(12) United States Patent
Subramanian et al.

(10) Patent No.: US 12,280,122 B2
(45) Date of Patent: *Apr. 22, 2025

(54) MUSCLE TARGETING COMPLEXES AND USES THEREOF FOR TREATING MYOTONIC DYSTROPHY

(71) Applicant: Dyne Therapeutics, Inc., Waltham, MA (US)

(72) Inventors: Romesh R. Subramanian, Framingham, MA (US); Mohammed T. Qatanani, Waltham, MA (US); Timothy Weeden, Waltham, MA (US); Cody A. Desjardins, Waltham, MA (US)

(73) Assignee: Dyne Therapeutics, Inc., Waltham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/799,447

(22) Filed: Aug. 9, 2024

(65) Prior Publication Data

US 2024/0398967 A1 Dec. 5, 2024

Related U.S. Application Data

(63) Continuation of application No. 18/416,981, filed on Jan. 19, 2024, now Pat. No. 12,097,263, which is a continuation of application No. 17/205,102, filed on Mar. 18, 2021, now Pat. No. 11,911,484, which is a continuation of application No. 17/264,905, filed as application No. PCT/US2019/044987 on Aug. 2, 2019, now abandoned.

(60) Provisional application No. 62/859,672, filed on Jun. 10, 2019, provisional application No. 62/858,888, filed on Jun. 7, 2019, provisional application No. 62/855,761, filed on May 31, 2019, provisional application No. 62/779,161, filed on Dec. 13, 2018, provisional application No. 62/713,914, filed on Aug. 2, 2018.

(51) Int. Cl.
| | | |
|---|---|---|
| *A61K 47/68* | (2017.01) | |
| *A61K 47/60* | (2017.01) | |
| *A61P 21/00* | (2006.01) | |
| *C07K 16/28* | (2006.01) | |
| *C12N 15/113* | (2010.01) | |

(52) U.S. Cl.
CPC .......... *A61K 47/6807* (2017.08); *A61K 47/60* (2017.08); *A61K 47/6849* (2017.08); *A61P 21/00* (2018.01); *C07K 16/2881* (2013.01); *C12N 15/1137* (2013.01); *C07K 2317/55* (2013.01); *C07K 2317/92* (2013.01); *C12N 2310/11* (2013.01); *C12N 2310/315* (2013.01); *C12N 2310/322* (2013.01); *C12N 2310/3513* (2013.01)

(58) Field of Classification Search
CPC . A61K 47/6807; A61K 47/6849; A61P 21/00; C07K 16/2881; C07K 2317/55; C12N 2310/11; C12N 2310/315; C12N 2310/322

See application file for complete search history.

(56) References Cited

U.S. PATENT DOCUMENTS

| | | |
|---|---|---|
| 2,631,173 A | 3/1953 | Hillyer et al. |
| 6,214,345 B1 | 4/2001 | Firestone et al. |
| 7,015,315 B1 | 3/2006 | Cook et al. |
| 7,064,142 B2 | 6/2006 | Sato et al. |
| 7,265,131 B2 | 9/2007 | Johnson et al. |
| 7,442,372 B2 | 10/2008 | Kakkis et al. |
| 7,575,886 B2 | 8/2009 | Venkataraman et al. |
| 8,580,756 B2 | 11/2013 | Hansen et al. |
| 8,846,639 B2 | 9/2014 | Swayze et al. |
| 8,859,629 B2 | 10/2014 | van Delft et al. |
| 8,952,147 B2 | 2/2015 | Bouchard et al. |
| 9,045,754 B2 | 6/2015 | Bhanot et al. |
| 9,222,940 B2 | 12/2015 | Van Delft et al. |
| 9,260,371 B2 | 2/2016 | Bertozzi et al. |
| 9,428,534 B2 | 8/2016 | Christensen et al. |
| 9,447,416 B2 | 9/2016 | Sazani et al. |
| 9,504,758 B2 | 11/2016 | van Delft et al. |
| 9,550,834 B2 | 1/2017 | Shirai et al. |
| 9,550,988 B2 | 1/2017 | Swayze |
| 9,610,362 B2 | 4/2017 | Armstrong |

(Continued)

FOREIGN PATENT DOCUMENTS

| | | |
|---|---|---|
| CN | 103443125 A | 12/2013 |
| CN | 103732259 A | 4/2014 |

(Continued)

OTHER PUBLICATIONS

Gong et al (Bioconjugate Chem. 2016, 27, 217-225) (Year: 2016).*
[No Author Listed] GenBank: NP_001121620. transferrin receptor protein 1 isoform 1 [*Homo sapiens*]. Dec. 28, 2017. Retrieved from the internet Aug. 2, 2023: https://www.ncbi.nlm.nih.gov/protein/NP_001121620.1, 4 pages.

(Continued)

*Primary Examiner* — Richard A Schnizer
(74) *Attorney, Agent, or Firm* — Wolf, Greenfield & Sacks, P.C.

(57) ABSTRACT

Aspects of the disclosure relate to complexes comprising a muscle-targeting agent covalently linked to a molecular payload. In some embodiments, the muscle-targeting agent specifically binds to an internalizing cell surface receptor on muscle cells. In some embodiments, the molecular payload inhibits expression or activity of a DMPK allele comprising a disease-associated-repeat. In some embodiments, the molecular payload is an oligonucleotide, such as an antisense oligonucleotide or RNAi oligonucleotide.

24 Claims, 21 Drawing Sheets

Specification includes a Sequence Listing.

(56) References Cited

U.S. PATENT DOCUMENTS

| | | |
|---|---|---|
| 9,617,540 B2 | 4/2017 | Bhanot et al. |
| 9,695,418 B2 | 7/2017 | Seth et al. |
| 9,708,406 B2 | 7/2017 | Zhang et al. |
| 9,708,614 B2 | 7/2017 | Christensen et al. |
| 9,765,338 B2 | 9/2017 | Bennett et al. |
| 10,131,682 B2 | 11/2018 | Zhao |
| 10,238,753 B2 | 3/2019 | Armstrong |
| 10,239,807 B2 | 3/2019 | van Delft et al. |
| 10,266,502 B2 | 4/2019 | van Delft et al. |
| 10,434,111 B2 | 10/2019 | Bertozzi et al. |
| 10,493,092 B2 | 12/2019 | Swayze |
| 10,550,188 B2 | 2/2020 | Geall et al. |
| 10,881,743 B2 | 1/2021 | Geall et al. |
| 11,111,309 B2 | 9/2021 | Subramanian et al. |
| 11,168,141 B2 | 11/2021 | Subramanian et al. |
| 11,179,472 B2 | 11/2021 | Levin et al. |
| 11,208,458 B2 | 12/2021 | Baik et al. |
| 11,230,605 B2 | 1/2022 | Launay et al. |
| 11,248,056 B1 | 2/2022 | Subramanian et al. |
| 11,286,305 B2 | 3/2022 | Subramanian et al. |
| 11,311,627 B1 | 4/2022 | Levin et al. |
| 11,369,689 B2 | 6/2022 | Subramanian et al. |
| 11,390,682 B2 | 7/2022 | Subramanian et al. |
| 11,400,163 B2 | 8/2022 | Levin et al. |
| 11,497,815 B2 | 11/2022 | Subramanian et al. |
| 11,518,816 B2 | 12/2022 | Subramanian et al. |
| 11,633,496 B2 | 4/2023 | Subramanian et al. |
| 11,633,498 B2 * | 4/2023 | Subramanian ..... C07K 16/2881 424/181.1 |
| 11,638,761 B2 | 5/2023 | Subramanian et al. |
| 11,648,318 B2 | 5/2023 | Subramanian et al. |
| 11,672,872 B2 | 6/2023 | Subramanian et al. |
| 11,679,161 B2 | 6/2023 | Subramanian et al. |
| 11,759,525 B1 | 9/2023 | Subramanian et al. |
| 11,771,776 B2 | 10/2023 | Subramanian et al. |
| 11,787,869 B2 | 10/2023 | Subramanian et al. |
| 11,795,233 B2 | 10/2023 | Subramanian et al. |
| 11,795,234 B2 | 10/2023 | Subramanian et al. |
| 11,833,217 B2 | 12/2023 | Subramanian et al. |
| 11,839,660 B2 | 12/2023 | Subramanian et al. |
| 11,844,843 B2 | 12/2023 | Subramanian et al. |
| 11,911,484 B2 * | 2/2024 | Subramanian ......... A61K 47/60 |
| 11,931,421 B2 * | 3/2024 | Hilderbrand ............ A61P 21/00 |
| 11,969,475 B2 | 4/2024 | Subramanian et al. |
| 11,986,537 B2 | 5/2024 | Subramanian et al. |
| 12,005,124 B2 | 6/2024 | Subramanian et al. |
| 12,012,460 B2 | 6/2024 | Subramanian et al. |
| 12,018,087 B2 * | 6/2024 | Subramanian .......... A61P 21/00 |
| 12,064,483 B2 | 8/2024 | Levin et al. |
| 12,097,263 B2 * | 9/2024 | Subramanian ......... A61K 47/60 |
| 12,102,687 B2 | 10/2024 | Subramanian et al. |
| 12,128,109 B2 | 10/2024 | Weeden et al. |
| 2004/0063654 A1 | 4/2004 | Davis et al. |
| 2004/0191243 A1 | 9/2004 | Chen et al. |
| 2005/0084906 A1 | 4/2005 | Goetsch et al. |
| 2005/0282252 A1 | 12/2005 | Siegel |
| 2006/0110782 A1 | 5/2006 | Bertozzi et al. |
| 2006/0252107 A1 | 11/2006 | Kubota et al. |
| 2011/0009471 A1 | 1/2011 | Kaneko et al. |
| 2011/0250199 A1 | 10/2011 | Fitzgerald et al. |
| 2011/0256157 A1 | 10/2011 | Howard et al. |
| 2012/0122801 A1 | 5/2012 | Platenburg |
| 2012/0201809 A1 | 8/2012 | Bhat et al. |
| 2012/0225013 A1 | 9/2012 | Dennis et al. |
| 2013/0028891 A1 | 1/2013 | Penichet et al. |
| 2013/0066063 A1 | 3/2013 | Berry et al. |
| 2013/0137763 A1 | 5/2013 | van Delft et al. |
| 2013/0177579 A1 | 7/2013 | Lin et al. |
| 2013/0237585 A1 | 9/2013 | Bennett et al. |
| 2014/0193436 A1 | 7/2014 | Prudent |
| 2014/0323552 A1 | 10/2014 | Burghes et al. |
| 2015/0064181 A1 | 3/2015 | Armstrong |
| 2015/0225722 A1 | 8/2015 | Ozsolak |
| 2015/0258210 A1 | 9/2015 | van Delft et al. |
| 2016/0015828 A1 | 1/2016 | Torgov et al. |
| 2016/0107999 A1 | 4/2016 | Debets et al. |
| 2016/0175460 A1 | 6/2016 | Arathoon et al. |
| 2016/0235861 A1 | 8/2016 | van Delft et al. |
| 2016/0250347 A1 | 9/2016 | van Delft et al. |
| 2016/0272973 A1 | 9/2016 | Shehadeh |
| 2016/0355599 A1 | 12/2016 | Sagert et al. |
| 2017/0002012 A1 | 1/2017 | van Delft et al. |
| 2017/0008858 A1 | 1/2017 | van Delft et al. |
| 2017/0072068 A1 | 3/2017 | Verkade et al. |
| 2017/0130256 A1 | 5/2017 | van Berkel et al. |
| 2017/0226554 A1 | 8/2017 | Wasiel et al. |
| 2017/0281795 A1 | 10/2017 | Geall et al. |
| 2017/0342169 A1 | 11/2017 | Akamatsu et al. |
| 2017/0348416 A1 | 12/2017 | Hasler et al. |
| 2018/0002433 A1 | 1/2018 | Zhang et al. |
| 2018/0021449 A1 | 1/2018 | Armstrong |
| 2018/0134797 A1 | 5/2018 | Zhang et al. |
| 2018/0369400 A1 | 12/2018 | Levin et al. |
| 2019/0000986 A1 | 1/2019 | Levin et al. |
| 2019/0038765 A1 | 2/2019 | van Berkel et al. |
| 2019/0092833 A1 | 3/2019 | Lin et al. |
| 2019/0092870 A1 | 3/2019 | Launay et al. |
| 2019/0153083 A1 | 5/2019 | Juste et al. |
| 2019/0211362 A1 | 7/2019 | Lundberg et al. |
| 2019/0240346 A1 * | 8/2019 | Sugo .................... A61K 39/395 |
| 2019/0298847 A1 | 10/2019 | Geall et al. |
| 2019/0336615 A1 | 11/2019 | Thompson et al. |
| 2020/0046742 A1 | 2/2020 | Bertozzi et al. |
| 2020/0048174 A1 | 2/2020 | van Delft et al. |
| 2020/0123267 A1 | 4/2020 | Zhang et al. |
| 2020/0282074 A1 | 9/2020 | Levin et al. |
| 2020/0325237 A1 | 10/2020 | Darimont et al. |
| 2021/0038739 A1 | 2/2021 | Takahashi et al. |
| 2021/0130486 A1 | 5/2021 | Darimont et al. |
| 2021/0187116 A1 | 6/2021 | Geall et al. |
| 2021/0206868 A1 | 7/2021 | Subramanian et al. |
| 2021/0220479 A1 | 7/2021 | Subramanian et al. |
| 2021/0228730 A1 | 7/2021 | Subramanian et al. |
| 2021/0230290 A1 | 7/2021 | Subramanian et al. |
| 2021/0261680 A1 | 8/2021 | Subramanian et al. |
| 2021/0308272 A1 | 10/2021 | Subramanian et al. |
| 2021/0308273 A1 | 10/2021 | Subramanian et al. |
| 2021/0308274 A1 | 10/2021 | Subramanian et al. |
| 2021/0317226 A1 | 10/2021 | Subramanian et al. |
| 2021/0322562 A1 | 10/2021 | Subramanian et al. |
| 2021/0322563 A1 | 10/2021 | Subramanian et al. |
| 2021/0324101 A1 | 10/2021 | Subramanian et al. |
| 2021/0380709 A1 | 12/2021 | Subramanian et al. |
| 2022/0025066 A1 | 1/2022 | Subramanian et al. |
| 2022/0143206 A1 | 5/2022 | Subramanian et al. |
| 2022/0169743 A1 | 6/2022 | Subramanian et al. |
| 2022/0193250 A1 | 6/2022 | Subramanian et al. |
| 2022/0288220 A1 | 9/2022 | Subramanian et al. |
| 2022/0306685 A1 | 9/2022 | Weeden et al. |
| 2022/0324992 A1 | 10/2022 | Subramanian et al. |
| 2022/0378934 A1 | 12/2022 | Subramanian et al. |
| 2023/0001002 A1 | 1/2023 | Subramanian et al. |
| 2023/0044278 A1 | 2/2023 | Subramanian et al. |
| 2023/0045002 A1 | 2/2023 | Subramanian et al. |
| 2023/0045314 A1 | 2/2023 | Subramanian et al. |
| 2023/0049450 A1 | 2/2023 | Subramanian et al. |
| 2023/0050911 A1 | 2/2023 | Subramanian et al. |
| 2023/0051954 A1 | 2/2023 | Subramanian et al. |
| 2023/0088865 A1 | 3/2023 | Subramanian et al. |
| 2023/0103793 A1 | 4/2023 | Subramanian et al. |
| 2023/0111147 A1 | 4/2023 | Subramanian et al. |
| 2023/0111212 A1 | 4/2023 | Subramanian et al. |
| 2023/0113823 A1 | 4/2023 | Subramanian et al. |
| 2023/0117883 A1 | 4/2023 | Subramanian et al. |
| 2023/0118799 A1 | 4/2023 | Subramanian et al. |
| 2023/0144436 A1 | 5/2023 | Subramanian et al. |
| 2023/0203180 A1 | 6/2023 | Subramanian et al. |
| 2023/0203181 A1 | 6/2023 | Subramanian et al. |
| 2023/0226212 A1 | 7/2023 | Subramanian et al. |
| 2023/0227569 A1 | 7/2023 | Subramanian et al. |
| 2023/0256112 A1 | 8/2023 | Subramanian et al. |
| 2023/0256113 A1 | 8/2023 | Subramanian et al. |
| 2023/0270873 A1 | 8/2023 | Subramanian et al. |
| 2023/0272065 A1 | 8/2023 | Subramanian et al. |

(56) References Cited

U.S. PATENT DOCUMENTS

| | | |
|---|---|---|
| 2023/0285582 A1 | 9/2023 | Subramanian et al. |
| 2023/0285586 A1 | 9/2023 | Subramanian et al. |
| 2023/0287108 A1 | 9/2023 | Subramanian et al. |
| 2023/0321264 A1 | 10/2023 | Subramanian et al. |
| 2023/0330247 A1 | 10/2023 | Hildebrand et al. |
| 2023/0330562 A1 | 10/2023 | Weeden et al. |
| 2023/0346966 A1 | 11/2023 | Subramanian et al. |
| 2023/0346967 A1 | 11/2023 | Subramanian et al. |
| 2024/0016950 A1 | 1/2024 | Weeden et al. |
| 2024/0016952 A1 | 1/2024 | Subramanian et al. |
| 2024/0066139 A1 | 2/2024 | Subramanian et al. |
| 2024/0066140 A1 | 2/2024 | Subramanian et al. |
| 2024/0067743 A1 | 2/2024 | Subramanian et al. |
| 2024/0067744 A1 | 2/2024 | Subramanian et al. |
| 2024/0100177 A1 | 3/2024 | Hildebrand et al. |
| 2024/0110184 A1 | 4/2024 | Brown et al. |
| 2024/0117356 A1 | 4/2024 | Subramanian et al. |
| 2024/0148891 A1 | 5/2024 | Subramanian et al. |
| 2024/0197901 A1 | 6/2024 | Subramanian et al. |
| 2024/0197905 A1 | 6/2024 | Subramanian et al. |
| 2024/0207430 A1 | 6/2024 | Subramanian et al. |
| 2024/0209119 A1 | 6/2024 | Subramanian et al. |
| 2024/0216522 A1 | 7/2024 | Subramanian et al. |
| 2024/0238435 A1 | 7/2024 | Subramanian et al. |
| 2024/0252666 A1 | 8/2024 | Hilderbrand et al. |
| 2024/0287201 A1 | 8/2024 | Subramanian et al. |
| 2024/0293568 A1 | 9/2024 | Subramanian et al. |
| 2024/0294921 A1 | 9/2024 | Subramanian et al. |
| 2024/0301416 A1 | 9/2024 | Tone et al. |
| 2024/0309107 A1 | 9/2024 | Subramanian et al. |
| 2024/0318176 A1 | 9/2024 | Desjardins et al. |
| 2024/0318177 A1 | 9/2024 | Desjardins et al. |
| 2024/0325558 A1 | 10/2024 | Zanotti et al. |

FOREIGN PATENT DOCUMENTS

| | | | |
|---|---|---|---|
| CN | 105142672 A | 12/2015 | |
| EP | 2149605 A2 | 2/2010 | |
| EP | 2410053 A1 | 1/2012 | |
| EP | 2410054 A1 | 1/2012 | |
| EP | 3031920 A1 | 6/2016 | |
| EP | 3067421 A1 | 9/2016 | |
| EP | 2623609 B1 | 1/2017 | |
| EP | 3202905 A1 | 8/2017 | |
| EP | 3315606 A1 | 5/2018 | |
| EP | 2922818 B1 | 9/2018 | |
| EP | 3436588 A1 | 2/2019 | |
| EP | 3473270 A1 | 4/2019 | |
| EP | 3489360 A2 | 5/2019 | |
| EP | 3560958 A1 | 10/2019 | |
| EP | 3565577 A1 | 11/2019 | |
| EP | 3684376 A1 | 7/2020 | |
| EP | 3691657 A1 | 8/2020 | |
| EP | 3720448 A1 | 10/2020 | |
| EP | 3735252 A2 | 11/2020 | |
| EP | 3898693 A1 | 10/2021 | |
| EP | 3980436 A1 | 4/2022 | |
| EP | 3980437 A1 | 4/2022 | |
| EP | 4126066 A1 | 2/2023 | |
| EP | 4146229 A1 | 3/2023 | |
| EP | 4314298 A1 | 2/2024 | |
| IL | 54795 A | 10/1980 | |
| JP | 2002-253259 A | 9/2002 | |
| JP | 2010-532168 A | 10/2010 | |
| JP | 2013-538560 A | 1/2012 | |
| JP | 2015-532264 A | 11/2015 | |
| JP | 2015-534996 A | 12/2015 | |
| JP | 2016-528258 A | 9/2016 | |
| WO | WO 1989/007970 A1 | 9/1989 | |
| WO | WO 1991/004753 A1 | 4/1991 | |
| WO | WO 2003/059951 A2 | 7/2003 | |
| WO | WO 2004/069991 A2 | 8/2004 | |
| WO | WO 2005/023825 A2 | 3/2005 | |
| WO | WO 2006/022688 A1 | 3/2006 | |
| WO | WO 2007/089612 A2 | 8/2007 | |
| WO | WO 2008/018795 A1 | 2/2008 | |
| WO | WO 2008/049085 A1 | 4/2008 | |
| WO | WO 2009/005793 A2 | 1/2009 | |
| WO | WO 2009/144481 A2 | 12/2009 | |
| WO | WO 2010/048586 A1 | 4/2010 | |
| WO | WO 2011/136645 A1 | 11/2011 | |
| WO | WO 2012/012443 A2 | 1/2012 | |
| WO | WO 2012/012467 A2 | 1/2012 | |
| WO | WO 2012/075037 A1 | 6/2012 | |
| WO | WO 2012/144906 A1 | 10/2012 | |
| WO | WO 2013/085550 A2 | 6/2013 | |
| WO | WO 2013/126746 A2 | 8/2013 | |
| WO | WO 2013/138662 A1 | 9/2013 | |
| WO | WO 2013/162363 A1 | 10/2013 | |
| WO | WO 2014/052276 A1 | 4/2014 | |
| WO | WO-2014065661 A1 * | 5/2014 | ............. A61K 47/61 |
| WO | WO 2015/021457 A2 | 2/2015 | |
| WO | WO 2015/023937 A1 | 2/2015 | |
| WO | WO 2015/042581 A1 | 3/2015 | |
| WO | WO 2015/179741 A1 | 11/2015 | |
| WO | WO 2016/081643 A1 | 5/2016 | |
| WO | WO 2016/081670 A2 | 5/2016 | |
| WO | WO 2016/187425 A1 | 11/2016 | |
| WO | WO 2017/062862 A2 | 4/2017 | |
| WO | WO 2017/100467 A2 | 6/2017 | |
| WO | WO 2017/106643 A1 | 6/2017 | |
| WO | WO 2017/143156 A1 | 8/2017 | |
| WO | WO 2017/173408 A1 | 10/2017 | |
| WO | WO 2017/192679 A1 | 11/2017 | |
| WO | WO 2017/205191 A1 | 11/2017 | |
| WO | WO 2017/221883 A1 | 12/2017 | |
| WO | WO 2018/129384 A1 | 7/2018 | |
| WO | WO 2018/226861 A1 | 12/2018 | |
| WO | WO 2019/060775 A1 | 3/2019 | |
| WO | WO 2019/071028 A1 | 4/2019 | |
| WO | WO 2019/113393 A1 | 6/2019 | |
| WO | WO 2019/136180 A2 | 7/2019 | |
| WO | WO 2019/151539 A1 | 8/2019 | |
| WO | WO 2019/157224 A1 | 8/2019 | |
| WO | WO 2019/215175 A1 | 11/2019 | |
| WO | WO 2019/229658 A1 | 12/2019 | |
| WO | WO 2020/028831 A1 | 2/2020 | |
| WO | WO 2020/028832 A1 | 2/2020 | |
| WO | WO 2020/028836 A1 | 2/2020 | |
| WO | WO 2020/028840 A1 | 2/2020 | |
| WO | WO 2020/028841 A1 | 2/2020 | |
| WO | WO 2020/028842 A1 | 2/2020 | |
| WO | WO 2020/028844 A1 | 2/2020 | |
| WO | WO 2020/028857 A1 | 2/2020 | |
| WO | WO 2020/028861 A1 | 2/2020 | |
| WO | WO 2020/028864 A1 | 2/2020 | |
| WO | WO 2020/084488 A1 | 4/2020 | |
| WO | WO 2020/094670 A1 | 5/2020 | |
| WO | WO 2020/132584 A1 | 6/2020 | |
| WO | WO 2020/163817 A1 | 8/2020 | |
| WO | WO 2020/209285 A1 | 10/2020 | |
| WO | WO 2020/247738 A1 | 12/2020 | |
| WO | WO 2020/247782 A1 | 12/2020 | |
| WO | WO 2020/247818 A1 | 12/2020 | |
| WO | WO 2021/076856 A1 | 4/2021 | |
| WO | WO 2021/108640 A1 | 6/2021 | |
| WO | WO 2021/142217 A1 | 7/2021 | |
| WO | WO 2021/142227 A1 | 7/2021 | |
| WO | WO 2021/142234 A1 | 7/2021 | |
| WO | WO 2021/142260 A1 | 7/2021 | |
| WO | WO 2021/142269 A1 | 7/2021 | |
| WO | WO 2021/142275 A1 | 7/2021 | |
| WO | WO 2021/142307 A1 | 7/2021 | |
| WO | WO 2021/142313 A1 | 7/2021 | |
| WO | WO 2021/142331 A1 | 7/2021 | |
| WO | WO 2021/150382 A1 | 7/2021 | |
| WO | WO 2021/154476 A1 | 8/2021 | |
| WO | WO 2021/154477 A1 | 8/2021 | |
| WO | WO 2022/020105 A1 | 1/2022 | |
| WO | WO 2022/020106 A1 | 1/2022 | |
| WO | WO 2022/020107 A1 | 1/2022 | |
| WO | WO 2022/020108 A1 | 1/2022 | |
| WO | WO 2022/020109 A1 | 1/2022 | |
| WO | WO 2022/026152 A1 | 2/2022 | |

(56) References Cited

FOREIGN PATENT DOCUMENTS

| WO | WO 2022/051665 A1 | 3/2022 |
|---|---|---|
| WO | WO 2022/056266 A2 | 3/2022 |
| WO | WO 2022/120132 A1 | 6/2022 |
| WO | WO 2022/147207 A1 | 7/2022 |
| WO | WO 2022/147209 A1 | 7/2022 |
| WO | WO 2022/212886 A1 | 10/2022 |
| WO | WO 2022/213118 A1 | 10/2022 |
| WO | WO 2022/270585 A1 | 12/2022 |
| WO | WO 2022/271543 A2 | 12/2022 |
| WO | WO 2022/271549 A1 | 12/2022 |
| WO | WO 2023/283531 A2 | 1/2023 |
| WO | WO 2023/283613 A1 | 1/2023 |
| WO | WO 2023/283614 A2 | 1/2023 |
| WO | WO 2023/283615 A1 | 1/2023 |
| WO | WO 2023/283619 A2 | 1/2023 |
| WO | WO 2023/283620 A1 | 1/2023 |
| WO | WO 2023/283623 A1 | 1/2023 |
| WO | WO 2023/283624 A2 | 1/2023 |
| WO | WO 2023/283629 A1 | 1/2023 |
| WO | WO 2023/022229 A1 | 2/2023 |
| WO | WO 2023/026994 A1 | 3/2023 |
| WO | WO 2023/044398 A1 | 3/2023 |
| WO | WO 2023/077120 A1 | 5/2023 |
| WO | WO 2023/086864 A1 | 5/2023 |
| WO | WO 2023/121444 A1 | 6/2023 |
| WO | WO 2023/121445 A1 | 6/2023 |
| WO | WO 2023/121446 A1 | 6/2023 |
| WO | WO 2023/168427 A1 | 9/2023 |
| WO | WO 2023/171820 A1 | 9/2023 |
| WO | WO 2023/196400 A2 | 10/2023 |
| WO | WO 2023/201318 A1 | 10/2023 |
| WO | WO 2023/201324 A1 | 10/2023 |
| WO | WO 2023/201332 A1 | 10/2023 |
| WO | WO 2024/011135 A1 | 1/2024 |
| WO | WO 2024/011150 A1 | 1/2024 |
| WO | WO 2024/097644 A1 | 5/2024 |
| WO | WO 2024/112809 A2 | 5/2024 |
| WO | WO 2024/149282 A1 | 7/2024 |
| WO | WO 2024/182358 A1 | 9/2024 |

OTHER PUBLICATIONS

[No Author Listed] UniProtKB/Swiss-Prot P02786. Transferrin receptor protein 1. Jul. 1, 20188. Retrieved from the Internet Oct. 23, 2019: https://www.uniprot.org/uniprot/P02786.txt?version=225, 20 pages.

[No Author Listed] Wikipedia, Mannose 6-phosphate receptor, Mar. 23, 2018. Retrieved from the internet Nov. 6, 2019: https://en.wikipedia.org/w/index.php?title=Mannose_6-phosphate_receptor&oldid=832003836, 8 pages.

[No Author Listed] Wikipedia, Myotonic dystrophy, Sep. 8, 2017. Retrieved from the internet Nov. 5, 2019: https://en.wikipedia.org/w/index.php?title=Myotonic_dystrophy&oldid=799605783, 9 pages.

[No Author Listed], Baliforsen—Ionis Pharmaceuticals Drug Profile. Springer Nature Switzerland AG. Nov. 15, 2016. 9 pages.

[No Author Listed], Building the world's leading muscle disease company. Dyne Company Overview. Jun. 2021. 42 pages.

[No Author Listed], IRDye® Peptide Labeling Application Guide. <https://licor.com/documents/nmekjs7iez6sw5p8fv7b7005chbrcog7> Published Apr. 2013. Retrieved Oct. 27, 2021. 8 pages.

[No Author Listed], Transferrin Receptor/CD71 Extracellular Domain (human, recombinant) 2021, retrieved from https://www.caymanchem.com/product/32031/transferrin-receptor-extracellular-domain-(human%2C-recombinant)#:-:text=Cayman's Transferrin Receptor%2FCD71 Extracellular,molecular weight of 103.6 kDa (Year: 2021). 3 pages.

Agard et al., A Comparative Study of Bioorthogonal Reactions with Azides. ACS Chem. Biol. 2006;1(10):644-8. Epub Oct. 20, 2006.

Agard et al., A Strain-Promoted [3 + 2] Azide-Alkyne Cycloaddition for Covalent Modification of Biomolecules in Living Systems. J. Am. Chem. Soc. Nov. 2004;126(46):15046-7.

Altshuler et al., Generation of recombinant antibodies and means for increasing their affinity. Biochemistry (Mosc). Dec. 2010;75(13):1584-605.

Anciaux et al., Transition-metal-catalyzed reactions of diazo compounds. 1. Cyclopropanation of double bonds. The Journal of Organic Chemistry. Feb. 1980;45(4):695-702.

Antony-Mayer et al., Bicyclo[6.1.0]nonynes. Chemische Berichte. Nov. 1988;121(11):2013-8.

Aoki et al., Challenges for antisense oligonucleotide-based therapeutics, in particular for exon 51-skipping in Duchenne muscular dystrophy, 2011 Fourth International Conference on Modeling, Simulation and Applied Optimization, 2011, 1-6, doi: 10.1109/ICMSAO.2011.5775520.

Arzumanov et al., A structure-activity study of the inhibition of HIV-1 Tat-dependent trans-activation by mixmer 2'-O-methyl oligoribonucleotides containing locked nucleic acid (LNA), alpha-L-LNA, or 2'-thio-LNA residues. Oligonucleotides. 2003;13(6):435-53. doi: 10.1089/154545703322860762.

Arzumanov et al., Inhibition of HIV-1 Tat-dependent trans activation by steric block chimeric 2'-O-methyl/LNA oligoribonucleotides. Biochemistry. Dec. 4, 2001;40(48):14645-54. doi: 10.1021/bi011279e.

Ast et al., Estergruppenhaltige Polyalkenylene durch Olefin-Metathese. Die Makromolekulare Chemie. May 1976;177(5):1349-55.

Barfield et al., A Novel HER2-targeted Antibody-drug Conjugate Offers the Possibility of Clinical Dosing at Trastuzumab-equivalent Exposure Levels. Mol Cancer Ther. Sep. 2020;19(9):1866-1874. doi: 10.1158/1535-7163.MCT-20-0190. Epub Jul. 10, 2020.

Barrientos et al., Metabolic Catastrophe in Mice Lacking Transferrin Receptor in Muscle. EBioMedicine. Oct. 4, 2015;2(11):1705-17. doi: 10.1016/j.ebiom.2015.09.041. eCollection Nov. 2015.

Baskin et al., Copper-free click chemistry for dynamic in vivo imaging. PNAS. Oct. 2007;104(43):16793-7.

Behlke, Chemical modification of siRNAs for in vivo use. Oligonucleotides. Dec. 2008;18(4):305-19.

Bennett et al., RNA targeting therapeutics: molecular mechanisms of antisense oligonucleotides as a therapeutic platform. Annu Rev Pharmacol Toxicol. 2010;50:259-93. Epub Oct. 19, 2009.

Beskrovnaya, FORCETM platform delivers exon skipping PMO, leads to durable increases in dystrophin protein in mdx mice and is well tolerated NHPs. Presented at Muscle Study Group Annual Scientific Meeting. Oct. 1, 2021. 29 pages.

Bien-Ly et al., Transferrin receptor (TfR) trafficking determines brain uptake of TfR antibody affinity variants. J Exp Med. Feb. 10, 2014;211(2):233-44. Epub Jan. 27, 2014.

Black, 9.13.4.1.1.3.2 Variation 2: C-Alkylation (and Arylation) by Carbenes and Free Radicals. Science of Synthesis. 2001;9:514.

Brown et al., Tolerance to single, but not multiple, amino acid replacements in antibody VH CDR 2: a means of minimizing B cell wastage from somatic hypermutation? J Immunol. May 1, 1996;156(9):3285-91.

Buntz et al., Quantitative fluorescence imaging determines the absolute No. of locked nucleic acid oligonucleotides needed for suppression of target gene expression. Nucleic Acids Res. Jan. 25, 2019;47(2):953-969. doi: 10.1093/nar/gky1158.

Bushel et al., Blood gene expression signatures predict exposure levels. Proc Natl Acad Sci USA. Nov. 13, 2007;104(46):18211-6. doi: 10.1073/pnas.0706987104. Epub Nov. 2, 2007.

Candelaria et al., Antibodies Targeting the Transferrin Receptor 1 (TfR1) as Direct Anti-cancer Agents. Front Immunol. Mar. 17, 2021;12:607692.

Carrell et al., Dmpk gene deletion or antisense knockdown does not compromise cardiac or skeletal muscle function in mice. Hum Mol Genet. Oct. 1, 2016;25(19):4328-4338. doi: 10.1093/hmg/ddw266. Epub Aug. 13, 2016.

Casi et al., Antibody-drug conjugates: basic concepts, examples and future perspectives. J Control Release. Jul. 20, 2012;161(2):422-8. doi: 10.1016/j.jconrel.2012.01.026. Epub Jan. 28, 2012.

Cenik et al., Argonaute proteins. Curr Biol. Jun. 21, 2011;21(12):R446-9.

Cho et al., Myotonic dystrophy: emerging mechanisms for DM1 and DM2. Biochim Biophys Acta. Feb. 2007;1772(2):195-204. Epub Jun. 20, 2006.

(56) References Cited

OTHER PUBLICATIONS

Chothia et al., Canonical structures for the hypervariable regions of immunoglobulins. J Mol Biol. Aug. 20, 1987;196(4):901-17. doi: 10.1016/0022-2836(87)90412-8.

Clark et al., Increased brain uptake of targeted nanoparticles by adding an acid-cleavable linkage between transferrin and the nanoparticle core. PNAS. Oct. 2015;112(40):12486-91.

Codelli et al., Second-Generation Difluorinated Cyclooctynes for Copper-Free Click Chemistry. J. Am. Chem. Soc. 2008;130(34):11486-11493. Epub Aug. 5, 2008.

Coico et al., Immunology: A short course. 2008 (originally published 2003): 61-2. 8 pages (including English translation).

Crook et al., Enrichment of early fetal-liver hemopoietic stem cells of the rat using monoclonal antibodies against the transferrin receptor, Thy-1, and MRC-OX82. Dev Immunol. 1996;4(4):235-46. doi: 10.1155/1995/85036.

Crooke et al., Antisense research and applications. 1993. p. 15-35.

Crooke et al., Kinetic characteristics of *Escherichia coli* RNase H1: cleavage of various antisense oligonucleotide-RNA duplexes. Biochem J. Dec. 1, 1995;312(Pt 2):599-608. doi: 10.1042/bj3120599.

Crooke et al., The Effects of 2'-O-Methoxyethyl Oligonucleotides on Renal Function in Humans. Nucleic Acid Ther. Feb. 2018;28(1):10-22. doi: 10.1089/nat.2017.0693. Epub Nov. 29, 2017.

Cuellar et al., Systematic evaluation of antibody-mediated siRNA delivery using an industrial platform of THIOMAB-siRNA conjugates. Nucleic Acids Res. Jan. 2015;43(2):1189-203. Epub Dec. 30, 2014.

Curtius, Ueber die Einwirkung von salpetriger Säure auf salzsauren Glycocolläther. Berichte der deutschen chemischen Gesellschaft. Jul.-Dec. 1883;16(2):2230-1.

Danis et al., Potential therapeutic application of antisense oligonucleotides in the treatment of ocular diseases. Expert Opin Pharmacother. Feb. 2001;2(2):277-91.

Darimont et al., A novel antibody-oligonucleotide conjugate (AOC) platform enables efficient regulation of muscle targets in mice. Abstract. 8-05. J. Cach Sarcopen Musc. 2017; 8:1065-66.

Davis et al., Improved targeting of miRNA with antisense oligonucleotides. Nucleic Acids Res. May 11, 2006;34(8):2294-304. doi: 10.1093/nar/gkl183. Print 2006.

Debets et al., Bioorthogonal labelling of biomolecules: new functional handles and ligation methods. Org Biomol Chem. Oct. 14, 2013;11(38):6439-55. Epub Aug. 23, 2013.

Demonceau et al., Novel Ruthenium-Based Catalyst Systems for the Ring-Opening Metathesis Polymerization of Low-Strain Cyclic Olefins. Macromolecules. 1997;30(11):3127-36. Epub Jun. 2, 1997.

Desjardins et al., Building a FORCETM platform-based DMD franchise for the treatment of individuals with mutations amenable to exon skipping. Neuromusc Dis. Oct. 2022; 32: S101-2. Abstract.

Desjardins et al., Building a ForceTM platform-based DMD franchise for the treatment of individuals with mutations amenable to exon skipping. Presented at 27th Int Hybrid Annual Congress of the World Muscle Society. Oct. 11-15, 2022. Poster. 1 page.

Desjardins et al., Enhanced exon skipping and prolonged dystrophin restoration achieved by TfR1-targeted delivery of antisense oligonucleotide using FORCE conjugation in mdx mice. Nucleic Acids Res. Nov. 11, 2022;50(20): 11401-11414.

Desjardins et al., Enhanced exon skipping and prolonged dystrophin restoration achieved by TfR1-targeted delivery of antisense oligonucleotide using FORCE conjugation in mdx mice. Nucleic Acids Res. Nov. 11, 2022;50(20):11401-11414. Supplemental Figures and Figure Legends. 34 pages.

Desjardins et al., ForceTM platform achieves robust exon skipping, restores dystrophin at the sarcolemma and halts progression of fibrosis in the severe D2-mdx model of DMD. Abstract. Mar. 2023. 1 page.

Desjardins et al., ForceTM platform achieves robust exon skipping, restores dystrophin at the sarcolemma and halts progression of fibrosis in the severe D2-mdx model of DMD. Poster. Presented at The Muscular Dystrophy Association Clinical and Scientific Conference. Mar. 19-22, 2023. 1 page.

Dommerholt et al., Readily accessible bicyclononynes for bioorthogonal labeling and three-dimensional imaging of living cells. Angew Chem Int Ed. Dec. 3, 2010;49(49):9422-5.

Dommerholt et al., Strain-Promoted 1,3-Dipolar Cycloaddition of Cycloalkynes and Organic Azides. Top Curr Chem. Apr. 2016;374(2):16. doi: 10.1007/s41061-016-0016-4. Epub Mar. 22, 2016.

Doucet et al., Abstract 150—RNA-based gene therapy for myotonic dystrophy type 1 (DM1). The Ottawa Conference on New Directions in Biology & Disease of Skeletal Muscle. Ottawa, CA. May 5-8, 2010:67. 6 pages total.

Efferth et al., Enhancement of cytotoxicity of artemisinins toward cancer cells by ferrous iron. Free Radic Biol Med. Oct. 1, 2004;37(7):998-1009. doi: 10.1016/j.freeradbiomed.2004.06.023.

Elangkovan et al., Gene Therapy for Duchenne Muscular Dystrophy. J Neuromuscul Dis. 2021;8(s2):S303-S316.

Fan, Research on humanized antibody-drug conjugates targeting prostate-specific membrane antigen. Chapter 7. Frontiers in Cancer Research. vol. 16. Xi'an Jiaotong University Press. Dec. 2016; 163-5. Chinese.

Fluiter et al., On the in vitro and in vivo properties of four locked nucleic acid nucleotides incorporated into an anti-H-Ras antisense oligonucleotide. Chembiochem. Jun. 2005;6(6):1104-9. doi: 10.1002/cbic.200400419.

Frazier, Antisense oligonucleotide therapies: the promise and the challenges from a toxicologic pathologist's perspective. Toxicol Pathol. Jan. 2015;43(1):78-89. doi: 10.1177/0192623314551840. Epub Nov. 9, 2014.

Frieden et al., Nuclease stability of LNA oligonucleotides and LNA-DNA chimeras. Nucleosides Nucleotides Nucleic Acids. May-Aug. 2003;22(5-8):1041-3. doi: 10.1081/NCN-120022731.

Furling et al., Abstract R.P.1.01 Therapeutic RNA strategies for myotonic dystrophy with CTG repeats. Neuromuscular Disorders. 2004;14:585. 2 pages total.

Furling et al., Viral vector producing antisense RNA restores myotonic dystrophy myoblast functions. Gene Ther. May 2003;10(9):795-802.

Gagnon et al., RNAi factors are present and active in human cell nuclei. Cell Rep. Jan. 16, 2014;6(1):211-21. Epub Jan. 2, 2014.

Galderisi et al., Myotonic dystrophy: antisense oligonucleotide inhibition of DMPK gene expression in vitro. Biochem Biophys Res Commun. Apr. 25, 1996;221(3):750-4.

Gao et al., Antisense oligonucleotides: rising stars in eliminating RNA toxicity in myotonic dystrophy. Hum Gene Ther. May 2013;24(5):499-507. doi: 10.1089/hum.2012.212. Epub Jan. 30, 2013.

Geary et al., Pharmacokinetics, biodistribution and cell uptake of antisense oligonucleotides. Adv Drug Deliv Rev. Jun. 29, 2015;87:46-51. doi: 10.1016/j.addr.2015.01.008. Epub Feb. 7, 2015.

Giles et al., Enhanced RNase H activity with methylphosphonodiester/phosphodiester chimeric antisense oligodeoxynucleotides. Anticancer Drug Des. Feb. 1992;7(1):37-48.

Girones et al. Comparison of the kinetics of cycling of the transferrin receptor in the presence or absence of bound diferric transferrin. Biochem J. Nov. 15, 1989;264(1):35-46.

Gong et al., Simple Method To Prepare Oligonucleotide—Conjugated Antibodies and Its Application in Multiplex Protein Detection in Single Cells. Bioconjug Chem. Jan. 20, 2016;27(1):217-25. doi: 10.1021/acs.bioconjchem.5b00613. Epub Jan. 4, 2016.

Gonzalez-Barriga et al., Intracellular Distribution and Nuclear Activity of Antisense Oligonucleotides After Unassisted Uptake in Myoblasts and Differentiated Myotubes In Vitro. Nucleic Acid Ther. Jun. 2017;27(3):144-158. doi: 10.1089/nat.2016.0641. Epub Apr. 4, 2017.

Gray et al., Combinatorial peptide libraries: mining for cell-binding peptides. Chem Rev. Jan. 22, 2014;114(2):1020-81.

Heemskerk et al., Preclinical PK and PD studies on 2'-O-methyl-phosphorothioate RNA antisense oligonucleotides in the mdx mouse model. Mol Ther. Jun. 2010;18(6):1210-7. doi: 10.1038/mt.2010.72. Epub Apr. 20, 2010.

Hein et al., Click chemistry, a powerful tool for pharmaceutical sciences. Pharm Res. Oct. 2008;25(10):2216-30. doi: 10.1007/s11095-008-9616-1. Epub May 29, 2008.

Helguera et al. An antibody recognizing the apical domain of human transferrin receptor 1 efficiently inhibits the entry of all new world

(56) References Cited

OTHER PUBLICATIONS hemorrhagic Fever arenaviruses. J Virol. Apr. 2012;86(7):4024-8. doi: 10.1128/JVI.06397-11. Epub Jan. 25, 2012.

Iwaki et al., Preparation of Chiral Stationary Phase via Activated Carbamate Intermediate for Liquid Chromatographic Optical Resolution. Chromatographia. Oct. 1987;23:727-30.

Jain et al., Current ADC Linker Chemistry. Pharm Res. Nov. 2015;32(11):3526-40. Epub Mar. 11, 2015.

Jauvin et al., Targeting DMPK with Antisense Oligonucleotide Improves Muscle Strength in Myotonic Dystrophy Type 1 Mice. Mol Ther Nucleic Acids. Jun. 16, 2017;7:465-474. Epub May 17, 2017.

Jearawiriyapaisarn et al., Sustained Dystrophin Expression Induced by Peptide-conjugated Morpholino Oligomers in the Muscles of mdx Mice. Mol Ther. Sep. 2008;16(9):1624-9. doi: 10.1038/mt.2008.120. Epub Jun. 10, 2008.

Jepsen et al., Locked nucleic acid: a potent nucleic acid analog in therapeutics and biotechnology. Oligonucleotides. 2004;14(2):130-46. doi: 10.1089/1545457041526317.

Juliano, The delivery of therapeutic oligonucleotides. Nucleic Acids Res. Aug. 19, 2016;44(14):6518-48. doi: 10.1093/nar/gkw236. Epub Apr. 15, 2016.

Kher et al., Antisense Oligonucleotides and RNA Interference. Challenges in Delivery of Therapeutic Genomics and Proteomics. Aug. 2011:325-86.

Kline et al., Methods to Make Homogenous Antibody Drug Conjugates. Pharm Res. Nov. 2015;32(11):3480-93. Epub Dec. 16, 2014.

Koshelev et al., Abstract 130—Therapeutic application for a cell culture model of myotonic dystrophy. New Directions in Biology & Disease of Skeletal Muscle. New Orleans, LA. Apr. 27-30, 2008:44. 10 pages total.

Koshelev et al., Heart-specific overexpression of CUGBP1 reproduces functional and molecular abnormalities of myotonic dystrophy type 1. Hum Mol Genet. Mar. 15, 2010;19(6):1066-75. Epub Jan. 5, 2010.

Kuran et al., Investigations on the Catalytic Systems Diethylzinc/Di- and Trihydroxybenzenes in the Copolymerization of Carbon Dioxide with Propylene Oxide. Makromol. Chem. 1976;177:1283-92.

Kurreck et al., Design of antisense oligonucleotides stabilized by locked nucleic acids. Nucleic Acids Res. May 1, 2002;30(9):1911-8. doi: 10.1093/nar/30.9.1911.

Kurreck, Antisense technologies. Improvement through novel chemical modifications. Eur J Biochem. Apr. 2003;270(8):1628-44.

Lai et al., Mechanism of action and spectrum of cell lines sensitive to a doxorubicin-transferrin conjugate. Cancer Chemother Pharmacol. 1998;41(2):155-60. doi: 10.1007/s002800050722.

Langlois et al., Abstract 831—Ribozyme and Antisense RNA-Based Gene Therapies for Myotonic Dystrophy. Molecular Therapy. May 2003;7(5, Part 2):S320.

Langlois et al., Cytoplasmic and nuclear retained DMPK mRNAs are targets for RNA interference in myotonic dystrophy cells. J Biol Chem. Apr. 29, 2005;280(17):16949-54. Epub Feb. 18, 2005.

Langlois et al., Hammerhead ribozyme-mediated destruction of nuclear foci in myotonic dystrophy myoblasts. Mol Ther. May 2003;7(5 Pt 1):670-80.

Lawrence et al., Crystal structure of the ectodomain of human transferrin receptor. Science. Oct. 22, 1999;286(5440):779-82. doi: 10.1126/science.286.5440.779.

Lee et al., Abstract—Targeted Degradation of Toxic RNA in Myotonic Dystrophy. RNA & Oligonucleotide Therapeutics. Cold Spring Harbor Laboratory. Cold Spring Harbor, NY. Apr. 7-10, 2010:35. 19 pages total.

Lee et al., RNase H-mediated degradation of toxic RNA in myotonic dystrophy type 1. Proc Natl Acad Sci U S A. Mar. 13, 2012;109(11):4221-6. doi: 10.1073/pnas.1117019109. Epub Feb. 27, 2012.

Lennox et al., Cellular localization of long non-coding RNAs affects silencing by RNAi more than by antisense oligonucleotides. Nucleic Acids Res. Jan. 29, 2016;44(2):863-77. doi: 10.1093/nar/gkv1206. Epub Nov. 17, 2015.

Lesley et al., Selection of cell lines resistant to anti-transferrin receptor antibody: evidence for a mutation in transferrin receptor. Mol Cell Biol. Sep. 1984;4(9):1675-81. doi: 10.1128/mcb.4.9.1675-1681.1984.

Levin, Targeting Therapeutic Oligonucleotides. N Engl J Med. Jan. 5, 2017;376(1):86-88. doi: 10.1056/NEJMcibr1613559.

Liang et al., RNase H1-Dependent Antisense Oligonucleotides Are Robustly Active in Directing RNA Cleavage in Both the Cytoplasm and the Nucleus. Mol Ther. Sep. 6, 2017;25(9):2075-2092. Epub Jun. 27, 2017.

Liang et al., Targeted delivery of plasmid DNA to myogenic cells via transferrin-conjugated peptide nucleic acid. Mol Ther. Mar. 2000;1(3):236-43. doi: 10.1006/mthe.2000.0043.

Lima et al., Structural requirements at the catalytic site of the heteroduplex substrate for human RNase H1 catalysis. J Biol Chem. Aug. 27, 2004;279(35):36317-26. doi: 10.1074/jbc.M405035200. Epub Jun. 17, 2004.

Lima et al., The positional influence of the helical geometry of the heteroduplex substrate on human RNase H1 catalysis. Mol Pharmacol. Jan. 2007;71(1):73-82. doi: 10.1124/mol.106.025429. Epub Oct. 6, 2006.

Liu, Exploring cell type-specific internalizing antibodies for targeted delivery of siRNA. Brief Funct Genomic Proteomic. Jun. 2007;6(2):112-9. doi: 10.1093/bfgp/elm015. Epub Jul. 31, 2007.

Luria-Perez et al., Antibody-mediated targeting of the transferrin receptor in cancer cells. Bol Med Hosp Infant Mex. Nov.-Dec. 2016;73(6):372-379. doi: 10.1016/j.bmhimx.2016.11.004. Epub Dec. 13, 2016.

Masters et al., Clinical toxicity of antibody drug conjugates: a meta-analysis of payloads. Invest New Drugs. Feb. 2018;36(1):121-135. doi: 10.1007/s10637-017-0520-6. Epub Oct. 13, 2017.

Meeuwissen et al., Cofactor regeneration in polymersome nanoreactors: Enzymatically catalysed Baeyer-Villiger reactions. Journal of Materials Chemistry. Dec. 2011;21(47):18923-6.

Mignon, Update on Ionis-DMPKRX Program. 2018 MDF Annual Conference. Nashville, TN. Sep. 14-15, 2018:22 pages.

Mojsov et al., A Quantitative Evaluation of Methods for Coupling Asparagine. The Journal of Organic Chemistry. Feb. 1980;45(4):555-60.

Monia et al., Evaluation of 2'-modified oligonucleotides containing 2'-deoxy gaps as antisense inhibitors of gene expression. J Biol Chem. Jul. 5, 1993;268(19):14514-22.

Mulders et al., Abstract S8-06—Chemically modified (CAG)n antisense oligonucleotides as molecular tools to silence toxic, expanded DMPK transcripts. 7th International Myotonic Dystrophy Consortium Meeting (IDMC-7). Wuerzburg, Germany. Sep 9-12, 2009:421-2. 12 pages total.

Mulders et al., Molecular therapy in myotonic dystrophy: focus on RNA gain-of-function. Human Molecular Genetics. 2010;19(1):R90-7. Epub Apr. 20, 2010.

Mulders et al., Triplet-repeat oligonucleotide-mediated reversal of RNA toxicity in myotonic dystrophy. PNAS. Aug. 18, 2009;106(33):13915-20. Supporting information included. 13 pages.

Murray et al., Human Biochemistry. "Mir." Moscow. 1993; 1:34. 5 pages (including English translation).

Naylor et al., DELIVER, a randomized, double-blind, placebo controlled, multiple ascending dose study of DYNE-251 in boys with DMD amenable to Exon 51 skipping. Poster. Presented at The Muscular Dystrophy Association Clinical and Scientific Conference. Mar. 19-22, 2023. 1 page.

Naylor et al., DELIVER, a randomized, double-blind, placebo controlled, multiple ascending dose study of DYNE-251 in boys with DMD amenable to Exon 51 skipping. Abstract. Mar. 2023. 1 page.

Overby et al., RNA-mediated therapies in myotonic dystrophy. Drug Discov Today. Dec. 2018;23(12):2013-2022. Epub Aug. 4, 2018.

(56) References Cited

OTHER PUBLICATIONS

Padlan et al., A possible procedure for reducing the immunogenicity of antibody variable domains while preserving their ligand-binding properties. Molecular Immunology. Apr.-May 1991;28(4-5):489-98.

Pandey et al., Identification and characterization of modified antisense oligonucleotides targeting DMPK in mice and nonhuman primates for the treatment of myotonic dystrophy type 1. J Pharmacol Exp Ther. Nov. 2015;355(2):329-40. doi: 10.1124/jpet.115.226969. Epub Sep. 1, 2015.

Panowski et al., Site-specific antibody drug conjugates for cancer therapy. MAbs. Jan.-Feb. 2014;6(1):34-45.

Picariello et al., Dyne-101 achieves durable knockdown of toxic human nuclear *DMPK* RNA and correction of splicing in the hTfR1/DMSXL mouse model of DM1. Presented at The Muscular Dystrophy Association Clinical and Scientific Conference. Mar. 13-16, 2022. 1 page.

Piche-Nicholas et al., Changes in complementarity-determining regions significantly alter IgG binding to the neonatal Fc receptor (FcRn) and pharmacokinetics. MAbs. Jan. 2018;10(1):81-94. doi: 10.1080/19420862.2017.1389355. Epub Nov. 3, 2017.

Pradeepkumar, Chemically modified oligonucleotides: synthesis, physicochemical and biochemical properties of their duplexes with DNA and RNA. Comprehensive Summaries of Uppsala Disserations from the Faculty of Science and Technology. 2004; 973: 56 pages.

Qian et al., Targeted drug delivery via the transferrin receptor-mediated endocytosis pathway. Pharmacol Rev. Dec. 2002;54(4):561-87. doi: 10.1124/pr.54.4.561.

Ramasamy et al., Remarkable enhancement of binding affinity of Heterocycle-modified DNA to DNA and RNA. Synthesis, characterization and biophysical evaluation of N2-imidazolylpropylguanine and N2-imidazolylpropyl-2-aminoadenine modified oligonucleotides. Tetrahedron Let. 1994;35(2):215-18.

Roberts et al., Advances in oligonucleotide drug delivery. Nat Rev Drug Discov. Oct. 2020;19(10):673-694. doi: 10.1038/s41573-020-0075-7. Epub Aug. 11, 2020.

Roberts et al., The Halogenation of Ethylenes. J. Am. Chem. Soc. May 1937;59(5):947-8.

Sahenk et al., The muscular dystrophies: distinct pathogenic mechanisms invite novel therapeutic approaches. Curr Rheumatol Rep. Jun. 2011;13(3):199-207.

Samoylova et al., Elucidation of muscle-binding peptides by phage display screening. Muscle Nerve. Apr. 1999;22(4):460-6.

Sazani et al., Systemically delivered antisense oligomers upregulate gene expression in mouse tissues. Nat Biotechnol. Dec. 2002;20(12):1228-33. doi: 10.1038/nbt759. Epub Nov. 11, 2002.

Scanlon, Anti-genes: siRNA, ribozymes and antisense. Curr Pharm Biotechnol. Oct. 2004;5(5):415-20.

Scherr et al., Detection of antisense and ribozyme accessible sites on native mRNAs: application to NCOA3 mRNA. Mol Ther. Nov. 2001;4(5):454-60.

Schneider et al., Structural features of the cell surface receptor for transferrin that is recognized by the monoclonal antibody OKT9. J Biol Chem. Jul. 25, 1982;257(14):8516-22.

Schnyder et al., Targeting of skeletal muscle in vitro using biotinylated immunoliposomes. Biochem J. Jan. 1, 2004;377(Pt 1):61-7. doi: 10.1042/BJ20031034.

Setten et al., The current state and future directions of RNAi-based therapeutics. Nat Rev Drug Discov. Jun. 2019;18(6):421-446. doi: 10.1038/s41573-019-0017-4.

Shen et al., Chemistry, mechanism and clinical status of antisense oligonucleotides and duplex RNAs. Nucleic Acids Res. Feb. 28, 2018;46(4):1584-1600.

Singh et al., Catalytic Enantioselective Cyclopropanation of Olefins Using Carbenoid Chemistry. Synthesis. Feb. 1997;137-49.

Stein, The experimental use of antisense oligonucleotides: a guide for the perplexed. J Clin Invest. Sep. 2001;108(5):641-4.

Stocki et al., Blood-brain barrier transport using a high affinity, brain-selective VNAR antibody targeting transferrin receptor 1. FASEB J. Feb. 2021;35(2):e21172. doi: 10.1096/fj.202001787R. Epub Nov. 25, 2020.

Strop et al., Location matters: site of conjugation modulates stability and pharmacokinetics of antibody drug conjugates. Chem Biol. Feb. 21, 2013;20(2):161-7.

Subramanian et al., Abstract 1074. Targeted delivery of oligonucleotide therapeutics to muscle demonstrates potential to treat duchenne muscular dystrophy. Abstract. Mol Ther. 28 (4S1): 465. (2020) 1 page.

Subramanian, Splice Correction and Reduction of Toxic DMPK RNA In Vitro and In Vivo Utilizing Novel Antibody Targeted Antisense Oligonucleotides. Presented at ASGST Annual Meeting; May 14, 2021. 19 pages.

Sugo et al., Development of antibody-siRNA conjugate targeted to cardiac and skeletal muscles. J Control Release. Sep. 10, 2016;237:1-13. doi: 10.1016/j.jconrel.2016.06.036. Epub Jun. 29, 2016.

Swayze et al., Antisense oligonucleotides containing locked nucleic acid improve potency but cause significant hepatotoxicity in animals. Nucleic Acids Res. 2007;35(2):687-700. doi: 10.1093/nar/gkl1071. Epub Dec. 19, 2006.

Swayze et al., The medicinal chemistry of oligonucleotides. In: Antisense Drug Technology, Second Edition. 2007. Crooke, Ed. Chapter 6: 143-182.

Thomas et al., Myotonic Dystrophy and Developmental Regulation of RNA Processing. Comprehensive Physiology. Apr. 2018;8(2):509-53. Epub Mar. 25, 2018.

Thornton et al., Abstract—Oligonucleotide Therapeutics in Myotonic Dystrophy. RNA & Oligonucleotide Therapeutics. Cold Spring Harbor Laboratory. Cold Spring Harbor, NY. Apr. 7-10, 2010:31. 19 pages total.

Thornton et al., Myotonic dystrophy: approach to therapy. Curr Opin Genet Dev. Jun. 2017;44:135-140. doi: 10.1016/j.gde.2017.03.007. Epub Apr. 1, 2017.

Tron et al., Click chemistry reactions in medicinal chemistry: applications of the 1,3-dipolar cycloaddition between azides and alkynes. Med Res Rev. Mar. 2008;28(2):278-308.

Trowbridge et al., Anti-transferrin receptor monoclonal antibody and toxin-antibody conjugates affect growth of human tumour cells. Nature. Nov. 12, 1981;294(5837):171-3. doi: 10.1038/294171a0.

Van Deutekom, Abstract—The Development of RNA-Modulating Therapies. RNA & Oligonucleotide Therapeutics. Cold Spring Harbor Laboratory. Cold Spring Harbor, NY. Apr. 7-10, 2010:3. 19 pages total.

Vickers et al., Efficient reduction of target RNAs by small interfering RNA and RNase H-dependent antisense agents. A comparative analysis. J Biol Chem. Feb. 28, 2003;278(9):7108-18. Epub Dec. 23, 2002.

Wagner et al., Transferrin-polycation conjugates as carriers for DNA uptake into cells. Proc Natl Acad Sci U S A. May 1990;87(9):3410-4. doi: 10.1073/pnas.87.9.3410.

Walder et al., Role of RNase H in hybrid-arrested translation by antisense oligonucleotides. Proc. Natl. Acad. Sci. Jul. 1988;85:5011-5.

Walker et al., Improved cellular delivery of antisense oligonucleotides using transferrin receptor antibody-oligonucleotide conjugates. Pharm Res. Oct. 1995;12(10):1548-53. doi: 10.1023/a:1016260110049.

Walles et al., ADME and Safety Aspects of Non-cleavable Linkers in Drug Discovery and Development. Curr Top Med Chem. 2017;17(32):3463-3475. doi: 10.2174/1568026618666180118153502.

Wheeler et al., Reversal of RNA dominance by displacement of protein sequestered on triplet repeat RNA. Science. Jul. 17, 2009;325(5938):336-9.

Wheeler et al., Targeting nuclear RNA for in vivo correction of myotonic dystrophy. Nature. Aug. 2, 2012;488(7409):111-5. doi: 10.1038/nature11362.

Wheeler, Myotonic dystrophy: therapeutic strategies for the future. Neurotherapeutics. Oct. 2008;5(4):592-600.

Wilton et al., Exon skipping and Duchenne muscular dystrophy: hope, hype and how feasible? Neurol India. Jul.-Sep. 2008;56(3):254-62. doi: 10.4103/0028-3886.43443.

(56) References Cited

OTHER PUBLICATIONS

Wolf et al., ACHIEVE trial, a randomized, placebo-controlled, multiple ascending dose study of Dyne-101 in individuals with myotonic dystrophy Type 1 (DM1). Abstract. Mar. 2023. 1 page.

Wolf et al., ACHIEVE trial, a randomized, placebo-controlled, multiple ascending dose study of Dyne-101 in individuals with myotonic dystrophy Type 1 (DM1). Presented at The Muscular Dystrophy Association Clinical and Scientific Conference. Poster. Mar. 19-22, 2023. 1 page.

Wu et al., Determination of the role of the human RNase H1 in the pharmacology of DNA-like antisense drugs. J Biol Chem. Apr. 23, 2004;279(17):17181-9. Epub Feb. 11, 2004.

Xia et al., Intravenous siRNA of brain cancer with receptor targeting and avidin-biotin technology. Pharm Res. Dec. 2007;24(12):2309-16. doi: 10.1007/s11095-007-9460-8. Epub Oct. 11, 2007.

Yao et al., Targeted Delivery of ASOs Demonstrates Potential to Treat Duchenne Muscular Dystrophy. Poster. Presented at ASGCT; May 12, 2020. 1 page.

Ye et al., Generation and functional characterization of the anti-transferrin receptor single-chain antibody-GAL4 (TfRscFv-GAL4) fusion protein. BMC Biotechnol. Nov. 28, 2012;12:91.

Yoshida et al., Evaluation of off-target effects of gapmer antisense oligonucleotides using human cells. Genes Cells. Dec. 2019;24(12):827-835. doi: 10.1111/gtc.12730. Epub Nov. 12, 2019.

Zanotti et al., Abstract 17. Repeat dosing with DYNE-101 is Well Tolerated and Leads to a Sustained Reduction of *DMPK* RNA expression in key muscles for DM1 pathology in hTfR1/DMSXL mice and NHPs. Abstract. Mol Ther. Apr. 2022;30(4S1): 9.

Zanotti et al., Abstract 247. The ForceTM platform achieves robust knock down of toxic human nuclear DMPK RNA and foci reduction in DM1 cells and in newly developed hTfR1/DMSXL mouse model. Mol Ther. 29(4S1): 127. Apr. 2021. 1 page.

Zanotti et al., Abstract 82. The ForceTM platform delivers oligonucleotides to the brain in a DM1 mouse model and in NHPs. Mol Ther. Apr. 2023; 31(4S1): 44.

Zanotti et al., Abstract EP.233. The ForceTM platform achieves durable knockdown of toxic human nuclear DMPK RNA and correction of splicing in the hTFR1/DMSXL mouse model. Neuromusc Disord. 2021; 31: S120.

Zanotti et al., DYNE-101 achieves durable knockdown of toxic human nuclear *DMPK* RNA and correction of splicing in the hTfR1/DMSXL mouse model of DM1. Abstract. Mar. 2022. 1 page.

Zanotti et al., The ForceTM platform achieves durable knockdown of toxic human nuclear DMPK RNA and correction of splicing in the hTFR1/DMSXL mouse model. Presented at WMS Meeting. Sep. 20-24, 2021. 1 page.

Zanotti, Repeat dosing with DYNE-101 is Well Tolerated and Leads to a Sustained Reduction of *DMPK* RNA expression in key muscles for DM1 pathology in hTfR1/DMSXL mice and NHPs. Presented at American Society of Gene & Cell Therapy Conference. May 16, 2022. 15 pages.

Zanotti, The ForceTM platform delivers oligonucleotides to the brain in a DM1 mouse model and in NHPs. Presented at American Society of Gene & Cell Therapy Conference. May 17, 2023. 16 pages.

Zanotti, The FORCE™ Platform Achieves Robust Knock Down of Toxic Human Nuclear DMPK RNA and Foci Reduction in DM1 Cells and in Newly Developed hTfR1/DMSXL Mouse Model. Presented at American Society of Gene & Cell Therapy Annual Meeting; May 14, 2021. 13 pages.

\* cited by examiner

NuPage 4-12% 1mm SDS-PAGE
MES running buffer, 150v 50min

SEQUENCE LISTING

```
Sequence total quantity: 516
SEQ ID NO: 1            moltype = AA  length = 760
FEATURE                 Location/Qualifiers
source                  1..760
                        mol_type = protein
                        organism = Homo sapiens
SEQUENCE: 1
MMDQARSAFS NLFGGEPLSY TRFSLARQVD GDNSHVEMKL AVDEEENADN NTKANVTKPK   60
RCSGSICYGT IAVIVFFLIG FMIGYLGYCK GVEPKTECER LAGTESPVRE EPGEDFPAAR  120
RLYWDDLKRK LSEKLDSTDF TGTIKLLNEN SYVPREAGSQ KDENLALYVE NQFREFKLSK  180
VWRDQHFVKI QVKDSAQNSV IIVDKNGRLV YLVENPGGYV AYSKAATVTG KLVHANFGTK  240
KDFEDLYTPV NGSIVIVRAG KITFAEKVAN AESLNAIGVL IYMDQTKFPI VNAELSFFGH  300
AHLGTGDPYT PGFPSFNHTQ FPPSRSSGLP NIPVQTISRA AAEKLFGNME GDCPSDWKTD  360
STCRMVTSES KNVKLTVSNV LKEIKILNIF GVIKGFVEPD HYVVVGAQRD AWGPGAAKSG  420
VGTALLLKLA QMFSDMVLKD GFQPSRSIIF ASWSAGDFGS VGATEWLEGY LSSLHLKAFT  480
YINLDKAVLG TSNFKVSASP LLYTLIEKTM QNVKHPVTGQ FLYQDSNWAS KVEKLTLDNA  540
AFPFLAYSGI PAVSFCFCED TDYPYLGTTM DTYKELIERI PELNKVARAA AEVAGQFVIK  600
LTHDVELNLD YERYNSQLLS FVRDLNQYRA DIKEMGLSLQ WLYSARGDFF RATSRLTTDF  660
GNAEKTDRFV MKKLNDRVMR VEYHFLSPYV SPKESPFRHV FWGSGSHTLP ALLENLKLRK  720
QNNGAFNETL FRNQLALATW TIQGAANALS GDVWDIDNEF                       760

SEQ ID NO: 2            moltype = AA  length = 760
FEATURE                 Location/Qualifiers
source                  1..760
                        mol_type = protein
                        organism = Macaca mulatta
SEQUENCE: 2
MMDQARSAFS NLFGGEPLSY TRFSLARQVD GDNSHVEMKL GVDEEENTDN NTKPNGTKPK   60
```

-continued

```
RCGGNICYGT IAVIIFFLIG FMIGYLGYCK GVEPKTECER LAGTESPARE EPEEDFPAAP    120
RLYWDDLKRK LSEKLDTTDF TSTIKLLNEN LYVPREAGSQ KDENLALYIE NQFREFKLSK    180
VWRDQHFVKI QVKDSAQNSV IIVDKNGGLV YLVENPGGYV AYSKAATVTG KLVHANFGTK    240
KDFEDLDSPV NGSIVIVRAG KITFAEKVAN AESLNAIGVL IYMDQTKFPI VKADLSFFGH    300
AHLGTGDPYT PGFPSFNHTQ FPPSQSSGLP NIPVQTISRA AAEKLFGNME GDCPSDWKTD    360
STCKMVTSEN KSVKLTVSNV LKETKILNIF GVIKGFVEPD HYVVVGAQRD AWGPGAAKSS    420
VGTALLLKLA QMFSDMVLKD GFQPSRSIIF ASWSAGDFGS VGATEWLEGY LSSLHLKAFT    480
YINLDKAVLG TSNFKVSASP LLYTLIEKTM QDVKHPVTGR SLYQDSNWAS KVEKLTLDNA    540
APPFLAYSGI PAVSFCFCED TDYPYLGTTM DTYKELVERI PELNKVARAA AEVAGQFVIK    600
LTHDTELNLD YERYNSQLLL FLRDLNQYRA DVKEMGLSLQ WLYSARGDFF RATSRLTTDF    660
RNAEKRDKFV MKKLNDRVMR VEYYFLSPYV SPKESPFRHV FWGSGSHTLS ALLESLKLRR    720
QNNSAFNETL FRNQLALATW TIQGAANALS GDVWDIDNEF                          760

SEQ ID NO: 3            moltype = AA   length = 760
FEATURE                 Location/Qualifiers
source                  1..760
                        mol_type = protein
                        organism = Macaca fascicularis
SEQUENCE: 3
MMDQARSAFS NLFGGEPLSY TRFSLARQVD GDNSHVEMKL GVDEEENTDN NTKANGTKPK     60
RCGGNICYGT IAVIIFFLIG FMIGYLGYCK GVEPKTECER LAGTESPARE EPEEDFPAAP    120
RLYWDDLKRK LSEKLDTTDF TSTIKLLNEN LYVPREAGSQ KDENLALYIE NQFREFKLSK    180
VWRDQHFVKI QVKDSAQNSV IIVDKNGGLV YLVENPGGYV AYSKAATVTG KLVHANFGTK    240
KDFEDLDSPV NGSIVIVRAG KITFAEKVAN AESLNAIGVL IYMDQTKFPI VKADLSFFGH    300
AHLGTGDPYT PGFPSFNHTQ FPPSQSSGLP NIPVQTISRA AAEKLFGNME GDCPSDWKTD    360
STCKMVTSEN KSVKLTVSNV LKETKILNIF GVIKGFVEPD HYVVVGAQRD AWGPGAAKSS    420
VGTALLLKLA QMFSDMVLKD GFQPSRSIIF ASWSAGDFGS VGATEWLEGY LSSLHLKAFT    480
YINLDKAVLG TSNFKVSASP LLYTLIEKTM QDVKHPVTGR SLYQDSNWAS KVEKLTLDNA    540
APPFLAYSGI PAVSFCFCED TDYPYLGTTM DTYKELVERI PELNKVARAA AEVAGQFVIK    600
LTHDTELNLD YERYNSQLLL FLRDLNQYRA DVKEMGLSLQ WLYSARGDFF RATSRLTTDF    660
RNAEKRDKFV MKKLNDRVMR VEYYFLSPYV SPKESPFRHV FWGSGSHTLS ALLESLKLRR    720
QNNSAFNETL FRNQLALATW TIQGAANALS GDVWDIDNEF                          760

SEQ ID NO: 4            moltype = AA   length = 763
FEATURE                 Location/Qualifiers
source                  1..763
                        mol_type = protein
                        organism = Mus musculus
SEQUENCE: 4
MMDQARSAFS NLFGGEPLSY TRFSLARQVD GDNSHVEMKL AADEEENADN NMKASVRKPK     60
RFNGRLCFAA IALVIFFLIG FMSGYLGYCK RVEQKEECVK LAETEETDKS ETMETEDVPT    120
SSRLYWADLK TLLSEKLNSI EFADTIKQLS QNTYTPREAG SQKDESLAYY IENQFHEFKF    180
SKVWRDEHYV KIQVKSSIGQ NMVTIVQSNG NLDPVESPEG YVAFSKPTEV SGKLVHANFG    240
TKKDFEELSY SVNGSLVIVR AGEITFAEKV ANAQSFNAIG VLIYMDKNKF PVVEADLALF    300
GHAHLGTGDP YTPGFPSFNH TQFPPSQSSG LPNIPVQTIS RAAAEKLFGK MEGSCPARWN    360
IDSSCKLELS QNQNVKLIVK NVLKERRILN IFGVIKGYEE PDRYVVVGAQ RDALGAGVAA    420
KSSVGTGLLL KLAQVFSDMI SKDGFRPSRS IIFASWTAGD FGAVGATEWL EGYLSSLHLK    480
AFTYINLDKV VLGTSNFKVS ASPLLYTLMG KIMQDVKHPV DGKSLYRDSN WISKVEKLSF    540
DNAAYPPLAY SGIPAVSFCF CEDADYPYLG TRLDTYEALT QKVPQLNQMV RTAAEVAGQL    600
IIKLTHDVEL NLDYEMYNSK LLSFMKDLNQ FKTDIRDMGL SLQWLYSARG DYFRATSRLT    660
TDFHNAEKTN RFVMREINDR IMKVEYHFLS PYVSPRESPF RHIFWGSGSH TLSALVENLK    720
LRQKNITAFN ETLFRNQLAL ATWTIQGVAN ALSGDIWNID NEF                      763

SEQ ID NO: 5            moltype = AA   length = 197
FEATURE                 Location/Qualifiers
REGION                  1..197
                        note = Synthetic polypeptide
source                  1..197
                        mol_type = protein
                        organism = synthetic construct
SEQUENCE: 5
FVKIQVKDSA QNSVIIVDKN GRLVYLVENP GGYVAYSKAA TVTGKLVHAN FGTKKDFEDL     60
YTPVNGSIVI VRAGKITFAE KVANAESLNA IGVLIYMDQT KFPIVNAELS FFGHAHLGTG    120
DPYTPGFPSF NHTQFPPSRS SGLPNIPVQT ISRAAAEKLF GNMEGDCPSD WKTDSTCRMV    180
TSESKNVKLT VSNVLKE                                                   197

SEQ ID NO: 6            moltype = AA   length = 7
FEATURE                 Location/Qualifiers
REGION                  1..7
                        note = Synthetic polypeptide
source                  1..7
                        mol_type = protein
                        organism = synthetic construct
SEQUENCE: 6
ASSLNIA                                                                7

SEQ ID NO: 7            moltype = AA   length = 12
FEATURE                 Location/Qualifiers
REGION                  1..12
```

```
                         note = Synthetic polypeptide
source                   1..12
                         mol_type = protein
                         organism = synthetic construct
SEQUENCE: 7
SKTFNTHPQS TP                                                              12

SEQ ID NO: 8             moltype = AA   length = 12
FEATURE                  Location/Qualifiers
REGION                   1..12
                         note = Synthetic polypeptide
source                   1..12
                         mol_type = protein
                         organism = synthetic construct
SEQUENCE: 8
TARGEHKEEE LI                                                              12

SEQ ID NO: 9             moltype = AA   length = 9
FEATURE                  Location/Qualifiers
REGION                   1..9
                         note = Synthetic polypeptide
source                   1..9
                         mol_type = protein
                         organism = synthetic construct
SEQUENCE: 9
CQAQGQLVC                                                                   9

SEQ ID NO: 10            moltype = AA   length = 9
FEATURE                  Location/Qualifiers
REGION                   1..9
                         note = Synthetic polypeptide
source                   1..9
                         mol_type = protein
                         organism = synthetic construct
SEQUENCE: 10
CSERSMNFC                                                                   9

SEQ ID NO: 11            moltype = AA   length = 9
FEATURE                  Location/Qualifiers
REGION                   1..9
                         note = Synthetic polypeptide
source                   1..9
                         mol_type = protein
                         organism = synthetic construct
SEQUENCE: 11
CPKTRRVPC                                                                   9

SEQ ID NO: 12            moltype = AA   length = 20
FEATURE                  Location/Qualifiers
REGION                   1..20
                         note = Synthetic polypeptide
source                   1..20
                         mol_type = protein
                         organism = synthetic construct
SEQUENCE: 12
WLSEAGPVVT VRALRGTGSW                                                      20

SEQ ID NO: 13            moltype = AA   length = 9
FEATURE                  Location/Qualifiers
REGION                   1..9
                         note = Synthetic polypeptide
source                   1..9
                         mol_type = protein
                         organism = synthetic construct
SEQUENCE: 13
CMQHSMRVC                                                                   9

SEQ ID NO: 14            moltype = AA   length = 7
FEATURE                  Location/Qualifiers
REGION                   1..7
                         note = Synthetic polypeptide
source                   1..7
                         mol_type = protein
                         organism = synthetic construct
SEQUENCE: 14
DDTRHWG                                                                     7

SEQ ID NO: 15            moltype = DNA   length = 2859
FEATURE                  Location/Qualifiers
```

```
source          1..2859
                mol_type = genomic DNA
                organism = Homo sapiens
SEQUENCE: 15
aggggggctg gaccaagggg tggggagaag gggaggaggc ctcggccggc cgcagagaga   60
agtggccaga gaggcccagg ggacagccag ggacaggcag acatgcagcc agggctccag  120
ggcctggaca ggggctgcca ggccctgtga caggaggacc ccgagccccc ggcccgggga  180
ggggccatgg tgctgcctgt ccaacatgtc agccgaggtg cggctgaggc ggctccagca  240
gctggtgttg gacccgggct tcctggggct ggagccctg ctcgaccttc tcctgggcgt  300
ccaccaggag ctgggcgcct ccgaactggc ccaggacaag tacgtggccg acttcttgca  360
gtgggcggga cccatcgtgg tgaggcttaa ggaggtccga ctgcagaggg acgacttcga  420
gattctgaag gtgatcggac gcggggcgtt cagcgaggta gcgtagtga agatgaagca  480
gacgggccag gtgtatgcca tgaagatcat gaacaagtgg gacatgctga gaggggcga  540
ggtgtcgtgc ttccgtgagg agagggacgt gttggtgaat ggggaccggc ggtggatcac  600
gcagctgcac ttcgccttcc aggatgagaa ctacctgtac ctggtcatgg agtattacgt  660
gggcggggac ctgctgacac tgctgagcaa gtttgggggag cggattccgg ccgagatggc  720
gcgcttctac ctggcggaga ttgtcatggc catagactcg gtgcaccggc ttggctacgt  780
gcacagggca atcaaaccg acaacatcct gctggaccgc tgtggccaca tccgcctggc  840
cgacttcggc tcttgcctca agctgcgggc agatgaacg gtgcggtcgc tgtggctgt  900
gggcaccca gactacctgt cccccgagat cctgcaggct gtgggcggtg ggcctgggac  960
aggcagctac gggcccgagt gtgactggtg ggcgctgggg gtattcgcct atgaaatgtt 1020
ctatgggcag acgcccttct acgcggattc cacggcggag acctatggca agatcgtcca 1080
ctacaaggag cacctctctc tgccgctggt ggacgaaggg gtccctgagg aggctcgaga 1140
cttcattcag cggttgctgt gtccccggga gacacgctg ggccggggtg gagcaggcga 1200
cttccggaca catcccttct tctttggcct cgactggat ggtctccggg acagcgtgcc 1260
cccctttaca ccggatttcg aaggtgccac cgacacatgc aacttcgact tgttggagga 1320
cgggctcact gccatggaga cactgtcgga cattcgggaa ggtcgcgcgc tagggggtcca 1380
cctgcctttt gtgggctact cctactcctg catggccctc agggacagtg aggtcccagg 1440
ccccacaccc atgaactgg aggccgagca gctgcttgag ccacgcgtgc aagcgcccag 1500
cctggagccc tcggtgtccc cacaggatga aacagctgga gtgcagttc cagcggctgt 1560
ccctgcggca gaggctgagg ccgaggtgac gctgcgggag ctccaggaag ccctggagga 1620
ggaggtgctc acccgcaga gcctgagccg ggagatggag gccatccgca cggacaacca 1680
gaacttcgcc agtcaactac gcgaggcaga ggctcggaac cgggacctag aggcacacgt 1740
ccggcagttg caggagcgga tggagtttgct gcaggcagag ggagccacag ctgtcacggg 1800
ggtcccagt cccccgggca cggatccacc ttcccatcta gatgccccc cggccgtggc 1860
tgtgggccag tgcccgctgg tggggccagg cccatgcac cgccgccacc tgctgctccc 1920
tgccagggtc cctaggcctg gccatcgga ggcgctttcc ctgctcctgt cgcgcgttgt 1980
tctgtctcgt gccgccgccc tgggctgcat gggttggtg gcccacgccg gccaactcac 2040
cgcagtctgg cgccgcccag gagccgcccg cgctccctga accctagaac tgtcttcgac 2100
tccggggccc cgttggaaga ctgagtgccc ggggcacggc acagaagccg cgcccaccgc 2160
ctgccagttc acaaccgctc cgagcgtggg tctccgccca gctccagtcc tgtgatccgg 2220
gcccgccccc tagcggccgg ggaggagggg gccgggtccg cggccggcga acggggctcg 2280
aagggtcctt gtagccggga atgctgctgc tgctgctgct gctgctgctg ctgctgctga 2340
tgctgctgct gctgctgctg ctgggggat cacagaccat ttctttcttt cggccaggct 2400
gaggccctga cgtggatggg caaactgcag gcctgggaag gcagcaagcc gggccgtccg 2460
tgttccatcc tccacgcacc cccacctatc gttggttcgc aaagtgcaaa gctttcttgt 2520
gcatgacgcc ctgctctggg gagcgtctgg cgcgatctct gctgcttac tcgggaaatt 2580
tgcttttgcc aaacccgctt tttcggggat cccgcgcccc cctcctcact gcgctgctc 2640
tcggagcccc agccggctcc gcccgcttcg cggtttgga tatttattga cctcgtcctc 2700
cgactcgctg acaggctaca ggaccccccaa caacccaat ccacgttttg gatgcactga 2760
gaccccgaca ttcctcggta tttattgtct gtccccacct aggacccca cccccgaccc 2820
tcgcgaataa aaggccctcc atctgcccaa agctctgga                        2859

SEQ ID NO: 16         moltype = DNA   length = 2683
FEATURE               Location/Qualifiers
source                1..2683
                      mol_type = genomic DNA
                      organism = Mus musculus
SEQUENCE: 16
gaactggcca gagagaccca agggatagtc agggacgggc agacatgcag ctagggttct   60
ggggcctgga caggggcagc caggccctgt gacgggaaga cccgagctc cggcccgggg  120
aggggccatg gtgttgcctg cccaacatgt cagccgaagt gcggctgagg cagctccagc  180
agctggtgct ggacccaggc ttcctggac tggagcccct gctcgacctt ctcctgggcg  240
tccaccagga gctgggtgcc tctcacctag cccaggacaa gtatgtggcc gacttcttga  300
gtgggtgga gcccattgca gcaaggctta aggaggtccg actgcagagg gatgattttg  360
agattttgaa ggtgatcggg cgtggggcgt tcagcgaggt agcggtggtg aagatgaaac  420
agacgggcca agtgtatgcc atgaagatta tgaataagtg gacatgctg aagagaggcg  480
aggtgtcgtg cttccgggaa gaaagggatg tattagtgaa aggggaccgg cgctggatca  540
cacagctgca ctttgccttc caggatgaga actacctgta cctggtcatg gaatactacg  600
tgggcgggga cctgctaacg ctgctgagca gtttggggga gcggatcccc gccgagatgc  660
ctcgcttcta cctggccgag attgtcatgg ccatagactc cgtgcaccgg ctgggctacg  720
tgcacaggga catcaaacca gataacattc tgctggaccg atgtgggcac attcgcctgg  780
cagacttcgg ctcctgcctc aaactgcagc ctgatggaat ggtgaggtcg ctggtggctg  840
tgggcacccc ggactacctg tctcctgaga ttctgcaggc cgttggtggga gggcctggga  900
caggcagcta cgggccagag tgtgactggt gggcactggg cgtgttcgcc tatgagatgt  960
tctatgggca gacccccttc tacgcggact ccacagccga gacatatgcc aagattgtgc 1020
actacaaggga acacttgtcg ctgccgctgg cagacacagt tgtccccgag gaagctcagg 1080
acctcattcg tgggctgctg tgtcctgctg agataaggcc aggtcgaggt ggggcagact 1140
tcgagggtgc cacggacaca tgcaatttcg atgtggtgga ggaccggctc actgccatgg 1200
```

```
tgagcggggg cggggagacg ctgtcagaca tgcaggaaga catgccccctt ggggtgcgcc   1260
tgcccttcgt gggctactcc tactgctgca tggccttcag agacaatcag gtccccggacc   1320
ccacccctat ggaactagag gcccctgcagt tgcctgtgtc agacttgcaa gggcttgact   1380
tgcagcccc agtgtcccca ccggatcaag tggctgaaga ggctgaccta gtggctgtcc    1440
ctgccctgt ggctgaggca gagaccacgg taacgctgca gcagctccag gaagccctgg    1500
aagaagaggt tctcacccgg cagagcctga gccgcgagct ggaggccatc cggaccgcca   1560
accagaactt ctccagccaa ctacaggagg ccgaggtccg aaaccgagac ctggaggcgc   1620
atgttcggca gctacaggaa cggatggaga tgctgcaggc cccaggagcc gcagccatca   1680
cggggggtccc cagtccccgg gccacggatc caccttccca tctagatggc ccccccggccg   1740
tggctgtggg ccagtgcccg ctggtggggc caggccccat gcaccgccgt cacctgctgc   1800
tccctgccag gatccctagg cctggcctat ccgaggcgcg ttgcctgctc ctgttcgccg    1860
ctgctctggc tgctgccgcc acactgggct gcactgggtt ggtggcctat accgcggtc    1920
tcaccccagt ctggtgtttc ccgggagcca ccttcgcccc ctgaaccta agactccaag   1980
ccatctttca tttaggcctc ctaggaaggt cgagcgacca gggagcgacc caaagcgtct   2040
ctgtgcccat cgcgccccc cccccccccc accgctccgc tccacacttc tgtgagcctg   2100
ggtccccacc cagctccgct cctgtgatcc aggcctgcca cctggcggcc ggggagggag   2160
gaacagggct cgtgcccagc accccctggtt cctgcagagc tggtagccac cgctgctgca   2220
gcagctgggc attcgcgac cttgcttttac tcagcccccga cgtggatggg caaactgctc   2280
agctcatccg atttcacttt ttcactctcc cagccatcag ttacaagcca taagcatgag   2340
cccctatt ccaggacat cccattccca tagtgatgga tcagcaagac ctctgccagc      2400
acacgcgag tctttggctt cggacagcct cactcctggg ggttgctgca actcttccc    2460
cgtgtacacg tctgcactct aacaacggag ccacagctgc actccccct ccccaaag     2520
agtgtgggta tttattgatc ttgttatctg actcactgac agactcgggg acccacgttt    2580
tagatgcatt gagactcgac attcctcggt atttattgtc tgtccccacc tacgacctcc    2640
actcccgacc cttgcgaata aaatacttct ggtctgccct aaa                     2683

SEQ ID NO: 17           moltype = AA   length = 5
FEATURE                 Location/Qualifiers
REGION                  1..5
                        note = Synthetic polypeptide
source                  1..5
                        mol_type = protein
                        organism = synthetic construct
SEQUENCE: 17
SYWMH                                                                5

SEQ ID NO: 18           moltype = AA   length = 17
FEATURE                 Location/Qualifiers
REGION                  1..17
                        note = Synthetic polypeptide
source                  1..17
                        mol_type = protein
                        organism = synthetic construct
SEQUENCE: 18
EINPTNGRTN YIEKFKS                                                  17

SEQ ID NO: 19           moltype = AA   length = 7
FEATURE                 Location/Qualifiers
REGION                  1..7
                        note = Synthetic polypeptide
source                  1..7
                        mol_type = protein
                        organism = synthetic construct
SEQUENCE: 19
GTRAYHY                                                              7

SEQ ID NO: 20           moltype = AA   length = 11
FEATURE                 Location/Qualifiers
REGION                  1..11
                        note = Synthetic polypeptide
source                  1..11
                        mol_type = protein
                        organism = synthetic construct
SEQUENCE: 20
RASDNLYSNL A                                                        11

SEQ ID NO: 21           moltype = AA   length = 7
FEATURE                 Location/Qualifiers
REGION                  1..7
                        note = Synthetic polypeptide
source                  1..7
                        mol_type = protein
                        organism = synthetic construct
SEQUENCE: 21
DATNLAD                                                              7

SEQ ID NO: 22           moltype = AA   length = 9
FEATURE                 Location/Qualifiers
REGION                  1..9
```

```
                        note = Synthetic polypeptide
source                  1..9
                        mol_type = protein
                        organism = synthetic construct
SEQUENCE: 22
QHFWGTPLT                                                                    9

SEQ ID NO: 23           moltype = AA   length = 7
FEATURE                 Location/Qualifiers
REGION                  1..7
                        note = Synthetic polypeptide
source                  1..7
                        mol_type = protein
                        organism = synthetic construct
SEQUENCE: 23
GYTFTSY                                                                      7

SEQ ID NO: 24           moltype = AA   length = 6
FEATURE                 Location/Qualifiers
REGION                  1..6
                        note = Synthetic polypeptide
source                  1..6
                        mol_type = protein
                        organism = synthetic construct
SEQUENCE: 24
NPTNGR                                                                       6

SEQ ID NO: 25           moltype = AA   length = 6
FEATURE                 Location/Qualifiers
REGION                  1..6
                        note = Synthetic polypeptide
source                  1..6
                        mol_type = protein
                        organism = synthetic construct
SEQUENCE: 25
TSYWMH                                                                       6

SEQ ID NO: 26           moltype = AA   length = 13
FEATURE                 Location/Qualifiers
REGION                  1..13
                        note = Synthetic polypeptide
source                  1..13
                        mol_type = protein
                        organism = synthetic construct
SEQUENCE: 26
WIGEINPTNG RTN                                                              13

SEQ ID NO: 27           moltype = AA   length = 6
FEATURE                 Location/Qualifiers
REGION                  1..6
                        note = Synthetic polypeptide
source                  1..6
                        mol_type = protein
                        organism = synthetic construct
SEQUENCE: 27
ARGTRA                                                                       6

SEQ ID NO: 28           moltype = AA   length = 7
FEATURE                 Location/Qualifiers
REGION                  1..7
                        note = Synthetic polypeptide
source                  1..7
                        mol_type = protein
                        organism = synthetic construct
SEQUENCE: 28
YSNLAWY                                                                      7

SEQ ID NO: 29           moltype = AA   length = 10
FEATURE                 Location/Qualifiers
REGION                  1..10
                        note = Synthetic polypeptide
source                  1..10
                        mol_type = protein
                        organism = synthetic construct
SEQUENCE: 29
LLVYDATNLA                                                                  10

SEQ ID NO: 30           moltype = AA   length = 8
FEATURE                 Location/Qualifiers
```

```
REGION                      1..8
                            note = Synthetic polypeptide
source                      1..8
                            mol_type = protein
                            organism = synthetic construct
SEQUENCE: 30
QHFWGTPL                                                                   8

SEQ ID NO: 31               moltype = AA  length = 9
FEATURE                     Location/Qualifiers
REGION                      1..9
                            note = Synthetic polypeptide
source                      1..9
                            mol_type = protein
                            organism = synthetic construct
SEQUENCE: 31
QHFAGTPLT                                                                  9

SEQ ID NO: 32               moltype = AA  length = 8
FEATURE                     Location/Qualifiers
REGION                      1..8
                            note = Synthetic polypeptide
source                      1..8
                            mol_type = protein
                            organism = synthetic construct
SEQUENCE: 32
QHFAGTPL                                                                   8

SEQ ID NO: 33               moltype = AA  length = 116
FEATURE                     Location/Qualifiers
REGION                      1..116
                            note = Synthetic polypeptide
source                      1..116
                            mol_type = protein
                            organism = synthetic construct
SEQUENCE: 33
QVQLQQPGAE LVKPGASVKL SCKASGYTFT SYWMHWVKQR PGQGLEWIGE INPTNGRTNY           60
IEKFKSKATL TVDKSSSTAY MQLSSLTSED SAVYYCARGT RAYHYWGQGT SVTVSS              116

SEQ ID NO: 34               moltype = AA  length = 107
FEATURE                     Location/Qualifiers
REGION                      1..107
                            note = Synthetic polypeptide
source                      1..107
                            mol_type = protein
                            organism = synthetic construct
SEQUENCE: 34
DIQMTQSPAS LSVSVGETVT ITCRASDNLY SNLAWYQQKQ GKSPQLLVYD ATNLADGVPS           60
RFSGSGSGTQ YSLKINSLQS EDFGTYYCQH FWGTPLTFGA GTKLELK                       107

SEQ ID NO: 35               moltype = AA  length = 116
FEATURE                     Location/Qualifiers
REGION                      1..116
                            note = Synthetic polypeptide
source                      1..116
                            mol_type = protein
                            organism = synthetic construct
SEQUENCE: 35
EVQLVQSGAE VKKPGASVKV SCKASGYTFT SYWMHWVRQA PGQRLEWIGE INPTNGRTNY           60
IEKFKSRATL TVDKSASTAY MELSSLRSED TAVYYCARGT RAYHYWGQGT MVTVSS              116

SEQ ID NO: 36               moltype = AA  length = 107
FEATURE                     Location/Qualifiers
REGION                      1..107
                            note = Synthetic polypeptide
source                      1..107
                            mol_type = protein
                            organism = synthetic construct
SEQUENCE: 36
DIQMTQSPSS LSASVGDRVT ITCRASDNLY SNLAWYQQKP GKSPKLLVYD ATNLADGVPS           60
RFSGSGSGTD YSLKINSLQS EDFGTYYCQH FWGTPLTFGA GTKLELK                       107

SEQ ID NO: 37               moltype = AA  length = 330
FEATURE                     Location/Qualifiers
REGION                      1..330
                            note = Synthetic polypeptide
source                      1..330
                            mol_type = protein
                            organism = synthetic construct
```

```
SEQUENCE: 37
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELLGG   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHNHYT QKSLSLSPGK                                   330

SEQ ID NO: 38            moltype = AA  length = 110
FEATURE                  Location/Qualifiers
REGION                   1..110
                         note = Synthetic polypeptide
source                   1..110
                         mol_type = protein
                         organism = synthetic construct
SEQUENCE: 38
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP              110

SEQ ID NO: 39            moltype = AA  length = 446
FEATURE                  Location/Qualifiers
REGION                   1..446
                         note = Synthetic polypeptide
source                   1..446
                         mol_type = protein
                         organism = synthetic construct
SEQUENCE: 39
QVQLQQPGAE LVKPGASVKL SCKASGYTFT SYWMHWVKQR PGQGLEWIGE INPTNGRTNY    60
IEKFKSKATL TVDKSSSTAY MQLSSLTSED SAVYYCARGT RAYHYWGQGT SVTVSSASTK   120
GPSVFPLAPS SKSTSGGTAA LGCLVKDYFP EPVTVSWNSG ALTSGVHTFP AVLQSSGLYS   180
LSSVVTVPSS SLGTQTYICN VNHKPSNTKV DKKVEPKSCD KTHTCPPCPA PELLGGPSVF   240
LFPPKPKDTL MISRTPEVTC VVVDVSHEDP EVKFNWYVDG VEVHNAKTKP REEQYNSTYR   300
VVSVLTVLHQ DWLNGKEYKC KVSNKALPAP IEKTISKAKG QPREPQVYTL PPSRDELTKN   360
QVSLTCLVKG FYPSDIAVEW ESNGQPENNY KTTPPVLDSD GSFFLYSKLT VDKSRWQQGN   420
VFSCSVMHEA LHNHYTQKSL SLSPGK                                       446

SEQ ID NO: 40            moltype = AA  length = 226
FEATURE                  Location/Qualifiers
REGION                   1..226
                         note = Synthetic polypeptide
source                   1..226
                         mol_type = protein
                         organism = synthetic construct
SEQUENCE: 40
QVQLQQPGAE LVKPGASVKL SCKASGYTFT SYWMHWVKQR PGQGLEWIGE INPTNGRTNY    60
IEKFKSKATL TVDKSSSTAY MQLSSLTSED SAVYYCARGT RAYHYWGQGT SVTVSSASTK   120
GPSVFPLAPS SKSTSGGTAA LGCLVKDYFP EPVTVSWNSG ALTSGVHTFP AVLQSSGLYS   180
LSSVVTVPSS SLGTQTYICN VNHKPSNTKV DKKVEPKSCD KTHTCP                 226

SEQ ID NO: 41            moltype = AA  length = 446
FEATURE                  Location/Qualifiers
REGION                   1..446
                         note = Synthetic polypeptide
source                   1..446
                         mol_type = protein
                         organism = synthetic construct
SEQUENCE: 41
EVQLVQSGAE VKKPGASVKV SCKASGYTFT SYWMHWVRQA PGQRLEWIGE INPTNGRTNY    60
IEKFKSRATL TVDKSASTAY MELSSLRSED TAVYYCARGT RAYHYWGQGT MVTVSSASTK   120
GPSVFPLAPS SKSTSGGTAA LGCLVKDYFP EPVTVSWNSG ALTSGVHTFP AVLQSSGLYS   180
LSSVVTVPSS SLGTQTYICN VNHKPSNTKV DKKVEPKSCD KTHTCPPCPA PELLGGPSVF   240
LFPPKPKDTL MISRTPEVTC VVVDVSHEDP EVKFNWYVDG VEVHNAKTKP REEQYNSTYR   300
VVSVLTVLHQ DWLNGKEYKC KVSNKALPAP IEKTISKAKG QPREPQVYTL PPSRDELTKN   360
QVSLTCLVKG FYPSDIAVEW ESNGQPENNY KTTPPVLDSD GSFFLYSKLT VDKSRWQQGN   420
VFSCSVMHEA LHNHYTQKSL SLSPGK                                       446

SEQ ID NO: 42            moltype = AA  length = 217
FEATURE                  Location/Qualifiers
REGION                   1..217
                         note = Synthetic polypeptide
source                   1..217
                         mol_type = protein
                         organism = synthetic construct
SEQUENCE: 42
DIQMTQSPSS LSASVGDRVT ITCRASDNLY SNLAWYQQKP GKSPKLLVYD ATNLADGVPS    60
RFSGSGSGTD YSLKINSLQS EDFGTYYCQH FWGTPLTFGA GTKLELKAST KGPSVFPLAP   120
SSKSTSGGTA ALGCLVKDYF PEPVTVSWNS GALTSGVHTF PAVLQSSGLY SLSSVVTVPS   180
SSLGTQTYIC NVNHKPSNTK VDKKVEPKSC DKTHTCP                           217
```

```
SEQ ID NO: 43            moltype = AA   length = 226
FEATURE                  Location/Qualifiers
REGION                   1..226
                         note = Synthetic polypeptide
source                   1..226
                         mol_type = protein
                         organism = synthetic construct
SEQUENCE: 43
QVQLQQPGAE LVKPGASVKL SCKASGYTFT SYWMHWVKQR PGQGLEWIGE INPTNGRTNY      60
IEKFKSKATL TVDKSSSTAY MQLSSLTSED SAVYYCARGT RAYHYWGQGT SVTVSSASTK     120
GPSVFPLAPS SKSTSGGTAA LGCLVKDYFP EPVTVSWNSG ALTSGVHTFP AVLQSSGLYS     180
LSSVVTVPSS SLGTQTYICN VNHKPSNTKV DKKVEPKSCD KTHTCP                    226

SEQ ID NO: 44            moltype = AA   length = 226
FEATURE                  Location/Qualifiers
REGION                   1..226
                         note = Synthetic polypeptide
source                   1..226
                         mol_type = protein
                         organism = synthetic construct
SEQUENCE: 44
EVQLVQSGAE VKKPGASVKV SCKASGYTFT SYWMHWVRQA PGQRLEWIGE INPTNGRTNY      60
IEKFKSRATL TVDKSASTAY MELSSLRSED TAVYYCARGT RAYHYWGQGT MVTVSSASTK     120
GPSVFPLAPS SKSTSGGTAA LGCLVKDYFP EPVTVSWNSG ALTSGVHTFP AVLQSSGLYS     180
LSSVVTVPSS SLGTQTYICN VNHKPSNTKV DKKVEPKSCD KTHTCP                    226

SEQ ID NO: 45            moltype = RNA   length = 20
FEATURE                  Location/Qualifiers
misc_feature             1..20
                         note = Synthetic Polynucleotide
source                   1..20
                         mol_type = other RNA
                         organism = synthetic construct
SEQUENCE: 45
ggacggcccg gcttgctgcc                                                  20

SEQ ID NO: 46            moltype = RNA   length = 20
FEATURE                  Location/Qualifiers
misc_feature             1..20
                         note = Synthetic Polynucleotide
source                   1..20
                         mol_type = other RNA
                         organism = synthetic construct
SEQUENCE: 46
gggcccggat cacaggactg                                                  20

SEQ ID NO: 47            moltype = RNA   length = 20
FEATURE                  Location/Qualifiers
misc_feature             1..20
                         note = Synthetic Polynucleotide
source                   1..20
                         mol_type = other RNA
                         organism = synthetic construct
SEQUENCE: 47
caaacttgct cagcagtgtc                                                  20

SEQ ID NO: 48            moltype = RNA   length = 20
FEATURE                  Location/Qualifiers
misc_feature             1..20
                         note = Synthetic Polynucleotide
source                   1..20
                         mol_type = other RNA
                         organism = synthetic construct
SEQUENCE: 48
aaacttgctc agcagtgtca                                                  20

SEQ ID NO: 49            moltype = RNA   length = 20
FEATURE                  Location/Qualifiers
misc_feature             1..20
                         note = Synthetic Polynucleotide
source                   1..20
                         mol_type = other RNA
                         organism = synthetic construct
SEQUENCE: 49
cggatggcct ccatctcccg                                                  20

SEQ ID NO: 50            moltype = RNA   length = 20
FEATURE                  Location/Qualifiers
misc_feature             1..20
```

```
                    note = Synthetic Polynucleotide
source              1..20
                    mol_type = other RNA
                    organism = synthetic construct
SEQUENCE: 50
ctcggccgga atccgctccc                                                    20

SEQ ID NO: 51       moltype = RNA   length = 20
FEATURE             Location/Qualifiers
misc_feature        1..20
                    note = Synthetic Polynucleotide
source              1..20
                    mol_type = other RNA
                    organism = synthetic construct
SEQUENCE: 51
tctcggccgg aatccgctcc                                                    20

SEQ ID NO: 52       moltype = RNA   length = 20
FEATURE             Location/Qualifiers
misc_feature        1..20
                    note = Synthetic Polynucleotide
source              1..20
                    mol_type = other RNA
                    organism = synthetic construct
SEQUENCE: 52
tgctcagcag tgtcagcagg                                                    20

SEQ ID NO: 53       moltype = RNA   length = 20
FEATURE             Location/Qualifiers
misc_feature        1..20
                    note = Synthetic Polynucleotide
source              1..20
                    mol_type = other RNA
                    organism = synthetic construct
SEQUENCE: 53
ttgtcgggtt tgatgtccct                                                    20

SEQ ID NO: 54       moltype = RNA   length = 20
FEATURE             Location/Qualifiers
misc_feature        1..20
                    note = Synthetic Polynucleotide
source              1..20
                    mol_type = other RNA
                    organism = synthetic construct
SEQUENCE: 54
gttgtcgggt tgatgtccc                                                     20

SEQ ID NO: 55       moltype = RNA   length = 20
FEATURE             Location/Qualifiers
misc_feature        1..20
                    note = Synthetic Polynucleotide
source              1..20
                    mol_type = other RNA
                    organism = synthetic construct
SEQUENCE: 55
tccgccaggt agaagcgcgc                                                    20

SEQ ID NO: 56       moltype = RNA   length = 20
FEATURE             Location/Qualifiers
misc_feature        1..20
                    note = Synthetic Polynucleotide
source              1..20
                    mol_type = other RNA
                    organism = synthetic construct
SEQUENCE: 56
catggcatac acctggcccg                                                    20

SEQ ID NO: 57       moltype = RNA   length = 20
FEATURE             Location/Qualifiers
misc_feature        1..20
                    note = Synthetic Polynucleotide
source              1..20
                    mol_type = other RNA
                    organism = synthetic construct
SEQUENCE: 57
aacttgctca gcagtgtcag                                                    20

SEQ ID NO: 58       moltype = RNA   length = 20
FEATURE             Location/Qualifiers
```

```
misc_feature             1..20
                         note = Synthetic Polynucleotide
source                   1..20
                         mol_type = other RNA
                         organism = synthetic construct
SEQUENCE: 58
cagctgcgtg atccaccgcc                                                    20

SEQ ID NO: 59            moltype = RNA  length = 20
FEATURE                  Location/Qualifiers
misc_feature             1..20
                         note = Synthetic Polynucleotide
source                   1..20
                         mol_type = other RNA
                         organism = synthetic construct
SEQUENCE: 59
cgaatgtccg acagtgtctc                                                    20

SEQ ID NO: 60            moltype = RNA  length = 20
FEATURE                  Location/Qualifiers
misc_feature             1..20
                         note = Synthetic Polynucleotide
source                   1..20
                         mol_type = other RNA
                         organism = synthetic construct
SEQUENCE: 60
gaagtcggcc aggcggatgt                                                    20

SEQ ID NO: 61            moltype = RNA  length = 20
FEATURE                  Location/Qualifiers
misc_feature             1..20
                         note = Synthetic Polynucleotide
source                   1..20
                         mol_type = other RNA
                         organism = synthetic construct
SEQUENCE: 61
tgtcgggttt gatgtccctg                                                    20

SEQ ID NO: 62            moltype = RNA  length = 20
FEATURE                  Location/Qualifiers
misc_feature             1..20
                         note = Synthetic Polynucleotide
source                   1..20
                         mol_type = other RNA
                         organism = synthetic construct
SEQUENCE: 62
ggatggcctc catctcccgg                                                    20

SEQ ID NO: 63            moltype = RNA  length = 20
FEATURE                  Location/Qualifiers
misc_feature             1..20
                         note = Synthetic Polynucleotide
source                   1..20
                         mol_type = other RNA
                         organism = synthetic construct
SEQUENCE: 63
aggatgttgt cgggtttgat                                                    20

SEQ ID NO: 64            moltype = RNA  length = 20
FEATURE                  Location/Qualifiers
misc_feature             1..20
                         note = Synthetic Polynucleotide
source                   1..20
                         mol_type = other RNA
                         organism = synthetic construct
SEQUENCE: 64
gtcgggtttg atgtccctgt                                                    20

SEQ ID NO: 65            moltype = RNA  length = 20
FEATURE                  Location/Qualifiers
misc_feature             1..20
                         note = Synthetic Polynucleotide
source                   1..20
                         mol_type = other RNA
                         organism = synthetic construct
SEQUENCE: 65
aatactccat gaccaggtac                                                    20

SEQ ID NO: 66            moltype = RNA  length = 20
```

```
FEATURE                     Location/Qualifiers
misc_feature                1..20
                            note = Synthetic Polynucleotide
source                      1..20
                            mol_type = other RNA
                            organism = synthetic construct
SEQUENCE: 66
cttgttcatg atcttcatgg                                                        20

SEQ ID NO: 67               moltype = RNA   length = 20
FEATURE                     Location/Qualifiers
misc_feature                1..20
                            note = Synthetic Polynucleotide
source                      1..20
                            mol_type = other RNA
                            organism = synthetic construct
SEQUENCE: 67
tcagtgcatc caaaacgtgg                                                        20

SEQ ID NO: 68               moltype = RNA   length = 20
FEATURE                     Location/Qualifiers
misc_feature                1..20
                            note = Synthetic Polynucleotide
source                      1..20
                            mol_type = other RNA
                            organism = synthetic construct
SEQUENCE: 68
ctgtcccgga gaccatccca                                                        20

SEQ ID NO: 69               moltype = RNA   length = 20
FEATURE                     Location/Qualifiers
misc_feature                1..20
                            note = Synthetic Polynucleotide
source                      1..20
                            mol_type = other RNA
                            organism = synthetic construct
SEQUENCE: 69
gggcctggga cctcactgtc                                                        20

SEQ ID NO: 70               moltype = RNA   length = 20
FEATURE                     Location/Qualifiers
misc_feature                1..20
                            note = Synthetic Polynucleotide
source                      1..20
                            mol_type = other RNA
                            organism = synthetic construct
SEQUENCE: 70
cccacgtaat actccatgac                                                        20

SEQ ID NO: 71               moltype = RNA   length = 20
FEATURE                     Location/Qualifiers
misc_feature                1..20
                            note = Synthetic Polynucleotide
source                      1..20
                            mol_type = other RNA
                            organism = synthetic construct
SEQUENCE: 71
ctctgccgca gggacagccg                                                        20

SEQ ID NO: 72               moltype = RNA   length = 20
FEATURE                     Location/Qualifiers
misc_feature                1..20
                            note = Synthetic Polynucleotide
source                      1..20
                            mol_type = other RNA
                            organism = synthetic construct
SEQUENCE: 72
ctgtgcacgt agccaagccg                                                        20

SEQ ID NO: 73               moltype = RNA   length = 20
FEATURE                     Location/Qualifiers
misc_feature                1..20
                            note = Synthetic Polynucleotide
source                      1..20
                            mol_type = other RNA
                            organism = synthetic construct
SEQUENCE: 73
tgcccatcca cgtcagggcc                                                        20
```

```
SEQ ID NO: 74        moltype = RNA   length = 20
FEATURE              Location/Qualifiers
misc_feature         1..20
                     note = Synthetic Polynucleotide
source               1..20
                     mol_type = other RNA
                     organism = synthetic construct
SEQUENCE: 74
agcgcctccg ataggccagg                                                 20

SEQ ID NO: 75        moltype = RNA   length = 20
FEATURE              Location/Qualifiers
misc_feature         1..20
                     note = Synthetic Polynucleotide
source               1..20
                     mol_type = other RNA
                     organism = synthetic construct
SEQUENCE: 75
tgtgcacgta gccaagccgg                                                 20

SEQ ID NO: 76        moltype = RNA   length = 20
FEATURE              Location/Qualifiers
misc_feature         1..20
                     note = Synthetic Polynucleotide
source               1..20
                     mol_type = other RNA
                     organism = synthetic construct
SEQUENCE: 76
gaccaggtac aggtagttct                                                 20

SEQ ID NO: 77        moltype = RNA   length = 20
FEATURE              Location/Qualifiers
misc_feature         1..20
                     note = Synthetic Polynucleotide
source               1..20
                     mol_type = other RNA
                     organism = synthetic construct
SEQUENCE: 77
ccatctcggc cggaatccgc                                                 20

SEQ ID NO: 78        moltype = RNA   length = 20
FEATURE              Location/Qualifiers
misc_feature         1..20
                     note = Synthetic Polynucleotide
source               1..20
                     mol_type = other RNA
                     organism = synthetic construct
SEQUENCE: 78
catctcggcc ggaatccgct                                                 20

SEQ ID NO: 79        moltype = RNA   length = 20
FEATURE              Location/Qualifiers
misc_feature         1..20
                     note = Synthetic Polynucleotide
source               1..20
                     mol_type = other RNA
                     organism = synthetic construct
SEQUENCE: 79
ttgccatagg tctccgccgt                                                 20

SEQ ID NO: 80        moltype = RNA   length = 20
FEATURE              Location/Qualifiers
misc_feature         1..20
                     note = Synthetic Polynucleotide
source               1..20
                     mol_type = other RNA
                     organism = synthetic construct
SEQUENCE: 80
acagcggtcc agcaggatgt                                                 20

SEQ ID NO: 81        moltype = RNA   length = 20
FEATURE              Location/Qualifiers
misc_feature         1..20
                     note = Synthetic Polynucleotide
source               1..20
                     mol_type = other RNA
                     organism = synthetic construct
SEQUENCE: 81
aaagcgcctc cgataggcca                                                 20
```

```
SEQ ID NO: 82              moltype = RNA   length = 20
FEATURE                    Location/Qualifiers
misc_feature               1..20
                           note = Synthetic Polynucleotide
source                     1..20
                           mol_type = other RNA
                           organism = synthetic construct
SEQUENCE: 82
gccaaagaag aagggatgtg                                                     20

SEQ ID NO: 83              moltype = RNA   length = 20
FEATURE                    Location/Qualifiers
misc_feature               1..20
                           note = Synthetic Polynucleotide
source                     1..20
                           mol_type = other RNA
                           organism = synthetic construct
SEQUENCE: 83
cacgtaatac tccatgacca                                                     20

SEQ ID NO: 84              moltype = RNA   length = 20
FEATURE                    Location/Qualifiers
misc_feature               1..20
                           note = Synthetic Polynucleotide
source                     1..20
                           mol_type = other RNA
                           organism = synthetic construct
SEQUENCE: 84
atctcggccg gaatccgctc                                                     20

SEQ ID NO: 85              moltype = RNA   length = 20
FEATURE                    Location/Qualifiers
misc_feature               1..20
                           note = Synthetic Polynucleotide
source                     1..20
                           mol_type = other RNA
                           organism = synthetic construct
SEQUENCE: 85
gcttcatctt cactaccgct                                                     20

SEQ ID NO: 86              moltype = RNA   length = 20
FEATURE                    Location/Qualifiers
misc_feature               1..20
                           note = Synthetic Polynucleotide
source                     1..20
                           mol_type = other RNA
                           organism = synthetic construct
SEQUENCE: 86
gccatctcgg ccggaatccg                                                     20

SEQ ID NO: 87              moltype = RNA   length = 20
FEATURE                    Location/Qualifiers
misc_feature               1..20
                           note = Synthetic Polynucleotide
source                     1..20
                           mol_type = other RNA
                           organism = synthetic construct
SEQUENCE: 87
cagggacagc cgctggaact                                                     20

SEQ ID NO: 88              moltype = RNA   length = 20
FEATURE                    Location/Qualifiers
misc_feature               1..20
                           note = Synthetic Polynucleotide
source                     1..20
                           mol_type = other RNA
                           organism = synthetic construct
SEQUENCE: 88
atgacaatct ccgccaggta                                                     20

SEQ ID NO: 89              moltype = RNA   length = 20
FEATURE                    Location/Qualifiers
misc_feature               1..20
                           note = Synthetic Polynucleotide
source                     1..20
                           mol_type = other RNA
                           organism = synthetic construct
SEQUENCE: 89
```

-continued ggccatgaca atctccgcca                                               20

SEQ ID NO: 90           moltype = RNA   length = 20
FEATURE                 Location/Qualifiers
misc_feature            1..20
                        note = Synthetic Polynucleotide
source                  1..20
                        mol_type = other RNA
                        organism = synthetic construct
SEQUENCE: 90
atactccatg accaggtaca                                               20

SEQ ID NO: 91           moltype = RNA   length = 20
FEATURE                 Location/Qualifiers
misc_feature            1..20
                        note = Synthetic Polynucleotide
source                  1..20
                        mol_type = other RNA
                        organism = synthetic construct
SEQUENCE: 91
gcctctgcct cgcgtagttg                                               20

SEQ ID NO: 92           moltype = RNA   length = 20
FEATURE                 Location/Qualifiers
misc_feature            1..20
                        note = Synthetic Polynucleotide
source                  1..20
                        mol_type = other RNA
                        organism = synthetic construct
SEQUENCE: 92
gaatgtccga cagtgtctcc                                               20

SEQ ID NO: 93           moltype = RNA   length = 20
FEATURE                 Location/Qualifiers
misc_feature            1..20
                        note = Synthetic Polynucleotide
source                  1..20
                        mol_type = other RNA
                        organism = synthetic construct
SEQUENCE: 93
cgttccatct gcccgcagct                                               20

SEQ ID NO: 94           moltype = RNA   length = 20
FEATURE                 Location/Qualifiers
misc_feature            1..20
                        note = Synthetic Polynucleotide
source                  1..20
                        mol_type = other RNA
                        organism = synthetic construct
SEQUENCE: 94
ccttgtagtg gacgatcttg                                               20

SEQ ID NO: 95           moltype = RNA   length = 20
FEATURE                 Location/Qualifiers
misc_feature            1..20
                        note = Synthetic Polynucleotide
source                  1..20
                        mol_type = other RNA
                        organism = synthetic construct
SEQUENCE: 95
atctccgcca ggtagaagcg                                               20

SEQ ID NO: 96           moltype = RNA   length = 20
FEATURE                 Location/Qualifiers
misc_feature            1..20
                        note = Synthetic Polynucleotide
source                  1..20
                        mol_type = other RNA
                        organism = synthetic construct
SEQUENCE: 96
ctcaggctct gccgggtgag                                               20

SEQ ID NO: 97           moltype = RNA   length = 20
FEATURE                 Location/Qualifiers
misc_feature            1..20
                        note = Synthetic Polynucleotide
source                  1..20
                        mol_type = other RNA
                        organism = synthetic construct

```
SEQUENCE: 97
tgcttcatct tcactaccgc                                                          20

SEQ ID NO: 98           moltype = RNA  length = 20
FEATURE                 Location/Qualifiers
misc_feature            1..20
                        note = Synthetic Polynucleotide
source                  1..20
                        mol_type = other RNA
                        organism = synthetic construct
SEQUENCE: 98
gcaggatgtt gtcgggtttg                                                          20

SEQ ID NO: 99           moltype = RNA  length = 20
FEATURE                 Location/Qualifiers
misc_feature            1..20
                        note = Synthetic Polynucleotide
source                  1..20
                        mol_type = other RNA
                        organism = synthetic construct
SEQUENCE: 99
ggcctcagcc tctgccgcag                                                          20

SEQ ID NO: 100          moltype = RNA  length = 20
FEATURE                 Location/Qualifiers
misc_feature            1..20
                        note = Synthetic Polynucleotide
source                  1..20
                        mol_type = other RNA
                        organism = synthetic construct
SEQUENCE: 100
tgttgtcggg tttgatgtcc                                                          20

SEQ ID NO: 101          moltype = RNA  length = 20
FEATURE                 Location/Qualifiers
misc_feature            1..20
                        note = Synthetic Polynucleotide
source                  1..20
                        mol_type = other RNA
                        organism = synthetic construct
SEQUENCE: 101
ccacgtaata ctccatgacc                                                          20

SEQ ID NO: 102          moltype = RNA  length = 20
FEATURE                 Location/Qualifiers
misc_feature            1..20
                        note = Synthetic Polynucleotide
source                  1..20
                        mol_type = other RNA
                        organism = synthetic construct
SEQUENCE: 102
ccgttccatc tgcccgcagc                                                          20

SEQ ID NO: 103          moltype = RNA  length = 20
FEATURE                 Location/Qualifiers
misc_feature            1..20
                        note = Synthetic Polynucleotide
source                  1..20
                        mol_type = other RNA
                        organism = synthetic construct
SEQUENCE: 103
ttcccgagta agcaggcaga                                                          20

SEQ ID NO: 104          moltype = RNA  length = 20
FEATURE                 Location/Qualifiers
misc_feature            1..20
                        note = Synthetic Polynucleotide
source                  1..20
                        mol_type = other RNA
                        organism = synthetic construct
SEQUENCE: 104
tgatcttcat ggcatacacc                                                          20

SEQ ID NO: 105          moltype = RNA  length = 20
FEATURE                 Location/Qualifiers
misc_feature            1..20
                        note = Synthetic Polynucleotide
source                  1..20
                        mol_type = other RNA
```

```
                         organism = synthetic construct
SEQUENCE: 105
agggacagcc gctggaactg                                                    20

SEQ ID NO: 106           moltype = RNA   length = 20
FEATURE                  Location/Qualifiers
misc_feature             1..20
                         note = Synthetic Polynucleotide
source                   1..20
                         mol_type = other RNA
                         organism = synthetic construct
SEQUENCE: 106
gggtttgatg tccctgtgca                                                    20

SEQ ID NO: 107           moltype = RNA   length = 20
FEATURE                  Location/Qualifiers
misc_feature             1..20
                         note = Synthetic Polynucleotide
source                   1..20
                         mol_type = other RNA
                         organism = synthetic construct
SEQUENCE: 107
tgacaatctc cgccaggtag                                                    20

SEQ ID NO: 108           moltype = RNA   length = 20
FEATURE                  Location/Qualifiers
misc_feature             1..20
                         note = Synthetic Polynucleotide
source                   1..20
                         mol_type = other RNA
                         organism = synthetic construct
SEQUENCE: 108
cacagcggtc cagcaggatg                                                    20

SEQ ID NO: 109           moltype = RNA   length = 20
FEATURE                  Location/Qualifiers
misc_feature             1..20
                         note = Synthetic Polynucleotide
source                   1..20
                         mol_type = other RNA
                         organism = synthetic construct
SEQUENCE: 109
gcgtagaagg gcgtctgccc                                                    20

SEQ ID NO: 110           moltype = RNA   length = 20
FEATURE                  Location/Qualifiers
misc_feature             1..20
                         note = Synthetic Polynucleotide
source                   1..20
                         mol_type = other RNA
                         organism = synthetic construct
SEQUENCE: 110
ctcagcctct gccgcaggga                                                    20

SEQ ID NO: 111           moltype = RNA   length = 20
FEATURE                  Location/Qualifiers
misc_feature             1..20
                         note = Synthetic Polynucleotide
source                   1..20
                         mol_type = other RNA
                         organism = synthetic construct
SEQUENCE: 111
gtctcagtgc atccaaaacg                                                    20

SEQ ID NO: 112           moltype = RNA   length = 20
FEATURE                  Location/Qualifiers
misc_feature             1..20
                         note = Synthetic Polynucleotide
source                   1..20
                         mol_type = other RNA
                         organism = synthetic construct
SEQUENCE: 112
ggacgatctt gccataggtc                                                    20

SEQ ID NO: 113           moltype = RNA   length = 20
FEATURE                  Location/Qualifiers
misc_feature             1..20
                         note = Synthetic Polynucleotide
source                   1..20
```

```
                        mol_type = other RNA
                        organism = synthetic construct
SEQUENCE: 113
tcagcagtgt cagcaggtcc                                                       20

SEQ ID NO: 114          moltype = RNA   length = 20
FEATURE                 Location/Qualifiers
misc_feature            1..20
                        note = Synthetic Polynucleotide
source                  1..20
                        mol_type = other RNA
                        organism = synthetic construct
SEQUENCE: 114
gctcctgggc ggcgccagac                                                       20

SEQ ID NO: 115          moltype = RNA   length = 20
FEATURE                 Location/Qualifiers
misc_feature            1..20
                        note = Synthetic Polynucleotide
source                  1..20
                        mol_type = other RNA
                        organism = synthetic construct
SEQUENCE: 115
agcaggatgt tgtcgggttt                                                       20

SEQ ID NO: 116          moltype = RNA   length = 20
FEATURE                 Location/Qualifiers
misc_feature            1..20
                        note = Synthetic Polynucleotide
source                  1..20
                        mol_type = other RNA
                        organism = synthetic construct
SEQUENCE: 116
atccgctcct gcaactgccg                                                       20

SEQ ID NO: 117          moltype = RNA   length = 20
FEATURE                 Location/Qualifiers
misc_feature            1..20
                        note = Synthetic Polynucleotide
source                  1..20
                        mol_type = other RNA
                        organism = synthetic construct
SEQUENCE: 117
aggagcaggg aaagcgcctc                                                       20

SEQ ID NO: 118          moltype = RNA   length = 20
FEATURE                 Location/Qualifiers
misc_feature            1..20
                        note = Synthetic Polynucleotide
source                  1..20
                        mol_type = other RNA
                        organism = synthetic construct
SEQUENCE: 118
acacctggcc cgtctgcttc                                                       20

SEQ ID NO: 119          moltype = RNA   length = 20
FEATURE                 Location/Qualifiers
misc_feature            1..20
                        note = Synthetic Polynucleotide
source                  1..20
                        mol_type = other RNA
                        organism = synthetic construct
SEQUENCE: 119
cccagcgccc accagtcaca                                                       20

SEQ ID NO: 120          moltype = RNA   length = 20
FEATURE                 Location/Qualifiers
misc_feature            1..20
                        note = Synthetic Polynucleotide
source                  1..20
                        mol_type = other RNA
                        organism = synthetic construct
SEQUENCE: 120
gctccctctg cctgcagcaa                                                       20

SEQ ID NO: 121          moltype = RNA   length = 20
FEATURE                 Location/Qualifiers
misc_feature            1..20
                        note = Synthetic Polynucleotide
```

-continued

```
source                  1..20
                        mol_type = other RNA
                        organism = synthetic construct
SEQUENCE: 121
gctcaggctc tgccgggtga                                                    20

SEQ ID NO: 122          moltype = RNA   length = 20
FEATURE                 Location/Qualifiers
misc_feature            1..20
                        note = Synthetic Polynucleotide
source                  1..20
                        mol_type = other RNA
                        organism = synthetic construct
SEQUENCE: 122
ttgatgtccc tgtgcacgta                                                    20

SEQ ID NO: 123          moltype = RNA   length = 20
FEATURE                 Location/Qualifiers
misc_feature            1..20
                        note = Synthetic Polynucleotide
source                  1..20
                        mol_type = other RNA
                        organism = synthetic construct
SEQUENCE: 123
gcctcagcct ctgccgcagg                                                    20

SEQ ID NO: 124          moltype = RNA   length = 20
FEATURE                 Location/Qualifiers
misc_feature            1..20
                        note = Synthetic Polynucleotide
source                  1..20
                        mol_type = other RNA
                        organism = synthetic construct
SEQUENCE: 124
ggtagttctc atcctggaag                                                    20

SEQ ID NO: 125          moltype = RNA   length = 20
FEATURE                 Location/Qualifiers
misc_feature            1..20
                        note = Synthetic Polynucleotide
source                  1..20
                        mol_type = other RNA
                        organism = synthetic construct
SEQUENCE: 125
cagcgcccac cagtcacact                                                    20

SEQ ID NO: 126          moltype = RNA   length = 20
FEATURE                 Location/Qualifiers
misc_feature            1..20
                        note = Synthetic Polynucleotide
source                  1..20
                        mol_type = other RNA
                        organism = synthetic construct
SEQUENCE: 126
cccaaacttg ctcagcagtg                                                    20

SEQ ID NO: 127          moltype = RNA   length = 20
FEATURE                 Location/Qualifiers
misc_feature            1..20
                        note = Synthetic Polynucleotide
source                  1..20
                        mol_type = other RNA
                        organism = synthetic construct
SEQUENCE: 127
cttgccatag gtctccgccg                                                    20

SEQ ID NO: 128          moltype = RNA   length = 20
FEATURE                 Location/Qualifiers
misc_feature            1..20
                        note = Synthetic Polynucleotide
source                  1..20
                        mol_type = other RNA
                        organism = synthetic construct
SEQUENCE: 128
tacacctggc ccgtctgctt                                                    20

SEQ ID NO: 129          moltype = RNA   length = 20
FEATURE                 Location/Qualifiers
misc_feature            1..20
```

```
                        note = Synthetic Polynucleotide
source                  1..20
                        mol_type = other RNA
                        organism = synthetic construct
SEQUENCE: 129
ccagcgccca ccagtcacac                                                   20

SEQ ID NO: 130          moltype = RNA   length = 20
FEATURE                 Location/Qualifiers
misc_feature            1..20
                        note = Synthetic Polynucleotide
source                  1..20
                        mol_type = other RNA
                        organism = synthetic construct
SEQUENCE: 130
ggcctcagcc tggccgaaag                                                   20

SEQ ID NO: 131          moltype = RNA   length = 20
FEATURE                 Location/Qualifiers
misc_feature            1..20
                        note = Synthetic Polynucleotide
source                  1..20
                        mol_type = other RNA
                        organism = synthetic construct
SEQUENCE: 131
aatctccgcc aggtagaagc                                                   20

SEQ ID NO: 132          moltype = RNA   length = 20
FEATURE                 Location/Qualifiers
misc_feature            1..20
                        note = Synthetic Polynucleotide
source                  1..20
                        mol_type = other RNA
                        organism = synthetic construct
SEQUENCE: 132
atggcataca cctggcccgt                                                   20

SEQ ID NO: 133          moltype = RNA   length = 20
FEATURE                 Location/Qualifiers
misc_feature            1..20
                        note = Synthetic Polynucleotide
source                  1..20
                        mol_type = other RNA
                        organism = synthetic construct
SEQUENCE: 133
ccatgacaat ctccgccagg                                                   20

SEQ ID NO: 134          moltype = RNA   length = 20
FEATURE                 Location/Qualifiers
misc_feature            1..20
                        note = Synthetic Polynucleotide
source                  1..20
                        mol_type = other RNA
                        organism = synthetic construct
SEQUENCE: 134
tccccaaact tgctcagcag                                                   20

SEQ ID NO: 135          moltype = RNA   length = 20
FEATURE                 Location/Qualifiers
misc_feature            1..20
                        note = Synthetic Polynucleotide
source                  1..20
                        mol_type = other RNA
                        organism = synthetic construct
SEQUENCE: 135
gatgttgtcg ggtttgatgt                                                   20

SEQ ID NO: 136          moltype = RNA   length = 20
FEATURE                 Location/Qualifiers
misc_feature            1..20
                        note = Synthetic Polynucleotide
source                  1..20
                        mol_type = other RNA
                        organism = synthetic construct
SEQUENCE: 136
gtttgcccat ccacgtcagg                                                   20

SEQ ID NO: 137          moltype = RNA   length = 20
FEATURE                 Location/Qualifiers
```

```
misc_feature                1..20
                            note = Synthetic Polynucleotide
source                      1..20
                            mol_type = other RNA
                            organism = synthetic construct
SEQUENCE: 137
cggacggccc ggcttgctgc                                                     20

SEQ ID NO: 138              moltype = RNA  length = 20
FEATURE                     Location/Qualifiers
misc_feature                1..20
                            note = Synthetic Polynucleotide
source                      1..20
                            mol_type = other RNA
                            organism = synthetic construct
SEQUENCE: 138
ctccgccagg tagaagcgcg                                                     20

SEQ ID NO: 139              moltype = RNA  length = 20
FEATURE                     Location/Qualifiers
misc_feature                1..20
                            note = Synthetic Polynucleotide
source                      1..20
                            mol_type = other RNA
                            organism = synthetic construct
SEQUENCE: 139
gtacaggtag ttctcatcct                                                     20

SEQ ID NO: 140              moltype = RNA  length = 20
FEATURE                     Location/Qualifiers
misc_feature                1..20
                            note = Synthetic Polynucleotide
source                      1..20
                            mol_type = other RNA
                            organism = synthetic construct
SEQUENCE: 140
agggcgtctg cccatagaac                                                     20

SEQ ID NO: 141              moltype = RNA  length = 20
FEATURE                     Location/Qualifiers
misc_feature                1..20
                            note = Synthetic Polynucleotide
source                      1..20
                            mol_type = other RNA
                            organism = synthetic construct
SEQUENCE: 141
tggccacagc ggtccagcag                                                     20

SEQ ID NO: 142              moltype = RNA  length = 20
FEATURE                     Location/Qualifiers
misc_feature                1..20
                            note = Synthetic Polynucleotide
source                      1..20
                            mol_type = other RNA
                            organism = synthetic construct
SEQUENCE: 142
cgtagttgac tggcgaagtt                                                     20

SEQ ID NO: 143              moltype = RNA  length = 20
FEATURE                     Location/Qualifiers
misc_feature                1..20
                            note = Synthetic Polynucleotide
source                      1..20
                            mol_type = other RNA
                            organism = synthetic construct
SEQUENCE: 143
tctgccgcag ggacagccgc                                                     20

SEQ ID NO: 144              moltype = RNA  length = 20
FEATURE                     Location/Qualifiers
misc_feature                1..20
                            note = Synthetic Polynucleotide
source                      1..20
                            mol_type = other RNA
                            organism = synthetic construct
SEQUENCE: 144
aagcgcctcc gataggccag                                                     20

SEQ ID NO: 145              moltype = RNA  length = 20
```

```
FEATURE              Location/Qualifiers
misc_feature         1..20
                     note = Synthetic Polynucleotide
source               1..20
                     mol_type = other RNA
                     organism = synthetic construct
SEQUENCE: 145
gacagaacaa cggcgaacag                                                  20

SEQ ID NO: 146       moltype = RNA   length = 20
FEATURE              Location/Qualifiers
misc_feature         1..20
                     note = Synthetic Polynucleotide
source               1..20
                     mol_type = other RNA
                     organism = synthetic construct
SEQUENCE: 146
gctcagcagt gtcagcaggt                                                  20

SEQ ID NO: 147       moltype = RNA   length = 20
FEATURE              Location/Qualifiers
misc_feature         1..20
                     note = Synthetic Polynucleotide
source               1..20
                     mol_type = other RNA
                     organism = synthetic construct
SEQUENCE: 147
atgatcttca tggcatacac                                                  20

SEQ ID NO: 148       moltype = RNA   length = 20
FEATURE              Location/Qualifiers
misc_feature         1..20
                     note = Synthetic Polynucleotide
source               1..20
                     mol_type = other RNA
                     organism = synthetic construct
SEQUENCE: 148
tttgcccatc cacgtcaggg                                                  20

SEQ ID NO: 149       moltype = RNA   length = 20
FEATURE              Location/Qualifiers
misc_feature         1..20
                     note = Synthetic Polynucleotide
source               1..20
                     mol_type = other RNA
                     organism = synthetic construct
SEQUENCE: 149
acttgctcag cagtgtcagc                                                  20

SEQ ID NO: 150       moltype = RNA   length = 20
FEATURE              Location/Qualifiers
misc_feature         1..20
                     note = Synthetic Polynucleotide
source               1..20
                     mol_type = other RNA
                     organism = synthetic construct
SEQUENCE: 150
tgatgtccct gtgcacgtag                                                  20

SEQ ID NO: 151       moltype = RNA   length = 20
FEATURE              Location/Qualifiers
misc_feature         1..20
                     note = Synthetic Polynucleotide
source               1..20
                     mol_type = other RNA
                     organism = synthetic construct
SEQUENCE: 151
aaataccgag gaatgtcggg                                                  20

SEQ ID NO: 152       moltype = RNA   length = 20
FEATURE              Location/Qualifiers
misc_feature         1..20
                     note = Synthetic Polynucleotide
source               1..20
                     mol_type = other RNA
                     organism = synthetic construct
SEQUENCE: 152
ggcgaataca cccagcgccc                                                  20
```

```
SEQ ID NO: 153              moltype = RNA   length = 20
FEATURE                     Location/Qualifiers
misc_feature                1..20
                            note = Synthetic Polynucleotide
source                      1..20
                            mol_type = other RNA
                            organism = synthetic construct
SEQUENCE: 153
agacaataaa taccgaggaa                                                       20

SEQ ID NO: 154              moltype = RNA   length = 20
FEATURE                     Location/Qualifiers
misc_feature                1..20
                            note = Synthetic Polynucleotide
source                      1..20
                            mol_type = other RNA
                            organism = synthetic construct
SEQUENCE: 154
cccgtctgct tcatcttcac                                                       20

SEQ ID NO: 155              moltype = RNA   length = 20
FEATURE                     Location/Qualifiers
misc_feature                1..20
                            note = Synthetic Polynucleotide
source                      1..20
                            mol_type = other RNA
                            organism = synthetic construct
SEQUENCE: 155
ctgcctgcag caactccatc                                                       20

SEQ ID NO: 156              moltype = RNA   length = 20
FEATURE                     Location/Qualifiers
misc_feature                1..20
                            note = Synthetic Polynucleotide
source                      1..20
                            mol_type = other RNA
                            organism = synthetic construct
SEQUENCE: 156
cctcagcctc tgccgcaggg                                                       20

SEQ ID NO: 157              moltype = RNA   length = 20
FEATURE                     Location/Qualifiers
misc_feature                1..20
                            note = Synthetic Polynucleotide
source                      1..20
                            mol_type = other RNA
                            organism = synthetic construct
SEQUENCE: 157
gtgtccggaa gtcgcctgct                                                       20

SEQ ID NO: 158              moltype = RNA   length = 20
FEATURE                     Location/Qualifiers
misc_feature                1..20
                            note = Synthetic Polynucleotide
source                      1..20
                            mol_type = other RNA
                            organism = synthetic construct
SEQUENCE: 158
tgcacgtgtg gctcaagcag                                                       20

SEQ ID NO: 159              moltype = RNA   length = 20
FEATURE                     Location/Qualifiers
misc_feature                1..20
                            note = Synthetic Polynucleotide
source                      1..20
                            mol_type = other RNA
                            organism = synthetic construct
SEQUENCE: 159
gacaataaat accgaggaat                                                       20

SEQ ID NO: 160              moltype = RNA   length = 20
FEATURE                     Location/Qualifiers
misc_feature                1..20
                            note = Synthetic Polynucleotide
source                      1..20
                            mol_type = other RNA
                            organism = synthetic construct
SEQUENCE: 160
gccatgacaa tctccgccag                                                       20
```

```
SEQ ID NO: 161          moltype = RNA   length = 20
FEATURE                 Location/Qualifiers
misc_feature            1..20
                        note = Synthetic Polynucleotide
source                  1..20
                        mol_type = other RNA
                        organism = synthetic construct
SEQUENCE: 161
gctgtcccgg agaccatccc                                                     20

SEQ ID NO: 162          moltype = RNA   length = 20
FEATURE                 Location/Qualifiers
misc_feature            1..20
                        note = Synthetic Polynucleotide
source                  1..20
                        mol_type = other RNA
                        organism = synthetic construct
SEQUENCE: 162
catgaccagg tacaggtagt                                                     20

SEQ ID NO: 163          moltype = RNA   length = 20
FEATURE                 Location/Qualifiers
misc_feature            1..20
                        note = Synthetic Polynucleotide
source                  1..20
                        mol_type = other RNA
                        organism = synthetic construct
SEQUENCE: 163
agcgcccacc agtcacactc                                                     20

SEQ ID NO: 164          moltype = RNA   length = 20
FEATURE                 Location/Qualifiers
misc_feature            1..20
                        note = Synthetic Polynucleotide
source                  1..20
                        mol_type = other RNA
                        organism = synthetic construct
SEQUENCE: 164
tctcagtgca tccaaaacgt                                                     20

SEQ ID NO: 165          moltype = RNA   length = 20
FEATURE                 Location/Qualifiers
misc_feature            1..20
                        note = Synthetic Polynucleotide
source                  1..20
                        mol_type = other RNA
                        organism = synthetic construct
SEQUENCE: 165
tttgggcaga tggagggcct                                                     20

SEQ ID NO: 166          moltype = RNA   length = 20
FEATURE                 Location/Qualifiers
misc_feature            1..20
                        note = Synthetic Polynucleotide
source                  1..20
                        mol_type = other RNA
                        organism = synthetic construct
SEQUENCE: 166
gatgtccctg tgcacgtagc                                                     20

SEQ ID NO: 167          moltype = RNA   length = 20
FEATURE                 Location/Qualifiers
misc_feature            1..20
                        note = Synthetic Polynucleotide
source                  1..20
                        mol_type = other RNA
                        organism = synthetic construct
SEQUENCE: 167
cagcagtgtc agcaggtccc                                                     20

SEQ ID NO: 168          moltype = RNA   length = 20
FEATURE                 Location/Qualifiers
misc_feature            1..20
                        note = Synthetic Polynucleotide
source                  1..20
                        mol_type = other RNA
                        organism = synthetic construct
SEQUENCE: 168
```
catgacaatc tccgccaggt                                                    20

SEQ ID NO: 169          moltype = RNA   length = 20
FEATURE                 Location/Qualifiers
misc_feature            1..20
                        note = Synthetic Polynucleotide
source                  1..20
                        mol_type = other RNA
                        organism = synthetic construct
SEQUENCE: 169
acttgttcat gatcttcatg                                                    20

SEQ ID NO: 170          moltype = RNA   length = 20
FEATURE                 Location/Qualifiers
misc_feature            1..20
                        note = Synthetic Polynucleotide
source                  1..20
                        mol_type = other RNA
                        organism = synthetic construct
SEQUENCE: 170
gtggaatccg cgtagaaggg                                                    20

SEQ ID NO: 171          moltype = RNA   length = 20
FEATURE                 Location/Qualifiers
misc_feature            1..20
                        note = Synthetic Polynucleotide
source                  1..20
                        mol_type = other RNA
                        organism = synthetic construct
SEQUENCE: 171
tggccatgac aatctccgcc                                                    20

SEQ ID NO: 172          moltype = RNA   length = 20
FEATURE                 Location/Qualifiers
misc_feature            1..20
                        note = Synthetic Polynucleotide
source                  1..20
                        mol_type = other RNA
                        organism = synthetic construct
SEQUENCE: 172
gggacagaca ataaataccg                                                    20

SEQ ID NO: 173          moltype = RNA   length = 20
FEATURE                 Location/Qualifiers
misc_feature            1..20
                        note = Synthetic Polynucleotide
source                  1..20
                        mol_type = other RNA
                        organism = synthetic construct
SEQUENCE: 173
ccgctcccca aacttgctca                                                    20

SEQ ID NO: 174          moltype = RNA   length = 20
FEATURE                 Location/Qualifiers
misc_feature            1..20
                        note = Synthetic Polynucleotide
source                  1..20
                        mol_type = other RNA
                        organism = synthetic construct
SEQUENCE: 174
cggctcaggc tctgccgggt                                                    20

SEQ ID NO: 175          moltype = RNA   length = 20
FEATURE                 Location/Qualifiers
misc_feature            1..20
                        note = Synthetic Polynucleotide
source                  1..20
                        mol_type = other RNA
                        organism = synthetic construct
SEQUENCE: 175
ggctcctggg cggcgccaga                                                    20

SEQ ID NO: 176          moltype = RNA   length = 20
FEATURE                 Location/Qualifiers
misc_feature            1..20
                        note = Synthetic Polynucleotide
source                  1..20
                        mol_type = other RNA
                        organism = synthetic construct

```
SEQUENCE: 176
tttcccgagt aagcaggcag                                                    20

SEQ ID NO: 177          moltype = RNA   length = 20
FEATURE                 Location/Qualifiers
misc_feature            1..20
                        note = Synthetic Polynucleotide
source                  1..20
                        mol_type = other RNA
                        organism = synthetic construct
SEQUENCE: 177
ggatgttgtc gggtttgatg                                                    20

SEQ ID NO: 178          moltype = RNA   length = 20
FEATURE                 Location/Qualifiers
misc_feature            1..20
                        note = Synthetic Polynucleotide
source                  1..20
                        mol_type = other RNA
                        organism = synthetic construct
SEQUENCE: 178
caggtagttc tcatcctgga                                                    20

SEQ ID NO: 179          moltype = RNA   length = 20
FEATURE                 Location/Qualifiers
misc_feature            1..20
                        note = Synthetic Polynucleotide
source                  1..20
                        mol_type = other RNA
                        organism = synthetic construct
SEQUENCE: 179
tgcccataga acatttcata                                                    20

SEQ ID NO: 180          moltype = RNA   length = 20
FEATURE                 Location/Qualifiers
misc_feature            1..20
                        note = Synthetic Polynucleotide
source                  1..20
                        mol_type = other RNA
                        organism = synthetic construct
SEQUENCE: 180
tagttctcat cctggaaggc                                                    20

SEQ ID NO: 181          moltype = RNA   length = 20
FEATURE                 Location/Qualifiers
misc_feature            1..20
                        note = Synthetic Polynucleotide
source                  1..20
                        mol_type = other RNA
                        organism = synthetic construct
SEQUENCE: 181
atgtccctgt gcacgtagcc                                                    20

SEQ ID NO: 182          moltype = RNA   length = 20
FEATURE                 Location/Qualifiers
misc_feature            1..20
                        note = Synthetic Polynucleotide
source                  1..20
                        mol_type = other RNA
                        organism = synthetic construct
SEQUENCE: 182
cgggcccgga tcacaggact                                                    20

SEQ ID NO: 183          moltype = RNA   length = 20
FEATURE                 Location/Qualifiers
misc_feature            1..20
                        note = Synthetic Polynucleotide
source                  1..20
                        mol_type = other RNA
                        organism = synthetic construct
SEQUENCE: 183
tggacgatct tgccataggt                                                    20

SEQ ID NO: 184          moltype = RNA   length = 20
FEATURE                 Location/Qualifiers
misc_feature            1..20
                        note = Synthetic Polynucleotide
source                  1..20
                        mol_type = other RNA
```

```
                          organism = synthetic construct
SEQUENCE: 184
gttggccggc gtgggccacc                                                  20

SEQ ID NO: 185           moltype = RNA  length = 20
FEATURE                  Location/Qualifiers
misc_feature             1..20
                         note = Synthetic Polynucleotide
source                   1..20
                         mol_type = other RNA
                         organism = synthetic construct
SEQUENCE: 185
ctcagtgcat ccaaaacgtg                                                  20

SEQ ID NO: 186           moltype = RNA  length = 20
FEATURE                  Location/Qualifiers
misc_feature             1..20
                         note = Synthetic Polynucleotide
source                   1..20
                         mol_type = other RNA
                         organism = synthetic construct
SEQUENCE: 186
tcgaagttgc atgtgtcggt                                                  20

SEQ ID NO: 187           moltype = RNA  length = 20
FEATURE                  Location/Qualifiers
misc_feature             1..20
                         note = Synthetic Polynucleotide
source                   1..20
                         mol_type = other RNA
                         organism = synthetic construct
SEQUENCE: 187
tggaacacgg acggcccggc                                                  20

SEQ ID NO: 188           moltype = RNA  length = 20
FEATURE                  Location/Qualifiers
misc_feature             1..20
                         note = Synthetic Polynucleotide
source                   1..20
                         mol_type = other RNA
                         organism = synthetic construct
SEQUENCE: 188
ccgagagcag cgcaagtgag                                                  20

SEQ ID NO: 189           moltype = RNA  length = 20
FEATURE                  Location/Qualifiers
misc_feature             1..20
                         note = Synthetic Polynucleotide
source                   1..20
                         mol_type = other RNA
                         organism = synthetic construct
SEQUENCE: 189
tcctgcaact gccggacgtg                                                  20

SEQ ID NO: 190           moltype = RNA  length = 20
FEATURE                  Location/Qualifiers
misc_feature             1..20
                         note = Synthetic Polynucleotide
source                   1..20
                         mol_type = other RNA
                         organism = synthetic construct
SEQUENCE: 190
tcaccaacac gtccctctcc                                                  20

SEQ ID NO: 191           moltype = RNA  length = 20
FEATURE                  Location/Qualifiers
misc_feature             1..20
                         note = Synthetic Polynucleotide
source                   1..20
                         mol_type = other RNA
                         organism = synthetic construct
SEQUENCE: 191
tgcctgcagc aactccatcc                                                  20

SEQ ID NO: 192           moltype = RNA  length = 20
FEATURE                  Location/Qualifiers
misc_feature             1..20
                         note = Synthetic Polynucleotide
source                   1..20
```

```
                    mol_type = other RNA
                    organism = synthetic construct
SEQUENCE: 192
ttggccggcg tgggccacca                                              20

SEQ ID NO: 193      moltype = RNA   length = 20
FEATURE             Location/Qualifiers
misc_feature        1..20
                    note = Synthetic Polynucleotide
source              1..20
                    mol_type = other RNA
                    organism = synthetic construct
SEQUENCE: 193
gagcctctgc ctcgcgtagt                                              20

SEQ ID NO: 194      moltype = RNA   length = 20
FEATURE             Location/Qualifiers
misc_feature        1..20
                    note = Synthetic Polynucleotide
source              1..20
                    mol_type = other RNA
                    organism = synthetic construct
SEQUENCE: 194
aagggcgtct gcccatagaa                                              20

SEQ ID NO: 195      moltype = RNA   length = 20
FEATURE             Location/Qualifiers
misc_feature        1..20
                    note = Synthetic Polynucleotide
source              1..20
                    mol_type = other RNA
                    organism = synthetic construct
SEQUENCE: 195
acagacaata aataccgagg                                              20

SEQ ID NO: 196      moltype = RNA   length = 20
FEATURE             Location/Qualifiers
misc_feature        1..20
                    note = Synthetic Polynucleotide
source              1..20
                    mol_type = other RNA
                    organism = synthetic construct
SEQUENCE: 196
ggacagacaa taaataccga                                              20

SEQ ID NO: 197      moltype = RNA   length = 20
FEATURE             Location/Qualifiers
misc_feature        1..20
                    note = Synthetic Polynucleotide
source              1..20
                    mol_type = other RNA
                    organism = synthetic construct
SEQUENCE: 197
acgtgtgcct ctaggtcccg                                              20

SEQ ID NO: 198      moltype = RNA   length = 20
FEATURE             Location/Qualifiers
misc_feature        1..20
                    note = Synthetic Polynucleotide
source              1..20
                    mol_type = other RNA
                    organism = synthetic construct
SEQUENCE: 198
ggcacgagac agaacaacgg                                              20

SEQ ID NO: 199      moltype = RNA   length = 20
FEATURE             Location/Qualifiers
misc_feature        1..20
                    note = Synthetic Polynucleotide
source              1..20
                    mol_type = other RNA
                    organism = synthetic construct
SEQUENCE: 199
tgaccaggta caggtagttc                                              20

SEQ ID NO: 200      moltype = RNA   length = 20
FEATURE             Location/Qualifiers
misc_feature        1..20
                    note = Synthetic Polynucleotide
```

```
source                  1..20
                        mol_type = other RNA
                        organism = synthetic construct
SEQUENCE: 200
ctctgccggg tgagcacctc                                                    20

SEQ ID NO: 201          moltype = RNA  length = 20
FEATURE                 Location/Qualifiers
misc_feature            1..20
                        note = Synthetic Polynucleotide
source                  1..20
                        mol_type = other RNA
                        organism = synthetic construct
SEQUENCE: 201
gacaatctcc gccaggtaga                                                    20

SEQ ID NO: 202          moltype = RNA  length = 20
FEATURE                 Location/Qualifiers
misc_feature            1..20
                        note = Synthetic Polynucleotide
source                  1..20
                        mol_type = other RNA
                        organism = synthetic construct
SEQUENCE: 202
tctccgccag gtagaagcgc                                                    20

SEQ ID NO: 203          moltype = RNA  length = 20
FEATURE                 Location/Qualifiers
misc_feature            1..20
                        note = Synthetic Polynucleotide
source                  1..20
                        mol_type = other RNA
                        organism = synthetic construct
SEQUENCE: 203
ctctgcctcg cgtagttgac                                                    20

SEQ ID NO: 204          moltype = RNA  length = 20
FEATURE                 Location/Qualifiers
misc_feature            1..20
                        note = Synthetic Polynucleotide
source                  1..20
                        mol_type = other RNA
                        organism = synthetic construct
SEQUENCE: 204
ctttgggcag atggagggcc                                                    20

SEQ ID NO: 205          moltype = RNA  length = 20
FEATURE                 Location/Qualifiers
misc_feature            1..20
                        note = Synthetic Polynucleotide
source                  1..20
                        mol_type = other RNA
                        organism = synthetic construct
SEQUENCE: 205
acaggtagtt ctcatcctgg                                                    20

SEQ ID NO: 206          moltype = RNA  length = 20
FEATURE                 Location/Qualifiers
misc_feature            1..20
                        note = Synthetic Polynucleotide
source                  1..20
                        mol_type = other RNA
                        organism = synthetic construct
SEQUENCE: 206
ccaaacttgc tcagcagtgt                                                    20

SEQ ID NO: 207          moltype = RNA  length = 20
FEATURE                 Location/Qualifiers
misc_feature            1..20
                        note = Synthetic Polynucleotide
source                  1..20
                        mol_type = other RNA
                        organism = synthetic construct
SEQUENCE: 207
tcgggtttga tgtccctgtg                                                    20

SEQ ID NO: 208          moltype = RNA  length = 20
FEATURE                 Location/Qualifiers
misc_feature            1..20
```

```
                           note = Synthetic Polynucleotide
source                     1..20
                           mol_type = other RNA
                           organism = synthetic construct
SEQUENCE: 208
ggcttgctgc cttcccaggc                                              20

SEQ ID NO: 209             moltype = RNA   length = 20
FEATURE                    Location/Qualifiers
misc_feature               1..20
                           note = Synthetic Polynucleotide
source                     1..20
                           mol_type = other RNA
                           organism = synthetic construct
SEQUENCE: 209
tacaggtagt tctcatcctg                                              20

SEQ ID NO: 210             moltype = RNA   length = 20
FEATURE                    Location/Qualifiers
misc_feature               1..20
                           note = Synthetic Polynucleotide
source                     1..20
                           mol_type = other RNA
                           organism = synthetic construct
SEQUENCE: 210
ttgcccatcc acgtcagggc                                              20

SEQ ID NO: 211             moltype = RNA   length = 20
FEATURE                    Location/Qualifiers
misc_feature               1..20
                           note = Synthetic Polynucleotide
source                     1..20
                           mol_type = other RNA
                           organism = synthetic construct
SEQUENCE: 211
aggtacaggt agttctcatc                                              20

SEQ ID NO: 212             moltype = RNA   length = 20
FEATURE                    Location/Qualifiers
misc_feature               1..20
                           note = Synthetic Polynucleotide
source                     1..20
                           mol_type = other RNA
                           organism = synthetic construct
SEQUENCE: 212
gacagacaat aaataccgag                                              20

SEQ ID NO: 213             moltype = RNA   length = 20
FEATURE                    Location/Qualifiers
misc_feature               1..20
                           note = Synthetic Polynucleotide
source                     1..20
                           mol_type = other RNA
                           organism = synthetic construct
SEQUENCE: 213
tagaacattt cataggcgaa                                              20

SEQ ID NO: 214             moltype = RNA   length = 20
FEATURE                    Location/Qualifiers
misc_feature               1..20
                           note = Synthetic Polynucleotide
source                     1..20
                           mol_type = other RNA
                           organism = synthetic construct
SEQUENCE: 214
agggccttt attcgcgagg                                               20

SEQ ID NO: 215             moltype = RNA   length = 20
FEATURE                    Location/Qualifiers
misc_feature               1..20
                           note = Synthetic Polynucleotide
source                     1..20
                           mol_type = other RNA
                           organism = synthetic construct
SEQUENCE: 215
gcctcgcgta gttgactggc                                              20

SEQ ID NO: 216             moltype = RNA   length = 20
FEATURE                    Location/Qualifiers
```

```
misc_feature               1..20
                           note = Synthetic Polynucleotide
source                     1..20
                           mol_type = other RNA
                           organism = synthetic construct
SEQUENCE: 216
ccagcaggat gttgtcgggt                                                    20

SEQ ID NO: 217             moltype = RNA   length = 20
FEATURE                    Location/Qualifiers
misc_feature               1..20
                           note = Synthetic Polynucleotide
source                     1..20
                           mol_type = other RNA
                           organism = synthetic construct
SEQUENCE: 217
gtagttgact ggcgaagttc                                                    20

SEQ ID NO: 218             moltype = RNA   length = 20
FEATURE                    Location/Qualifiers
misc_feature               1..20
                           note = Synthetic Polynucleotide
source                     1..20
                           mol_type = other RNA
                           organism = synthetic construct
SEQUENCE: 218
tgcggatggc ctccatctcc                                                    20

SEQ ID NO: 219             moltype = RNA   length = 20
FEATURE                    Location/Qualifiers
misc_feature               1..20
                           note = Synthetic Polynucleotide
source                     1..20
                           mol_type = other RNA
                           organism = synthetic construct
SEQUENCE: 219
acaatctccg ccaggtagaa                                                    20

SEQ ID NO: 220             moltype = RNA   length = 20
FEATURE                    Location/Qualifiers
misc_feature               1..20
                           note = Synthetic Polynucleotide
source                     1..20
                           mol_type = other RNA
                           organism = synthetic construct
SEQUENCE: 220
gcgaatacac ccagcgccca                                                    20

SEQ ID NO: 221             moltype = RNA   length = 20
FEATURE                    Location/Qualifiers
misc_feature               1..20
                           note = Synthetic Polynucleotide
source                     1..20
                           mol_type = other RNA
                           organism = synthetic construct
SEQUENCE: 221
gtagttctca tcctggaagg                                                    20

SEQ ID NO: 222             moltype = RNA   length = 20
FEATURE                    Location/Qualifiers
misc_feature               1..20
                           note = Synthetic Polynucleotide
source                     1..20
                           mol_type = other RNA
                           organism = synthetic construct
SEQUENCE: 222
ggctcaggct ctgccgggtg                                                    20

SEQ ID NO: 223             moltype = RNA   length = 20
FEATURE                    Location/Qualifiers
misc_feature               1..20
                           note = Synthetic Polynucleotide
source                     1..20
                           mol_type = other RNA
                           organism = synthetic construct
SEQUENCE: 223
ccattcacca acacgtccct                                                    20

SEQ ID NO: 224             moltype = RNA   length = 20
```

```
FEATURE                 Location/Qualifiers
misc_feature            1..20
                        note = Synthetic Polynucleotide
source                  1..20
                        mol_type = other RNA
                        organism = synthetic construct
SEQUENCE: 224
accaggtaca ggtagttctc                                                   20

SEQ ID NO: 225          moltype = RNA   length = 20
FEATURE                 Location/Qualifiers
misc_feature            1..20
                        note = Synthetic Polynucleotide
source                  1..20
                        mol_type = other RNA
                        organism = synthetic construct
SEQUENCE: 225
ctgcagtttg cccatccacg                                                   20

SEQ ID NO: 226          moltype = RNA   length = 20
FEATURE                 Location/Qualifiers
misc_feature            1..20
                        note = Synthetic Polynucleotide
source                  1..20
                        mol_type = other RNA
                        organism = synthetic construct
SEQUENCE: 226
ttgttcatga tcttcatggc                                                   20

SEQ ID NO: 227          moltype = RNA   length = 20
FEATURE                 Location/Qualifiers
misc_feature            1..20
                        note = Synthetic Polynucleotide
source                  1..20
                        mol_type = other RNA
                        organism = synthetic construct
SEQUENCE: 227
tttgatgtcc ctgtgcacgt                                                   20

SEQ ID NO: 228          moltype = RNA   length = 20
FEATURE                 Location/Qualifiers
misc_feature            1..20
                        note = Synthetic Polynucleotide
source                  1..20
                        mol_type = other RNA
                        organism = synthetic construct
SEQUENCE: 228
gcggtccagc aggatgttgt                                                   20

SEQ ID NO: 229          moltype = RNA   length = 20
FEATURE                 Location/Qualifiers
misc_feature            1..20
                        note = Synthetic Polynucleotide
source                  1..20
                        mol_type = other RNA
                        organism = synthetic construct
SEQUENCE: 229
gtctatggcc atgacaatct                                                   20

SEQ ID NO: 230          moltype = RNA   length = 20
FEATURE                 Location/Qualifiers
misc_feature            1..20
                        note = Synthetic Polynucleotide
source                  1..20
                        mol_type = other RNA
                        organism = synthetic construct
SEQUENCE: 230
ggagcaggga aagcgcctcc                                                   20

SEQ ID NO: 231          moltype = RNA   length = 20
FEATURE                 Location/Qualifiers
misc_feature            1..20
                        note = Synthetic Polynucleotide
source                  1..20
                        mol_type = other RNA
                        organism = synthetic construct
SEQUENCE: 231
tgcctcgcgt agttgactgg                                                   20
```

```
SEQ ID NO: 232           moltype = RNA  length = 20
FEATURE                  Location/Qualifiers
misc_feature             1..20
                         note = Synthetic Polynucleotide
source                   1..20
                         mol_type = other RNA
                         organism = synthetic construct
SEQUENCE: 232
gcggatggcc tccatctccc                                                       20

SEQ ID NO: 233           moltype = RNA  length = 20
FEATURE                  Location/Qualifiers
misc_feature             1..20
                         note = Synthetic Polynucleotide
source                   1..20
                         mol_type = other RNA
                         organism = synthetic construct
SEQUENCE: 233
tttcataggc gaatacaccc                                                       20

SEQ ID NO: 234           moltype = RNA  length = 20
FEATURE                  Location/Qualifiers
misc_feature             1..20
                         note = Synthetic Polynucleotide
source                   1..20
                         mol_type = other RNA
                         organism = synthetic construct
SEQUENCE: 234
gcctgtcagc gagtcggagg                                                       20

SEQ ID NO: 235           moltype = RNA  length = 20
FEATURE                  Location/Qualifiers
misc_feature             1..20
                         note = Synthetic Polynucleotide
source                   1..20
                         mol_type = other RNA
                         organism = synthetic construct
SEQUENCE: 235
ccacttcagc tgtttcatcc                                                       20

SEQ ID NO: 236           moltype = RNA  length = 20
FEATURE                  Location/Qualifiers
misc_feature             1..20
                         note = Synthetic Polynucleotide
source                   1..20
                         mol_type = other RNA
                         organism = synthetic construct
SEQUENCE: 236
catccgctcc tgcaactgcc                                                       20

SEQ ID NO: 237           moltype = RNA  length = 20
FEATURE                  Location/Qualifiers
misc_feature             1..20
                         note = Synthetic Polynucleotide
source                   1..20
                         mol_type = other RNA
                         organism = synthetic construct
SEQUENCE: 237
tctagggttc agggagcgcg                                                       20

SEQ ID NO: 238           moltype = RNA  length = 20
FEATURE                  Location/Qualifiers
misc_feature             1..20
                         note = Synthetic Polynucleotide
source                   1..20
                         mol_type = other RNA
                         organism = synthetic construct
SEQUENCE: 238
caccaacacg tccctctcct                                                       20

SEQ ID NO: 239           moltype = RNA  length = 20
FEATURE                  Location/Qualifiers
misc_feature             1..20
                         note = Synthetic Polynucleotide
source                   1..20
                         mol_type = other RNA
                         organism = synthetic construct
SEQUENCE: 239
caggagcagg gaaagcgcct                                                       20
```

```
SEQ ID NO: 240            moltype = RNA   length = 20
FEATURE                   Location/Qualifiers
misc_feature              1..20
                          note = Synthetic Polynucleotide
source                    1..20
                          mol_type = other RNA
                          organism = synthetic construct
SEQUENCE: 240
caatctccgc caggtagaag                                                    20

SEQ ID NO: 241            moltype = RNA   length = 20
FEATURE                   Location/Qualifiers
misc_feature              1..20
                          note = Synthetic Polynucleotide
source                    1..20
                          mol_type = other RNA
                          organism = synthetic construct
SEQUENCE: 241
atgttgtcgg gtttgatgtc                                                    20

SEQ ID NO: 242            moltype = RNA   length = 20
FEATURE                   Location/Qualifiers
misc_feature              1..20
                          note = Synthetic Polynucleotide
source                    1..20
                          mol_type = other RNA
                          organism = synthetic construct
SEQUENCE: 242
ccatccgctc ctgcaactgc                                                    20

SEQ ID NO: 243            moltype = RNA   length = 20
FEATURE                   Location/Qualifiers
misc_feature              1..20
                          note = Synthetic Polynucleotide
source                    1..20
                          mol_type = other RNA
                          organism = synthetic construct
SEQUENCE: 243
gcgtcacctc ggcctcagcc                                                    20

SEQ ID NO: 244            moltype = RNA   length = 20
FEATURE                   Location/Qualifiers
misc_feature              1..20
                          note = Synthetic Polynucleotide
source                    1..20
                          mol_type = other RNA
                          organism = synthetic construct
SEQUENCE: 244
gagggccttt tattcgcgag                                                    20

SEQ ID NO: 245            moltype = RNA   length = 20
FEATURE                   Location/Qualifiers
misc_feature              1..20
                          note = Synthetic Polynucleotide
source                    1..20
                          mol_type = other RNA
                          organism = synthetic construct
SEQUENCE: 245
agcggcagag agaggtgctc                                                    20

SEQ ID NO: 246            moltype = RNA   length = 20
FEATURE                   Location/Qualifiers
misc_feature              1..20
                          note = Synthetic Polynucleotide
source                    1..20
                          mol_type = other RNA
                          organism = synthetic construct
SEQUENCE: 246
catccaaaac gtggattggg                                                    20

SEQ ID NO: 247            moltype = RNA   length = 20
FEATURE                   Location/Qualifiers
misc_feature              1..20
                          note = Synthetic Polynucleotide
source                    1..20
                          mol_type = other RNA
                          organism = synthetic construct
SEQUENCE: 247
```
ttgggcagat ggagggcctt 20

SEQ ID NO: 248      moltype = RNA   length = 20
FEATURE             Location/Qualifiers
misc_feature        1..20
                    note = Synthetic Polynucleotide
source              1..20
                    mol_type = other RNA
                    organism = synthetic construct
SEQUENCE: 248
cctctgcctc gcgtagttga 20

SEQ ID NO: 249      moltype = RNA   length = 20
FEATURE             Location/Qualifiers
misc_feature        1..20
                    note = Synthetic Polynucleotide
source              1..20
                    mol_type = other RNA
                    organism = synthetic construct
SEQUENCE: 249
acagaacaac ggcgaacagg 20

SEQ ID NO: 250      moltype = RNA   length = 20
FEATURE             Location/Qualifiers
misc_feature        1..20
                    note = Synthetic Polynucleotide
source              1..20
                    mol_type = other RNA
                    organism = synthetic construct
SEQUENCE: 250
caggatgttg tcgggtttga 20

SEQ ID NO: 251      moltype = RNA   length = 20
FEATURE             Location/Qualifiers
misc_feature        1..20
                    note = Synthetic Polynucleotide
source              1..20
                    mol_type = other RNA
                    organism = synthetic construct
SEQUENCE: 251
cggcctcagc ctctgccgca 20

SEQ ID NO: 252      moltype = RNA   length = 20
FEATURE             Location/Qualifiers
misc_feature        1..20
                    note = Synthetic Polynucleotide
source              1..20
                    mol_type = other RNA
                    organism = synthetic construct
SEQUENCE: 252
cagcaggatg ttgtcgggtt 20

SEQ ID NO: 253      moltype = RNA   length = 20
FEATURE             Location/Qualifiers
misc_feature        1..20
                    note = Synthetic Polynucleotide
source              1..20
                    mol_type = other RNA
                    organism = synthetic construct
SEQUENCE: 253
gcagagagag gtgctccttg 20

SEQ ID NO: 254      moltype = RNA   length = 20
FEATURE             Location/Qualifiers
misc_feature        1..20
                    note = Synthetic Polynucleotide
source              1..20
                    mol_type = other RNA
                    organism = synthetic construct
SEQUENCE: 254
tccagttcca tgggtgtggg 20

SEQ ID NO: 255      moltype = RNA   length = 20
FEATURE             Location/Qualifiers
misc_feature        1..20
                    note = Synthetic Polynucleotide
source              1..20
                    mol_type = other RNA
                    organism = synthetic construct

```
SEQUENCE: 255
cctcagcctg gccgaaagaa                                                20

SEQ ID NO: 256          moltype = RNA  length = 20
FEATURE                 Location/Qualifiers
misc_feature            1..20
                        note = Synthetic Polynucleotide
source                  1..20
                        mol_type = other RNA
                        organism = synthetic construct
SEQUENCE: 256
gggccttta ttcgcgaggg                                                 20

SEQ ID NO: 257          moltype = RNA  length = 20
FEATURE                 Location/Qualifiers
misc_feature            1..20
                        note = Synthetic Polynucleotide
source                  1..20
                        mol_type = other RNA
                        organism = synthetic construct
SEQUENCE: 257
gtcggccagg cggatgtggc                                                20

SEQ ID NO: 258          moltype = RNA  length = 20
FEATURE                 Location/Qualifiers
misc_feature            1..20
                        note = Synthetic Polynucleotide
source                  1..20
                        mol_type = other RNA
                        organism = synthetic construct
SEQUENCE: 258
gcttgctgcc ttcccaggcc                                                20

SEQ ID NO: 259          moltype = RNA  length = 20
FEATURE                 Location/Qualifiers
misc_feature            1..20
                        note = Synthetic Polynucleotide
source                  1..20
                        mol_type = other RNA
                        organism = synthetic construct
SEQUENCE: 259
ggtccagcag gatgttgtcg                                                20

SEQ ID NO: 260          moltype = RNA  length = 20
FEATURE                 Location/Qualifiers
misc_feature            1..20
                        note = Synthetic Polynucleotide
source                  1..20
                        mol_type = other RNA
                        organism = synthetic construct
SEQUENCE: 260
cggagaccat cccagtcgag                                                20

SEQ ID NO: 261          moltype = RNA  length = 20
FEATURE                 Location/Qualifiers
misc_feature            1..20
                        note = Synthetic Polynucleotide
source                  1..20
                        mol_type = other RNA
                        organism = synthetic construct
SEQUENCE: 261
tctgcctcgc gtagttgact                                                20

SEQ ID NO: 262          moltype = RNA  length = 20
FEATURE                 Location/Qualifiers
misc_feature            1..20
                        note = Synthetic Polynucleotide
source                  1..20
                        mol_type = other RNA
                        organism = synthetic construct
SEQUENCE: 262
aggtagttct catcctggaa                                                20

SEQ ID NO: 263          moltype = RNA  length = 20
FEATURE                 Location/Qualifiers
misc_feature            1..20
                        note = Synthetic Polynucleotide
source                  1..20
                        mol_type = other RNA
```

```
                              organism = synthetic construct
SEQUENCE: 263
tccttgtagt ggacgatctt                                                     20

SEQ ID NO: 264       moltype = RNA  length = 20
FEATURE              Location/Qualifiers
misc_feature         1..20
                     note = Synthetic Polynucleotide
source               1..20
                     mol_type = other RNA
                     organism = synthetic construct
SEQUENCE: 264
gcatccaaaa cgtggattgg                                                     20

SEQ ID NO: 265       moltype = RNA  length = 20
FEATURE              Location/Qualifiers
misc_feature         1..20
                     note = Synthetic Polynucleotide
source               1..20
                     mol_type = other RNA
                     organism = synthetic construct
SEQUENCE: 265
gtccagcagg atgttgtcgg                                                     20

SEQ ID NO: 266       moltype = RNA  length = 20
FEATURE              Location/Qualifiers
misc_feature         1..20
                     note = Synthetic Polynucleotide
source               1..20
                     mol_type = other RNA
                     organism = synthetic construct
SEQUENCE: 266
agctcccgca gcgtcacctc                                                     20

SEQ ID NO: 267       moltype = RNA  length = 20
FEATURE              Location/Qualifiers
misc_feature         1..20
                     note = Synthetic Polynucleotide
source               1..20
                     mol_type = other RNA
                     organism = synthetic construct
SEQUENCE: 267
cgagagcagc gcaagtgagg                                                     20

SEQ ID NO: 268       moltype = RNA  length = 20
FEATURE              Location/Qualifiers
misc_feature         1..20
                     note = Synthetic Polynucleotide
source               1..20
                     mol_type = other RNA
                     organism = synthetic construct
SEQUENCE: 268
cagggaaagc gcctccgata                                                     20

SEQ ID NO: 269       moltype = RNA  length = 20
FEATURE              Location/Qualifiers
misc_feature         1..20
                     note = Synthetic Polynucleotide
source               1..20
                     mol_type = other RNA
                     organism = synthetic construct
SEQUENCE: 269
atttcatagg cgaatacacc                                                     20

SEQ ID NO: 270       moltype = RNA  length = 20
FEATURE              Location/Qualifiers
misc_feature         1..20
                     note = Synthetic Polynucleotide
source               1..20
                     mol_type = other RNA
                     organism = synthetic construct
SEQUENCE: 270
tcggccaggc ggatgtggcc                                                     20

SEQ ID NO: 271       moltype = RNA  length = 20
FEATURE              Location/Qualifiers
misc_feature         1..20
                     note = Synthetic Polynucleotide
source               1..20
```

```
                        mol_type = other RNA
                        organism = synthetic construct
SEQUENCE: 271
aaggqatgtg tccggaagtc                                                      20

SEQ ID NO: 272         moltype = RNA   length = 20
FEATURE                Location/Qualifiers
misc_feature           1..20
                       note = Synthetic Polynucleotide
source                 1..20
                       mol_type = other RNA
                       organism = synthetic construct
SEQUENCE: 272
cttgtagtgg acgatcttgc                                                      20

SEQ ID NO: 273         moltype = RNA   length = 20
FEATURE                Location/Qualifiers
misc_feature           1..20
                       note = Synthetic Polynucleotide
source                 1..20
                       mol_type = other RNA
                       organism = synthetic construct
SEQUENCE: 273
agtcggccag gcggatgtgg                                                      20

SEQ ID NO: 274         moltype = RNA   length = 20
FEATURE                Location/Qualifiers
misc_feature           1..20
                       note = Synthetic Polynucleotide
source                 1..20
                       mol_type = other RNA
                       organism = synthetic construct
SEQUENCE: 274
gcctcagcct ggccgaaaga                                                      20

SEQ ID NO: 275         moltype = RNA   length = 20
FEATURE                Location/Qualifiers
misc_feature           1..20
                       note = Synthetic Polynucleotide
source                 1..20
                       mol_type = other RNA
                       organism = synthetic construct
SEQUENCE: 275
agcgtcacct cggcctcagc                                                      20

SEQ ID NO: 276         moltype = RNA   length = 20
FEATURE                Location/Qualifiers
misc_feature           1..20
                       note = Synthetic Polynucleotide
source                 1..20
                       mol_type = other RNA
                       organism = synthetic construct
SEQUENCE: 276
cagcggcaga gagaggtgct                                                      20

SEQ ID NO: 277         moltype = RNA   length = 20
FEATURE                Location/Qualifiers
misc_feature           1..20
                       note = Synthetic Polynucleotide
source                 1..20
                       mol_type = other RNA
                       organism = synthetic construct
SEQUENCE: 277
ccagcggcag agagaggtgc                                                      20

SEQ ID NO: 278         moltype = RNA   length = 20
FEATURE                Location/Qualifiers
misc_feature           1..20
                       note = Synthetic Polynucleotide
source                 1..20
                       mol_type = other RNA
                       organism = synthetic construct
SEQUENCE: 278
ttgtagtgga cgatcttgcc                                                      20

SEQ ID NO: 279         moltype = RNA   length = 20
FEATURE                Location/Qualifiers
misc_feature           1..20
                       note = Synthetic Polynucleotide
```

```
source                          1..20
                                mol_type = other RNA
                                organism = synthetic construct
SEQUENCE: 279
agggaaagcg cctccgatag                                                    20

SEQ ID NO: 280                  moltype = RNA   length = 20
FEATURE                         Location/Qualifiers
misc_feature                    1..20
                                note = Synthetic Polynucleotide
source                          1..20
                                mol_type = other RNA
                                organism = synthetic construct
SEQUENCE: 280
gggaaagcgc ctccgatagg                                                    20

SEQ ID NO: 281                  moltype = DNA   length = 20
FEATURE                         Location/Qualifiers
misc_feature                    1..20
                                note = Synthetic Polynucleotide
source                          1..20
                                mol_type = other DNA
                                organism = synthetic construct
SEQUENCE: 281
ggcagcaagc cgggccgtcc                                                    20

SEQ ID NO: 282                  moltype = DNA   length = 20
FEATURE                         Location/Qualifiers
misc_feature                    1..20
                                note = Synthetic Polynucleotide
source                          1..20
                                mol_type = other DNA
                                organism = synthetic construct
SEQUENCE: 282
cagtcctgtg atccgggccc                                                    20

SEQ ID NO: 283                  moltype = DNA   length = 20
FEATURE                         Location/Qualifiers
misc_feature                    1..20
                                note = Synthetic Polynucleotide
source                          1..20
                                mol_type = other DNA
                                organism = synthetic construct
SEQUENCE: 283
gacactgctg agcaagtttg                                                    20

SEQ ID NO: 284                  moltype = DNA   length = 20
FEATURE                         Location/Qualifiers
misc_feature                    1..20
                                note = Synthetic Polynucleotide
source                          1..20
                                mol_type = other DNA
                                organism = synthetic construct
SEQUENCE: 284
tgacactgct gagcaagttt                                                    20

SEQ ID NO: 285                  moltype = DNA   length = 20
FEATURE                         Location/Qualifiers
misc_feature                    1..20
                                note = Synthetic Polynucleotide
source                          1..20
                                mol_type = other DNA
                                organism = synthetic construct
SEQUENCE: 285
cgggagatgg aggccatccg                                                    20

SEQ ID NO: 286                  moltype = DNA   length = 20
FEATURE                         Location/Qualifiers
misc_feature                    1..20
                                note = Synthetic Polynucleotide
source                          1..20
                                mol_type = other DNA
                                organism = synthetic construct
SEQUENCE: 286
gggagcggat tccggccgag                                                    20

SEQ ID NO: 287                  moltype = DNA   length = 20
FEATURE                         Location/Qualifiers
misc_feature                    1..20
```

```
                        note = Synthetic Polynucleotide
source                  1..20
                        mol_type = other DNA
                        organism = synthetic construct
SEQUENCE: 287
ggagcggatt ccggccgaga                                              20

SEQ ID NO: 288          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 288
cctgctgaca ctgctgagca                                              20

SEQ ID NO: 289          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 289
agggacatca aacccgacaa                                              20

SEQ ID NO: 290          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 290
gggacatcaa acccgacaac                                              20

SEQ ID NO: 291          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 291
gcgcgcttct acctggcgga                                              20

SEQ ID NO: 292          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 292
cgggccaggt gtatgccatg                                              20

SEQ ID NO: 293          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 293
ctgacactgc tgagcaagtt                                              20

SEQ ID NO: 294          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 294
ggcggtggat cacgcagctg                                              20

SEQ ID NO: 295          moltype = DNA  length = 20
FEATURE                 Location/Qualifiers
```

```
                        misc_feature         1..20
                                             note = Synthetic Polynucleotide
                        source               1..20
                                             mol_type = other DNA
                                             organism = synthetic construct
                        SEQUENCE: 295
                        gagacactgt cggacattcg                                                  20

SEQ ID NO: 296       moltype = DNA   length = 20
                        FEATURE              Location/Qualifiers
                        misc_feature         1..20
                                             note = Synthetic Polynucleotide
                        source               1..20
                                             mol_type = other DNA
                                             organism = synthetic construct
                        SEQUENCE: 296
                        acatccgcct ggccgacttc                                                  20

SEQ ID NO: 297       moltype = DNA   length = 20
                        FEATURE              Location/Qualifiers
                        misc_feature         1..20
                                             note = Synthetic Polynucleotide
                        source               1..20
                                             mol_type = other DNA
                                             organism = synthetic construct
                        SEQUENCE: 297
                        cagggacatc aaacccgaca                                                  20

SEQ ID NO: 298       moltype = DNA   length = 20
                        FEATURE              Location/Qualifiers
                        misc_feature         1..20
                                             note = Synthetic Polynucleotide
                        source               1..20
                                             mol_type = other DNA
                                             organism = synthetic construct
                        SEQUENCE: 298
                        ccgggagatg gaggccatcc                                                  20

SEQ ID NO: 299       moltype = DNA   length = 20
                        FEATURE              Location/Qualifiers
                        misc_feature         1..20
                                             note = Synthetic Polynucleotide
                        source               1..20
                                             mol_type = other DNA
                                             organism = synthetic construct
                        SEQUENCE: 299
                        atcaaacccg acaacatcct                                                  20

SEQ ID NO: 300       moltype = DNA   length = 20
                        FEATURE              Location/Qualifiers
                        misc_feature         1..20
                                             note = Synthetic Polynucleotide
                        source               1..20
                                             mol_type = other DNA
                                             organism = synthetic construct
                        SEQUENCE: 300
                        acagggacat caaacccgac                                                  20

SEQ ID NO: 301       moltype = DNA   length = 20
                        FEATURE              Location/Qualifiers
                        misc_feature         1..20
                                             note = Synthetic Polynucleotide
                        source               1..20
                                             mol_type = other DNA
                                             organism = synthetic construct
                        SEQUENCE: 301
                        gtacctggtc atggagtatt                                                  20

SEQ ID NO: 302       moltype = DNA   length = 20
                        FEATURE              Location/Qualifiers
                        misc_feature         1..20
                                             note = Synthetic Polynucleotide
                        source               1..20
                                             mol_type = other DNA
                                             organism = synthetic construct
                        SEQUENCE: 302
                        ccatgaagat catgaacaag                                                  20

SEQ ID NO: 303       moltype = DNA   length = 20
```

```
FEATURE              Location/Qualifiers
misc_feature         1..20
                     note = Synthetic Polynucleotide
source               1..20
                     mol_type = other DNA
                     organism = synthetic construct
SEQUENCE: 303
ccacgttttg gatgcactga                                               20

SEQ ID NO: 304       moltype = DNA   length = 20
FEATURE              Location/Qualifiers
misc_feature         1..20
                     note = Synthetic Polynucleotide
source               1..20
                     mol_type = other DNA
                     organism = synthetic construct
SEQUENCE: 304
tgggatggtc tccgggacag                                               20

SEQ ID NO: 305       moltype = DNA   length = 20
FEATURE              Location/Qualifiers
misc_feature         1..20
                     note = Synthetic Polynucleotide
source               1..20
                     mol_type = other DNA
                     organism = synthetic construct
SEQUENCE: 305
gacagtgagg tcccaggccc                                               20

SEQ ID NO: 306       moltype = DNA   length = 20
FEATURE              Location/Qualifiers
misc_feature         1..20
                     note = Synthetic Polynucleotide
source               1..20
                     mol_type = other DNA
                     organism = synthetic construct
SEQUENCE: 306
gtcatggagt attacgtggg                                               20

SEQ ID NO: 307       moltype = DNA   length = 20
FEATURE              Location/Qualifiers
misc_feature         1..20
                     note = Synthetic Polynucleotide
source               1..20
                     mol_type = other DNA
                     organism = synthetic construct
SEQUENCE: 307
cggctgtccc tgcggcagag                                               20

SEQ ID NO: 308       moltype = DNA   length = 20
FEATURE              Location/Qualifiers
misc_feature         1..20
                     note = Synthetic Polynucleotide
source               1..20
                     mol_type = other DNA
                     organism = synthetic construct
SEQUENCE: 308
cggcttggct acgtgcacag                                               20

SEQ ID NO: 309       moltype = DNA   length = 20
FEATURE              Location/Qualifiers
misc_feature         1..20
                     note = Synthetic Polynucleotide
source               1..20
                     mol_type = other DNA
                     organism = synthetic construct
SEQUENCE: 309
ggccctgacg tggatgggca                                               20

SEQ ID NO: 310       moltype = DNA   length = 20
FEATURE              Location/Qualifiers
misc_feature         1..20
                     note = Synthetic Polynucleotide
source               1..20
                     mol_type = other DNA
                     organism = synthetic construct
SEQUENCE: 310
cctggcctat cggaggcgct                                               20
```

```
SEQ ID NO: 311            moltype = DNA   length = 20
FEATURE                   Location/Qualifiers
misc_feature              1..20
                          note = Synthetic Polynucleotide
source                    1..20
                          mol_type = other DNA
                          organism = synthetic construct
SEQUENCE: 311
ccggcttggc tacgtgcaca                                                 20

SEQ ID NO: 312            moltype = DNA   length = 20
FEATURE                   Location/Qualifiers
misc_feature              1..20
                          note = Synthetic Polynucleotide
source                    1..20
                          mol_type = other DNA
                          organism = synthetic construct
SEQUENCE: 312
agaactacct gtacctggtc                                                 20

SEQ ID NO: 313            moltype = DNA   length = 20
FEATURE                   Location/Qualifiers
misc_feature              1..20
                          note = Synthetic Polynucleotide
source                    1..20
                          mol_type = other DNA
                          organism = synthetic construct
SEQUENCE: 313
gcggattccg gccgagatgg                                                 20

SEQ ID NO: 314            moltype = DNA   length = 20
FEATURE                   Location/Qualifiers
misc_feature              1..20
                          note = Synthetic Polynucleotide
source                    1..20
                          mol_type = other DNA
                          organism = synthetic construct
SEQUENCE: 314
agcggattcc ggccgagatg                                                 20

SEQ ID NO: 315            moltype = DNA   length = 20
FEATURE                   Location/Qualifiers
misc_feature              1..20
                          note = Synthetic Polynucleotide
source                    1..20
                          mol_type = other DNA
                          organism = synthetic construct
SEQUENCE: 315
acggcggaga cctatggcaa                                                 20

SEQ ID NO: 316            moltype = DNA   length = 20
FEATURE                   Location/Qualifiers
misc_feature              1..20
                          note = Synthetic Polynucleotide
source                    1..20
                          mol_type = other DNA
                          organism = synthetic construct
SEQUENCE: 316
acatcctgct ggaccgctgt                                                 20

SEQ ID NO: 317            moltype = DNA   length = 20
FEATURE                   Location/Qualifiers
misc_feature              1..20
                          note = Synthetic Polynucleotide
source                    1..20
                          mol_type = other DNA
                          organism = synthetic construct
SEQUENCE: 317
tggcctatcg gaggcgcttt                                                 20

SEQ ID NO: 318            moltype = DNA   length = 20
FEATURE                   Location/Qualifiers
misc_feature              1..20
                          note = Synthetic Polynucleotide
source                    1..20
                          mol_type = other DNA
                          organism = synthetic construct
SEQUENCE: 318
cacatccctt cttctttggc                                                 20
```

```
SEQ ID NO: 319          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 319
tggtcatgga gtattacgtg                                                     20

SEQ ID NO: 320          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 320
gagcggattc cggccgagat                                                     20

SEQ ID NO: 321          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 321
agcggtagtg aagatgaagc                                                     20

SEQ ID NO: 322          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 322
cggattccgg ccgagatggc                                                     20

SEQ ID NO: 323          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 323
agttccagcg gctgtccctg                                                     20

SEQ ID NO: 324          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 324
tacctggcgg agattgtcat                                                     20

SEQ ID NO: 325          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 325
tggcggagat tgtcatggcc                                                     20

SEQ ID NO: 326          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 326
```

```
tgtacctggt catggagtat                                                  20

SEQ ID NO: 327          moltype = DNA   length = 20
FEATURE                 Location/Qualifiers
misc_feature            1..20
                        note = Synthetic Polynucleotide
source                  1..20
                        mol_type = other DNA
                        organism = synthetic construct
SEQUENCE: 327
caactacgcg aggcagaggc                                                  20

SEQ ID NO: 328          moltype = DNA   length = 20
FEATURE                 Location/Qualifiers
misc_feature            1..20
                        note = Synthetic Polynucleotide
source                  1..20
                        mol_type = other DNA
                        organism = synthetic construct
SEQUENCE: 328
ggagacactg tcggacattc                                                  20

SEQ ID NO: 329          moltype = DNA   length = 20
FEATURE                 Location/Qualifiers
misc_feature            1..20
                        note = Synthetic Polynucleotide
source                  1..20
                        mol_type = other DNA
                        organism = synthetic construct
SEQUENCE: 329
agctgcgggc agatggaacg                                                  20

SEQ ID NO: 330          moltype = DNA   length = 20
FEATURE                 Location/Qualifiers
misc_feature            1..20
                        note = Synthetic Polynucleotide
source                  1..20
                        mol_type = other DNA
                        organism = synthetic construct
SEQUENCE: 330
caagatcgtc cactacaagg                                                  20

SEQ ID NO: 331          moltype = DNA   length = 20
FEATURE                 Location/Qualifiers
misc_feature            1..20
                        note = Synthetic Polynucleotide
source                  1..20
                        mol_type = other DNA
                        organism = synthetic construct
SEQUENCE: 331
cgcttctacc tggcggagat                                                  20

SEQ ID NO: 332          moltype = DNA   length = 20
FEATURE                 Location/Qualifiers
misc_feature            1..20
                        note = Synthetic Polynucleotide
source                  1..20
                        mol_type = other DNA
                        organism = synthetic construct
SEQUENCE: 332
ctcacccggc agagcctgag                                                  20

SEQ ID NO: 333          moltype = DNA   length = 20
FEATURE                 Location/Qualifiers
misc_feature            1..20
                        note = Synthetic Polynucleotide
source                  1..20
                        mol_type = other DNA
                        organism = synthetic construct
SEQUENCE: 333
gcggtagtga agatgaagca                                                  20

SEQ ID NO: 334          moltype = DNA   length = 20
FEATURE                 Location/Qualifiers
misc_feature            1..20
                        note = Synthetic Polynucleotide
source                  1..20
                        mol_type = other DNA
                        organism = synthetic construct
```

```
SEQUENCE: 334
caaacccgac aacatcctgc                                              20

SEQ ID NO: 335          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 335
ctgcggcaga ggctgaggcc                                              20

SEQ ID NO: 336          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 336
ggacatcaaa cccgacaaca                                              20

SEQ ID NO: 337          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 337
ggtcatggag tattacgtgg                                              20

SEQ ID NO: 338          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 338
gctgcgggca gatggaacgg                                              20

SEQ ID NO: 339          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 339
tctgcctgct tactcgggaa                                              20

SEQ ID NO: 340          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 340
ggtgtatgcc atgaagatca                                              20

SEQ ID NO: 341          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 341
cagttccagc ggctgtccct                                              20

SEQ ID NO: 342          moltype = DNA  length = 20
FEATURE                 Location/Qualifiers
misc_feature            1..20
                        note = Synthetic Polynucleotide
source                  1..20
                        mol_type = other DNA
```

```
                        organism = synthetic construct
SEQUENCE: 342
tgcacaggga catcaaaccc                                               20

SEQ ID NO: 343          moltype = DNA   length = 20
FEATURE                 Location/Qualifiers
misc_feature            1..20
                        note = Synthetic Polynucleotide
source                  1..20
                        mol_type = other DNA
                        organism = synthetic construct
SEQUENCE: 343
ctacctggcg gagattgtca                                               20

SEQ ID NO: 344          moltype = DNA   length = 20
FEATURE                 Location/Qualifiers
misc_feature            1..20
                        note = Synthetic Polynucleotide
source                  1..20
                        mol_type = other DNA
                        organism = synthetic construct
SEQUENCE: 344
catcctgctg gaccgctgtg                                               20

SEQ ID NO: 345          moltype = DNA   length = 20
FEATURE                 Location/Qualifiers
misc_feature            1..20
                        note = Synthetic Polynucleotide
source                  1..20
                        mol_type = other DNA
                        organism = synthetic construct
SEQUENCE: 345
gggcagacgc ccttctacgc                                               20

SEQ ID NO: 346          moltype = DNA   length = 20
FEATURE                 Location/Qualifiers
misc_feature            1..20
                        note = Synthetic Polynucleotide
source                  1..20
                        mol_type = other DNA
                        organism = synthetic construct
SEQUENCE: 346
tccctgcggc agaggctgag                                               20

SEQ ID NO: 347          moltype = DNA   length = 20
FEATURE                 Location/Qualifiers
misc_feature            1..20
                        note = Synthetic Polynucleotide
source                  1..20
                        mol_type = other DNA
                        organism = synthetic construct
SEQUENCE: 347
cgttttggat gcactgagac                                               20

SEQ ID NO: 348          moltype = DNA   length = 20
FEATURE                 Location/Qualifiers
misc_feature            1..20
                        note = Synthetic Polynucleotide
source                  1..20
                        mol_type = other DNA
                        organism = synthetic construct
SEQUENCE: 348
gacctatggc aagatcgtcc                                               20

SEQ ID NO: 349          moltype = DNA   length = 20
FEATURE                 Location/Qualifiers
misc_feature            1..20
                        note = Synthetic Polynucleotide
source                  1..20
                        mol_type = other DNA
                        organism = synthetic construct
SEQUENCE: 349
ggacctgctg acactgctga                                               20

SEQ ID NO: 350          moltype = DNA   length = 20
FEATURE                 Location/Qualifiers
misc_feature            1..20
                        note = Synthetic Polynucleotide
source                  1..20
```

```
                    mol_type = other DNA
                    organism = synthetic construct
SEQUENCE: 350
gtctggcgcc gcccaggagc                                                 20

SEQ ID NO: 351      moltype = DNA   length = 20
FEATURE             Location/Qualifiers
misc_feature        1..20
                    note = Synthetic Polynucleotide
source              1..20
                    mol_type = other DNA
                    organism = synthetic construct
SEQUENCE: 351
aaacccgaca acatcctgct                                                 20

SEQ ID NO: 352      moltype = DNA   length = 20
FEATURE             Location/Qualifiers
misc_feature        1..20
                    note = Synthetic Polynucleotide
source              1..20
                    mol_type = other DNA
                    organism = synthetic construct
SEQUENCE: 352
cggcagttgc aggagcggat                                                 20

SEQ ID NO: 353      moltype = DNA   length = 20
FEATURE             Location/Qualifiers
misc_feature        1..20
                    note = Synthetic Polynucleotide
source              1..20
                    mol_type = other DNA
                    organism = synthetic construct
SEQUENCE: 353
gaggcgcttt ccctgctcct                                                 20

SEQ ID NO: 354      moltype = DNA   length = 20
FEATURE             Location/Qualifiers
misc_feature        1..20
                    note = Synthetic Polynucleotide
source              1..20
                    mol_type = other DNA
                    organism = synthetic construct
SEQUENCE: 354
gaagcagacg ggccaggtgt                                                 20

SEQ ID NO: 355      moltype = DNA   length = 20
FEATURE             Location/Qualifiers
misc_feature        1..20
                    note = Synthetic Polynucleotide
source              1..20
                    mol_type = other DNA
                    organism = synthetic construct
SEQUENCE: 355
tgtgactggt gggcgctggg                                                 20

SEQ ID NO: 356      moltype = DNA   length = 20
FEATURE             Location/Qualifiers
misc_feature        1..20
                    note = Synthetic Polynucleotide
source              1..20
                    mol_type = other DNA
                    organism = synthetic construct
SEQUENCE: 356
ttgctgcagg cagagggagc                                                 20

SEQ ID NO: 357      moltype = DNA   length = 20
FEATURE             Location/Qualifiers
misc_feature        1..20
                    note = Synthetic Polynucleotide
source              1..20
                    mol_type = other DNA
                    organism = synthetic construct
SEQUENCE: 357
tcacccggca gagcctgagc                                                 20

SEQ ID NO: 358      moltype = DNA   length = 20
FEATURE             Location/Qualifiers
misc_feature        1..20
                    note = Synthetic Polynucleotide
```

```
source                          1..20
                                mol_type = other DNA
                                organism = synthetic construct
SEQUENCE: 358
tacgtgcaca gggacatcaa                                                      20

SEQ ID NO: 359                  moltype = DNA  length = 20
FEATURE                         Location/Qualifiers
misc_feature                    1..20
                                note = Synthetic Polynucleotide
source                          1..20
                                mol_type = other DNA
                                organism = synthetic construct
SEQUENCE: 359
cctgcggcag aggctgaggc                                                      20

SEQ ID NO: 360                  moltype = DNA  length = 20
FEATURE                         Location/Qualifiers
misc_feature                    1..20
                                note = Synthetic Polynucleotide
source                          1..20
                                mol_type = other DNA
                                organism = synthetic construct
SEQUENCE: 360
cttccaggat gagaactacc                                                      20

SEQ ID NO: 361                  moltype = DNA  length = 20
FEATURE                         Location/Qualifiers
misc_feature                    1..20
                                note = Synthetic Polynucleotide
source                          1..20
                                mol_type = other DNA
                                organism = synthetic construct
SEQUENCE: 361
agtgtgactg gtgggcgctg                                                      20

SEQ ID NO: 362                  moltype = DNA  length = 20
FEATURE                         Location/Qualifiers
misc_feature                    1..20
                                note = Synthetic Polynucleotide
source                          1..20
                                mol_type = other DNA
                                organism = synthetic construct
SEQUENCE: 362
cactgctgag caagtttggg                                                      20

SEQ ID NO: 363                  moltype = DNA  length = 20
FEATURE                         Location/Qualifiers
misc_feature                    1..20
                                note = Synthetic Polynucleotide
source                          1..20
                                mol_type = other DNA
                                organism = synthetic construct
SEQUENCE: 363
cggcggagac ctatggcaag                                                      20

SEQ ID NO: 364                  moltype = DNA  length = 20
FEATURE                         Location/Qualifiers
misc_feature                    1..20
                                note = Synthetic Polynucleotide
source                          1..20
                                mol_type = other DNA
                                organism = synthetic construct
SEQUENCE: 364
aagcagacgg gccaggtgta                                                      20

SEQ ID NO: 365                  moltype = DNA  length = 20
FEATURE                         Location/Qualifiers
misc_feature                    1..20
                                note = Synthetic Polynucleotide
source                          1..20
                                mol_type = other DNA
                                organism = synthetic construct
SEQUENCE: 365
gtgtgactgg tgggcgctgg                                                      20

SEQ ID NO: 366                  moltype = DNA  length = 20
FEATURE                         Location/Qualifiers
misc_feature                    1..20
```

```
                    note = Synthetic Polynucleotide
source              1..20
                    mol_type = other DNA
                    organism = synthetic construct
SEQUENCE: 366
ctttcggcca ggctgaggcc                                                    20

SEQ ID NO: 367      moltype = DNA   length = 20
FEATURE             Location/Qualifiers
misc_feature        1..20
                    note = Synthetic Polynucleotide
source              1..20
                    mol_type = other DNA
                    organism = synthetic construct
SEQUENCE: 367
gcttctacct ggcggagatt                                                    20

SEQ ID NO: 368      moltype = DNA   length = 20
FEATURE             Location/Qualifiers
misc_feature        1..20
                    note = Synthetic Polynucleotide
source              1..20
                    mol_type = other DNA
                    organism = synthetic construct
SEQUENCE: 368
acgggccagg tgtatgccat                                                    20

SEQ ID NO: 369      moltype = DNA   length = 20
FEATURE             Location/Qualifiers
misc_feature        1..20
                    note = Synthetic Polynucleotide
source              1..20
                    mol_type = other DNA
                    organism = synthetic construct
SEQUENCE: 369
cctggcggag attgtcatgg                                                    20

SEQ ID NO: 370      moltype = DNA   length = 20
FEATURE             Location/Qualifiers
misc_feature        1..20
                    note = Synthetic Polynucleotide
source              1..20
                    mol_type = other DNA
                    organism = synthetic construct
SEQUENCE: 370
ctgctgagca agtttgggga                                                    20

SEQ ID NO: 371      moltype = DNA   length = 20
FEATURE             Location/Qualifiers
misc_feature        1..20
                    note = Synthetic Polynucleotide
source              1..20
                    mol_type = other DNA
                    organism = synthetic construct
SEQUENCE: 371
acatcaaacc cgacaacatc                                                    20

SEQ ID NO: 372      moltype = DNA   length = 20
FEATURE             Location/Qualifiers
misc_feature        1..20
                    note = Synthetic Polynucleotide
source              1..20
                    mol_type = other DNA
                    organism = synthetic construct
SEQUENCE: 372
cctgacgtgg atgggcaaac                                                    20

SEQ ID NO: 373      moltype = DNA   length = 20
FEATURE             Location/Qualifiers
misc_feature        1..20
                    note = Synthetic Polynucleotide
source              1..20
                    mol_type = other DNA
                    organism = synthetic construct
SEQUENCE: 373
gcagcaagcc gggccgtccg                                                    20

SEQ ID NO: 374      moltype = DNA   length = 20
FEATURE             Location/Qualifiers
```

```
                          -continued misc_feature              1..20
                          note = Synthetic Polynucleotide
source                    1..20
                          mol_type = other DNA
                          organism = synthetic construct
SEQUENCE: 374
cgcgcttcta cctggcggag                                                   20

SEQ ID NO: 375            moltype = DNA  length = 20
FEATURE                   Location/Qualifiers
misc_feature              1..20
                          note = Synthetic Polynucleotide
source                    1..20
                          mol_type = other DNA
                          organism = synthetic construct
SEQUENCE: 375
aggatgagaa ctacctgtac                                                   20

SEQ ID NO: 376            moltype = DNA  length = 20
FEATURE                   Location/Qualifiers
misc_feature              1..20
                          note = Synthetic Polynucleotide
source                    1..20
                          mol_type = other DNA
                          organism = synthetic construct
SEQUENCE: 376
gttctatggg cagacgccct                                                   20

SEQ ID NO: 377            moltype = DNA  length = 20
FEATURE                   Location/Qualifiers
misc_feature              1..20
                          note = Synthetic Polynucleotide
source                    1..20
                          mol_type = other DNA
                          organism = synthetic construct
SEQUENCE: 377
ctgctggacc gctgtggcca                                                   20

SEQ ID NO: 378            moltype = DNA  length = 20
FEATURE                   Location/Qualifiers
misc_feature              1..20
                          note = Synthetic Polynucleotide
source                    1..20
                          mol_type = other DNA
                          organism = synthetic construct
SEQUENCE: 378
aacttcgcca gtcaactacg                                                   20

SEQ ID NO: 379            moltype = DNA  length = 20
FEATURE                   Location/Qualifiers
misc_feature              1..20
                          note = Synthetic Polynucleotide
source                    1..20
                          mol_type = other DNA
                          organism = synthetic construct
SEQUENCE: 379
gcggctgtcc ctgcggcaga                                                   20

SEQ ID NO: 380            moltype = DNA  length = 20
FEATURE                   Location/Qualifiers
misc_feature              1..20
                          note = Synthetic Polynucleotide
source                    1..20
                          mol_type = other DNA
                          organism = synthetic construct
SEQUENCE: 380
ctggcctatc ggaggcgctt                                                   20

SEQ ID NO: 381            moltype = DNA  length = 20
FEATURE                   Location/Qualifiers
misc_feature              1..20
                          note = Synthetic Polynucleotide
source                    1..20
                          mol_type = other DNA
                          organism = synthetic construct
SEQUENCE: 381
ctgttcgccg ttgttctgtc                                                   20

SEQ ID NO: 382            moltype = DNA  length = 20
```

```
FEATURE                Location/Qualifiers
misc_feature           1..20
                       note = Synthetic Polynucleotide
source                 1..20
                       mol_type = other DNA
                       organism = synthetic construct
SEQUENCE: 382
acctgctgac actgctgagc                                                  20

SEQ ID NO: 383         moltype = DNA   length = 20
FEATURE                Location/Qualifiers
misc_feature           1..20
                       note = Synthetic Polynucleotide
source                 1..20
                       mol_type = other DNA
                       organism = synthetic construct
SEQUENCE: 383
gtgtatgcca tgaagatcat                                                  20

SEQ ID NO: 384         moltype = DNA   length = 20
FEATURE                Location/Qualifiers
misc_feature           1..20
                       note = Synthetic Polynucleotide
source                 1..20
                       mol_type = other DNA
                       organism = synthetic construct
SEQUENCE: 384
ccctgacgtg gatgggcaaa                                                  20

SEQ ID NO: 385         moltype = DNA   length = 20
FEATURE                Location/Qualifiers
misc_feature           1..20
                       note = Synthetic Polynucleotide
source                 1..20
                       mol_type = other DNA
                       organism = synthetic construct
SEQUENCE: 385
gctgacactg ctgagcaagt                                                  20

SEQ ID NO: 386         moltype = DNA   length = 20
FEATURE                Location/Qualifiers
misc_feature           1..20
                       note = Synthetic Polynucleotide
source                 1..20
                       mol_type = other DNA
                       organism = synthetic construct
SEQUENCE: 386
ctacgtgcac agggacatca                                                  20

SEQ ID NO: 387         moltype = DNA   length = 20
FEATURE                Location/Qualifiers
misc_feature           1..20
                       note = Synthetic Polynucleotide
source                 1..20
                       mol_type = other DNA
                       organism = synthetic construct
SEQUENCE: 387
cccgacattc ctcggtattt                                                  20

SEQ ID NO: 388         moltype = DNA   length = 20
FEATURE                Location/Qualifiers
misc_feature           1..20
                       note = Synthetic Polynucleotide
source                 1..20
                       mol_type = other DNA
                       organism = synthetic construct
SEQUENCE: 388
gggcgctggg tgtattcgcc                                                  20

SEQ ID NO: 389         moltype = DNA   length = 20
FEATURE                Location/Qualifiers
misc_feature           1..20
                       note = Synthetic Polynucleotide
source                 1..20
                       mol_type = other DNA
                       organism = synthetic construct
SEQUENCE: 389
ttcctcggta tttattgtct                                                  20
```

```
SEQ ID NO: 390              moltype = DNA   length = 20
FEATURE                     Location/Qualifiers
misc_feature                1..20
                            note = Synthetic Polynucleotide
source                      1..20
                            mol_type = other DNA
                            organism = synthetic construct
SEQUENCE: 390
gtgaagatga agcagacggg                                                20

SEQ ID NO: 391              moltype = DNA   length = 20
FEATURE                     Location/Qualifiers
misc_feature                1..20
                            note = Synthetic Polynucleotide
source                      1..20
                            mol_type = other DNA
                            organism = synthetic construct
SEQUENCE: 391
gatggagttg ctgcaggcag                                                20

SEQ ID NO: 392              moltype = DNA   length = 20
FEATURE                     Location/Qualifiers
misc_feature                1..20
                            note = Synthetic Polynucleotide
source                      1..20
                            mol_type = other DNA
                            organism = synthetic construct
SEQUENCE: 392
ccctgcggca gaggctgagg                                                20

SEQ ID NO: 393              moltype = DNA   length = 20
FEATURE                     Location/Qualifiers
misc_feature                1..20
                            note = Synthetic Polynucleotide
source                      1..20
                            mol_type = other DNA
                            organism = synthetic construct
SEQUENCE: 393
agcaggcgac ttccggacac                                                20

SEQ ID NO: 394              moltype = DNA   length = 20
FEATURE                     Location/Qualifiers
misc_feature                1..20
                            note = Synthetic Polynucleotide
source                      1..20
                            mol_type = other DNA
                            organism = synthetic construct
SEQUENCE: 394
ctgcttgagc cacacgtgca                                                20

SEQ ID NO: 395              moltype = DNA   length = 20
FEATURE                     Location/Qualifiers
misc_feature                1..20
                            note = Synthetic Polynucleotide
source                      1..20
                            mol_type = other DNA
                            organism = synthetic construct
SEQUENCE: 395
attcctcggt atttattgtc                                                20

SEQ ID NO: 396              moltype = DNA   length = 20
FEATURE                     Location/Qualifiers
misc_feature                1..20
                            note = Synthetic Polynucleotide
source                      1..20
                            mol_type = other DNA
                            organism = synthetic construct
SEQUENCE: 396
ctggcggaga ttgtcatggc                                                20

SEQ ID NO: 397              moltype = DNA   length = 20
FEATURE                     Location/Qualifiers
misc_feature                1..20
                            note = Synthetic Polynucleotide
source                      1..20
                            mol_type = other DNA
                            organism = synthetic construct
SEQUENCE: 397
gggatggtct ccgggacagc                                                20
```

```
SEQ ID NO: 398         moltype = DNA   length = 20
FEATURE                Location/Qualifiers
misc_feature           1..20
                       note = Synthetic Polynucleotide
source                 1..20
                       mol_type = other DNA
                       organism = synthetic construct
SEQUENCE: 398
actacctgta cctggtcatg                                                    20

SEQ ID NO: 399         moltype = DNA   length = 20
FEATURE                Location/Qualifiers
misc_feature           1..20
                       note = Synthetic Polynucleotide
source                 1..20
                       mol_type = other DNA
                       organism = synthetic construct
SEQUENCE: 399
gagtgtgact ggtgggcgct                                                    20

SEQ ID NO: 400         moltype = DNA   length = 20
FEATURE                Location/Qualifiers
misc_feature           1..20
                       note = Synthetic Polynucleotide
source                 1..20
                       mol_type = other DNA
                       organism = synthetic construct
SEQUENCE: 400
acgttttgga tgcactgaga                                                    20

SEQ ID NO: 401         moltype = DNA   length = 20
FEATURE                Location/Qualifiers
misc_feature           1..20
                       note = Synthetic Polynucleotide
source                 1..20
                       mol_type = other DNA
                       organism = synthetic construct
SEQUENCE: 401
aggccctcca tctgcccaaa                                                    20

SEQ ID NO: 402         moltype = DNA   length = 20
FEATURE                Location/Qualifiers
misc_feature           1..20
                       note = Synthetic Polynucleotide
source                 1..20
                       mol_type = other DNA
                       organism = synthetic construct
SEQUENCE: 402
gctacgtgca cagggacatc                                                    20

SEQ ID NO: 403         moltype = DNA   length = 20
FEATURE                Location/Qualifiers
misc_feature           1..20
                       note = Synthetic Polynucleotide
source                 1..20
                       mol_type = other DNA
                       organism = synthetic construct
SEQUENCE: 403
gggacctgct gacactgctg                                                    20

SEQ ID NO: 404         moltype = DNA   length = 20
FEATURE                Location/Qualifiers
misc_feature           1..20
                       note = Synthetic Polynucleotide
source                 1..20
                       mol_type = other DNA
                       organism = synthetic construct
SEQUENCE: 404
acctggcgga gattgtcatg                                                    20

SEQ ID NO: 405         moltype = DNA   length = 20
FEATURE                Location/Qualifiers
misc_feature           1..20
                       note = Synthetic Polynucleotide
source                 1..20
                       mol_type = other DNA
                       organism = synthetic construct
SEQUENCE: 405
```

```
catgaagatc atgaacaagt                                            20

SEQ ID NO: 406          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 406
cccttctacg cggattccac                                            20

SEQ ID NO: 407          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 407
ggcggagatt gtcatggcca                                            20

SEQ ID NO: 408          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 408
cggtatttat tgtctgtccc                                            20

SEQ ID NO: 409          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 409
tgagcaagtt tggggagcgg                                            20

SEQ ID NO: 410          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 410
acccggcaga gcctgagccg                                            20

SEQ ID NO: 411          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 411
tctggcgccg cccaggagcc                                            20

SEQ ID NO: 412          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 412
ctgcctgctt actcgggaaa                                            20

SEQ ID NO: 413          moltype = DNA  length = 20
FEATURE                 Location/Qualifiers
misc_feature            1..20
                        note = Synthetic Polynucleotide
source                  1..20
                        mol_type = other DNA
                        organism = synthetic construct
```

```
SEQUENCE: 413
catcaaaccc gacaacatcc                                                   20

SEQ ID NO: 414          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 414
tccaggatga gaactacctg                                                   20

SEQ ID NO: 415          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 415
tatgaaatgt tctatgggca                                                   20

SEQ ID NO: 416          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 416
gccttccagg atgagaacta                                                   20

SEQ ID NO: 417          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 417
ggctacgtgc acagggacat                                                   20

SEQ ID NO: 418          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 418
agtcctgtga tccgggcccg                                                   20

SEQ ID NO: 419          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 419
acctatggca agatcgtcca                                                   20

SEQ ID NO: 420          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 420
ggtggcccac gccggccaac                                                   20

SEQ ID NO: 421          moltype = DNA  length = 20
FEATURE                 Location/Qualifiers
misc_feature            1..20
                        note = Synthetic Polynucleotide
source                  1..20
                        mol_type = other DNA
```

```
                              organism = synthetic construct
SEQUENCE: 421
cacgttttgg atgcactgag                                                    20

SEQ ID NO: 422         moltype = DNA  length = 20
FEATURE                Location/Qualifiers
misc_feature           1..20
                       note = Synthetic Polynucleotide
source                 1..20
                       mol_type = other DNA
                       organism = synthetic construct
SEQUENCE: 422
accgacacat gcaacttcga                                                    20

SEQ ID NO: 423         moltype = DNA  length = 20
FEATURE                Location/Qualifiers
misc_feature           1..20
                       note = Synthetic Polynucleotide
source                 1..20
                       mol_type = other DNA
                       organism = synthetic construct
SEQUENCE: 423
gccgggccgt ccgtgttcca                                                    20

SEQ ID NO: 424         moltype = DNA  length = 20
FEATURE                Location/Qualifiers
misc_feature           1..20
                       note = Synthetic Polynucleotide
source                 1..20
                       mol_type = other DNA
                       organism = synthetic construct
SEQUENCE: 424
ctcacttgcg ctgctctcgg                                                    20

SEQ ID NO: 425         moltype = DNA  length = 20
FEATURE                Location/Qualifiers
misc_feature           1..20
                       note = Synthetic Polynucleotide
source                 1..20
                       mol_type = other DNA
                       organism = synthetic construct
SEQUENCE: 425
cacgtccggc agttgcagga                                                    20

SEQ ID NO: 426         moltype = DNA  length = 20
FEATURE                Location/Qualifiers
misc_feature           1..20
                       note = Synthetic Polynucleotide
source                 1..20
                       mol_type = other DNA
                       organism = synthetic construct
SEQUENCE: 426
ggagagggac gtgttggtga                                                    20

SEQ ID NO: 427         moltype = DNA  length = 20
FEATURE                Location/Qualifiers
misc_feature           1..20
                       note = Synthetic Polynucleotide
source                 1..20
                       mol_type = other DNA
                       organism = synthetic construct
SEQUENCE: 427
ggatggagtt gctgcaggca                                                    20

SEQ ID NO: 428         moltype = DNA  length = 20
FEATURE                Location/Qualifiers
misc_feature           1..20
                       note = Synthetic Polynucleotide
source                 1..20
                       mol_type = other DNA
                       organism = synthetic construct
SEQUENCE: 428
tggtggccca cgccggccaa                                                    20

SEQ ID NO: 429         moltype = DNA  length = 20
FEATURE                Location/Qualifiers
misc_feature           1..20
                       note = Synthetic Polynucleotide
source                 1..20
```

```
                        mol_type = other DNA
                        organism = synthetic construct
SEQUENCE: 429
actacgcgag gcagaggctc                                                       20

SEQ ID NO: 430          moltype = DNA   length = 20
FEATURE                 Location/Qualifiers
misc_feature            1..20
                        note = Synthetic Polynucleotide
source                  1..20
                        mol_type = other DNA
                        organism = synthetic construct
SEQUENCE: 430
ttctatgggc agacgccctt                                                       20

SEQ ID NO: 431          moltype = DNA   length = 20
FEATURE                 Location/Qualifiers
misc_feature            1..20
                        note = Synthetic Polynucleotide
source                  1..20
                        mol_type = other DNA
                        organism = synthetic construct
SEQUENCE: 431
cctcggtatt tattgtctgt                                                       20

SEQ ID NO: 432          moltype = DNA   length = 20
FEATURE                 Location/Qualifiers
misc_feature            1..20
                        note = Synthetic Polynucleotide
source                  1..20
                        mol_type = other DNA
                        organism = synthetic construct
SEQUENCE: 432
tcggtattta ttgtctgtcc                                                       20

SEQ ID NO: 433          moltype = DNA   length = 20
FEATURE                 Location/Qualifiers
misc_feature            1..20
                        note = Synthetic Polynucleotide
source                  1..20
                        mol_type = other DNA
                        organism = synthetic construct
SEQUENCE: 433
cgggacctag aggcacacgt                                                       20

SEQ ID NO: 434          moltype = DNA   length = 20
FEATURE                 Location/Qualifiers
misc_feature            1..20
                        note = Synthetic Polynucleotide
source                  1..20
                        mol_type = other DNA
                        organism = synthetic construct
SEQUENCE: 434
ccgttgttct gtctcgtgcc                                                       20

SEQ ID NO: 435          moltype = DNA   length = 20
FEATURE                 Location/Qualifiers
misc_feature            1..20
                        note = Synthetic Polynucleotide
source                  1..20
                        mol_type = other DNA
                        organism = synthetic construct
SEQUENCE: 435
gaactacctg tacctggtca                                                       20

SEQ ID NO: 436          moltype = DNA   length = 20
FEATURE                 Location/Qualifiers
misc_feature            1..20
                        note = Synthetic Polynucleotide
source                  1..20
                        mol_type = other DNA
                        organism = synthetic construct
SEQUENCE: 436
gaggtgctca cccggcagag                                                       20

SEQ ID NO: 437          moltype = DNA   length = 20
FEATURE                 Location/Qualifiers
misc_feature            1..20
                        note = Synthetic Polynucleotide
```

```
source                    1..20
                          mol_type = other DNA
                          organism = synthetic construct
SEQUENCE: 437
tctacctggc ggagattgtc                                                    20

SEQ ID NO: 438            moltype = DNA  length = 20
FEATURE                   Location/Qualifiers
misc_feature              1..20
                          note = Synthetic Polynucleotide
source                    1..20
                          mol_type = other DNA
                          organism = synthetic construct
SEQUENCE: 438
gcgcttctac ctggcggaga                                                    20

SEQ ID NO: 439            moltype = DNA  length = 20
FEATURE                   Location/Qualifiers
misc_feature              1..20
                          note = Synthetic Polynucleotide
source                    1..20
                          mol_type = other DNA
                          organism = synthetic construct
SEQUENCE: 439
gtcaactacg cgaggcagag                                                    20

SEQ ID NO: 440            moltype = DNA  length = 20
FEATURE                   Location/Qualifiers
misc_feature              1..20
                          note = Synthetic Polynucleotide
source                    1..20
                          mol_type = other DNA
                          organism = synthetic construct
SEQUENCE: 440
ggccctccat ctgcccaaag                                                    20

SEQ ID NO: 441            moltype = DNA  length = 20
FEATURE                   Location/Qualifiers
misc_feature              1..20
                          note = Synthetic Polynucleotide
source                    1..20
                          mol_type = other DNA
                          organism = synthetic construct
SEQUENCE: 441
ccaggatgag aactacctgt                                                    20

SEQ ID NO: 442            moltype = DNA  length = 20
FEATURE                   Location/Qualifiers
misc_feature              1..20
                          note = Synthetic Polynucleotide
source                    1..20
                          mol_type = other DNA
                          organism = synthetic construct
SEQUENCE: 442
acactgctga gcaagtttgg                                                    20

SEQ ID NO: 443            moltype = DNA  length = 20
FEATURE                   Location/Qualifiers
misc_feature              1..20
                          note = Synthetic Polynucleotide
source                    1..20
                          mol_type = other DNA
                          organism = synthetic construct
SEQUENCE: 443
cacagggaca tcaaacccga                                                    20

SEQ ID NO: 444            moltype = DNA  length = 20
FEATURE                   Location/Qualifiers
misc_feature              1..20
                          note = Synthetic Polynucleotide
source                    1..20
                          mol_type = other DNA
                          organism = synthetic construct
SEQUENCE: 444
gcctgggaag gcagcaagcc                                                    20

SEQ ID NO: 445            moltype = DNA  length = 20
FEATURE                   Location/Qualifiers
misc_feature              1..20
```

```
                         note = Synthetic Polynucleotide
source                   1..20
                         mol_type = other DNA
                         organism = synthetic construct
SEQUENCE: 445
caggatgaga actacctgta                                                   20

SEQ ID NO: 446           moltype = DNA  length = 20
FEATURE                  Location/Qualifiers
misc_feature             1..20
                         note = Synthetic Polynucleotide
source                   1..20
                         mol_type = other DNA
                         organism = synthetic construct
SEQUENCE: 446
gccctgacgt ggatgggcaa                                                   20

SEQ ID NO: 447           moltype = DNA  length = 20
FEATURE                  Location/Qualifiers
misc_feature             1..20
                         note = Synthetic Polynucleotide
source                   1..20
                         mol_type = other DNA
                         organism = synthetic construct
SEQUENCE: 447
gatgagaact acctgtacct                                                   20

SEQ ID NO: 448           moltype = DNA  length = 20
FEATURE                  Location/Qualifiers
misc_feature             1..20
                         note = Synthetic Polynucleotide
source                   1..20
                         mol_type = other DNA
                         organism = synthetic construct
SEQUENCE: 448
ctcggtattt attgtctgtc                                                   20

SEQ ID NO: 449           moltype = DNA  length = 20
FEATURE                  Location/Qualifiers
misc_feature             1..20
                         note = Synthetic Polynucleotide
source                   1..20
                         mol_type = other DNA
                         organism = synthetic construct
SEQUENCE: 449
ttcgcctatg aaatgttcta                                                   20

SEQ ID NO: 450           moltype = DNA  length = 20
FEATURE                  Location/Qualifiers
misc_feature             1..20
                         note = Synthetic Polynucleotide
source                   1..20
                         mol_type = other DNA
                         organism = synthetic construct
SEQUENCE: 450
cctcgcgaat aaaaggccct                                                   20

SEQ ID NO: 451           moltype = DNA  length = 20
FEATURE                  Location/Qualifiers
misc_feature             1..20
                         note = Synthetic Polynucleotide
source                   1..20
                         mol_type = other DNA
                         organism = synthetic construct
SEQUENCE: 451
gccagtcaac tacgcgaggc                                                   20

SEQ ID NO: 452           moltype = DNA  length = 20
FEATURE                  Location/Qualifiers
misc_feature             1..20
                         note = Synthetic Polynucleotide
source                   1..20
                         mol_type = other DNA
                         organism = synthetic construct
SEQUENCE: 452
acccgacaac atcctgctgg                                                   20

SEQ ID NO: 453           moltype = DNA  length = 20
FEATURE                  Location/Qualifiers
```

```
misc_feature                   1..20
                               note = Synthetic Polynucleotide
source                         1..20
                               mol_type = other DNA
                               organism = synthetic construct
SEQUENCE: 453
gaacttcgcc agtcaactac                                                       20

SEQ ID NO: 454                 moltype = DNA  length = 20
FEATURE                        Location/Qualifiers
misc_feature                   1..20
                               note = Synthetic Polynucleotide
source                         1..20
                               mol_type = other DNA
                               organism = synthetic construct
SEQUENCE: 454
ggagatggag gccatccgca                                                       20

SEQ ID NO: 455                 moltype = DNA  length = 20
FEATURE                        Location/Qualifiers
misc_feature                   1..20
                               note = Synthetic Polynucleotide
source                         1..20
                               mol_type = other DNA
                               organism = synthetic construct
SEQUENCE: 455
ttctacctgg cggagattgt                                                       20

SEQ ID NO: 456                 moltype = DNA  length = 20
FEATURE                        Location/Qualifiers
misc_feature                   1..20
                               note = Synthetic Polynucleotide
source                         1..20
                               mol_type = other DNA
                               organism = synthetic construct
SEQUENCE: 456
tgggcgctgg gtgtattcgc                                                       20

SEQ ID NO: 457                 moltype = DNA  length = 20
FEATURE                        Location/Qualifiers
misc_feature                   1..20
                               note = Synthetic Polynucleotide
source                         1..20
                               mol_type = other DNA
                               organism = synthetic construct
SEQUENCE: 457
ccttccagga tgagaactac                                                       20

SEQ ID NO: 458                 moltype = DNA  length = 20
FEATURE                        Location/Qualifiers
misc_feature                   1..20
                               note = Synthetic Polynucleotide
source                         1..20
                               mol_type = other DNA
                               organism = synthetic construct
SEQUENCE: 458
cacccggcag agcctgagcc                                                       20

SEQ ID NO: 459                 moltype = DNA  length = 20
FEATURE                        Location/Qualifiers
misc_feature                   1..20
                               note = Synthetic Polynucleotide
source                         1..20
                               mol_type = other DNA
                               organism = synthetic construct
SEQUENCE: 459
agggacgtgt tggtgaatgg                                                       20

SEQ ID NO: 460                 moltype = DNA  length = 20
FEATURE                        Location/Qualifiers
misc_feature                   1..20
                               note = Synthetic Polynucleotide
source                         1..20
                               mol_type = other DNA
                               organism = synthetic construct
SEQUENCE: 460
gagaactacc tgtacctggt                                                       20

SEQ ID NO: 461                 moltype = DNA  length = 20
```

```
FEATURE                 Location/Qualifiers
misc_feature            1..20
                        note = Synthetic Polynucleotide
source                  1..20
                        mol_type = other DNA
                        organism = synthetic construct
SEQUENCE: 461
cgtggatggg caaactgcag                                                    20

SEQ ID NO: 462          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 462
gccatgaaga tcatgaacaa                                                    20

SEQ ID NO: 463          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 463
acgtgcacag ggacatcaaa                                                    20

SEQ ID NO: 464          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 464
acaacatcct gctggaccgc                                                    20

SEQ ID NO: 465          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 465
agattgtcat ggccatagac                                                    20

SEQ ID NO: 466          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 466
ggaggcgctt tccctgctcc                                                    20

SEQ ID NO: 467          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 467
ccagtcaact acgcgaggca                                                    20

SEQ ID NO: 468          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 468
gggagatgga ggccatccgc                                                    20
```

```
SEQ ID NO: 469            moltype = DNA  length = 20
FEATURE                   Location/Qualifiers
misc_feature              1..20
                          note = Synthetic Polynucleotide
source                    1..20
                          mol_type = other DNA
                          organism = synthetic construct
SEQUENCE: 469
gggtgtattc gcctatgaaa                                                       20

SEQ ID NO: 470            moltype = DNA  length = 20
FEATURE                   Location/Qualifiers
misc_feature              1..20
                          note = Synthetic Polynucleotide
source                    1..20
                          mol_type = other DNA
                          organism = synthetic construct
SEQUENCE: 470
cctccgactc gctgacaggc                                                       20

SEQ ID NO: 471            moltype = DNA  length = 20
FEATURE                   Location/Qualifiers
misc_feature              1..20
                          note = Synthetic Polynucleotide
source                    1..20
                          mol_type = other DNA
                          organism = synthetic construct
SEQUENCE: 471
ggatgaaaca gctgaagtgg                                                       20

SEQ ID NO: 472            moltype = DNA  length = 20
FEATURE                   Location/Qualifiers
misc_feature              1..20
                          note = Synthetic Polynucleotide
source                    1..20
                          mol_type = other DNA
                          organism = synthetic construct
SEQUENCE: 472
ggcagttgca ggagcggatg                                                       20

SEQ ID NO: 473            moltype = DNA  length = 20
FEATURE                   Location/Qualifiers
misc_feature              1..20
                          note = Synthetic Polynucleotide
source                    1..20
                          mol_type = other DNA
                          organism = synthetic construct
SEQUENCE: 473
cgcgctccct gaaccctaga                                                       20

SEQ ID NO: 474            moltype = DNA  length = 20
FEATURE                   Location/Qualifiers
misc_feature              1..20
                          note = Synthetic Polynucleotide
source                    1..20
                          mol_type = other DNA
                          organism = synthetic construct
SEQUENCE: 474
aggagaggga cgtgttggtg                                                       20

SEQ ID NO: 475            moltype = DNA  length = 20
FEATURE                   Location/Qualifiers
misc_feature              1..20
                          note = Synthetic Polynucleotide
source                    1..20
                          mol_type = other DNA
                          organism = synthetic construct
SEQUENCE: 475
aggcgctttc cctgctcctg                                                       20

SEQ ID NO: 476            moltype = DNA  length = 20
FEATURE                   Location/Qualifiers
misc_feature              1..20
                          note = Synthetic Polynucleotide
source                    1..20
                          mol_type = other DNA
                          organism = synthetic construct
SEQUENCE: 476
cttctacctg gcggagattg                                                       20
```

| | | |
|---|---|---|
| SEQ ID NO: 477<br>FEATURE<br>misc_feature<br><br>source | moltype = DNA length = 20<br>Location/Qualifiers<br>1..20<br>note = Synthetic Polynucleotide<br>1..20<br>mol_type = other DNA<br>organism = synthetic construct | |
| SEQUENCE: 477<br>gacatcaaac ccgacaacat | | 20 |
| SEQ ID NO: 478<br>FEATURE<br>misc_feature<br><br>source | moltype = DNA length = 20<br>Location/Qualifiers<br>1..20<br>note = Synthetic Polynucleotide<br>1..20<br>mol_type = other DNA<br>organism = synthetic construct | |
| SEQUENCE: 478<br>gcagttgcag gagcggatgg | | 20 |
| SEQ ID NO: 479<br>FEATURE<br>misc_feature<br><br>source | moltype = DNA length = 20<br>Location/Qualifiers<br>1..20<br>note = Synthetic Polynucleotide<br>1..20<br>mol_type = other DNA<br>organism = synthetic construct | |
| SEQUENCE: 479<br>ggctgaggcc gaggtgacgc | | 20 |
| SEQ ID NO: 480<br>FEATURE<br>misc_feature<br><br>source | moltype = DNA length = 20<br>Location/Qualifiers<br>1..20<br>note = Synthetic Polynucleotide<br>1..20<br>mol_type = other DNA<br>organism = synthetic construct | |
| SEQUENCE: 480<br>ctcgcgaata aaaggccctc | | 20 |
| SEQ ID NO: 481<br>FEATURE<br>misc_feature<br><br>source | moltype = DNA length = 20<br>Location/Qualifiers<br>1..20<br>note = Synthetic Polynucleotide<br>1..20<br>mol_type = other DNA<br>organism = synthetic construct | |
| SEQUENCE: 481<br>gagcacctct ctctgccgct | | 20 |
| SEQ ID NO: 482<br>FEATURE<br>misc_feature<br><br>source | moltype = DNA length = 20<br>Location/Qualifiers<br>1..20<br>note = Synthetic Polynucleotide<br>1..20<br>mol_type = other DNA<br>organism = synthetic construct | |
| SEQUENCE: 482<br>cccaatccac gttttggatg | | 20 |
| SEQ ID NO: 483<br>FEATURE<br>misc_feature<br><br>source | moltype = DNA length = 20<br>Location/Qualifiers<br>1..20<br>note = Synthetic Polynucleotide<br>1..20<br>mol_type = other DNA<br>organism = synthetic construct | |
| SEQUENCE: 483<br>aaggccctcc atctgcccaa | | 20 |
| SEQ ID NO: 484<br>FEATURE<br>misc_feature<br><br>source | moltype = DNA length = 20<br>Location/Qualifiers<br>1..20<br>note = Synthetic Polynucleotide<br>1..20<br>mol_type = other DNA<br>organism = synthetic construct | |
| SEQUENCE: 484 | | |

```
tcaactacgc gaggcagagg                                           20

SEQ ID NO: 485         moltype = DNA  length = 20
FEATURE                Location/Qualifiers
misc_feature           1..20
                       note = Synthetic Polynucleotide
source                 1..20
                       mol_type = other DNA
                       organism = synthetic construct
SEQUENCE: 485
cctgttcgcc gttgttctgt                                           20

SEQ ID NO: 486         moltype = DNA  length = 20
FEATURE                Location/Qualifiers
misc_feature           1..20
                       note = Synthetic Polynucleotide
source                 1..20
                       mol_type = other DNA
                       organism = synthetic construct
SEQUENCE: 486
tcaacccga caacatcctg                                            20

SEQ ID NO: 487         moltype = DNA  length = 20
FEATURE                Location/Qualifiers
misc_feature           1..20
                       note = Synthetic Polynucleotide
source                 1..20
                       mol_type = other DNA
                       organism = synthetic construct
SEQUENCE: 487
tgcggcagag gctgaggccg                                           20

SEQ ID NO: 488         moltype = DNA  length = 20
FEATURE                Location/Qualifiers
misc_feature           1..20
                       note = Synthetic Polynucleotide
source                 1..20
                       mol_type = other DNA
                       organism = synthetic construct
SEQUENCE: 488
aacccgacaa catcctgctg                                           20

SEQ ID NO: 489         moltype = DNA  length = 20
FEATURE                Location/Qualifiers
misc_feature           1..20
                       note = Synthetic Polynucleotide
source                 1..20
                       mol_type = other DNA
                       organism = synthetic construct
SEQUENCE: 489
caaggagcac ctctctctgc                                           20

SEQ ID NO: 490         moltype = DNA  length = 20
FEATURE                Location/Qualifiers
misc_feature           1..20
                       note = Synthetic Polynucleotide
source                 1..20
                       mol_type = other DNA
                       organism = synthetic construct
SEQUENCE: 490
cccacaccca tggaactgga                                           20

SEQ ID NO: 491         moltype = DNA  length = 20
FEATURE                Location/Qualifiers
misc_feature           1..20
                       note = Synthetic Polynucleotide
source                 1..20
                       mol_type = other DNA
                       organism = synthetic construct
SEQUENCE: 491
ttctttcggc caggctgagg                                           20

SEQ ID NO: 492         moltype = DNA  length = 20
FEATURE                Location/Qualifiers
misc_feature           1..20
                       note = Synthetic Polynucleotide
source                 1..20
                       mol_type = other DNA
                       organism = synthetic construct
```

```
SEQUENCE: 492
ccctcgcgaa taaaaggccc                                                     20

SEQ ID NO: 493          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 493
gccacatccg cctggccgac                                                     20

SEQ ID NO: 494          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 494
ggcctgggaa ggcagcaagc                                                     20

SEQ ID NO: 495          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 495
cgacaacatc ctgctggacc                                                     20

SEQ ID NO: 496          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 496
ctcgactggg atggtctccg                                                     20

SEQ ID NO: 497          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 497
agtcaactac gcgaggcaga                                                     20

SEQ ID NO: 498          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 498
ttccaggatg agaactacct                                                     20

SEQ ID NO: 499          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 499
aagatcgtcc actacaagga                                                     20

SEQ ID NO: 500          moltype = DNA  length = 20
FEATURE                 Location/Qualifiers
misc_feature            1..20
                        note = Synthetic Polynucleotide
source                  1..20
                        mol_type = other DNA
```

```
                            organism = synthetic construct
SEQUENCE: 500
ccaatccacg ttttggatgc                                                    20

SEQ ID NO: 501              moltype = DNA  length = 20
FEATURE                     Location/Qualifiers
misc_feature                1..20
                            note = Synthetic Polynucleotide
source                      1..20
                            mol_type = other DNA
                            organism = synthetic construct
SEQUENCE: 501
ccgacaacat cctgctggac                                                    20

SEQ ID NO: 502              moltype = DNA  length = 20
FEATURE                     Location/Qualifiers
misc_feature                1..20
                            note = Synthetic Polynucleotide
source                      1..20
                            mol_type = other DNA
                            organism = synthetic construct
SEQUENCE: 502
gaggtgacgc tgcgggagct                                                    20

SEQ ID NO: 503              moltype = DNA  length = 20
FEATURE                     Location/Qualifiers
misc_feature                1..20
                            note = Synthetic Polynucleotide
source                      1..20
                            mol_type = other DNA
                            organism = synthetic construct
SEQUENCE: 503
cctcacttgc gctgctctcg                                                    20

SEQ ID NO: 504              moltype = DNA  length = 20
FEATURE                     Location/Qualifiers
misc_feature                1..20
                            note = Synthetic Polynucleotide
source                      1..20
                            mol_type = other DNA
                            organism = synthetic construct
SEQUENCE: 504
tatcggaggc gctttccctg                                                    20

SEQ ID NO: 505              moltype = DNA  length = 20
FEATURE                     Location/Qualifiers
misc_feature                1..20
                            note = Synthetic Polynucleotide
source                      1..20
                            mol_type = other DNA
                            organism = synthetic construct
SEQUENCE: 505
ggtgtattcg cctatgaaat                                                    20

SEQ ID NO: 506              moltype = DNA  length = 20
FEATURE                     Location/Qualifiers
misc_feature                1..20
                            note = Synthetic Polynucleotide
source                      1..20
                            mol_type = other DNA
                            organism = synthetic construct
SEQUENCE: 506
ggccacatcc gcctggccga                                                    20

SEQ ID NO: 507              moltype = DNA  length = 20
FEATURE                     Location/Qualifiers
misc_feature                1..20
                            note = Synthetic Polynucleotide
source                      1..20
                            mol_type = other DNA
                            organism = synthetic construct
SEQUENCE: 507
gacttccgga cacatccctt                                                    20

SEQ ID NO: 508              moltype = DNA  length = 20
FEATURE                     Location/Qualifiers
misc_feature                1..20
                            note = Synthetic Polynucleotide
source                      1..20
```

```
                        mol_type = other DNA
                        organism = synthetic construct
SEQUENCE: 508
gcaagatcgt ccactacaag                                                   20

SEQ ID NO: 509          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 509
ccacatccgc ctggccgact                                                   20

SEQ ID NO: 510          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 510
tctttcggcc aggctgaggc                                                   20

SEQ ID NO: 511          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 511
gctgaggccg aggtgacgct                                                   20

SEQ ID NO: 512          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 512
agcacctctc tctgccgctg                                                   20

SEQ ID NO: 513          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 513
gcacctctct ctgccgctgg                                                   20

SEQ ID NO: 514          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 514
ggcaagatcg tccactacaa                                                   20

SEQ ID NO: 515          moltype = DNA  length = 20
FEATURE                 Location/Qualifiers
misc_feature            1..20
                        note = Synthetic Polynucleotide
source                  1..20
                        mol_type = other DNA
                        organism = synthetic construct
SEQUENCE: 515
ctatcggagg cgctttccct                                                   20

SEQ ID NO: 516          moltype = DNA  length = 20
FEATURE                 Location/Qualifiers
misc_feature            1..20
                        note = Synthetic Polynucleotide
```

```
source          1..20
                mol_type = other DNA
                organism = synthetic construct
SEQUENCE: 516
cctatcggag gcgctttccc                                                     20
```

MUSCLE TARGETING COMPLEXES AND USES THEREOF FOR TREATING MYOTONIC DYSTROPHY

RELATED APPLICATIONS

This application is a continuation of U.S. application Ser. No. 18/416,981, entitled "MUSCLE TARGETING COMPLEXES AND USES THEREOF FOR TREATING MYOTONIC DYSTROPHY", filed Jan. 19, 2024, which is a continuation of U.S. application Ser. No. 17/205,102, entitled "MUSCLE TARGETING COMPLEXES AND USES THEREOF FOR TREATING MYOTONIC DYSTROPHY", filed Mar. 18, 2021, now U.S. Pat. No. 11,911,484, which is a continuation of U.S. application Ser. No. 17/264,905, entitled "MUSCLE TARGETING COMPLEXES AND USES THEREOF FOR TREATING MYOTONIC DYSTROPHY", filed Feb. 1, 2021, now Abandoned, which is a national stage filing under 35 U.S.C. § 371 of International Application No. PCT/US2019/044987, entitled "MUSCLE TARGETING COMPLEXES AND USES THEREOF FOR TREATING MYOTONIC DYSTROPHY", filed Aug. 2, 2019, which claims the benefit of the filing date of U.S. Provisional Application No. 62/713,914, entitled "MUSCLE TARGETING COMPLEXES AND USES THEREOF FOR TREATING MYOTONIC DYSTROPHY" filed Aug. 2, 2018; U.S. Application No. 62/779,161, entitled "MUSCLE TARGETING COMPLEXES AND USES THEREOF FOR TREATING MYOTONIC DYSTROPHY", filed Dec. 13, 2018; U.S. Application No. 62/855,761, entitled "MUSCLE TARGETING COMPLEXES AND USES THEREOF FOR TREATING MYOTONIC DYSTROPHY", filed May 31, 2019; U.S. Application No. 62/858,888, entitled "MUSCLE TARGETING COMPLEXES AND USES THEREOF FOR TREATING MYOTONIC DYSTROPHY", filed Jun. 7, 2019 and U.S. Application No. 62/859,672, entitled "MUSCLE TARGETING COMPLEXES AND USES THEREOF FOR TREATING MYOTONIC DYSTROPHY", filed Jun. 10, 2019; the contents of each of which are incorporated herein by reference in their entirety.

FIELD OF THE INVENTION

The present application relates to targeting complexes for delivering molecular payloads (e.g., oligonucleotides) to cells and uses thereof, particularly uses relating to treatment of disease.

REFERENCE TO AN ELECTRONIC SEQUENCE LISTING

The contents of the electronic sequence listing (D082470000US08-SEQ-CBD.xml; Size: bytes; and Date of Creation: Jul. 22, 2024) is herein incorporated by reference in its entirety.

BACKGROUND OF INVENTION

Myotonic dystrophy (DM) is a dominantly inherited genetic disease that is characterized by myotonia, muscle loss or degeneration, diminished muscle function, insulin resistance, cardiac arrhythmia, smooth muscle dysfunction, and neurological abnormalities. DM is the most common form of adult-onset muscular dystrophy, with a worldwide incidence of about 1 in 8000 people worldwide. Two types of the disease, myotonic dystrophy type 1 (DM1) and myotonic dystrophy type 2 (DM2), have been described. DM1, the more common form of the disease, results from a repeat expansion of a CTG trinucleotide repeat in the 3' non-coding region of DMPK on chromosome 19; DM2 results from a repeat expansion of a CCTG tetranucleotide repeat in the first intron of ZNF9 on chromosome 3. In DM1 patients, the repeat expansion of a CTG trinucleotide repeat, which may comprise greater than ~50 to ~3,000+ total repeats, leads to generation of toxic RNA repeats capable of forming hairpin structures that bind essential intracellular proteins, e.g. muscleblind-like proteins, with high affinity resulting in protein sequestration and the loss-of-function phenotypes that are characteristic of the disease. Apart from supportive care and treatments to address the symptoms of the disease, no effective therapeutic for DM1 is currently available.

SUMMARY OF INVENTION

According to some aspects, the disclosure provides complexes that target muscle cells for purposes of delivering molecular payloads to those cells. In some embodiments, complexes provided herein are particularly useful for delivering molecular payloads that inhibit the expression or activity of a DMPK allele comprising an expanded disease-associated-repeat, e.g., in a subject having or suspected of having myotonic dystrophy. Accordingly, in some embodiments, complexes provided herein comprise muscle-targeting agents (e.g., muscle targeting antibodies) that specifically bind to receptors on the surface of muscle cells for purposes of delivering molecular payloads to the muscle cells. In some embodiments, the complexes are taken up into the cells via a receptor mediated internalization, following which the molecular payload may be released to perform a function inside the cells. For example, complexes engineered to deliver oligonucleotides may release the oligonucleotides such that the oligonucleotides can inhibit mutant DMPK expression in the muscle cells. In some embodiments, the oligonucleotides are released by endosomal cleavage of covalent linkers connecting oligonucleotides and muscle-targeting agents of the complexes.

Aspects of the disclosure related to complexes comprising a muscle-targeting agent covalently linked to a molecular payload configured for inhibiting expression or activity of a DMPK allele comprising a disease-associated-repeat. In some embodiments, the muscle-targeting agent specifically binds to an internalizing cell surface receptor on muscle cells. In some embodiments, the muscle-targeting agent is a muscle-targeting antibody. In some embodiments, the muscle-targeting antibody specifically binds to an extracellular epitope of a transferrin receptor. In some embodiments, the extracellular epitope of the transferrin receptor comprises an epitope of the apical domain of the transferrin receptor.

In some embodiments, the muscle-targeting antibody specifically binds to an epitope of a sequence in the range of C89 to F760 of SEQ ID NO: 1-3. In some embodiments, the equilibrium dissociation constant (Kd) of binding of the muscle-targeting antibody to the transferrin receptor is in a range from $10^{-11}$ M to $10^{-6}$ M. In some embodiments, the muscle-targeting antibody competes for specific binding to an epitope of a transferrin receptor with an antibody listed in Table 1. In some embodiments, the muscle-targeting antibody competes for specific binding to an epitope of a transferrin receptor with an Kd of less than or equal to $10^{-6}$ M. In some embodiments, the Kd is in a range of $10^{-11}$ M to $10^{-6}$ M.

In some embodiments, the muscle-targeting antibody does not specifically bind to the transferrin binding site of the transferrin receptor and/or wherein the muscle-targeting antibody does not inhibit binding of transferrin to the transferrin receptor. In some embodiments, the muscle-targeting antibody is cross-reactive with extracellular epitopes of two or more of a human, non-human primate and rodent transferrin receptor.

In some embodiments, the complex is configured to promote transferrin receptor mediated internalization of the molecular payload into a muscle cell. In some embodiments, the muscle-targeting antibody is a chimeric antibody, optionally wherein the chimeric antibody is a humanized monoclonal antibody.

In some embodiments, the muscle-targeting antibody is in the form of a ScFv, Fab fragment, Fab' fragment, F(ab')$_2$ fragment, or Fv fragment. In some embodiments, the molecular payload is an oligonucleotide.

In some embodiments, the oligonucleotide comprises at least 15 consecutive nucleotides of a sequence comprising any one of SEQ ID NO: 45-280. In some embodiments, the oligonucleotide comprises a sequence comprising any one of SEQ ID NO: 45-280. In some embodiments, the oligonucleotide comprises a sequence comprising any one of SEQ ID NO: 56, 59, 69, 71, 77, 79, 85, 87, 92, 93, 98, 100, 109, 112, 115, 119, 145, or 161.

In some embodiments, the oligonucleotide comprises a region of complementarity to any one of SEQ ID NO: 281-516. In some embodiments, the oligonucleotide comprises a region of complementarity to at least 15 consecutive nucleotides of any one of SEQ ID NO: 281-516. In some embodiments, the oligonucleotide comprises a region of complementarity to the DMPK allele comprising the disease-associated-repeat expansion.

In some embodiments, the molecular payload is a polypeptide. In some embodiments, the polypeptide is a muscleblind-like (MBNL) polypeptide.

In some embodiments, the oligonucleotide comprises an antisense strand that hybridizes, in a cell, with a wild-type DMPK mRNA transcript encoded by the allele, wherein the DMPK mRNA transcript comprises repeating units of a CUG trinucleotide sequence. In some embodiments, the oligonucleotide comprises an antisense strand that hybridizes, in a cell, with a mutant DMPK mRNA transcript encoded by the allele, wherein the DMPK mRNA transcript comprises repeating units of a CUG trinucleotide sequence. In some embodiments, the disease-associated-repeat is 38 to 200 repeating units in length. In some embodiments, the disease-associated-repeat is associated with late onset myotonic dystrophy. In some embodiments, the disease-associated-repeat is 100 to 10,000 repeat units in length. In some embodiments, the disease-associated-repeat is associated with congenital myotonic dystrophy.

In some embodiments, the oligonucleotide comprises at least one modified internucleotide linkage. In some embodiments, the at least one modified internucleotide linkage is a phosphorothioate linkage. In some embodiments, the oligonucleotide comprises phosphorothioate linkages in the Rp stereochemical conformation and/or in the Sp stereochemical conformation. In some embodiments, the oligonucleotide comprises phosphorothioate linkages that are all in the Rp stereochemical conformation or that are all in the Sp stereochemical conformation.

In some embodiments, the oligonucleotide comprises one or more modified nucleotides. In some embodiments, the one or more modified nucleotides are 2'-modified nucleotides.

In some embodiments, the oligonucleotide is a gapmer oligonucleotide that directs RNAse H-mediated cleavage of a DMPK mRNA transcript in a cell. In some embodiments, the gapmer oligonucleotide comprises a central portion of 5 to 15 deoxyribonucleotides flanked by wings of 2 to 8 modified nucleotides. In some embodiments, the modified nucleotides of the wings are 2'-modified nucleotides.

In some embodiments, the oligonucleotide is a mixmer oligonucleotide. In some embodiments, the mixmer oligonucleotide inhibits binding of muscleblind-like protein 1, muscleblind-like protein 2, or muscleblind-like protein 3 to the DMPK mRNA transcript. In some embodiments, the mixmer oligonucleotide comprises two or more different 2' modified nucleotides.

In some embodiments, the oligonucleotide is an RNAi oligonucleotide that promotes RNAi-mediated cleavage of the DMPK mRNA transcript. In some embodiments, the RNAi oligonucleotide is a double-stranded oligonucleotide of 19 to 25 nucleotides in length.

In some embodiments, the RNAi oligonucleotide comprises at least one 2' modified nucleotide. In some embodiments, each 2' modified nucleotide is selected from the group consisting of: 2'-O-methyl, 2'-fluoro (2'-F), 2'-O-methoxyethyl (2'-MOE), and 2',4'-bridged nucleotides. In some embodiments, the one or more modified nucleotides are bridged nucleotides. In some embodiments, at least one 2' modified nucleotide is a 2',4'-bridged nucleotide selected from: 2',4'-constrained 2'-O-ethyl (cEt) and locked nucleic acid (LNA) nucleotides.

In some embodiments, the oligonucleotide comprises a guide sequence for a genome editing nuclease.

In some embodiments, the oligonucleotide is phosphorodiamidite morpholino oligomer.

In some embodiments, the muscle-targeting agent is covalently linked to the molecular payload via a cleavable linker. In some embodiments, the cleavable linker is selected from: a protease-sensitive linker, pH-sensitive linker, and glutathione-sensitive linker. In some embodiments, the cleavable linker is a protease-sensitive linker. In some embodiments, the protease-sensitive linker comprises a sequence cleavable by a lysosomal protease and/or an endosomal protease. In some embodiments, the protease-sensitive linker comprises a valine-citrulline dipeptide sequence. In some embodiments, the linker is pH-sensitive linker that is cleaved at a pH in a range of 4 to 6.

In some embodiments, the muscle-targeting agent is covalently linked to the molecular payload via a non-cleavable linker. In some embodiments, the non-cleavable linker is an alkane linker. In some embodiments, the muscle-targeting antibody comprises a non-natural amino acid to which the oligonucleotide is covalently linked. In some embodiments, the muscle-targeting antibody is covalently linked to the oligonucleotide via conjugation to a lysine residue or a cysteine residue of the antibody.

In some embodiments, the muscle-targeting antibody is conjugated to the cysteine via a maleimide-containing linker, optionally wherein the maleimide-containing linker comprises a maleimidocaproyl or maleimidomethyl cyclohexane-1-carboxylate group.

In some embodiments, the muscle-targeting antibody is a glycosylated antibody that comprises at least one sugar moiety to which the oligonucleotide is covalently linked. In some embodiments, the sugar moiety is a branched mannose. In some embodiments, the muscle-targeting antibody is a glycosylated antibody that comprises one to four sugar moieties each of which is covalently linked to a separate oligonucleotide.

In some embodiments, the muscle-targeting antibody is a fully-glycosylated antibody. In some embodiments, the muscle-targeting antibody is a partially-glycosylated antibody. In some embodiments, the partially-glycosylated antibody is produced via chemical or enzymatic means. In some embodiments, the partially-glycosylated antibody is produced in a cell, cell that is deficient for an enzyme in the N- or O-glycosylation pathway.

According to some aspects of the disclosure, methods are provided for delivering a molecular payload to a cell expressing transferrin receptor. In some embodiments, the methods comprise contacting the cell with the complex provided herein.

According to some aspects of the disclosure, methods are provided for inhibiting activity of DMPK in a cell. In some embodiments, the methods comprise contacting the cell with the complex provided herein in an amount effective for promoting internalization of the molecular payload to the cell. In some embodiments, the cell is in vitro. In some embodiments, the cell is in a subject. In some embodiments, the subject is a human.

According to some aspects of the disclosure, methods are provided for treating a subject having an expansion of a disease-associated-repeat of a DMPK allele that is associated with myotonic dystrophy. In some embodiments, the methods comprise administering to the subject an effective amount of the complex provided herein. In some embodiments, the disease-associated-repeat comprises repeating units of a trinucleotide sequence. In some embodiments, the trinucleotide sequence is a CTG trinucleotide sequence. In some embodiments, the disease-associated-repeat is 38 to 200 repeating units in length. In some embodiments, the disease-associated-repeat is associated with late onset myotonic dystrophy. In some embodiments, the disease-associated-repeat is 100 to 10,000 repeating units in length. In some embodiments, the disease-associated-repeat is associated with congenital myotonic dystrophy.

DETAILED DESCRIPTION OF INVENTION

Figure 1:
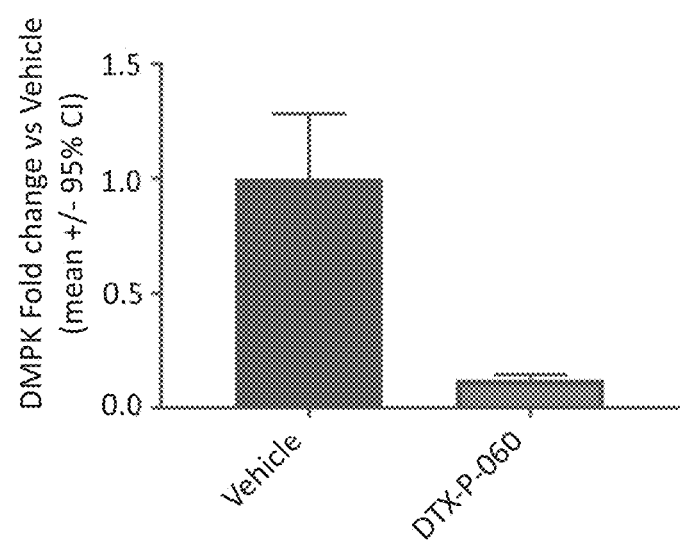
FIG. 1 depicts a non-limiting schematic showing the effect of transfecting Hepa 1-6 cells with an antisense oligonucleotide that targets DMPK (DTX-P-060) on expression levels of DMPK relative to a vehicle transfection.

Aspects of the disclosure relate to a recognition that while certain molecular payloads (e.g., oligonucleotides, peptides, small molecules) can have beneficial effects in muscle cells, it has proven challenging to effectively target such cells. As described herein, the present disclosure provides complexes comprising muscle-targeting agents covalently linked to molecular payloads in order to overcome such challenges. In some embodiments, the complexes are particularly useful for delivering molecular payloads that inhibit the expression or activity of target genes in muscle cells, e.g., in a subject having or suspected of having a rare muscle disease. For example, in some embodiments, complexes are provided for targeting a DMPK allele that comprises an expanded disease-associated-repeat to treat subjects having DM1. In some embodiments, complexes provided herein may comprise oligonucleotides that inhibit expression of a DMPK allele comprising an expanded disease-associated-repeat. As another example, complexes may comprise oligonucleotides that interfere with the binding of a disease-associated DMPK mRNA to a muscleblind-like protein (e.g., MBNL1, 2, and/or 3), thereby reducing a toxic effect of a disease-associated DMPK allele. In some embodiments, synthetic nucleic acid payloads (e.g., DNA or RNA payloads) may be used that express one or more proteins that reduce a toxic effect of a disease-associated DMPK allele. In some embodiments, complexes may comprise molecular payloads of synthetic cDNAs and/or synthetic mRNAs, e.g., that express one or more muscleblind-like-proteins (e.g.. MBNL1, 2, and/or 3) or fragments thereof. In some embodiments, complexes may comprise molecular payloads such as guide molecules (e.g., guide RNAs) that are capable of targeting nucleic acid programmable nucleases (e.g., Cas9) to a sequence at or near a disease-associated repeat sequence of DMPK. In some embodiments, such nucleic programmable nucleases could be used to cleave part or all of a disease-associated repeat sequence from a DMPK gene.

Further aspects of the disclosure, including a description of defined terms, are provided below.

I. Definitions

Administering: As used herein, the terms "administering" or "administration" means to provide a complex to a subject in a manner that is physiologically and/or pharmacologically useful (e.g., to treat a condition in the subject).

Approximately: As used herein, the term "approximately" or "about," as applied to one or more values of interest, refers to a value that is similar to a stated reference value. In certain embodiments, the term "approximately" or "about" refers to a range of values that fall within 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Antibody: As used herein, the term "antibody" refers to a polypeptide that includes at least one immunoglobulin variable domain or at least one antigenic determinant, e.g., paratope that specifically binds to an antigen. In some embodiments, an antibody is a full-length antibody. In some embodiments, an antibody is a chimeric antibody. In some embodiments, an antibody is a humanized antibody. However, in some embodiments, an antibody is a Fab fragment, a F(ab')$_2$ fragment, a Fv fragment or a scFv fragment. In some embodiments, an antibody is a nanobody derived from a camelid antibody or a nanobody derived from shark antibody. In some embodiments, an antibody is a diabody. In some embodiments, an antibody comprises a framework having a human germline sequence. In another embodiment, an antibody comprises a heavy chain constant domain selected from the group consisting of IgG, IgG1, IgG2, IgG2A, IgG2B, IgG2C, IgG3, IgG4, IgA1, IgA2, IgD, IgM, and IgE constant domains. In some embodiments, an antibody comprises a heavy (H) chain variable region (abbreviated herein as VH), and/or a light (L) chain variable region (abbreviated herein as VL). In some embodiments, an antibody comprises a constant domain, e.g., an Fc region. An immunoglobulin constant domain refers to a heavy or light chain constant domain. Human IgG heavy chain and light chain constant domain amino acid sequences and their functional variations are known. With respect to the heavy chain, in some embodiments, the heavy chain of an antibody described herein can be an alpha (α), delta (Δ), epsilon (ε), gamma (γ) or mu (μ) heavy chain. In some embodiments, the heavy chain of an antibody described herein can comprise a human alpha (α), delta (Δ), epsilon (ε), gamma (γ) or mu (μ) heavy chain. In a particular embodiment, an antibody described herein comprises a human gamma 1 CH1, CH2, and/or CH3 domain. In some embodiments, the amino acid sequence of the VH domain comprises the amino acid sequence of a human gamma (γ) heavy chain constant region, such as any known in the art. Non-limiting examples of human constant region sequences have been described in the art, e.g., see U.S. Pat. No. 5,693,780 and Kabat E A et al., (1991) supra. In some embodiments, the VH domain comprises an amino acid sequence that is at least 70%, 75%, 80%, 85%, 90%, 95%, 98%, or at least 99% identical to any of the variable chain constant regions provided herein. In some embodiments, an antibody is modified, e.g., modified via glycosylation, phosphorylation, sumoylation, and/or methylation. In some embodiments, an antibody is a glycosylated antibody, which is conjugated to one or more sugar or carbohydrate molecules. In some embodiments, the one or more sugar or carbohydrate molecule are conjugated to the antibody via N-glycosylation, O-glycosylation, C-glycosylation, glypiation (GPI anchor attachment), and/or phosphoglycosylation. In some embodiments, the one or more sugar or carbohydrate molecule are monosaccharides, disaccharides, oligosaccharides, or glycans. In some embodiments, the one or more sugar or carbohydrate molecule is a branched oligosaccharide or a branched glycan. In some embodiments, the one or more sugar or carbohydrate molecule includes a mannose unit, a glucose unit, an N-acetylglucosamine unit, an N-acetylgalactosamine unit, a galactose unit, a fucose unit, or a phospholipid unit. In some embodiments, an antibody is a construct that comprises a polypeptide comprising one or more antigen binding fragments of the disclosure linked to a linker polypeptide or an immunoglobulin constant domain. Linker polypeptides comprise two or more amino acid residues joined by peptide bonds and are used to link one or more antigen binding portions. Examples of linker polypeptides have been reported (see e.g., Holliger, P., et al. (1993) Proc. Natl. Acad. Sci. USA 90:6444-6448; Poljak, R. J., et al. (1994) Structure 2:1121-1123). Still further, an antibody may be part of a larger immunoadhesion molecule, formed by covalent or noncovalent association of the antibody or antibody portion with one or more other proteins or peptides. Examples of such immunoadhesion molecules include use of the streptavidin core region to make a tetrameric scFv molecule (Kipriyanov, S. M., et al. (1995) Human Antibodies and Hybridomas 6:93-101) and use of a cysteine residue, a marker peptide and a C-terminal polyhistidine tag to make bivalent and biotinylated scFv molecules (Kipriyanov, S. M., et al. (1994) Mol. Immunol. 31:1047-1058).

CDR: As used herein, the term "CDR" refers to the complementarity determining region within antibody variable sequences. There are three CDRs in each of the variable regions of the heavy chain and the light chain, which are designated CDR1, CDR2 and CDR3, for each of the variable regions. The term "CDR set" as used herein refers to a group of three CDRs that occur in a single variable region capable of binding the antigen. The exact boundaries of these CDRs have been defined differently according to different systems. The system described by Kabat (Kabat et al., Sequences of Proteins of Immunological Interest (National Institutes of Health, Bethesda, Md. (1987) and (1991)) not only provides an unambiguous residue numbering system applicable to any variable region of an antibody, but also provides precise residue boundaries defining the three CDRs. These CDRs may be referred to as Kabat CDRs. Sub-portions of CDRs may be designated as L1, L2 and L3 or H1, H2 and H3 where the "L" and the "H" designates the light chain and the heavy chains regions, respectively. These regions may be referred to as Chothia CDRs, which have boundaries that overlap with Kabat CDRs. Other boundaries defining CDRs overlapping with the Kabat CDRs have been described by Padlan (FASEB J. 9:133-139 (1995)) and MacCallum (J Mol Biol 262(5):732-45 (1996)). Still other CDR boundary definitions may not strictly follow one of the above systems, but will nonetheless overlap with the Kabat CDRs, although they may be shortened or lengthened in light of prediction or experimental findings that particular residues or groups of residues or even entire CDRs do not significantly impact antigen binding. The methods used herein may utilize CDRs defined according to any of these systems, although preferred embodiments use Kabat or Chothia defined CDRs.

CDR-grafted antibody: The term "CDR-grafted antibody" refers to antibodies which comprise heavy and light chain variable region sequences from one species but in which the sequences of one or more of the CDR regions of VH and/or VL are replaced with CDR sequences of another species, such as antibodies having murine heavy and light chain variable regions in which one or more of the murine CDRs (e.g., CDR3) has been replaced with human CDR sequences.

Chimeric antibody: The term "chimeric antibody" refers to antibodies which comprise heavy and light chain variable region sequences from one species and constant region sequences from another species, such as antibodies having murine heavy and light chain variable regions linked to human constant regions.

Complementary: As used herein, the term "complementary" refers to the capacity for precise pairing between two nucleotides or two sets of nucleotides. In particular, complementary is a term that characterizes an extent of hydrogen bond pairing that brings about binding between two nucleotides or two sets of nucleotides. For example, if a base at one position of an oligonucleotide is capable of hydrogen bonding with a base at the corresponding position of a target nucleic acid (e.g., an mRNA), then the bases are considered to be complementary to each other at that position. Base pairings may include both canonical Watson-Crick base pairing and non-Watson-Crick base pairing (e.g., Wobble base pairing and Hoogsteen base pairing). For example, in some embodiments, for complementary base pairings, adenosine-type bases (A) are complementary to thymidine-type bases (T) or uracil-type bases (U), that cytosine-type bases (C) are complementary to guanosine-type bases (G), and that universal bases such as 3-nitropyrrole or 5-nitroindole can hybridize to and are considered complementary to any A, C, U, or T. Inosine (I) has also been considered in the art to be a universal base and is considered complementary to any A, C, U or T.

Conservative amino acid substitution: As used herein, a "conservative amino acid substitution" refers to an amino acid substitution that does not alter the relative charge or size characteristics of the protein in which the amino acid substitution is made. Variants can be prepared according to methods for altering polypeptide sequence known to one of ordinary skill in the art such as are found in references which compile such methods, e.g. Molecular Cloning: A Laboratory Manual, J. Sambrook, et al., eds., Fourth Edition, Cold Spring Harbor Laboratory Press, Cold Spring Harbor, New York, 2012, or Current Protocols in Molecular Biology, F. M. Ausubel, et al., eds., John Wiley & Sons, Inc., New York. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D.

Covalently linked: As used herein, the term "covalently linked" refers to a characteristic of two or more molecules being linked together via at least one covalent bond. In some embodiments, two molecules can be covalently linked together by a single bond, e.g., a disulfide bond or disulfide bridge, that serves as a linker between the molecules. However, in some embodiments, two or more molecules can be covalently linked together via a molecule that serves as a linker that joins the two or more molecules together through multiple covalent bonds. In some embodiments, a linker may be a cleavable linker. However, in some embodiments, a linker may be a non-cleavable linker.

Cross-reactive: As used herein and in the context of a targeting agent (e.g., antibody), the term "cross-reactive," refers to a property of the agent being capable of specifically binding to more than one antigen of a similar type or class (e.g., antigens of multiple homologs, paralogs, or orthologs) with similar affinity or avidity. For example, in some embodiments, an antibody that is cross-reactive against human and non-human primate antigens of a similar type or class (e.g., a human transferrin receptor and non-human primate transferring receptor) is capable of binding to the human antigen and non-human primate antigens with a similar affinity or avidity. In some embodiments, an antibody is cross-reactive against a human antigen and a rodent antigen of a similar type or class. In some embodiments, an antibody is cross-reactive against a rodent antigen and a non-human primate antigen of a similar type or class. In some embodiments, an antibody is cross-reactive against a human antigen, a non-human primate antigen, and a rodent antigen of a similar type or class.

Disease-associated-repeat: As used herein, the term "disease-associated-repeat" refers to a repeated nucleotide sequence at a genomic location for which the number of units of the repeated nucleotide sequence is correlated with and/or directly or indirectly contributes to, or causes, genetic disease. Each repeating unit of a disease associated repeat may be 2, 3, 4, 5 or more nucleotides in length. For example, in some embodiments, a disease associated repeat is a dinucleotide repeat. In some embodiments, a disease associated repeat is a trinucleotide repeat. In some embodiments, a disease associated repeat is a tetranucleotide repeat. In some embodiments, a disease associated repeat is a pentanucleotide repeat. In some embodiments, embodiments, the disease-associated-repeat comprises CAG repeats, CTG repeats, CUG repeats, CGG repeats, CCTG repeats, or a nucleotide complement of any thereof. In some embodiments, a disease-associated-repeat is in a non-coding portion of a gene. However, in some embodiments, a disease-associated-repeat is in a coding region of a gene. In some embodiments, a disease-associated-repeat is expanded from a normal state to a length that directly or indirectly contributes to, or causes, genetic disease. In some embodiments, a disease-associated-repeat is in RNA (e.g., an RNA transcript). In some embodiments, a disease-associated-repeat is in DNA (e.g., a chromosome, a plasmid). In some embodiments, a disease-associated-repeat is expanded in a chromosome of a germline cell. In some embodiments, a disease-associated-repeat is expanded in a chromosome of a somatic cell. In some embodiments, a disease-associated-repeat is expanded to a number of repeating units that is associated with congenital onset of disease. In some embodiments, a disease-associated-repeat is expanded to a number of repeating units that is associated with childhood onset of disease. In some embodiments, a disease-associated-repeat is expanded to a number of repeating units that is associated with adult onset of disease.

DMPK: As used herein, the term "DMPK" refers to a gene that encodes myotonin-protein kinase (also known as myotonic dystrophy protein kinase or dystrophia myotonica protein kinase), a serine/threonine protein kinase. Substrates for this enzyme may include myogenin, the beta-subunit of the L-type calcium channels, and phospholemman. In some embodiments, DMPK may be a human (Gene ID: 1760), non-human primate (e.g., Gene ID: 456139, Gene ID: 715328), or rodent gene (e.g., Gene ID: 13400). In humans, a CTG repeat expansion in the 3' non-coding, untranslated region of DMPK is associated with myotonic dystrophy type I (DM1). In addition, multiple human transcript variants (e.g., as annotated under GenBank RefSeq Accession Numbers: NM_001081563.2, NM_004409.4, NM_001081560.2, NM_001081562.2, NM_001288764.1, NM_001288765.1, and NM_001288766.1) have been characterized that encode different protein isoforms.

DMPK allele: As used herein, the term "DMPK allele" refers to any one of alternative forms (e.g., wild-type or mutant forms) of a DMPK gene. In some embodiments, a DMPK allele may encode for wild-type myotonin-protein kinase that retains its normal and typical functions. In some embodiments, a DMPK allele may comprise one or more disease-associated-repeat expansions. In some embodiments, normal subjects have two DMPK alleles comprising in the range of 5 to 37 repeat units. In some embodiments, the number of CTG repeat units in subjects having DM1 is in the range of ~50 to ~3,000+ with higher numbers of repeats leading to an increased severity of disease. In some embodiments, mildly affected DM1 subjects have at least one DMPK allele having in the range of 50 to 150 repeat units. In some embodiments, subjects with classic DM1 have at least one DMPK allele having in the range of 100 to 1,000 or more repeat units. In some embodiments, subjects having DM1 with congenital onset may have at least one DMPK allele comprising more than 2,000 repeat units.

Framework: As used herein, the term "framework" or "framework sequence" refers to the remaining sequences of a variable region minus the CDRs. Because the exact definition of a CDR sequence can be determined by different systems, the meaning of a framework sequence is subject to correspondingly different interpretations. The six CDRs (CDR-L1, CDR-L2, and CDR-L3 of light chain and CDR-H1, CDR-H2, and CDR-H3 of heavy chain) also divide the framework regions on the light chain and the heavy chain into four sub-regions (FR1, FR2, FR3 and FR4) on each chain, in which CDR1 is positioned between FR1 and FR2. CDR2 between FR2 and FR3, and CDR3 between FR3 and FR4. Without specifying the particular sub-regions as FR1, FR2, FR3 or FR4, a framework region, as referred by others, represents the combined FRs within the variable region of a single, naturally occurring immunoglobulin chain. As used herein, a FR represents one of the four sub-regions, and FRs represents two or more of the four sub-regions constituting a framework region. Human heavy chain and light chain acceptor sequences are known in the art. In one embodiment, the acceptor sequences known in the art may be used in the antibodies disclosed herein.

Human antibody: The term "human antibody", as used herein, is intended to include antibodies having variable and constant regions derived from human germline immunoglobulin sequences. The human antibodies of the disclosure may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include antibodies in which CDR sequences derived from the germline of another mammalian species, such as a mouse, have been grafted onto human framework sequences.

Humanized antibody: The term "humanized antibody" refers to antibodies which comprise heavy and light chain variable region sequences from a non-human species (e.g., a mouse) but in which at least a portion of the VH and/or VL sequence has been altered to be more "human-like", i.e., more similar to human germline variable sequences. One type of humanized antibody is a CDR-grafted antibody, in which human CDR sequences are introduced into non-human VH and VL sequences to replace the corresponding nonhuman CDR sequences. In one embodiment, humanized anti-transferrin receptor antibodies and antigen binding portions are provided. Such antibodies may be generated by obtaining murine anti-transferrin receptor monoclonal antibodies using traditional hybridoma technology followed by humanization using in vitro genetic engineering, such as those disclosed in Kasaian et al PCT publication No. WO 2005/123126 A2.

Internalizing cell surface receptor: As used herein, the term, "internalizing cell surface receptor" refers to a cell surface receptor that is internalized by cells, e.g., upon external stimulation, e.g., ligand binding to the receptor. In some embodiments, an internalizing cell surface receptor is internalized by endocytosis. In some embodiments, an internalizing cell surface receptor is internalized by clathrin-mediated endocytosis. However, in some embodiments, an internalizing cell surface receptor is internalized by a clathrin-independent pathway, such as, for example, phagocytosis, macropinocytosis, caveolae- and raft-mediated uptake or constitutive clathrin-independent endocytosis. In some embodiments, the internalizing cell surface receptor comprises an intracellular domain, a transmembrane domain, and/or an extracellular domain, which may optionally further comprise a ligand-binding domain. In some embodiments, a cell surface receptor becomes internalized by a cell after ligand binding. In some embodiments, a ligand may be a muscle-targeting agent or a muscle-targeting antibody. In some embodiments, an internalizing cell surface receptor is a transferrin receptor.

Isolated antibody: An "isolated antibody", as used herein, is intended to refer to an antibody that is substantially free of other antibodies having different antigenic specificities (e.g., an isolated antibody that specifically binds transferrin receptor is substantially free of antibodies that specifically bind antigens other than transferrin receptor). An isolated antibody that specifically binds transferrin receptor complex may, however, have cross-reactivity to other antigens, such as transferrin receptor molecules from other species. Moreover, an isolated antibody may be substantially free of other cellular material and/or chemicals.

Kabat numbering: The terms "Kabat numbering", "Kabat definitions and "Kabat labeling" are used interchangeably herein. These terms, which are recognized in the art, refer to a system of numbering amino acid residues which are more variable (i.e. hypervariable) than other amino acid residues in the heavy and light chain variable regions of an antibody, or an antigen binding portion thereof (Kabat et al. (1971) Ann. NY Acad, Sci. 190:382-391 and, Kabat, E. A., et al. (1991) Sequences of Proteins of Immunological Interest, Fifth Edition, U.S. Department of Health and Human Services, NIH Publication No. 91-3242). For the heavy chain variable region, the hypervariable region ranges from amino acid positions 31 to 35 for CDR1, amino acid positions 50 to 65 for CDR2, and amino acid positions 95 to 102 for CDR3. For the light chain variable region, the hypervariable region ranges from amino acid positions 24 to 34 for CDR1, amino acid positions 50 to 56 for CDR2, and amino acid positions 89 to 97 for CDR3.

Molecular payload: As used herein, the term "molecular payload" refers to a molecule or species that functions to modulate a biological outcome. In some embodiments, a molecular payload is linked to, or otherwise associated with a muscle-targeting agent. In some embodiments, the molecular payload is a small molecule, a protein, a peptide, a nucleic acid, or an oligonucleotide. In some embodiments, the molecular payload functions to modulate the transcription of a DNA sequence, to modulate the expression of a protein, or to modulate the activity of a protein. In some embodiments, the molecular payload is an oligonucleotide that comprises a strand having a region of complementarity to a target gene.

Muscle-targeting agent: As used herein, the term, "muscle-targeting agent," refers to a molecule that specifically binds to an antigen expressed on muscle cells. The antigen in or on muscle cells may be a membrane protein, for example an integral membrane protein or a peripheral membrane protein. Typically, a muscle-targeting agent specifically binds to an antigen on muscle cells that facilitates internalization of the muscle-targeting agent (and any associated molecular payload) into the muscle cells. In some embodiments, a muscle-targeting agent specifically binds to an internalizing, cell surface receptor on muscles and is capable of being internalized into muscle cells through receptor mediated internalization. In some embodiments, the muscle-targeting agent is a small molecule, a protein, a peptide, a nucleic acid (e.g., an aptamer), or an antibody. In some embodiments, the muscle-targeting agent is linked to a molecular payload.

Muscle-targeting antibody: As used herein, the term, "muscle-targeting antibody," refers to a muscle-targeting agent that is an antibody that specifically binds to an antigen found in or on muscle cells. In some embodiments, a muscle-targeting antibody specifically binds to an antigen on muscle cells that facilitates internalization of the muscle-targeting antibody (and any associated molecular payment) into the muscle cells. In some embodiments, the muscle-targeting antibody specifically binds to an internalizing, cell surface receptor present on muscle cells. In some embodiments, the muscle-targeting antibody is an antibody that specifically binds to a transferrin receptor.

Myotonic dystrophy (DM): As used herein, the term "Myotonic dystrophy (DM)" refers to a genetic disease caused by mutations in the DMPK gene or CNBP (ZNF9) gene that is characterized by muscle loss, muscle weakening, and muscle function. Two types of the disease, myotonic dystrophy type 1 (DM1) and myotonic dystrophy type 2 (DM2), have been described. DM1 is associated with an expansion of a CTG trinucleotide repeat in the 3' non-coding region of DMPK. DM2 is associated with an expansion of a CCTG tetranucleotide repeat in the first intron of ZNF9. In both DM1 and DM2, the nucleotide expansions lead to toxic RNA repeats capable of forming hairpin structures that bind critical intracellular proteins. e.g., muscleblind-like proteins, with high affinity. Myotonic dystrophy, the genetic basis for the disease, and related symptoms are described in the art (see, e.g. Thornton, C. A., "Myotonic Dystrophy" Neurol Clin. (2014), 32(3): 705-719.; and Konieczny et al. "Myotonic dystrophy: candidate small molecule therapeutics" Drug Discovery Today (2017), 22:11.) In some embodiments, subjects are born with a variation of DM1 called congenital myotonic dystrophy. Symptoms of congenital myotonic dystrophy are present from birth and include weakness of all muscles, breathing problems, clubfeet, developmental delays and intellectual disabilities. DM1 is associated with Online Mendelian Inheritance in Man (OMIM) Entry #160900. DM2 is associated with OMIM Entry #602668.

Oligonucleotide: As used herein, the term "oligonucleotide" refers to an oligomeric nucleic acid compound of up to 200 nucleotides in length. Examples of oligonucleotides include, but are not limited to, RNAi oligonucleotides (e.g., siRNAs, shRNAs), microRNAs, gapmers, mixmers, phosphorodiamidite morpholinos, peptide nucleic acids, aptamers, guide nucleic acids (e.g., Cas9 guide RNAs), etc. Oligonucleotides may be single-stranded or double-stranded. In some embodiments, an oligonucleotide may comprise one or more modified nucleotides (e.g. 2'-O-methyl sugar modifications, purine or pyrimidine modifications). In some embodiments, an oligonucleotide may comprise one or more modified internucleotide linkage. In some embodiments, an oligonucleotide may comprise one or more phosphorothioate linkages, which may be in the Rp or Sp stereochemical conformation.

Recombinant antibody: The term "recombinant human antibody", as used herein, is intended to include all human antibodies that are prepared, expressed, created or isolated by recombinant means, such as antibodies expressed using a recombinant expression vector transfected into a host cell (described in more details in this disclosure), antibodies isolated from a recombinant, combinatorial human antibody library (Hoogenboom H. R., (1997) TIB Tech. 15:62-70; Azzazy H., and Highsmith W. E., (2002) Clin. Biochem. 35:425-445: Gavilondo J. V., and Larrick J. W. (2002) BioTechniques 29:128-145; Hoogenboom H., and Chames P. (2000) Immunology Today 21:371-378), antibodies isolated from an animal (e.g., a mouse) that is transgenic for human immunoglobulin genes (see e.g., Taylor, L. D., et al. (1992) Nucl. Acids Res. 20:6287-6295; Kellermann S-A., and Green L. L. (2002) Current Opinion in Biotechnology 13:593-597; Little M. et al (2000) Immunology Today 21:364-370) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo. One embodiment of the disclosure provides fully human antibodies capable of binding human transferrin receptor which can be generated using techniques well known in the art, such as, but not limited to, using human Ig phage libraries such as those disclosed in Jermutus et al., PCT publication No. WO 2005/007699 A2.

Region of complementarity: As used herein, the term "region of complementarity" refers to a nucleotide sequence, e.g., of a oligonucleotide, that is sufficiently complementary to a cognate nucleotide sequence, e.g., of a target nucleic acid, such that the two nucleotide sequences are capable of annealing to one another under physiological conditions (e.g., in a cell). In some embodiments, a region of complementarity is fully complementary to a cognate nucleotide sequence of target nucleic acid. However, in some embodiments, a region of complementarity is partially complementary to a cognate nucleotide sequence of target nucleic acid (e.g., at least 80%, 90%, 95% or 99% complementarity). In some embodiments, a region of complementarity contains 1, 2, 3, or 4 mismatches compared with a cognate nucleotide sequence of a target nucleic acid.

Specifically binds: As used herein, the term "specifically binds" refers to the ability of a molecule to bind to a binding partner with a degree of affinity or avidity that enables the molecule to be used to distinguish the binding partner from an appropriate control in a binding assay or other binding context. With respect to an antibody, the term, "specifically binds", refers to the ability of the antibody to bind to a specific antigen with a degree of affinity or avidity, compared with an appropriate reference antigen or antigens, that enables the antibody to be used to distinguish the specific antigen from others, e.g., to an extent that permits preferential targeting to certain cells, e.g., muscle cells, through binding to the antigen, as described herein. In some embodiments, an antibody specifically binds to a target if the antibody has a $K_D$ for binding the target of at least about $10^{-4}$ M, $10^{-5}$ M, $10^{-6}$ M, $10^{-7}$ M, $10^{-8}$ M, $10^{-9}$ M, $10^{-10}$ M, $10^{-11}$ M, $10^{-12}$, $10^{-13}$ M, or less. In some embodiments, an antibody specifically binds to the transferrin receptor, e.g., an epitope of the apical domain of transferrin receptor.

Subject: As used herein, the term "subject" refers to a mammal. In some embodiments, a subject is non-human primate, or rodent. In some embodiments, a subject is a human. In some embodiments, a subject is a patient, e.g., a human patient that has or is suspected of having a disease. In some embodiments, the subject is a human patient who has or is suspected of having a disease resulting from a disease-associated-repeat expansion, e.g., in a DMPK allele.

Transferrin receptor: As used herein, the term, "transferrin receptor" (also known as TFRC, CD71, p90, or TFR1) refers to an internalizing cell surface receptor that binds transferrin to facilitate iron uptake by endocytosis. In some embodiments, a transferrin receptor may be of human (NCBI Gene ID 7037), non-human primate (e.g., NCBI Gene ID 711568 or NCBI Gene ID 102136007), or rodent (e.g., NCBI Gene ID 22042) origin. In addition, multiple human transcript variants have been characterized that encoded different isoforms of the receptor (e.g., as annotated under GenBank RefSeq Accession Numbers: NP_001121620.1, NP_003225.2, NP_001300894.1, and NP_001300895.1).

II. Complexes

Provided herein are complexes that comprise a targeting agent, e.g. an antibody, covalently linked to a molecular payload. In some embodiments, a complex comprises a muscle-targeting antibody covalently linked to a oligonucleotide. A complex may comprise an antibody that specifically binds a single antigenic site or that binds to at least two antigenic sites that may exist on the same or different antigens.

A complex may be used to modulate the activity or function of at least one gene, protein, and/or nucleic acid. In some embodiments, the molecular payload present with a complex is responsible for the modulation of a gene, protein, and/or nucleic acids. A molecular payload may be a small molecule, protein, nucleic acid, oligonucleotide, or any molecular entity capable of modulating the activity or function of a gene, protein, and/or nucleic acid in a cell. In some embodiments, a molecular payload is an oligonucleotide that targets a disease-associated repeat in muscle cells.

In some embodiments, a complex comprises a muscle-targeting agent, e.g. an anti-transferrin receptor antibody, covalently linked to a molecular payload, e.g. an antisense oligonucleotide that targets a disease-associated repeat, e.g. DMPK allele.

A. Muscle-Targeting Agents

Some aspects of the disclosure provide muscle-targeting agents, e.g., for delivering a molecular payload to a muscle cell. In some embodiments, such muscle-targeting agents are capable of binding to a muscle cell, e.g., via specifically binding to an antigen on the muscle cell, and delivering an associated molecular payload to the muscle cell. In some embodiments, the molecular payload is bound (e.g., covalently bound) to the muscle targeting agent and is internalized into the muscle cell upon binding of the muscle targeting agent to an antigen on the muscle cell, e.g., via endocytosis. It should be appreciated that various types of muscle-targeting agents may be used in accordance with the disclosure. For example, the muscle-targeting agent may comprise, or consist of, a nucleic acid (e.g., DNA or RNA), a peptide (e.g., an antibody), a lipid (e.g., a microvesicle), or a sugar moiety (e.g., a polysaccharide). Exemplary muscle-targeting agents are described in further detail herein, however, it should be appreciated that the exemplary muscle-targeting agents provided herein are not meant to be limiting.

Some aspects of the disclosure provide muscle-targeting agents that specifically bind to an antigen on muscle, such as skeletal muscle, smooth muscle, or cardiac muscle. In some embodiments, any of the muscle-targeting agents provided herein bind to (e.g., specifically bind to) an antigen on a skeletal muscle cell, a smooth muscle cell, and/or a cardiac muscle cell.

By interacting with muscle-specific cell surface recognition elements (e.g., cell membrane proteins), both tissue localization and selective uptake into muscle cells can be achieved. In some embodiments, molecules that are substrates for muscle uptake transporters are useful for delivering a molecular payload into muscle tissue. Binding to muscle surface recognition elements followed by endocytosis can allow even large molecules such as antibodies to enter muscle cells. As another example molecular payloads conjugated to transferrin or anti-transferrin receptor antibodies can be taken up by muscle cells via binding to transferrin receptor, which may then be endocytosed, e.g., via clathrin-mediated endocytosis.

The use of muscle-targeting agents may be useful for concentrating a molecular payload (e.g., oligonucleotide) in muscle while reducing toxicity associated with effects in other tissues. In some embodiments, the muscle-targeting agent concentrates a bound molecular payload in muscle cells as compared to another cell type within a subject. In some embodiments, the muscle-targeting agent concentrates a bound molecular payload in muscle cells (e.g., skeletal, smooth, or cardiac muscle cells) in an amount that is at least 1, 2, 3, 4, 5, 6, 7, 8, 9, 10, 15, 20, 30, 40, 50, 60, 70, 80, 90, or 100 times greater than an amount in non-muscle cells (e.g., liver, neuronal, blood, or fat cells). In some embodiments, a toxicity of the molecular payload in a subject is reduced by at least 1%, 2%, 3%, 4%, 5%, 10%, 15%, 20%, 25%, 30%, 35%, 40%, 45%, 50%, 55%, 60%, 65%, 70%, 75%, 80%, 90%, or 95% when it is delivered to the subject when bound to the muscle-targeting agent.

In some embodiments, to achieve muscle selectivity, a muscle recognition element (e.g., a muscle cell antigen) may be required. As one example, a muscle-targeting agent may be a small molecule that is a substrate for a muscle-specific uptake transporter. As another example, a muscle-targeting agent may be an antibody that enters a muscle cell via transporter-mediated endocytosis. As another example, a muscle targeting agent may be a ligand that binds to cell surface receptor on a muscle cell. It should be appreciated that while transporter-based approaches provide a direct path for cellular entry, receptor-based targeting may involve stimulated endocytosis to reach the desired site of action.

i. Muscle-Targeting Antibodies

In some embodiments, the muscle-targeting agent is an antibody. Generally, the high specificity of antibodies for their target antigen provides the potential for selectively targeting muscle cells (e.g., skeletal, smooth, and/or cardiac muscle cells). This specificity may also limit off-target toxicity. Examples of antibodies that are capable of targeting a surface antigen of muscle cells have been reported and are within the scope of the disclosure. For example, antibodies that target the surface of muscle cells are described in Arahata K., et al. "Immunostaining of skeletal and cardiac muscle surface membrane with antibody against Duchenne muscular dystrophy peptide" *Nature* 1988; 333: 861-3; Song K. S., et al. "Expression of caveolin-3 in skeletal, cardiac, and smooth muscle cells. Caveolin-3 is a component of the sarcolemma and co-fractionates with dystrophin and dystrophin-associated glycoproteins" *J Biol Chem* 1996; 271: 15160-5; and Weisbart R. H. et al., "Cell type specific targeted intracellular delivery into muscle of a monoclonal antibody that binds myosin IIb" *Mol Immunol.* 2003 March, 39(13):78309; the entire contents of each of which are incorporated herein by reference.

a. Anti-Transferrin Receptor Antibodies

Some aspects of the disclosure are based on the recognition that agents binding to transferrin receptor, e.g., anti-transferrin-receptor antibodies, are capable of targeting muscle cell. Transferrin receptors are internalizing cell surface receptors that transport transferrin across the cellular membrane and participate in the regulation and homeostasis of intracellular iron levels. Some aspects of the disclosure provide transferrin receptor binding proteins, which are capable of binding to transferrin receptor. Accordingly, aspects of the disclosure provide binding proteins (e.g., antibodies) that bind to transferrin receptor. In some embodiments, binding proteins that bind to transferrin receptor are internalized, along with any bound molecular payload, into a muscle cell. As used herein, an antibody that binds to a transferrin receptor may be referred to as an anti-transferrin receptor antibody. Antibodies that bind, e.g. specifically bind, to a transferrin receptor may be internalized into the cell, e.g. through receptor-mediated endocytosis, upon binding to a transferrin receptor.

It should be appreciated that anti-transferrin receptor antibodies may be produced, synthesized, and/or derivatized using several known methodologies, e.g. library design using phage display. Exemplary methodologies have been characterized in the art and are incorporated by reference (Díez, P. et al. "High-throughput phage-display screening in array format", Enzyme and microbial technology, 2015, 79, 34-41.; Christoph M. H. and Stanley, J. R. "Antibody Phage Display: Technique and Applications" J Invest Dermatol. 2014, 134:2.; Engleman, Edgar (Ed.) "Human Hybridomas and Monoclonal Antibodies." 1985, Springer.). In other embodiments, an anti-transferrin antibody has been previously characterized or disclosed. Antibodies that specifically bind to transferrin receptor are known in the art (see, e.g. U.S. Pat. No. 4,364,934, filed Dec. 4, 1979, "Monoclonal antibody to a human early thymocyte antigen and methods for preparing same"; U.S. Pat. No. 8,409,573, filed Jun. 14, 2006, "Anti-CD71 monoclonal antibodies and uses thereof for treating malignant tumor cells"; U.S. Pat. No. 9,708,406, filed May 20, 2014, "Anti-transferrin receptor antibodies and methods of use"; U.S. Pat. No. 9,611,323, filed Dec. 19, 2014, "Low affinity blood brain barrier receptor antibodies and uses therefor"; WO 2015/098989, filed Dec. 24, 2014, "Novel anti-Transferrin receptor antibody that passes through blood-brain barrier"; Schneider C. et al. "Structural features of the cell surface receptor for transferrin that is recognized by the monoclonal antibody OKT9." J Biol Chem. 1982, 257:14, 8516-8522.; Lee et al. "Targeting Rat Anti-Mouse Transferrin Receptor Monoclonal Antibodies through Blood-Brain Barrier in Mouse" 2000, J Pharmacol. Exp. Ther., 292: 1048-1052.).

Any appropriate anti-transferrin receptor antibodies may be used in the complexes disclosed herein. Examples of anti-transferrin receptor antibodies, including associated references and binding epitopes are listed in Table 1. In some embodiments, the anti-transferrin receptor antibody comprises the complementarity determining regions (CDR-H, CDR-H2, CDR-H3, CDR-L1, CDR-L2, and CDR-L3) of any of the anti-transferrin receptor antibodies provided herein, e.g., anti-transferrin receptor antibodies listed in Table 1.

TABLE 1

List of anti-transferrin receptor antibody clones, including associated references and binding epitope information.

| Antibody Clone Name | Reference(s) | Epitope/Notes |
|---|---|---|
| OKT9 | U.S. Pat. No. 4,364,934, filed Dec. 4, 1979, entitled "MONOCLONAL ANTIBODY TO A HUMAN EARLY THYMOCYTE ANTIGEN AND METHODS FOR PREPARING SAME" Schneider C. et al. "Structural features of the cell surface receptor for transferrin that is recognized by the monoclonal antibody OKT9." J Biol Chem. 1982, 257:14, 8516-8522. | Apical domain of TfR (residues 305-366 of human TfR sequence XM_052730.3, available in GenBank) |
| (From JCR) Clone M11 Clone M23 Clone M27 Clone B84 | WO 2015/098989, filed Dec. 24, 2014, "Novel anti-Transferrin receptor antibody that passes through blood-brain barrier" U.S. Pat. No. 9,994,641, filed Dec. 24, 2014, "Novel anti-Transferrin receptor antibody that passes through blood-brain barrier" | Apical domain (residues 230-244 and 326-347 of TfR) and protease-like domain (residues 461-473) |

TABLE 1-continued

List of anti-transferrin receptor antibody clones, including associated references and binding epitope information.

| Antibody Clone Name | Reference(s) | Epitope/Notes |
|---|---|---|
| (From Genentech) 7A4, 8A2, 15D2, 10D11, 7B10, 15G11, 16G5, 13C3, 16G4, 16F6, 7G7, 4C2, 1B12, and 13D4 | WO 2016/081643, filed May 26, 2016, entitled "ANTI-TRANSFERRIN RECEPTOR ANTIBODIES AND METHODS OF USE" U.S. Pat. No. 9,708,406, filed May 20, 2014, "Anti-transferrin receptor antibodies and methods of use" | Apical domain and non-apical regions |
| (From Armagen) 8D3 | Lee et al. "Targeting Rat Anti-Mouse Transferrin Receptor Monoclonal Antibodies through Blood-Brain Barrier in Mouse" 2000, J Pharmacol. Exp. Ther., 292: 1048-1052. U.S. patent application 2010/077498, filed Sep. 11, 2008, entitled "COMPOSITIONS AND METHODS FOR BLOOD-BRAIN BARRIER DELIVERY IN THE MOUSE" | |
| OX26 | Haobam, B. et al. 2014. Rab17-mediated recycling endosomes contribute to autophagosome formation in response to Group A Streptococcus invasion. Cellular microbiology. 16: 1806-21. | |
| DF1513 | Ortiz-Zapater E et al. Trafficking of the human transferrin receptor in plant cells: effects of tyrphostin A23 and brefeldin A. Plant J 48: 757-70 (2006). | |
| 1A1B2, 66IG10, MEM-189, JF0956, 29806, 1A1B2, TFRC/1818, 1E6, 66Ig10, TFRC/1059, Q1/71, 23D10, 13E4, TFRC/1149, ER-MP21, YTA74.4, BU54, 2B6, RI7 217 | Commercially available anti-transferrin receptor antibodies. | Novus Biologicals 8100 Southpark Way, A-8 Littleton CO 80120 |
| (From INSERM) BA120g | U.S. patent application 2011/0311544A1, filed Jun. 15, 2005, entitled "ANTI-CD71 MONOCLONAL ANTIBODIES AND USES THEREOF FOR TREATING MALIGNANT TUMOR CELLS" | Does not compete with OKT9 |
| LUCA31 | U.S. Pat. No. 7,572,895, filed Jun. 7, 2004, entitled "TRANSFERRIN RECEPTOR ANTIBODIES" | "LUCA31 epitope" |
| (Salk Institute) B3/25 T58/30 | Trowbridge, I. S. et al. "Anti-transferrin receptor monoclonal antibody and toxin-antibody conjugates affect growth of human tumour cells." Nature, 1981, volume 294, pages 171-173 | |
| R17 217.1.3, 5E9C11, OKT9 (BE0023 clone) | Commercially available anti-transferrin receptor antibodies. | BioXcell 10 Technology Dr., Suite 2B West Lebanon, NH 03784-1671 USA |
| BK19.9, B3/25, T56/14 and T58/1 | Gatter, K. C. et al. "Transferrin receptors in human tissues: their distribution and possible clinical relevance." J Clin Pathol. 1983 May; 36(5): 539-45. | |

In some embodiments, the muscle-targeting agent is an anti-transferrin receptor antibody. In some embodiment, an anti-transferrin receptor antibody specifically binds to a transferrin protein having an amino acid sequence as disclosed herein. In some embodiments, an anti-transferrin receptor antibody may specifically bind to any extracellular epitope of a transferrin receptor or an epitope that becomes exposed to an antibody, including the apical domain, the transferrin binding domain, and the protease-like domain. In some embodiments, an anti-transferrin receptor antibody binds to an amino acid segment of a human or non-human primate transferrin receptor, as provided in SEQ ID Nos. 1-3 in the range of amino acids C89 to F760. In some embodiments, an anti-transferrin receptor antibody specifically binds with binding affinity of at least about $10^{-4}$ M, $10^{-5}$ M, $10^{-6}$ M, $10^{-7}$ M, $10^{-8}$ M, $10^{-9}$ M, $10^{-10}$ M, $10^{-11}$ M, $10^{-12}$ M, $10^{-13}$ M, or less. Anti-transferrin receptor antibodies used herein may be capable of competing for binding with other anti-transferrin receptor antibodies, e.g. OKT9, 8D3, that bind to transferrin receptor with $10^{-3}$ M, $10^{-4}$ M, $10^{-5}$ M, $10^{-6}$ M, $10^{-7}$ M, or less.

An example human transferrin receptor amino acid sequence, corresponding to NCBI sequence NP_003225.2 (transferrin receptor protein 1 isoform 1, *Homo sapiens*) is as follows:

(SEQ ID NO: 1)
MMDQARSAFSNLFGGEPLSYTRFSLARQVDGDNSHVEMKLAVDEEENADN

NTKANVTKPKRCSGSICYGTIAVIVFFLIGFMIGYLGYCKGVEPKTECER

LAGTESPVREEPGEDFPAARRLYWDDLKRKLSEKLDSTDFTGTIKLLNEN

SYVPREAGSQKDENLALYVENQFREFKLSKVWRDQHFVKIQVKDSAQNSV

IIVDKNGRLVYLVENPGGYVAYSKAATVTGKLVHANFGTKKDFEDLYTPV

NGSIVIVRAGKITFAEKVANAESLNAIGVLIYMDQTKFPIVNAELSFFGH

AHLGTGDPYTPGFPSFNHTQFPPSRSSGLPNIPVQTISRAAAEKLFGNME

GDCPSDWKTDSTCRMVTSESKNVKLTVSNVLKEIKILNIFGVIKGFVEPD

HYVVVGAQRDAWGPGAAKSGVGTALLLKLAQMFSDMVLKDGFQPSRSIIF

ASWSAGDFGSVGATEWLEGYLSSLHLKAFTYINLDKAVLGTSNFKVSASP

LLYTLIEKTMQNVKHPVTGQFLYQDSNWASKVEKLTLDNAAFPPLAYSGI

PAVSFCFCEDTDYPYLGTTMDTYKELIERIPELNKVARAAAEVAGQFVIK

LTHDVELNLDYERYNSQLLSFVRDLNQYRADIKEMGLSLQWLYSARGDFF

RATSRLTTDFGNAEKTDRFVMKKLNDRVMRVEYHFLSPYVSPKESPFRHV

FWGSGSHTLPALLENLKLRKQNNGAFNETLFRNQLALATWTIQGAANALS

GDVWDIDNEF.

An example non-human primate transferrin receptor amino acid sequence, corresponding to NCBI sequence NP_001244232.1 (transferrin receptor protein 1, *Macaca mulatta*) is as follows:

(SEQ ID NO: 2)
MMDQARSAFSNLFGGEPLSYTRFSLARQVDGDNSHVEMKLGVDEEENTDN

NTKPNGTKPKRCGGNICYGTIAVIIFFLIGFMIGYLGYCKGVEPKTECER

LAGTESPAREEPEEDFPAAPRLYWDDLKRKLSEKLDTTDFTSTIKLLNEN

LYVPREAGSQKDENLALYIENQFREFKLSKVWRDQHFVKIQVKDSAQNSV

IIVDKNGGLVYLVENPGGYVAYSKAATVTGKLVHANFGTKKDFEDLDSPV

NGSIVIVRAGKITFAEKVANAESLNAIGVLIYMDQTKFPIVKADLSFFGH

AHLGTGDPYTPGFPSFNHTQFPPSQSSGLPNIPVQTISRAAAEKLFGNME

GDCPSDWKTDSTCKMVTSENKSVKLTVSNVLKETKILNIFGVIKGFVEPD

HYVVVGAQRDAWGPGAAKSSVGTALLLKLAQMFSDMVLKDGFQPSRSIIF

ASWSAGDFGSVGATEWLEGYLSSLHLKAFTYINLDKAVLGTSNFKVSASP

-continued
LLYTLIEKTMQDVKHPVTGRSLYQDSNWASKVEKLTLDNAAFPPLAYSGI

PAVSFCFCEDTDYPYLGTTMDTYKELVERIPELNKVARAAAEVAGQFVIK

LTHDTELNLDYERYNSQLLLFLRDLNQYRADVKEMGLSLQWLYSARGDFF

RATSRLTTDFRNAEKRDKFVMKKLNDRVMRVEYYFLSPYVSPKESPFRHV

FWGSGSHTLSALLESLKLRRQNNSAFNETLFRNQLALATWTIQGAANALS

GDVWDIDNEF

An example non-human primate transferrin receptor amino acid sequence, corresponding to NCBI sequence XP_005545315.1 (transferrin receptor protein 1, *Macaca fascicularis*) is as follows:

(SEQ ID NO: 3)
MMDQARSAFSNLFGGEPLSYTRFSLARQVDGDNSHVEMKLGVDEEENTDN

NTKANGTKPKRCGGNICYGTIAVIIFFLIGFMIGYLGYCKGVEPKTECER

LAGTESPAREEPEEDFPAAPRLYWDDLKRKLSEKLDTTDFTSTIKLLNEN

LYVPREAGSQKDENLALYIENQFREFKLSKVWRDQHFVKIQVKDSAQNSV

IIVDKNGGLVYLVENPGGYVAYSKAATVTGKLVHANFGTKKDFEDLDSPV

NGSIVIVRAGKITFAEKVANAESLNAIGVLIYMDQTKFPIVKADLSFFGH

AHLGTGDPYTPGFPSFNHTQFPPSQSSGLPNIPVQTISRAAAEKLFGNME

GDCPSDWKTDSTCKMVTSENKSVKLTVSNVLKETKILNIFGVIKGFVEPD

HYVVVGAQRDAWGPGAAKSSVGTALLLKLAQMFSDMVLKDGFQPSRSIIF

ASWSAGDFGSVGATEWLEGYLSSLHLKAFTYINLDKAVLGTSNFKVSASP

LLYTLIEKTMQDVKHPVTGRSLYQDSNWASKVEKLTLDNAAFPPLAYSGI

PAVSFCFCEDTDYPYLGTTMDTYKELVERIPELNKVARAAAEVAGQFVIK

LTHDTELNLDYERYNSQLLLFLRDLNQYRADVKEMGLSLQWLYSARGDFF

RATSRLTTDFRNAEKRDKFVMKKLNDRVMRVEYYFLSPYVSPKESPFRHV

FWGSGSHTLSALLESLKLRRQNNSAFNETLFRNQLALATWTIQGAANALS

GDVWDIDNEF.

An example mouse transferrin receptor amino acid sequence, corresponding to NCBI sequence NP_001344227.1 (transferrin receptor protein 1, *Mus musculus*) is as follows:

(SEQ ID NO: 4)
MMDQARSAFSNLFGGEPLSYTRFSLARQVDGDNSHVEMKLAADEEENADN

NMKASVRKPKRFNGRLCFAAIALVIFFLIGFMSGYLGYCKRVEQKEECVK

LAETEETDKSETMETEDVPTSSRLYWADLKTLLSEKLNSIEFADTIKQLS

QNTYTPREAGSQKDESLAYYIENQFHEFKFSKVWRDEHYVKIQVKSSIGQ

NMVTIVQSNGNLDPVESPEGYVAFSKPTEVSGKLVHANFGTKKDFEELSY

SVNGSLVIVRAGEITFAEKVANAQSFNAIGVLIYMDKNKFPVVEADLALF

GHAHLGTGDPYTPGFPSFNHTQFPPSQSSGLPNIPVQTISRAAAEKLFGK

MEGSCPARWNIDSSCKLELSQNQNVKLIVKNVLKERRILNIFGVIKGYEE

PDRYVVVGAQRDALGAGVAAKSSVGTGLLLKLAQVFSDMISKDGFRPSRS

IIFASWTAGDFGAVGATEWLEGYLSSLHLKAFTYINLDKVVLGTSNFKVS

ASPLLYTLMGKIMQDVKHPVDGKSLYRDSNWISKVEKLSFDNAAYPFLAY

-continued

SGIPAVSFCFCEDADYPYLGTRLDTYEALTQKVPQLNQMVRTAAEVAGQL

IIKLTHDVELNLDYEMYNSKLLSFMKDLNQFKTDIRDMGLSLQWLYSARG

DYFRATSRLTTDFHNAEKTNRFVMREINDRIMKVEYHFLSPYVSPRESPF

RHIFWGSGSHTLSALVENLKLRQKNITAFNETLFRNQLALATWTIQGVAN

ALSGDIWNIDNEF

In some embodiments, an anti-transferrin receptor antibody binds to an amino acid segment of the receptor as follows:

(SEQ ID NO: 5)
FVKIQVKDSAQNSVIIVDKNGRLVYLVENPGGYVAYSKAATVTGKLVHAN

FGTKKDFEDLYTPVNGSIVIVRAGKITFAEKVANAESLNAIGVLIYMDQT

KFPIVNAELSFFGHAHLGTGDPYTPGFPSFNHTQFPPSRSSGLPNIPVQT

ISRAAAEKLFGNMEGDCPSDWKTDSTCRMVTSESKNVKLTVSNVLKE and does not inhibit the binding interactions between transferrin receptors and transferrin and/or human hemochromatosis protein (also as HFE).

Appropriate methodologies may be used to obtain and/or produce antibodies, antibody fragments, or antigen-binding agents, e.g., through the use of recombinant DNA protocols. In some embodiments, an antibody may also be produced through the generation of hybridomas (see, e.g., Kohler, G and Milstein, C. "Continuous cultures of fused cells secreting antibody of predefined specificity" Nature, 1975, 256: 495-497). The antigen-of-interest may be used as the immunogen in any form or entity, e.g., recombinant or a naturally occurring form or entity. Hybridomas are screened using standard methods, e.g. ELISA screening, to find at least one hybridoma that produces an antibody that targets a particular antigen. Antibodies may also be produced through screening of protein expression libraries that express antibodies, e.g., phage display libraries. Phage display library design may also be used, in some embodiments, (see, e.g. U.S. Pat. No. 5,223,409, filed Mar. 1, 1991, "Directed evolution of novel binding proteins"; WO 1992/18619, filed Apr. 10, 1992, "Heterodimeric receptor libraries using phagemids"; WO 1991/17271, filed May 1, 1991, "Recombinant library screening methods"; WO 1992/20791, filed May 15, 1992, "Methods for producing members of specific binding pairs"; WO 1992/15679, filed Feb. 28, 1992, and "Improved epitope displaying phage"). In some embodiments, an antigen-of-interest may be used to immunize a non-human animal, e.g., a rodent or a goat. In some embodiments, an antibody is then obtained from the non-human animal, and may be optionally modified using a number of methodologies, e.g., using recombinant DNA techniques. Additional examples of antibody production and methodologies are known in the art (see, e.g. Harlow et al. "Antibodies: A Laboratory Manual", Cold Spring Harbor Laboratory, 1988.).

In some embodiments, an antibody is modified, e.g., modified via glycosylation, phosphorylation, sumoylation, and/or methylation. In some embodiments, an antibody is a glycosylated antibody, which is conjugated to one or more sugar or carbohydrate molecules. In some embodiments, the one or more sugar or carbohydrate molecule are conjugated to the antibody via N-glycosylation, O-glycosylation, C-glycosylation, glypiation (GPI anchor attachment), and/or phosphoglycosylation. In some embodiments, the one or more sugar or carbohydrate molecules are monosaccharides, disaccharides, oligosaccharides, or glycans. In some embodiments, the one or more sugar or carbohydrate molecule is a branched oligosaccharide or a branched glycan. In some embodiments, the one or more sugar or carbohydrate molecule includes a mannose unit, a glucose unit, an N-acetylglucosamine unit, an N-acetylgalactosamine unit, a galactose unit, a fucose unit, or a phospholipid unit. In some embodiments, there are about 1-10, about 1-5, about 5-10, about 1-4, about 1-3, or about 2 sugar molecules. In some embodiments, a glycosylated antibody is fully or partially glycosylated. In some embodiments, an antibody is glycosylated by chemical reactions or by enzymatic means. In some embodiments, an antibody is glycosylated in vitro or inside a cell, which may optionally be deficient in an enzyme in the N- or O-glycosylation pathway, e.g. a glycosyltransferase. In some embodiments, an antibody is functionalized with sugar or carbohydrate molecules as described in International Patent Application Publication WO2014065661, published on May 1, 2014, entitled, "Modified antibody, antibody-conjugate and process for the preparation thereof".

Some aspects of the disclosure provide proteins that bind to transferrin receptor (e.g., an extracellular portion of the transferrin receptor). In some embodiments, transferrin receptor antibodies provided herein bind specifically to transferrin receptor (e.g., human transferrin receptor). Transferrin receptors are internalizing cell surface receptors that transport transferrin across the cellular membrane and participate in the regulation and homeostasis of intracellular iron levels. In some embodiments, transferrin receptor antibodies provided herein bind specifically to transferrin receptor from human, non-human primates, mouse, rat, etc. In some embodiments, transferrin receptor antibodies provided herein bind to human transferrin receptor. In some embodiments, transferrin receptor antibodies provided herein specifically bind to human transferrin receptor. In some embodiments, transferrin receptor antibodies provided herein bind to an apical domain of human transferrin receptor. In some embodiments, transferrin receptor antibodies provided herein specifically bind to an apical domain of human transferrin receptor.

In some embodiments, transferrin receptor antibodies of the present disclosure include one or more of the CDR-H (e.g., CDR-H1, CDR-H2, and CDR-H3) amino acid sequences from any one of the anti-transferrin receptor antibodies selected from Table 1. In some embodiments, transferrin receptor antibodies include the CDR-H1, CDR-H2, and CDR-H3 as provided for any one of the anti-transferrin receptor antibodies selected from Table 1. In some embodiments, anti-transferrin receptor antibodies include the CDR-L1, CDR-L2, and CDR-L3 as provided for any one of the anti-transferrin receptor antibodies selected from Table 1. In some embodiments, anti-transferrin antibodies include the CDR-H1, CDR-H2, CDR-H3, CDR-L1, CDR-L2, and CDR-L3 as provided for any one of the anti-transferrin receptor antibodies selected from Table 1. The disclosure also includes any nucleic acid sequence that encodes a molecule comprising a CDR-H1, CDR-H2, CDR-H3, CDR-L1, CDR-L2, or CDR-L3 as provided for any one of the anti-transferrin receptor antibodies selected from Table 1. In some embodiments, antibody heavy and light chain CDR3 domains may play a particularly important role in the binding specificity/affinity of an antibody for an antigen. Accordingly, anti-transferrin receptor antibodies of the disclosure may include at least the heavy and/or light chain CDR3s of any one of the anti-transferrin receptor antibodies selected from Table 1.

In some examples, any of the anti-transferrin receptor antibodies of the disclosure have one or more CDR (e.g., CDR-H or CDR-L) sequences substantially similar to any of the CDR-H1. CDR-H2, CDR-H3, CDR-L1, CDR-L2, and/or CDR-L3 sequences from one of the anti-transferrin receptor antibodies selected from Table 1. In some embodiments, the position of one or more CDRs along the VH (e.g., CDR-H1, CDR-H2, or CDR-H3) and/or VL (e.g., CDR-L1, CDR-L2, or CDR-L3) region of an antibody described herein can vary by one, two, three, four, five, or six amino acid positions so long as immunospecific binding to transferrin receptor (e.g., human transferrin receptor) is maintained (e.g., substantially maintained, for example, at least 50%, at least 60%, at least 70%, at least 80%, at least 90%, at least 95% of the binding of the original antibody from which it is derived). For example, in some embodiments, the position defining a CDR of any antibody described herein can vary by shifting the N-terminal and/or C-terminal boundary of the CDR by one, two, three, four, five, or six amino acids, relative to the CDR position of any one of the antibodies described herein, so long as immunospecific binding to transferrin receptor (e.g., human transferrin receptor) is maintained (e.g., substantially maintained, for example, at least 50%, at least 60%, at least 70%, at least 80%, at least 90%, at least 95% of the binding of the original antibody from which it is derived). In another embodiment, the length of one or more CDRs along the VH (e.g., CDR-H1, CDR-H2, or CDR-H3) and/or VL (e.g., CDR-L1, CDR-L2, or CDR-L3) region of an antibody described herein can vary (e.g., be shorter or longer) by one, two, three, four, five, or more amino acids, so long as immunospecific binding to transferrin receptor (e.g., human transferrin receptor) is maintained (e.g., substantially maintained, for example, at least 50%, at least 60%, at least 70%, at least 80%, at least 90%, at least 95% of the binding of the original antibody from which it is derived).

Accordingly, in some embodiments, a CDR-L1, CDR-L2, CDR-L3, CDR-H1, CDR-H2, and/or CDR-H3 described herein may be one, two, three, four, five or more amino acids shorter than one or more of the CDRs described herein (e.g., CDRS from any of the anti-transferrin receptor antibodies selected from Table 1) so long as immunospecific binding to transferrin receptor (e.g., human transferrin receptor) is maintained (e.g., substantially maintained, for example, at least 50%, at least 60%, at least 70%, at least 80%, at least 90%, at least 95% relative to the binding of the original antibody from which it is derived). In some embodiments, a CDR-L1, CDR-L2, CDR-L3, CDR-H1, CDR-H2, and/or CDR-H3 described herein may be one, two, three, four, five or more amino acids longer than one or more of the CDRs described herein (e.g., CDRS from any of the anti-transferrin receptor antibodies selected from Table 1) so long as immunospecific binding to transferrin receptor (e.g., human transferrin receptor) is maintained (e.g., substantially maintained, for example, at least 50%, at least 60%, at least 70%, at least 80%, at least 90%, at least 95% relative to the binding of the original antibody from which it is derived). In some embodiments, the amino portion of a CDR-L1, CDR-L2, CDR-L3, CDR-H1, CDR-H2, and/or CDR-H3 described herein can be extended by one, two, three, four, five or more amino acids compared to one or more of the CDRs described herein (e.g., CDRS from any of the anti-transferrin receptor antibodies selected from Table 1) so long as immunospecific binding to transferrin receptor (e.g., human transferrin receptor) is maintained (e.g., substantially maintained, for example, at least 50%, at least 60%, at least 70%, at least 80%, at least 90%, at least 95% relative to the binding of the original antibody from which it is derived). In some embodiments, the carboxy portion of a CDR-L1, CDR-L2, CDR-L3, CDR-H1, CDR-H2, and/or CDR-H3 described herein can be extended by one, two, three, four, five or more amino acids compared to one or more of the CDRs described herein (e.g., CDRS from any of the anti-transferrin receptor antibodies selected from Table 1) so long as immunospecific binding to transferrin receptor (e.g., human transferrin receptor) is maintained (e.g., substantially maintained, for example, at least 50%, at least 60%, at least 70%, at least 80%, at least 90%, at least 95% relative to the binding of the original antibody from which it is derived). In some embodiments, the amino portion of a CDR-L1, CDR-L2, CDR-L3, CDR-H1, CDR-H2, and/or CDR-H3 described herein can be shortened by one, two, three, four, five or more amino acids compared to one or more of the CDRs described herein (e.g., CDRS from any of the anti-transferrin receptor antibodies selected from Table 1) so long as immunospecific binding to transferrin receptor (e.g., human transferrin receptor) is maintained (e.g., substantially maintained, for example, at least 50%, at least 60%, at least 70%, at least 80%, at least 90%, at least 95% relative to the binding of the original antibody from which it is derived). In some embodiments, the carboxy portion of a CDR-L1, CDR-L2, CDR-L3, CDR-H1, CDR-H2, and/or CDR-H3 described herein can be shortened by one, two, three, four, five or more amino acids compared to one or more of the CDRs described herein (e.g., CDRS from any of the anti-transferrin receptor antibodies selected from Table 1) so long as immunospecific binding to transferrin receptor (e.g., human transferrin receptor) is maintained (e.g., substantially maintained, for example, at least 50%, at least 60%, at least 70%, at least 80%, at least 90%, at least 95% relative to the binding of the original antibody from which it is derived). Any method can be used to ascertain whether immunospecific binding to transferrin receptor (e.g., human transferrin receptor) is maintained, for example, using binding assays and conditions described in the art.

In some examples, any of the anti-transferrin receptor antibodies of the disclosure have one or more CDR (e.g., CDR-H or CDR-L) sequences substantially similar to any one of the anti-transferrin receptor antibodies selected from Table 1. For example, the antibodies may include one or more CDR sequence(s) from any of the anti-transferrin receptor antibodies selected from Table 1 containing up to 5, 4, 3, 2, or 1 amino acid residue variations as compared to the corresponding CDR region in any one of the CDRs provided herein (e.g., CDRs from any of the anti-transferrin receptor antibodies selected from Table 1) so long as immunospecific binding to transferrin receptor (e.g., human transferrin receptor) is maintained (e.g., substantially maintained, for example, at least 50%, at least 60%, at least 70%, at least 80%, at least 90%, at least 95% relative to the binding of the original antibody from which it is derived). In some embodiments, any of the amino acid variations in any of the CDRs provided herein may be conservative variations. Conservative variations can be introduced into the CDRs at positions where the residues are not likely to be involved in interacting with a transferrin receptor protein (e.g., a human transferrin receptor protein), for example, as determined based on a crystal structure. Some aspects of the disclosure provide transferrin receptor antibodies that comprise one or more of the heavy chain variable (VH) and/or light chain variable (VL) domains provided herein. In some embodiments, any of the VH domains provided herein include one or more of the CDR-H sequences (e.g., CDR-H1, CDR-H2, and CDR-H3) provided herein, for example, any of the CDR-H sequences provided in any one of the anti-transferrin receptor antibodies selected from Table 1. In some embodiments, any of the V L domains provided herein include one or more of the CDR-L sequences (e.g., CDR-L1, CDR-L2, and CDR-L3) provided herein, for example, any of the CDR-L sequences provided in any one of the anti-transferrin receptor antibodies selected from Table 1.

In some embodiments, anti-transferrin receptor antibodies of the disclosure include any antibody that includes a heavy chain variable domain and/or a light chain variable domain of any anti-transferrin receptor antibody, such as any one of the anti-transferrin receptor antibodies selected from Table 1. In some embodiments, anti-transferrin receptor antibodies of the disclosure include any antibody that includes the heavy chain variable and light chain variable pairs of any anti-transferrin receptor antibody, such as any one of the anti-transferrin receptor antibodies selected from Table 1.

Aspects of the disclosure provide anti-transferrin receptor antibodies having a heavy chain variable (VH) and/or a light chain variable (VL) domain amino acid sequence homologous to any of those described herein. In some embodiments, the anti-transferrin receptor antibody comprises a heavy chain variable sequence or a light chain variable sequence that is at least 75% (e.g., 80%, 85%, 90%, 95%, 98%, or 99%) identical to the heavy chain variable sequence and/or any light chain variable sequence of any anti-transferrin receptor antibody, such as any one of the anti-transferrin receptor antibodies selected from Table 1. In some embodiments, the homologous heavy chain variable and/or a light chain variable amino acid sequences do not vary within any of the CDR sequences provided herein. For example, in some embodiments, the degree of sequence variation (e.g., 75%, 80%, 85%, 90%, 95%, 98%, or 99%) may occur within a heavy chain variable and/or a light chain variable sequence excluding any of the CDR sequences provided herein. In some embodiments, any of the anti-transferrin receptor antibodies provided herein comprise a heavy chain variable sequence and a light chain variable sequence that comprises a framework sequence that is at least 75%, 80%, 85%, 90%, 95%, 98%, or 99% identical to the framework sequence of any anti-transferrin receptor antibody, such as any one of the anti-transferrin receptor antibodies selected from Table 1.

In some embodiments, an anti-transferrin receptor antibody, which specifically binds to transferrin receptor (e.g., human transferrin receptor), comprises a light chain variable VL domain comprising any of the CDR-L domains (CDR-L1, CDR-L2, and CDR-L3), or CDR-L domain variants provided herein, of any of the anti-transferrin receptor antibodies selected from Table 1. In some embodiments, an anti-transferrin receptor antibody, which specifically binds to transferrin receptor (e.g., human transferrin receptor), comprises a light chain variable VL domain comprising the CDR-L1, the CDR-L2, and the CDR-L3 of any anti-transferrin receptor antibody, such as any one of the anti-transferrin receptor antibodies selected from Table 1. In some embodiments, the anti-transferrin receptor antibody comprises a light chain variable (VL) region sequence comprising one, two, three or four of the framework regions of the light chain variable region sequence of any anti-transferrin receptor antibody, such as any one of the anti-transferrin receptor antibodies selected from Table 1. In some embodiments, the anti-transferrin receptor antibody comprises one, two, three or four of the framework regions of a light chain variable region sequence which is at least 75%, 80%, 85%, 90%, 95%, or 100% identical to one, two, three or four of the framework regions of the light chain variable region sequence of any anti-transferrin receptor antibody, such as any one of the anti-transferrin receptor antibodies selected from Table 1. In some embodiments, the light chain variable framework region that is derived from said amino acid sequence consists of said amino acid sequence but for the presence of up to 10 amino acid substitutions, deletions, and/or insertions, preferably up to 10 amino acid substitutions. In some embodiments, the light chain variable framework region that is derived from said amino acid sequence consists of said amino acid sequence with 1, 2, 3, 4, 5, 6, 7, 8, 9 or 10 amino acid residues being substituted for an amino acid found in an analogous position in a corresponding non-human, primate, or human light chain variable framework region.

In some embodiments, an anti-transferrin receptor antibody that specifically binds to transferrin receptor comprises the CDR-L1, the CDR-L2, and the CDR-L3 of any anti-transferrin receptor antibody, such as any one of the anti-transferrin receptor antibodies selected from Table 1. In some embodiments, the antibody further comprises one, two, three or all four VL framework regions derived from the VL of a human or primate antibody. The primate or human light chain framework region of the antibody selected for use with the light chain CDR sequences described herein, can have, for example, at least 70% (e.g., at least 75%, 80%, 85%, 90%, 95%, 98%, or at least 99%) identity with a light chain framework region of a non-human parent antibody. The primate or human antibody selected can have the same or substantially the same number of amino acids in its light chain complementarity determining regions to that of the light chain complementarity determining regions of any of the antibodies provided herein, e.g., any of the anti-transferrin receptor antibodies selected from Table 1. In some embodiments, the primate or human light chain framework region amino acid residues are from a natural primate or human antibody light chain framework region having at least 75% identity, at least 80% identity, at least 85% identity, at least 90% identity, at least 95% identity, at least 98% identity, at least 99% (or more) identity with the light chain framework regions of any anti-transferrin receptor antibody, such as any one of the anti-transferrin receptor antibodies selected from Table 1. In some embodiments, an anti-transferrin receptor antibody further comprises one, two, three or all four VL framework regions derived from a human light chain variable kappa subfamily. In some embodiments, an anti-transferrin receptor antibody further comprises one, two, three or all four VL framework regions derived from a human light chain variable lambda subfamily.

In some embodiments, any of the anti-transferrin receptor antibodies provided herein comprise a light chain variable domain that further comprises a light chain constant region. In some embodiments, the light chain constant region is a kappa, or a lambda light chain constant region. In some embodiments, the kappa or lambda light chain constant region is from a mammal, e.g., from a human, monkey, rat, or mouse. In some embodiments, the light chain constant region is a human kappa light chain constant region. In some embodiments, the light chain constant region is a human lambda light chain constant region. It should be appreciated that any of the light chain constant regions provided herein may be variants of any of the light chain constant regions provided herein. In some embodiments, the light chain constant region comprises an amino acid sequence that is at least 75%, 80%, 85%, 90%, 95%, 98%, or 99% identical to any of the light chain constant regions of any anti-transferrin receptor antibody, such as any one of the anti-transferrin receptor antibodies selected from Table 1.

In some embodiments, the anti-transferrin receptor antibody is any anti-transferrin receptor antibody, such as any one of the anti-transferrin receptor antibodies selected from Table 1.

In some embodiments, an anti-transferrin receptor antibody comprises a VL domain comprising the amino acid sequence of any anti-transferrin receptor antibody, such as any one of the anti-transferrin receptor antibodies selected from Table 1, and wherein the constant regions comprise the amino acid sequences of the constant regions of an IgG, IgE, IgM, IgD, IgA or IgY immunoglobulin molecule, or a human IgG, IgE, IgM, IgD, IgA or IgY immunoglobulin molecule. In some embodiments, an anti-transferrin receptor antibody comprises any of the VL domains, or VL domain variants, and any of the VH domains, or VH domain variants, wherein the VL and VH domains, or variants thereof, are from the same antibody clone, and wherein the constant regions comprise the amino acid sequences of the constant regions of an IgG, IgE, IgM, IgD, IgA or IgY immunoglobulin molecule, any class (e.g., IgG1, IgG2, IgG3, IgG4, IgA1 and IgA2), or any subclass (e.g., IgG2a and IgG2b) of immunoglobulin molecule. Non-limiting examples of human constant regions are described in the art, e.g., see Kabat E A et al., (1991) supra.

In some embodiments, an antibody of the disclosure can bind to a target antigen (e.g., transferrin receptor) with relatively high affinity, e.g., with a $K_D$ less than $10^{-6}$ M, $10^{-7}$ M, $10^{-8}$ M, $10^{-9}$ M. $10^{-10}$ M, $10^{-11}$ M or lower. For example, anti-transferrin receptor antibodies can bind to a transferrin receptor protein (e.g., human transferrin receptor) with an affinity between 5 pM and 500 nM, e.g., between 50 pM and 100 nM, e.g., between 500 pM and 50 nM. The disclosure also includes antibodies that compete with any of the antibodies described herein for binding to a transferrin receptor protein (e.g., human transferrin receptor) and that have an affinity of 50 nM or lower (e.g., 20 nM or lower, 10 nM or lower, 500 pM or lower, 50 pM or lower, or 5 pM or lower). The affinity and binding kinetics of the anti-transferrin receptor antibody can be tested using any suitable method including but not limited to biosensor technology (e.g., OCTET or BIACORE).

In some embodiments, an antibody of the disclosure can bind to a target antigen (e.g., transferrin receptor) with relatively high affinity, e.g., with a $K_D$ less than $10^{-6}$ M, $10^{-7}$ M, $10^{-8}$ M, $10^{-9}$ M, $10^{-10}$ M, $10^{-11}$ M or lower. For example, anti-transferrin receptor antibodies can bind to a transferrin receptor protein (e.g., human transferrin receptor) with an affinity between 5 pM and 500 nM, e.g., between 50 pM and 100 nM, e.g., between 500 pM and 50 nM. The disclosure also includes antibodies that compete with any of the antibodies described herein for binding to a transferrin receptor protein (e.g., human transferrin receptor) and that have an affinity of 50 nM or lower (e.g., 20 nM or lower, 10 nM or lower, 500 pM or lower, 50 pM or lower, or 5 pM or lower). The affinity and binding kinetics of the anti-transferrin receptor antibody can be tested using any suitable method including but not limited to biosensor technology (e.g., OCTET or BIACORE).

In some embodiments, the muscle-targeting agent is a transferrin receptor antibody (e.g., an antibody and variants thereof as described in International Application Publication WO 2016/081643, incorporated herein by reference).

In some embodiments, the heavy chain and light chain CDRs of an example antibody according to different definition systems are provided in Table 1.1. The different definition systems, e.g., the Kabat definition, the Chothia definition, and/or the contact definition have been described. See, e.g., (e.g., Kabat, E. A., et al. (1991) Sequences of Proteins of Immunological interest, Fifth Edition, U.S. Department of Health and Human Services, NIH Publication No. 91-3242, Chothia et al., (1989) Nature 342:877, Chothia, C. et al. (1987) J. Mol. Biol. 196:901-917, Al-lazikani et al (1997) J. Molec. Biol. 273:927-948; and Almagro, J. Mol. Recognit. 17:132-143 (2004). See also hgmp.mrc.ac.uk and bioinf.org.uk/abs).

TABLE 1.1

Heavy chain and light chain CDRs of a transferrin receptor antibody

| CDRs | Kabat | Chothia | Contact |
| --- | --- | --- | --- |
| CDR-H1 | SYWMH (SEQ ID NO: 17) | GYTFTSY (SEQ ID NO: 23) | TSYWMH (SEQ ID NO: 25) |
| CDR-H2 | EINPTNGRTNYIEKFKS (SEQ ID NO: 18) | NPTNGR (SEQ ID NO: 24) | WIGEINPTNGRTN (SEQ ID NO: 26) |
| CDR-H3 | GTRAYHY (SEQ ID NO: 19) | GTRAYHY (SEQ ID NO: 19) | ARGTRA (SEQ ID NO: 27) |
| CDR-L1 | RASDNLYSNLA (SEQ ID NO: 20) | RASDNLYSNLA (SEQ ID NO: 20) | YSNLAWY (SEQ ID NO: 28) |
| CDR-L2 | DATNLAD (SEQ ID NO: 21) | DATNLAD (SEQ ID NO: 21) | LLVYDATNLA (SEQ ID NO: 29) |
| CDR-L3 | QHFWGTPLT (SEQ ID NO: 22) | QHFWGTPLT (SEQ ID NO: 22) | QHFWGTPL (SEQ ID NO: 30) |

The heavy chain variable domain (VH) and light chain variable domain sequences are for also provided:

VH (SEQ ID NO: 33)
QVQLQQPGAELVKPGASVKLSCKASGYTFTSYWMHWVKQRPGQGLEWIGE

INPTNGRTNYIEKFKSKATLTVDKSSSTAYMQLSSLTSEDSAVYYCARGT

RAYHYWGQGTSVTVSS

-continued

VL
(SEQ ID NO: 34)
DIQMTQSPASLSVSVGETVTITCRASDNLYSNLAWYQQKQGKSPQLLVYD

ATNLADGVPSRFSGSGSGTQYSLKINSLQSEDFGTYYCQHFWGTPLTFGA

GTKLELK

In some embodiments, the transferrin receptor antibody of the present disclosure comprises a CDR-H1, a CDR-H2, and a CDR-H3 that are the same as the CDR-H1, CDR-H2, and CDR-H3 shown in Table 1.1. Alternatively or in addition, the transferrin receptor antibody of the present disclosure comprises a CDR-L1, a CDR-L2, and a CDR-L3 that are the same as the CDR-L1, CDR-L2, and CDR-L3 shown in Table 1.1.

In some embodiments, the transferrin receptor antibody of the present disclosure comprises a CDR-H1, a CDR-H2, and a CDR-H3, which collectively contains no more than 5 amino acid variations (e.g., no more than 5, 4, 3, 2, or 1 amino acid variation) as compared with the CDR-H1, CDR-H2, and CDR-H3 as shown in Table 1.1. "Collectively" means that the total number of amino acid variations in all of the three heavy chain CDRs is within the defined range. Alternatively or in addition, the transferrin receptor antibody of the present disclosure may comprise a CDR-L1, a CDR-L2, and a CDR-L3, which collectively contains no more than 5 amino acid variations (e.g., no more than 5, 4, 3, 2 or 1 amino acid variation) as compared with the CDR-L1, CDR-L2, and CDR-L3 as shown in Table 1.1.

In some embodiments, the transferrin receptor antibody of the present disclosure comprises a CDR-H1, a CDR-H2, and a CDR-H3, at least one of which contains no more than 3 amino acid variations (e.g., no more than 3, 2, or 1 amino acid variation) as compared with the counterpart heavy chain CDR as shown in Table 1.1. Alternatively or in addition, the transferrin receptor antibody of the present disclosure may comprise CDR-L1, a CDR-L2, and a CDR-L3, at least one of which contains no more than 3 amino acid variations (e.g., no more than 3, 2, or 1 amino acid variation) as compared with the counterpart light chain CDR as shown in Table 1.1.

In some embodiments, the transferrin receptor antibody of the present disclosure comprises a CDR-L3, which contains no more than 3 amino acid variations (e.g., no more than 3, 2, or 1 amino acid variation) as compared with the CDR-L3 as shown in Table 1.1. In some embodiments, the transferrin receptor antibody of the present disclosure comprises a CDR-L3 containing one amino acid variation as compared with the CDR-L3 as shown in Table 1.1. In some embodiments, the transferrin receptor antibody of the present disclosure comprises a CDR-L3 of QHFAGTPLT (SEQ ID NO: 31 according to the Kabat and Chothia definition system) or QHFAGTPL (SEQ ID NO: 32 according to the Contact definition system). In some embodiments, the transferrin receptor antibody of the present disclosure comprises a CDR-H1, a CDR-H2, a CDR-H3, a CDR-L1 and a CDR-L2 that are the same as the CDR-H1, CDR-H2, and CDR-H3 shown in Table 1.1, and comprises a CDR-L3 of QHFAGTPLT (SEQ ID NO: 31 according to the Kabat and Chothia definition system) or QHFAGTPL (SEQ ID NO: 32 according to the Contact definition system).

In some embodiments, the transferrin receptor antibody of the present disclosure comprises heavy chain CDRs that collectively are at least 80% (e.g., 80%, 85%, 90%, 95%, or 98%) identical to the heavy chain CDRs as shown in Table 1.1. Alternatively or in addition, the transferrin receptor antibody of the present disclosure comprises light chain CDRs that collectively are at least 80% (e.g., 80%, 85%, 90%, 95%, or 98%) identical to the light chain CDRs as shown in Table 1.1.

In some embodiments, the transferrin receptor antibody of the present disclosure comprises a VH comprising the amino acid sequence of SEQ ID NO: 33. Alternatively or in addition, the transferrin receptor antibody of the present disclosure comprises a VL comprising the amino acid sequence of SEQ ID NO: 34.

In some embodiments, the transferrin receptor antibody of the present disclosure comprises a VH containing no more than 20 amino acid variations (e.g., no more than 20, 19, 18, 17, 16, 15, 14, 13, 12, 11, 10, 9, 8, 7, 6, 5, 4, 3, 2, or 1 amino acid variation) as compared with the VH as set forth in SEQ ID NO: 33. Alternatively or in addition, the transferrin receptor antibody of the present disclosure comprises a VL containing no more than 15 amino acid variations (e.g., no more than 20, 19, 18, 17, 16, 15, 14, 13, 12, 11, 9, 8, 7, 6, 5, 4, 3, 2, or 1 amino acid variation) as compared with the VL as set forth in SEQ ID NO: 34.

In some embodiments, the transferrin receptor antibody of the present disclosure comprises a VH comprising an amino acid sequence that is at least 80% (e.g., 80%, 85%, 90%, 95%, or 98%) identical to the VH as set forth in SEQ ID NO: 33. Alternatively or in addition, the transferrin receptor antibody of the present disclosure comprises a VL comprising an amino acid sequence that is at least 80% (e.g., 80%, 85%, 90%, 95%, or 98%) identical to the VL as set forth in SEQ ID NO: 34.

In some embodiments, the transferrin receptor antibody of the present disclosure is a humanized antibody (e.g., a humanized variant containing one or more CDRs of Table 1.1). In some embodiments, the transferrin receptor antibody of the present disclosure comprises a CDR-H1, a CDR-H2, a CDR-H3, a CDR-L1, a CDR-L2, and a CDR-L3 that are the same as the CDR-H1, CDR-H2, and CDR-H3 shown in Table 1.1, and comprises a humanized heavy chain variable region and/or a humanized light chain variable region.

Humanized antibodies are human immunoglobulins (recipient antibody) in which residues from a complementary determining region (CDR) of the recipient are replaced by residues from a CDR of a non-human species (donor antibody) such as mouse, rat, or rabbit having the desired specificity, affinity, and capacity. In some embodiments, Fv framework region (FR) residues of the human immunoglobulin are replaced by corresponding non-human residues. Furthermore, the humanized antibody may comprise residues that are found neither in the recipient antibody nor in the imported CDR or framework sequences, but are included to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region or domain (Fc), typically that of a human immunoglobulin. Antibodies may have Fc regions modified as described in WO 99/58572. Other forms of humanized antibodies have one or more CDRs (one, two, three, four, live, six) which are altered with respect to the original antibody, which are also termed one or more CDRs derived from one or more CDRs from the original antibody. Humanized antibodies may also involve affinity maturation.

In some embodiments, humanization is achieved by grafting the CDRs (e.g., as shown in Table 1.1) into the IGKV1-NL1*01 and IGHV1-3*01 human variable domains. In some embodiments, the transferrin receptor antibody of the present disclosure is a humanized variant comprising one or more amino acid substitutions at positions 9, 13, 17, 18, 40, 45, and 70 as compared with the VL as set forth in SEQ ID NO: 34, and/or one or more amino acid substitutions at positions 1, 5, 7, 11, 12, 20, 38, 40, 44, 66, 75, 81, 83, 87, and 108 as compared with the VH as set forth in SEQ ID NO: 33. In some embodiments, the transferrin receptor antibody of the present disclosure is a humanized variant comprising amino acid substitutions at all of positions 9, 13, 17, 18, 40, 45, and 70 as compared with the VL as set forth in SEQ ID NO: 34, and/or amino acid substitutions at all of positions 1, 5, 7, 11, 12, 20, 38, 40, 44, 66, 75, 81, 83, 87, and 108 as compared with the VH as set forth in SEQ ID NO: 33.

In some embodiments, the transferrin receptor antibody of the present disclosure is a humanized antibody and contains the residues at positions 43 and 48 of the V L as set forth in SEQ ID NO: 34. Alternatively or in addition, the transferrin receptor antibody of the present disclosure is a humanized antibody and contains the residues at positions 48, 67, 69, 71, and 73 of the VH as set forth in SEQ ID NO: 33.

The VH and VL amino acid sequences of an example humanized antibody that may be used in accordance with the present disclosure are provided:

```
Humanized VH
                                          (SEQ ID NO: 35)
EVQLVQSGAEVKKPGASVKVSCKASGYTFTSYWMHWVRQAPGQRLEWIGE

INPTNGRTNYIEKFKSRATLTVDKSASTAYMELSSLRSEDTAVYYCARGT

RAYHYWGQGTMVTVSS

Humanized VL
                                          (SEQ ID NO: 36)
DIQMTQSPSSLSASVGDRVTITCRASDNLYSNLAWYQQKPGKSPKLLVYD

ATNLADGVPSRFSGSGSGTDYSLKINSLQSEDFGTYYCQHFWGTPLTFGA

GTKLELK
```

In some embodiments, the transferrin receptor antibody of the present disclosure comprises a VH comprising the amino acid sequence of SEQ ID NO: 35. Alternatively or in addition, the transferrin receptor antibody of the present disclosure comprises a VL comprising the amino acid sequence of SEQ ID NO: 36.

In some embodiments, the transferrin receptor antibody of the present disclosure comprises a VH containing no more than 20 amino acid variations (e.g., no more than 20, 19, 18, 17, 16, 15, 14, 13, 12, 11, 10, 9, 8, 7, 6, 5, 4, 3, 2, or 1 amino acid variation) as compared with the VH as set forth in SEQ ID NO: 35. Alternatively or in addition, the transferrin receptor antibody of the present disclosure comprises a VL containing no more than 15 amino acid variations (e.g., no more than 20, 19, 18, 17, 16, 15, 14, 13, 12, 11, 9, 8, 7, 6, 5, 4, 3, 2, or 1 amino acid variation) as compared with the V L as set forth in SEQ ID NO: 36.

In some embodiments, the transferrin receptor antibody of the present disclosure comprises a VH comprising an amino acid sequence that is at least 80% (e.g., 80%, 85%, 90%, 95%, or 98%) identical to the VH as set forth in SEQ ID NO: 35. Alternatively or in addition, the transferrin receptor antibody of the present disclosure comprises a VL comprising an amino acid sequence that is at least 80% (e.g., 80%, 85%, 90%, 95%, or 98%) identical to the VL as set forth in SEQ ID NO: 36.

In some embodiments, the transferrin receptor antibody of the present disclosure is a humanized variant comprising amino acid substitutions at one or more of positions 43 and 48 as compared with the VL as set forth in SEQ ID NO: 34, and/or amino acid substitutions at one or more of positions 48, 67, 69, 71, and 73 as compared with the VH as set forth in SEQ ID NO: 33. In some embodiments, the transferrin receptor antibody of the present disclosure is a humanized variant comprising a S43A and/or a V48L mutation as compared with the VL as set forth in SEQ ID NO: 34, and/or one or more of A67V, L69I, V71R, and K73T mutations as compared with the VH as set forth in SEQ ID NO: 33

In some embodiments, the transferrin receptor antibody of the present disclosure is a humanized variant comprising amino acid substitutions at one or more of positions 9, 13, 17, 18, 40, 43, 48, 45, and 70 as compared with the VL as set forth in SEQ ID NO: 34, and/or amino acid substitutions at one or more of positions 1, 5, 7, 11, 12, 20, 38, 40, 44, 48, 66, 67, 69, 71, 73, 75, 81, 83, 87, and 108 as compared with the VH as set forth in SEQ ID NO: 33.

In some embodiments, the transferrin receptor antibody of the present disclosure is a chimeric antibody, which can include a heavy constant region and a light constant region from a human antibody. Chimeric antibodies refer to antibodies having a variable region or part of variable region from a first species and a constant region from a second species. Typically, in these chimeric antibodies, the variable region of both light and heavy chains mimics the variable regions of antibodies derived from one species of mammals (e.g., a non-human mammal such as mouse, rabbit, and rat), while the constant portions are homologous to the sequences in antibodies derived from another mammal such as human. In some embodiments, amino acid modifications can be made in the variable region and/or the constant region.

In some embodiments, the transferrin receptor antibody described herein is a chimeric antibody, which can include a heavy constant region and a light constant region from a human antibody. Chimeric antibodies refer to antibodies having a variable region or part of variable region from a first species and a constant region from a second species. Typically, in these chimeric antibodies, the variable region of both light and heavy chains mimics the variable regions of antibodies derived from one species of mammals (e.g., a non-human mammal such as mouse, rabbit, and rat), while the constant portions are homologous to the sequences in antibodies derived from another mammal such as human. In some embodiments, amino acid modifications can be made in the variable region and/or the constant region.

In some embodiments, the heavy chain of any of the transferrin receptor antibodies as described herein may comprises a heavy chain constant region (CH) or a portion thereof (e.g., CH1. CH2, CH3, or a combination thereof). The heavy chain constant region can of any suitable origin, e.g., human, mouse, rat, or rabbit. In one specific example, the heavy chain constant region is from a human IgG (a gamma heavy chain), e.g., IgG1, IgG2, or IgG4. An exemplary human IgG1 constant region is given below:

```
                                          (SEQ ID NO: 37)
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEP
```

```
KSCDKTHTCPPCPAPELLGGPSVFLFPPKPKDTLMISRTPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVYTLPPSRDELTKNQVSLTC

LVKGFYPSDIAVEWESNGQPENNYKTTPPVLDSDGSFFLYSKLTVDKSRW

QQGNVFSCSVMHEALHNHYTQKSLSLSPGK
```

In some embodiments, the light chain of any of the transferrin receptor antibodies described herein may further comprise a light chain constant region (CL), which can be any CL known in the art. In some examples, the CL is a kappa light chain. In other examples, the CL is a lambda light chain. In some embodiments, the CL is a kappa light chain, the sequence of which is provided below:

```
                                      (SEQ ID NO: 38)
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEP

KSCDKTHTCP
```

Other antibody heavy and light chain constant regions are well known in the art, e.g., those provided in the IMGT database (www.imgt.org) or at www.vbase2.org/vbstat.php., both of which are incorporated by reference herein.

Exemplary heavy chain and light chain amino acid sequences of the transferrin receptor antibodies described are provided below:

```
Heavy Chain (VH + human IgG1 constant region)
                                      (SEQ ID NO: 39)
QVQLQQPGAELVKPGASVKLSCKASGYTFTSYWMHWVKQRPGQGLEWIGE

INPTNGRTNYIEKFKSKATLTVDKSSSTAYMQLSSLTSEDSAVYYCARGT

RAYHYWGQGTSVTVSSASTKGPSVFPLAPSSKSTSGGTAALGCLVKDYFP

EPVTVSWNSGALTSGVHTFPAVLQSSGLYSLSSVVTVPSSSLGTQTYICN

VNHKPSNTKVDKKVEPKSCDKTHTCPPCPAPELLGGPSVFLFPPKPKDTL

MISRTPEVTCVVVDVSHEDPEVKFNWYVDGVEVHNAKTKPREEQYNSTYR

VVSVLTVLHQDWLNGKEYKCKVSNKALPAPIEKTISKAKGQPREPQVYTL

PPSRDELTKNQVSLTCLVKGFYPSDIAVEWESNGQPENNYKTTPPVLDSD

GSFFLYSKLTVDKSRWQQGNVFSCSVMHEALHNHYTQKSLSLSPGK

Light Chain (VL + kappa light chain)
                                      (SEQ ID NO: 40)
QVQLQQPGAELVKPGASVKLSCKASGYTFTSYWMHWVKQRPGQGLEWIGE

INPTNGRTNYIEKFKSKATLTVDKSSSTAYMQLSSLTSEDSAVYYCARGT

RAYHYWGQGTSVTVSSASTKGPSVFPLAPSSKSTSGGTAALGCLVKDYFP

EPVTVSWNSGALTSGVHTFPAVLQSSGLYSLSSVVTVPSSSLGTQTYICN

VNHKPSNTKVDKKVEPKSCDKTHTCP

Heavy Chain (humanized VH + human IgG1 constant
region)
                                      (SEQ ID NO: 41)
EVQLVQSGAEVKKPGASVKVSCKASGYTFTSYWMHWVRQAPGQRLEWIGE

INPTNGRTNYIEKFKSRATLTVDKSASTAYMELSSLRSEDTAVYYCARGT

RAYHYWGQGTMVTVSSASTKGPSVFPLAPSSKSTSGGTAALGCLVKDYFP

EPVTVSWNSGALTSGVHTFPAVLQSSGLYSLSSVVTVPSSSLGTQTYICN

VNHKPSNTKVDKKVEPKSCDKTHTCPPCPAPELLGGPSVFLFPPKPKDTL

MISRTPEVTCVVVDVSHEDPEVKFNWYVDGVEVHNAKTKPREEQYNSTYR

VVSVLTVLHQDWLNGKEYKCKVSNKALPAPIEKTISKAKGQPREPQVYTL

PPSRDELTKNQVSLTCLVKGFYPSDIAVEWESNGQPENNYKTTPPVLDSD

GSFFLYSKLTVDKSRWQQGNVFSCSVMHEALHNHYTQKSLSLSPGK

Light Chain (humanized VL + kappa light chain)
                                      (SEQ ID NO: 42)
DIQMTQSPSSLSASVGDRVTITCRASDNLYSNLAWYQQKPGKSPKLLVYD

ATNLADGVPSRFSGSGSGTDYSLKINSLQSEDFGTYYCQHFWGTPLTFGA

GTKLELKASTKGPSVFPLAPSSKSTSGGTAALGCLVKDYFPEPVTVSWNS

GALTSGVHTFPAVLQSSGLYSLSSVVTVPSSSLGTQTYICNVNHKPSNTK

VDKKVEPKSCDKTHTCP
```

In some embodiments, the transferrin receptor antibody described herein comprises a heavy chain comprising an amino acid sequence that is at least 80% (e.g., 80%, 85%, 90%, 95%, or 98%) identical to SEQ ID NO: 39. Alternatively or in addition, the transferrin receptor antibody described herein comprises a light chain comprising an amino acid sequence that is at least 80% (e.g., 80%, 85%, 90%, 95%, or 98%) identical to SEQ ID NO: 40. In some embodiments, the transferrin receptor antibody described herein comprises a heavy chain comprising the amino acid sequence of SEQ ID NO: 39. Alternatively or in addition, the transferrin receptor antibody described herein comprises a light chain comprising the amino acid sequence of SEQ ID NO: 40.

In some embodiments, the transferrin receptor antibody of the present disclosure comprises a heavy chain containing no more than 20 amino acid variations (e.g., no more than 20, 19, 18, 17, 16, 15, 14, 13, 12, 11, 10, 9, 8, 7, 6, 5, 4, 3, 2, or 1 amino acid variation) as compared with the heavy chain as set forth in SEQ ID NO: 39. Alternatively or in addition, the transferrin receptor antibody of the present disclosure comprises a light chain containing no more than 15 amino acid variations (e.g., no more than 20, 19, 18, 17, 16, 15, 14, 13, 12, 11, 9, 8, 7, 6, 5, 4, 3, 2, or 1 amino acid variation) as compared with the light chain as set forth in SEQ ID NO: 40.

In some embodiments, the transferrin receptor antibody described herein comprises a heavy chain comprising an amino acid sequence that is at least 80% (e.g., 80%, 85%, 90%, 95%, or 98%) identical to SEQ ID NO: 41. Alternatively or in addition, the transferrin receptor antibody described herein comprises a light chain comprising an amino acid sequence that is at least 80% (e.g., 80%, 85%, 90%, 95%, or 98%) identical to SEQ ID NO: 42. In some embodiments, the transferrin receptor antibody described herein comprises a heavy chain comprising the amino acid sequence of SEQ ID NO: 41. Alternatively or in addition, the transferrin receptor antibody described herein comprises a light chain comprising the amino acid sequence of SEQ ID NO: 42.

In some embodiments, the transferrin receptor antibody of the present disclosure comprises a heavy chain containing no more than 20 amino acid variations (e.g., no more than 20, 19, 18, 17, 16, 15, 14, 13, 12, 11, 10, 9, 8, 7, 6, 5, 4, 3, 2, or 1 amino acid variation) as compared with the heavy chain of a humanized sequence as set forth in SEQ ID NO: 39. Alternatively or in addition, the transferrin receptor antibody of the present disclosure comprises a light chain containing no more than 15 amino acid variations (e.g., no more than 20, 19, 18, 17, 16, 15, 14, 13, 12, 11, 9, 8, 7, 6, 5, 4, 3, 2, or 1 amino acid variation) as compared with the light chain of a humanized sequence as set forth in SEQ ID NO: 40.

In some embodiments, the transferrin receptor antibody is an antigen binding fragment (FAB) of an intact antibody (full-length antibody). Antigen binding fragment of an intact antibody (full-length antibody) can be prepared via routine methods. For example, F(ab')$_2$ fragments can be produced by pepsin digestion of an antibody molecule, and Fab fragments that can be generated by reducing the disulfide bridges of F(ab')$_2$ fragments. Exemplary FABs amino acid sequences of the transferrin receptor antibodies described herein are provided below:

```
Heavy Chain FAB (VH + a portion of human IgG1
constant region)
                                    (SEQ ID NO: 43)
QVQLQQPGAELVKPGASVKLSCKASGYTFTSYWMHWVKQRPGQGLEWIGE

INPTNGRTNYIEKFKSKATLTVDKSSSTAYMQLSSLTSEDSAVYYCARGT

RAYHYWGQGTSVTVSSASTKGPSVFPLAPSSKSTSGGTAALGCLVKDYFP

EPVTVSWNSGALTSGVHTFPAVLQSSGLYSLSSVVTVPSSSLGTQTYICN

VNHKPSNTKVDKKVEPKSCDKTHTCP

Heavy Chain FAB (humanized VH + a portion of
human IgGI constant region)
                                    (SEQ ID NO: 44)
EVQLVQSGAEVKKPGASVKVSCKASGYTFTSYWMHWVRQAPGQRLEWIGE

INPTNGRTNYIEKFKSRATLTVDKSASTAYMELSSLRSEDTAVYYCARGT

RAYHYWGQGTMVTVSSASTKGPSVFPLAPSSKSTSGGTAALGCLVKDYFP

EPVTVSWNSGALTSGVHTFPAVLQSSGLYSLSSVVTVPSSSLGTQTYICN

VNHKPSNTKVDKKVEPKSCDKTHTCP
```

The transferrin receptor antibodies described herein can be in any antibody form, including, but not limited to, intact (i.e., full-length) antibodies, antigen-binding fragments thereof (such as Fab, Fab', F(ab')$_2$, Fv), single chain antibodies, bi-specific antibodies, or nanobodies. In some embodiments, the transferrin receptor antibody described herein is a scFv. In some embodiments, the transferrin receptor antibody described herein is a scFv-Fab (e.g., scFv fused to a portion of a constant region). In some embodiments, the transferrin receptor antibody described herein is a scFv fused to a constant region (e.g., human IgG1 constant region as set forth in SEQ ID NO: 39).

b. Other Muscle-Targeting Antibodies

In some embodiments, the muscle-targeting antibody is an antibody that specifically binds hemojuvelin, caveolin-3, Duchenne muscular dystrophy peptide, myosin lib, or CD63. In some embodiments, the muscle-targeting antibody is an antibody that specifically binds a myogenic precursor protein. Exemplary myogenic precursor proteins include, without limitation, ABCG2, M-Cadherin/Cadherin-15, Caveolin-1, CD34, FoxK1, Integrin alpha 7, Integrin alpha 7 beta 1, MYF-5, MyoD, Myogenin, NCAM-1/CD56, Pax3, Pax7, and Pax9. In some embodiments, the muscle-targeting antibody is an antibody that specifically binds a skeletal muscle protein. Exemplary skeletal muscle proteins include, without limitation, alpha-Sarcoglycan, beta-Sarcoglycan, Calpain Inhibitors, Creatine Kinase MM/CKMM, eIF5A, Enolase 2/Neuron-specific Enolase, epsilon-Sarcoglycan, FABP3/H-FABP, GDF-8/Myostatin, GDF-11/GDF-8, Integrin alpha 7, Integrin alpha 7 beta 1, Integrin beta 1/CD29, MCAM/CD146, MyoD, Myogenin, Myosin Light Chain Kinase Inhibitors, NCAM-1/CD56, and Troponin 1. In some embodiments, the muscle-targeting antibody is an antibody that specifically binds a smooth muscle protein. Exemplary smooth muscle proteins include, without limitation, alpha-Smooth Muscle Actin, VE-Cadherin, Caldesmon/CALD1, Calponin 1, Desmin, Histamine H2 R, Motilin R/GPR38, Transgelin/TAGLN, and Vimentin. However, it should be appreciated that antibodies to additional targets are within the scope of this disclosure and the exemplary lists of targets provided herein are not meant to be limiting.

c. Antibody Features/Alterations

In some embodiments, conservative mutations can be introduced into antibody sequences (e.g., CDRs or framework sequences) at positions where the residues are not likely to be involved in interacting with a target antigen (e.g., transferrin receptor), for example, as determined based on a crystal structure. In some embodiments, one, two or more mutations (e.g., amino acid substitutions) are introduced into the Fc region of a muscle-targeting antibody described herein (e.g., in a CH2 domain (residues 231-340 of human IgG1) and/or CH3 domain (residues 341-447 of human IgG1) and/or the hinge region, with numbering according to the Kabat numbering system (e.g., the EU index in Kabat)) to alter one or more functional properties of the antibody, such as serum half-life, complement fixation. Fc receptor binding and/or antigen-dependent cellular cytotoxicity.

In some embodiments, one, two or more mutations (e.g., amino acid substitutions) are introduced into the hinge region of the Fc region (CH1 domain) such that the number of cysteine residues in the hinge region are altered (e.g., increased or decreased) as described in, e.g., U.S. Pat. No. 5,677,425. The number of cysteine residues in the hinge region of the CH1 domain can be altered to, e.g., facilitate assembly of the light and heavy chains, or to alter (e.g., increase or decrease) the stability of the antibody or to facilitate linker conjugation.

In some embodiments, one, two or more mutations (e.g., amino acid substitutions) are introduced into the Fc region of a muscle-targeting antibody described herein (e.g., in a CH2 domain (residues 231-340 of human IgG1) and/or CH3 domain (residues 341-447 of human IgG1) and/or the hinge region, with numbering according to the Kabat numbering system (e.g., the EU index in Kabat)) to increase or decrease the affinity of the antibody for an Fc receptor (e.g., an activated Fc receptor) on the surface of an effector cell. Mutations in the Fc region of an antibody that decrease or increase the affinity of an antibody for an Fc receptor and techniques for introducing such mutations into the Fc receptor or fragment thereof are known to one of skill in the art. Examples of mutations in the Fc receptor of an antibody that can be made to alter the affinity of the antibody for an Fc receptor are described in, e.g., Smith P et al., (2012) PNAS 109: 6181-6186, U.S. Pat. No. 6,737,056, and International Publication Nos. WO 02/060919; WO 98/23289; and WO 97/34631, which are incorporated herein by reference.

In some embodiments, one, two or more amino acid mutations (i.e., substitutions, insertions or deletions) are introduced into an IgG constant domain, or FcRn-binding fragment thereof (preferably an Fc or hinge-Fc domain fragment) to alter (e.g., decrease or increase) half-life of the antibody in vivo. See, e.g., International Publication Nos. WO 02/060919: WO 98/23289; and WO 97/34631; and U.S. Pat. Nos. 5,869,046, 6,121,022, 6,277,375 and 6,165.745 for examples of mutations that will alter (e.g., decrease or increase) the half-life of an antibody in vivo.

In some embodiments, one, two or more amino acid mutations (i.e., substitutions, insertions or deletions) are introduced into an IgG constant domain, or FcRn-binding fragment thereof (preferably an Fc or hinge-Fc domain fragment) to decrease the half-life of the anti-transferrin receptor antibody in vivo. In some embodiments, one, two or more amino acid mutations (i.e., substitutions, insertions or deletions) are introduced into an IgG constant domain, or FcRn-binding fragment thereof (preferably an Fc or hinge-Fc domain fragment) to increase the half-life of the antibody in vivo. In some embodiments, the antibodies can have one or more amino acid mutations (e.g., substitutions) in the second constant (CH2) domain (residues 231-340 of human IgG1) and/or the third constant (CH3) domain (residues 341-447 of human IgG1), with numbering according to the EU index in Kabat (Kabat E A et al., (1991) supra). In some embodiments, the constant region of the IgG1 of an antibody described herein comprises a methionine (M) to tyrosine (Y) substitution in position 252, a serine (S) to threonine (T) substitution in position 254, and a threonine (T) to glutamic acid (E) substitution in position 256, numbered according to the EU index as in Kabat. See U.S. Pat. No. 7,658,921, which is incorporated herein by reference. This type of mutant IgG, referred to as "YTE mutant" has been shown to display fourfold increased half-life as compared to wild-type versions of the same antibody (see Dall'Acqua W F et al., (2006) J Biol Chem 281: 23514-24). In some embodiments, an antibody comprises an IgG constant domain comprising one, two, three or more amino acid substitutions of amino acid residues at positions 251-257, 285-290, 308-314, 385-389, and 428-436, numbered according to the EU index as in Kabat.

In some embodiments, one, two or more amino acid substitutions are introduced into an IgG constant domain Fc region to alter the effector function(s) of the anti-transferrin receptor antibody. The effector ligand to which affinity is altered can be, for example, an Fc receptor or the C1 component of complement. This approach is described in further detail in U.S. Pat. Nos. 5,624,821 and 5,648,260. In some embodiments, the deletion or inactivation (through point mutations or other means) of a constant region domain can reduce Fc receptor binding of the circulating antibody thereby increasing tumor localization. See, e.g., U.S. Pat. Nos. 5,585,097 and 8,591,886 for a description of mutations that delete or inactivate the constant domain and thereby increase tumor localization. In some embodiments, one or more amino acid substitutions may be introduced into the Fc region of an antibody described herein to remove potential glycosylation sites on Fc region, which may reduce Fc receptor binding (see, e.g., Shields R L et al., (2001) J Biol Chem 276: 6591-604).

In some embodiments, one or more amino in the constant region of a muscle-targeting antibody described herein can be replaced with a different amino acid residue such that the antibody has altered C1q binding and/or reduced or abolished complement dependent cytotoxicity (CDC). This approach is described in further detail in U.S. Pat. No. 6,194,551 (Idusogie et al). In some embodiments, one or more amino acid residues in the N-terminal region of the CH2 domain of an antibody described herein are altered to thereby alter the ability of the antibody to fix complement. This approach is described further in International Publication No. WO 94/29351. In some embodiments, the Fc region of an antibody described herein is modified to increase the ability of the antibody to mediate antibody dependent cellular cytotoxicity (ADCC) and/or to increase the affinity of the antibody for an Fcy receptor. This approach is described further in International Publication No. WO 00/42072.

In some embodiments, the heavy and/or light chain variable domain(s) sequence(s) of the antibodies provided herein can be used to generate, for example, CDR-grafted, chimeric, humanized, or composite human antibodies or antigen-binding fragments, as described elsewhere herein. As understood by one of ordinary skill in the art, any variant, CDR-grafted, chimeric, humanized, or composite antibodies derived from any of the antibodies provided herein may be useful in the compositions and methods described herein and will maintain the ability to specifically bind transferrin receptor, such that the variant, CDR-grafted, chimeric, humanized, or composite antibody has at least 50%, at least 60%, at least 70%, at least 80%, at least 90%, at least 95% or more binding to transferrin receptor relative to the original antibody from which it is derived.

In some embodiments, the antibodies provided herein comprise mutations that confer desirable properties to the antibodies. For example, to avoid potential complications due to Fab-arm exchange, which is known to occur with native IgG4 mAbs, the antibodies provided herein may comprise a stabilizing 'Adair' mutation (Angal S., et al., "A single amino acid substitution abolishes the heterogeneity of chimeric mouse/human (IgG4) antibody," Mol Immunol 30, 105-108; 1993), where serine 228 (EU numbering; residue 241 Kabat numbering) is converted to proline resulting in an IgG1-like hinge sequence. Accordingly, any of the antibodies may include a stabilizing 'Adair' mutation.

As provided herein, antibodies of this disclosure may optionally comprise constant regions or parts thereof. For example, a VL domain may be attached at its C-terminal end to a light chain constant domain like Cκ or Cλ. Similarly, a VH domain or portion thereof may be attached to all or part of a heavy chain like IgA, IgD, IgE, IgG, and IgM, and any isotype subclass. Antibodies may include suitable constant regions (see, for example, Kabat et al., Sequences of Proteins of Immunological Interest, No. 91-3242, National Institutes of Health Publications, Bethesda, Md. (1991)). Therefore, antibodies within the scope of this may disclosure include VH and VL domains, or an antigen binding portion thereof, combined with any suitable constant regions.

ii. Muscle-Targeting Peptides

Some aspects of the disclosure provide muscle-targeting peptides as muscle-targeting agents. Short peptide sequences (e.g., peptide sequences of 5-20 amino acids in length) that bind to specific cell types have been described. For example, cell-targeting peptides have been described in Vines e., et al., A. "Cell-penetrating and cell-targeting peptides in drug delivery" *Biochim Biophys Acta* 2008, 1786: 126-38; Jarver P., et al., "In vivo biodistribution and efficacy of peptide mediated delivery" *Trends Pharmacol Sci* 2010; 31: 528-35; Samoylova T. I., et al., "Elucidation of muscle-binding peptides by phage display screening" *Muscle Nerve* 1999; 22: 460-6: U.S. Pat. No. 6,329,501, issued on Dec. 11, 2001, entitled "METHODS AND COMPOSITIONS FOR TARGETING COMPOUNDS TO MUSCLE"; and Samoylov A. M., et al., "Recognition of cell-specific binding of phage display derived peptides using an acoustic wave sensor." *Biomol Eng* 2002; 18: 269-72; the entire contents of each of which are incorporated herein by reference. By designing peptides to interact with specific cell surface antigens (e.g., receptors), selectivity for a desired tissue, e.g., muscle, can be achieved. Skeletal muscle-targeting has been investigated and a range of molecular payloads are able to be delivered. These approaches may have high selectivity for muscle tissue without many of the practical disadvantages of a large antibody or viral particle. Accordingly, in some embodiments, the muscle-targeting agent is a muscle-targeting peptide that is from 4 to 50 amino acids in length. In some embodiments, the muscle-targeting peptide is 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 amino acids in length. Muscle-targeting peptides can be generated using any of several methods, such as phage display.

In some embodiments, a muscle-targeting peptide may bind to an internalizing cell surface receptor that is overexpressed or relatively highly expressed in muscle cells, e.g. a transferrin receptor, compared with certain other cells. In some embodiments, a muscle-targeting peptide may target, e.g., bind to, a transferrin receptor. In some embodiments, a peptide that targets a transferrin receptor may comprise a segment of a naturally occurring ligand, e.g., transferrin. In some embodiments, a peptide that targets a transferrin receptor is as described in U.S. Pat. No. 6,743,893, filed Nov. 30, 2000, "RECEPTOR-MEDIATED UPTAKE OF PEPTIDES THAT BIND THE HUMAN TRANSFERRIN RECEPTOR". In some embodiments, a peptide that targets a transferrin receptor is as described in Kawamoto, M. et al, "A novel transferrin receptor-targeted hybrid peptide disintegrates cancer cell membrane to induce rapid killing of cancer cells." BMC Cancer. 2011 Aug. 18; 11:359. In some embodiments, a peptide that targets a transferrin receptor is as described in U.S. Pat. No. 8,399,653, filed May 20, 2011, "TRANSFERRIN/TRANSFERRIN RECEPTOR-MEDIATED SIRNA DELIVERY".

As discussed above, examples of muscle targeting peptides have been reported. For example, muscle-specific peptides were identified using phage display library presenting surface heptapeptides. As one example a peptide having the amino acid sequence ASSLNIA (SEQ ID NO: 6) bound to C2C12 murine myotubes in vitro, and bound to mouse muscle tissue in vivo. Accordingly, in some embodiments, the muscle-targeting agent comprises the amino acid sequence ASSLNIA (SEQ ID NO: 6). This peptide displayed improved specificity for binding to heart and skeletal muscle tissue after intravenous injection in mice with reduced binding to liver, kidney, and brain. Additional muscle-specific peptides have been identified using phage display. For example, a 12 amino acid peptide was identified by phage display library for muscle targeting in the context of treatment for DMD. See, Yoshida D., et al., "Targeting of salicylate to skin and muscle following topical injections in rats." *Int J Pharm* 2002; 231: 177-84; the entire contents of which are hereby incorporated by reference. Here, a 12 amino acid peptide having the sequence SKTFNTHPQSTP (SEQ ID NO: 7) was identified and this muscle-targeting peptide showed improved binding to C2C12 cells relative to the ASSLNIA (SEQ ID NO: 6) peptide.

An additional method for identifying peptides selective for muscle (e.g., skeletal muscle) over other cell types includes in vitro selection, which has been described in Ghosh D., et al., "Selection of muscle-binding peptides from context-specific peptide-presenting phage libraries for adenoviral vector targeting" *J Virol* 2005; 79: 13667-72; the entire contents of which are incorporated herein by reference. By pre-incubating a random 12-mer peptide phage display library with a mixture of non-muscle cell types, non-specific cell binders were selected out. Following rounds of selection the 12 amino acid peptide TARGEHKEEELI (SEQ ID NO: 8) appeared most frequently. Accordingly, in some embodiments, the muscle-targeting agent comprises the amino acid sequence TARGEHKEEELI (SEQ ID NO: 8).

A muscle-targeting agent may an amino acid-containing molecule or peptide. A muscle-targeting peptide may correspond to a sequence of a protein that preferentially binds to a protein receptor found in muscle cells. In some embodiments, a muscle-targeting peptide contains a high propensity of hydrophobic amino acids, e.g. valine, such that the peptide preferentially targets muscle cells. In some embodiments, a muscle-targeting peptide has not been previously characterized or disclosed. These peptides may be conceived of, produced, synthesized, and/or derivatized using any of several methodologies, e.g. phage displayed peptide libraries, one-bead one-compound peptide libraries, or positional scanning synthetic peptide combinatorial libraries. Exemplary methodologies have been characterized in the art and are incorporated by reference (Gray, B. P. and Brown, K. C. "Combinatorial Peptide Libraries: Mining for Cell-Binding Peptides" Chem Rev. 2014, 114:2, 1020-1081.; Samoylova, T. I. and Smith, B. F. "Elucidation of muscle-binding peptides by phage display screening." Muscle Nerve, 1999, 22:4, 460-6.). In some embodiments, a muscle-targeting peptide has been previously disclosed (see, e.g. Writer M. J. et al. "Targeted gene delivery to human airway epithelial cells with synthetic vectors incorporating novel targeting peptides selected by phage display." J. Drug Targeting. 2004; 12:185; Cai, D. "BDNF-mediated enhancement of inflammation and injury in the aging heart." Physiol Genomics. 2006, 24:3, 191-7.; Zhang, L. "Molecular profiling of heart endothelial cells." Circulation, 2005, 112:11, 1601-11.; McGuire, M. J. et al. "In vitro selection of a peptide with high selectivity for cardiomyocytes in vivo." J Mol Biol. 2004, 342:1, 171-82.). Exemplary muscle-targeting peptides comprise an amino acid sequence of the following group: CQAQGQLVC (SEQ ID NO: 9), CSERSMNFC (SEQ ID NO: 10), CPKTRRVPC (SEQ ID NO: 11), WLSEAGPVVTVRALRGTGSW (SEQ ID NO: 12), ASSLNIA (SEQ ID NO: 6), CMQHSMRVC (SEQ ID NO: 13), and DDTRHWG (SEQ ID NO: 14). In some embodiments, a muscle-targeting peptide may comprise about 2-25 amino acids, about 2-20 amino acids, about 2-15 amino acids, about 2-10 amino acids, or about 2-5 amino acids. Muscle-targeting peptides may comprise naturally-occurring amino acids, e.g. cysteine, alanine, or non-naturally-occurring or modified amino acids. Non-naturally occurring amino acids include β-amino acids, homo-amino acids, proline derivatives, 3-substituted alanine derivatives, linear core amino acids, N-methyl amino acids, and others known in the art. In some embodiments, a muscle-targeting peptide may be linear; in other embodiments, a muscle-targeting peptide may be cyclic, e.g. bicyclic (see, e.g. Silvana, M. G. et al. Mol. Therapy, 2018, 26:1, 132-147.).

iii. Muscle-Targeting Receptor Ligands

A muscle-targeting agent may be a ligand, e.g. a ligand that binds to a receptor protein. A muscle-targeting ligand may be a protein, e.g. transferrin, which binds to an internalizing cell surface receptor expressed by a muscle cell. Accordingly, in some embodiments, the muscle-targeting agent is transferrin, or a derivative thereof that binds to a transferrin receptor. A muscle-targeting ligand may alternatively be a small molecule, e.g. a lipophilic small molecule that preferentially targets muscle cells relative to other cell types. Exemplary lipophilic small molecules that may target muscle cells include compounds comprising cholesterol, cholesteryl, stearic acid, palmitic acid, oleic acid, oleyl, linolene, linoleic acid, myristic acid, sterols, dihydrotestosterone, testosterone derivatives, glycerine, alkyl chains, trityl groups, and alkoxy acids.

iv. Muscle-Targeting Aptamers

A muscle-targeting agent may be an aptamer, e.g. an RNA aptamer, which preferentially targets muscle cells relative to other cell types. In some embodiments, a muscle-targeting aptamer has not been previously characterized or disclosed. These aptamers may be conceived of, produced, synthesized, and/or derivatized using any of several methodologies, e.g. Systematic Evolution of Ligands by Exponential Enrichment. Exemplary methodologies have been characterized in the art and are incorporated by reference (Yan, A. C. and Levy, M. "Aptamers and aptamer targeted delivery" RNA biology, 2009, 6:3, 316-20.; Germer, K. et al. "RNA aptamers and their therapeutic and diagnostic applications." Int. J. Biochem. Mol. Biol. 2013; 4: 27-40.). In some embodiments, a muscle-targeting aptamer has been previously disclosed (see, e.g. Phillippou, S. et al. "Selection and Identification of Skeletal-Muscle-Targeted RNA Aptamers." Mol Ther Nucleic Acids. 2018, 10:199-214.; Thiel, W. H. et al. "Smooth Muscle Cell-targeted RNA Aptamer Inhibits Neointimal Formation." Mol Ther. 2016, 24:4, 779-87.). Exemplary muscle-targeting aptamers include the A01B RNA aptamer and RNA Apt 14. In some embodiments, an aptamer is a nucleic acid-based aptamer, an oligonucleotide aptamer or a peptide aptamer. In some embodiments, an aptamer may be about 5-15 kDa, about 5-10 kDa, about 10-15 kDa, about 1-5 Da, about 1-3 kDa, or smaller.

v. Other Muscle-Targeting Agents

One strategy for targeting a muscle cell (e.g., a skeletal muscle cell) is to use a substrate of a muscle transporter protein, such as a transporter protein expressed on the sarcolemma. In some embodiments, the muscle-targeting agent is a substrate of an influx transporter that is specific to muscle tissue. In some embodiments, the influx transporter is specific to skeletal muscle tissue. Two main classes of transporters are expressed on the skeletal muscle sarcolemma, (1) the adenosine triphosphate (ATP) binding cassette (ABC) superfamily, which facilitate efflux from skeletal muscle tissue and (2) the solute carrier (SLC) superfamily, which can facilitate the influx of substrates into skeletal muscle. In some embodiments, the muscle-targeting agent is a substrate that binds to an ABC superfamily or an SLC superfamily of transporters. In some embodiments, the substrate that binds to the ABC or SLC superfamily of transporters is a naturally-occurring substrate. In some embodiments, the substrate that binds to the ABC or SLC superfamily of transporters is a non-naturally occurring substrate, for example, a synthetic derivative thereof that binds to the ABC or SLC superfamily of transporters.

In some embodiments, the muscle-targeting agent is a substrate of an SLC superfamily of transporters. SLC transporters are either equilibrative or use proton or sodium ion gradients created across the membrane to drive transport of substrates. Exemplary SLC transporters that have high skeletal muscle expression include, without limitation, the SATT transporter (ASCT1; SLC1A4), GLUT4 transporter (SLC2A4), GLUT7 transporter (GLUT7; SLC2A7), ATRC2 transporter (CAT-2; SLC7A2), LAT3 transporter (KIAA0245; SLC7A6), PHT1 transporter (PTR4; SLC15A4), OATP-J transporter (OATP5A1; SLC21A15), OCT3 transporter (EMT; SLC22A3), OCTN2 transporter (FU46769; SLC22A5), ENT transporters (ENT1; SLC29A1 and ENT2; SLC29A2), PAT2 transporter (SLC36A2), and SAT2 transporter (KIAA1382; SLC38A2). These transporters can facilitate the influx of substrates into skeletal muscle, providing opportunities for muscle targeting.

In some embodiments, the muscle-targeting agent is a substrate of an equilibrative nucleoside transporter 2 (ENT2) transporter. Relative to other transporters, ENT2 has one of the highest mRNA expressions in skeletal muscle. While human ENT2 (hENT2) is expressed in most body organs such as brain, heart, placenta, thymus, pancreas, prostate, and kidney, it is especially abundant in skeletal muscle. Human ENT2 facilitates the uptake of its substrates depending on their concentration gradient. ENT2 plays a role in maintaining nucleoside homeostasis by transporting a wide range of purine and pyrimidine nucleobases. The hENT2 transporter has a low affinity for all nucleosides (adenosine, guanosine, uridine, thymidine, and cytidine) except for inosine. Accordingly, in some embodiments, the muscle-targeting agent is an ENT2 substrate. Exemplary ENT2 substrates include, without limitation, inosine, 2',3'-dideoxyinosine, and calofarabine. In some embodiments, any of the muscle-targeting agents provided herein are associated with a molecular payload (e.g., oligonucleotide payload). In some embodiments, the muscle-targeting agent is covalently linked to the molecular payload. In some embodiments, the muscle-targeting agent is non-covalently linked to the molecular payload.

In some embodiments, the muscle-targeting agent is a substrate of an organic cation/carnitine transporter (OCTN2), which is a sodium ion-dependent, high affinity carnitine transporter. In some embodiments, the muscle-targeting agent is carnitine, mildronate, acetylcarnitine, or any derivative thereof that binds to OCTN2. In some embodiments, the carnitine, mildronate, acetylcarnitine, or derivative thereof is covalently linked to the molecular payload (e.g., oligonucleotide payload).

A muscle-targeting agent may be a protein that is protein that exists in at least one soluble form that targets muscle cells. In some embodiments, a muscle-targeting protein may be hemojuvelin (also known as repulsive guidance molecule C or hemochromatosis type 2 protein), a protein involved in iron overload and homeostasis. In some embodiments, hemojuvelin may be full length or a fragment, or a mutant with at least 75%, at least 80%, at least 85%, at least 90%, at least 95%, at least 98% or at least 99% sequence identity to a functional hemojuvelin protein. In some embodiments, a hemojuvelin mutant may be a soluble fragment, may lack a N-terminal signaling, and/or lack a C-terminal anchoring domain. In some embodiments, hemojuvelin may be annotated under GenBank RefSeq Accession Numbers NM_001316767.1, NM_145277.4. NM_202004.3, NM_213652.3, or NM_213653.3. It should be appreciated that a hemojuvelin may be of human, non-human primate, or rodent origin.

B. Molecular Payloads

Some aspects of the disclosure provide molecular payloads, e.g., for modulating a biological outcome, e.g., the transcription of a DNA sequence, the expression of a protein, or the activity of a protein. In some embodiments, a molecular payload is linked to, or otherwise associated with a muscle-targeting agent. In some embodiments, such molecular payloads are capable of targeting to a muscle cell, e.g., via specifically binding to a nucleic acid or protein in the muscle cell following delivery to the muscle cell by an associated muscle-targeting agent. It should be appreciated that various types of muscle-targeting agents may be used in accordance with the disclosure. For example, the molecular payload may comprise, or consist of, an oligonucleotide (e.g., antisense oligonucleotide), a peptide (e.g., a peptide that binds a nucleic acid or protein associated with disease in a muscle cell), a protein (e.g., a protein that binds a nucleic acid or protein associated with disease in a muscle cell), or a small molecule (e.g., a small molecule that modulates the function of a nucleic acid or protein associated with disease in a muscle cell). In some embodiments, the molecular payload is an oligonucleotide that comprises a strand having a region of complementarity to a DMPK allele comprising a disease-associated-repeat expansion. Exemplary molecular payloads are described in further detail herein, however, it should be appreciated that the exemplary molecular payloads provided herein are not meant to be limiting.

i. Oligonucleotides

Any suitable oligonucleotide may be used as a molecular payload, as described herein. In some embodiments, the oligonucleotide may be designed to cause degradation of an mRNA (e.g., the oligonucleotide may be a gapmer, an siRNA, a ribozyme or an aptamer that causes degradation). In some embodiments, the oligonucleotide may be designed to block translation of an mRNA (e.g., the oligonucleotide may be a mixmer, an siRNA or an aptamer that blocks translation). In some embodiments, an oligonucleotide may be designed to caused degradation and block translation of an mRNA. In some embodiments, an oligonucleotide may be a guide nucleic acid (e.g., guide RNA) for directing activity of an enzyme (e.g., a gene editing enzyme). Other examples of oligonucleotides are provided herein. It should be appreciated that, in some embodiments, oligonucleotides in one format (e.g., antisense oligonucleotides) may be suitably adapted to another format (e.g., siRNA oligonucleotides) by incorporating functional sequences (e.g., antisense strand sequences) from one format to the other format.

Examples of oligonucleotides useful for targeting DMPK are provided in US Patent Application Publication 20100016215A1, published on Jan. 1, 2010, entitled Compound And Method For Treating Myotonic Dystrophy; US Patent Application Publication 20130237585A1, published Jul. 19, 2010, Modulation Of Dystrophia Myotonica-Protein Kinase (DMPK) Expression; US Patent Application Publication 20150064181A1, published on Mar. 5, 2015, entitled "Antisense Conjugates For Decreasing Expression Of Dmpk"; US Patent Application Publication 20150238627A1, published on Aug. 27, 2015, entitled "Peptide-Linked Morpholino Antisense Oligonucleotides For Treatment Of Myotonic Dystrophy"; and US Patent Application Publication 20160304877A1, published on Oct. 20, 2016, entitled "Compounds And Methods For Modulation Of Dystrophia Myotonica-Protein Kinase (Dmpk) Expression," the contents of each of which are incorporated herein in their entireties.

Examples of oligonucleotides for promoting DMPK gene editing include US Patent Application Publication 20170088819A1, published on Mar. 3, 2017, entitled "Genetic Correction Of Myotonic Dystrophy Type 1"; and international Patent Application Publication WO18002812A1, published on Apr. 1, 2018, entitled "Materials And Methods For Treatment Of Myotonic Dystrophy Type 1 (DM1) And Other Related Disorders," the contents of each of which are incorporated herein in their entireties.

In some embodiments, oligonucleotides may have a region of complementarity to a sequence set forth as follows, which is an example human DMPK gene sequence (Gene ID 1760; NM_001081560.2):

```
                                                  (SEQ ID NO. 15)
AGGGGGGCTGGACCAAGGGGTGGGGAGAAGGGGAGGAGGCCTCGGCCGG

CCGCAGAGAGAAGTGGCCAGAGAGGCCCAGGGGACAGCCAGGGACAGGC

AGACATGCAGCCAGGGCTCCAGGGCCTGGACAGGGGCTGCCAGGCCCTG

TGACAGGAGGACCCCGAGCCCCCGGCCCGGGGAGGGGCCATGGTGCTGC

CTGTCCAACATGTCAGCCGAGGTGCGGCTGAGGCGGCTCCAGCAGCTGG

TGTTGGACCCGGGCTTCCTGGGGCTGGAGCCCCTGCTCGACCTTCTCCT

GGGCGTCCACCAGGAGCTGGGCGCCTCCGAACTGGCCCAGGACAAGTAC

GTGGCCGACTTCTTGCAGTGGGCGGAGCCCATCGTGGTGAGGCTTAAGG

AGGTCCGACTGCAGAGGGACGACTTCGAGATTCTGAAGGTGATCGGACG

CGGGGCGTTCAGCGAGGTAGCGGTAGTGAAGATGAAGCAGACGGGCCAG

GTGTATGCCATGAAGATCATGAACAAGTGGGACATGCTGAAGAGGGGCG

AGGTGTCGTGCTTCCGTGAGGAGAGGGACGTGTTGGTGAATGGGGACCG

GCGGTGGATCACGCAGCTGCACTTCGCCTTCCAGGATGAGAACTACCTG

TACCTGGTCATGGAGTATTACGTGGGCGGGGACCTGCTGACACTGCTGA

GCAAGTTTGGGGAGCGGATTCCGGCCGAGATGGCGCGCTTCTACCTGGC

GGAGATTGTCATGGCCATAGACTCGGTGCACCGGCTTGGCTACGTGCAC

AGGGACATCAAACCCGACAACATCCTGCTGGACCGCTGTGGCCACATCC

GCCTGGCCGACTTCGGCTCTTGCCTCAAGCTGCGGGCAGATGGAACGGT

GCGGTCGCTGGTGGCTGTGGGCACCCCAGACTACCTGTCCCCCGAGATC

CTGCAGGCTGTGGGCGGTGGGCCTGGACAGGCAGCTACGGGCCCGAGT

GTGACTGGTGGGCGCTGGGTGTATTCGCCTATGAAATGTTCTATGGGCA

GACGCCCTTCTACGCGGATTCCACGGCGGAGACCTATGGCAAGATCGTC

CACTACAAGGAGCACCTCTCTCTGCCGCTGGTGGACGAAGGGGTCCCTG

AGGAGGCTCGAGACTTCATTCAGCGGTTGCTGTGTCCCCGGAGACACG

GCTGGGCCGGGGTGGAGCAGGCGACTTCCGGACACATCCCTTCTTCTTT

GGCCTCGACTGGGATGGTCTCCGGGACAGCGTGCCCCCCTTTACACCGG

ATTTCGAAGGTGCCACCGACACATGCAACTTCGACTTGGTGGAGGACGG

GCTCACTGCCATGGAGACACTGTCGGACATTCGGGAAGGTGCGCCGCTA

GGGGTCCACCTGCCTTTTGTGGGCTACTCCTACTCCTGCATGGCCCTCA

GGGACAGTGAGGTCCCAGGCCCCACACCCATGGAACTGGAGGCCGAGCA

GCTGCTTGAGCCACACGTGCAAGCGCCCAGCCTGGAGCCCTCGGTGTCC

CCACAGGATGAAACAGCTGAAGTGGCAGTTCCAGCGGCTGTCCCTGCGG

CAGAGGCTGAGGCCGAGGTGACGCTGCGGGAGCTCCAGGAAGCCCTGGA

GGAGGAGGTGCTCACCCGGCAGAGCCTGAGCCGGGAGATGGAGGCCATC

CGCACGGACAACCAGAACTTCGCCAGTCAACTACGCGAGGCAGAGGCTC

GGAACCGGGACCTAGAGGCACACGTCCGGCAGTTGCAGGAGCGGATGGA

GTTGCTGCAGGCAGAGGGAGCCACAGCTGTCACGGGGGTCCCCAGTCCC

CGGGCCACGGATCCACCTTCCCATCTAGATGGCCCCCGGCCGTGGCTG

TGGGCCAGTGCCCGCTGGTGGGGCCAGGCCCCATGCACCGCCGCCACCT

GCTGCTCCCTGCCAGGGTCCCTAGGCCTGGCCTATCGGAGGCGCTTTCC
```

```
CTGCTCCTGTTCGCCGTTGTTCTGTCTCGTGCCGCCGCCCTGGGCTGCA
TTGGGTTGGTGGCCCACGCCGGCCAACTCACCGCAGTCTGGCGCCGCCC
AGGAGCCGCCCGCGCTCCCTGAACCCTAGAACTGTCTTCGACTCCGGGG
CCCCGTTGGAAGACTGAGTGCCCGGGGCACGGCACAGAAGCGCGCCCA
CCGCCTGCCAGTTCACAACCGCTCCGAGCGTGGGTCTCCGCCCAGCTCC
AGTCCTGTGATCCGGGCCCGCCCCCTAGCGGCCGGGGAGGGAGGGGCCG
GGTCCGCGGCCGGCGAACGGGGCTCGAAGGGTCCTTGTAGCCGGGAATG
CTGCTGCTGCTGCTGCTGCTGCTGCTGCTGCTGCTGCTGCTGCTGCTGC
TGCTGCTGCTGGGGGGATCACAGACCATTTCTTTCTTTCGGCCAGGCTG
AGGCCCTGACGTGGATGGGCAAACTGCAGGCCTGGGAAGGCAGCAAGCC
GGGCCGTCCGTGTTCCATCCTCCACGCACCCCCACCTATCGTTGGTTCG
CAAAGTGCAAAGCTTTCTTGTGCATGACGCCCTGCTCTGGGGAGCGTCT
GGCGCGATCTCTGCCTGCTTACTCGGGAAATTTGCTTTTGCCAAACCCG
CTTTTTCGGGGATCCCGCGCCCCCCTCCTCACTTGCGCTGCTCTCGGAG
CCCCAGCCGGCTCCGCCCGCTTCGGCGGTTTGGATATTTATTGACCTCG
TCCTCCGACTCGCTGACAGGCTACAGGACCCCCAACAACCCCAATCCAC
GTTTTGGATGCACTGAGACCCCGACATTCCTCGGTATTTATTGTCTGTC
CCCACCTAGGACCCCCACCCCCGACCCTCGCGAATAAAAGGCCCTCCAT
CTGCCCAAAGCTCTGGA.
```

In some embodiments, oligonucleotides may have a region of complementarity to a sequence set forth as follows, which is an example mouse DMPK gene sequence (Gene ID 13400; NM 001190490.1).

```
                                     (SEQ ID NO. 16)
GAACTGGCCAGAGAGACCCAAGGGATAGTCAGGGACGGGCAGACATGCA
GCTAGGGTTCTGGGGCCTGGACAGGGGCAGCCAGGCCCTGTGACGGGAA
GACCCCGAGCTCCGGCCCGGGGAGGGGCCATGGTGTTGCCTGCCCAACA
TGTCAGCCGAAGTGCGGCTGAGGCAGCTCCAGCAGCTGGTGCTGGACCC
AGGCTTCCTGGGACTGGAGCCCCTGCTCGACCTTCTCCTGGGCGTCCAC
CAGGAGCTGGGTGCCTCTCACCTAGCCCAGGACAAGTATGTGGCCGACT
TCTTGCAGTGGGTGGAGCCCATTGCAGCAAGGCTTAAGGAGGTCCGACT
GCAGAGGGATGATTTTGAGATTTTGAAGGTGATCGGGCGTGGGCGTTC
AGCGAGGTAGCGGTGGTGAAGATGAAACAGACGGGCCAAGTGTATGCCA
TGAAGATTATGAATAAGTGGGACATGCTGAAGAGAGGCGAGGTGTCGTG
CTTCCGGGAAGAAAGGGATGTATTAGTGAAAGGGGACCGGCGCTGGATC
ACACAGCTGCACTTTGCCTTCCAGGATGAGAACTACCTGTACCTGGTCA
TGGAATACTACGTGGGCGGGACCTGCTAACGCTGCTGAGCAAGTTTGG
GGAGCGGATCCCCGCCGAGATGGCTCGCTTCTACCTGGCCGAGATTGTC
ATGGCCATAGACTCCGTGCACCGGCTGGGCTACGTGCACAGGGACATCA
AACCAGATAACATTCTGCTGGACCGATGTGGGCACATTCGCCTGGCAGA
CTTCGGCTCCTGCCTCAAACTGCAGCCTGATGGAATGGTGAGGTCGCTG
GTGGCTGTGGGCACCCCGGACTACCTGTCTCCTGAGATTCTGCAGGCCG
TTGGTGGAGGGCCTGGGGCAGGCAGCTACGGGCCAGAGTGTGACTGGTG
GGCACTGGGCGTGTTCGCCTATGAGATGTTCTATGGGCAGACCCCCTTC
TACGCGGACTCCACAGCCGAGACATATGCCAAGATTGTGCACTACAGGG
AACACTTGTCGCTGCCGCTGGCAGACACAGTTGTCCCCGAGGAAGCTCA
GGACCTCATTCGTGGGCTGCTGTGTCCTGCTGAGATAAGGCTAGGTCGA
GGTGGGGCAGACTTCGAGGGTGCCACGGACACATGCAATTTCGATGTGG
TGGAGGACCGGCTCACTGCCATGGTGAGCGGGGGGGGAGACGCTGTCA
GACATGCAGGAAGACATGCCCCTTGGGGTGCGCCTGCCCTTCGTGGGCT
ACTCCTACTGCTGCATGGCCTTCAGAGACAATCAGGTCCCGGACCCCAC
CCCTATGGAACTAGAGGCCCTGCAGTTGCCTGTGTCAGACTTGCAAGGG
CTTGACTTGCAGCCCCAGTGTCCCACCGGATCAAGTGGCTGAAGAGG
CTGACCTAGTGGCTGTCCCTGCCCCTGTGGCTGAGGCAGAGACCACGGT
AACGCTGCAGCAGCTCCAGGAAGCCCTGGAAGAAGAGGTTCTCACCCGG
CAGAGCCTGAGCCGCGAGCTGGAGGCCATCCGGACCGCCAACCAGAACT
TCTCCAGCCAACTACAGGAGGCCGAGGTCCGAAACCGAGACCTGGAGGC
GCATGTTCGGCAGCTACAGGAACGGATGGAGATGCTGCAGGCCCCAGGA
GCCGCAGCCATCACGGGGGTCCCCAGTCCCGGGCCACGGATCCACCTT
CCCATCTAGATGGCCCCCCGGCCGTGGCTGTGGGCCAGTGCCCGCTGGT
GGGGCCAGGCCCCATGCACCGCCGTCACCTGCTGCTCCCTGCCAGGATC
CCTAGGCCTGGCCTATCCGAGGCGCGTTGCCTGCTCCTGTTCGCCGCTG
CTCTGGCTGCTGCCGCCACACTGGGCTGCACTGGGTTGGTGGCCTATAC
CGGCGGTCTCACCCCAGTCTGGTGTTTCCCGGGAGCCACCTTCGCCCCC
TGAACCCTAAGACTCCAAGCCATCTTTCATTTAGGCCTCCTAGGAAGGT
CGAGCGACCAGGGAGCGACCCAAAGCGTCTCTGTGCCCATCGCGCCCCC
CCCCCCCCCCCACCGCTCCGCTCCACACTTCTGTGAGCCTGGGTCCCCA
CCCAGCTCCGCTCCTGTGATCCAGGCCTGCCACCTGGCGGCCGGGGAGG
GAGGAACAGGGCTCGTGCCCAGCACCCCTGGTTCCTGCAGAGCTGGTAG
CCACCGCTGCTGCAGCAGCTGGGCATTCGCCGACCTTGCTTTACTCAGC
CCCGACGTGGATGGGCAAACTGCTCAGCTCATCCGATTTCACTTTTTCA
CTCTCCCAGCCATCAGTTACAAGCCATAAGCATGAGCCCCCTATTTCCA
GGGACATCCCATTCCCATAGTGATGGATCAGCAAGACCTCTGCCAGCAC
ACACGGAGTCTTTGGCTTCGGACAGCCTCACTCCTGGGGGTTGCTGCAA
CTCCTTCCCCGTGTACACGTCTGCACTCTAACAACGGAGCCACAGCTGC
ACTCCCCCCTCCCCCAAAGCAGTGTGGGTATTTATTGATCTTGTTATCT
GACTCACTGACAGACTCCGGGACCCACGTTTTAGATGCATTGAGACTCG
ACATTCCTCGGTATTTATTGTCTGTCCCCACCTACGACCTCCACTCCCG
ACCCTTGCGAATAAAATACTTCTGGTCTGCCCTAAA.
```

In some embodiments, an oligonucleotide may have a region of complementarity to DMPK gene sequences of multiple species, e.g., selected from human, mouse and non-human species.

In some embodiments, the oligonucleotide may have region of complementarity to a mutant form of DMPK, for example, a mutant form as reported in Botta A. et al. "The CTG repeat expansion size correlates with the splicing defects observed in muscles from myotonic dystrophy type 1 patients." J Med Genet. 2008 October; 45(10):639-46.; and Machuca-Tzili L. et al. "Clinical and molecular aspects of the myotonic dystrophies: a review." Muscle Nerve. 2005 July; 32(1):1-18.; the contents of each of which are incorporated herein by reference in their entireties.

In some embodiments, the oligonucleotide may target lncRNA or mRNA, e.g., for degradation. In some embodiments, the oligonucleotide may target, e.g., for degradation, a nucleic acid encoding a protein involved in a mismatch repair pathway, e.g., MSH2, MutLalpha, MutSbeta, MutLalpha. Non-limiting examples of proteins involved in mismatch repair pathways, for which mRNAs encoding such proteins may be targeted by oligonucleotides described herein, are described in Iyer, R. R. et al., "DNA triplet repeat expansion and mismatch repair" Annu Rev Biochem. 2015; 84:199-226.; and Schmidt M. H. and Pearson C. E., "Disease-associated repeat instability and mismatch repair" DNA Repair (Amst). 2016 February; 38:117-26.

In some embodiments, an oligonucleotide provided herein is an antisense oligonucleotide targeting DMPK. In some embodiments, the oligonucleotide targeting is any one of the antisense oligonucleotides (e.g., a Gapmer) targeting DMPK as described in US Patent Application Publication US20160304877A1, published on Oct. 20, 2016, entitled "Compounds And Methods For Modulation Of Dystrophia Myotonica-Protein Kinase (DMPK) Expression," incorporated herein by reference). In some embodiments, the DMPK targeting oligonucleotide targets a region of the DMPK gene sequence as set forth in Genbank accession No. NM_001081560.2 (SEQ ID NO: 15) or as set forth in Genbank accession No. NG_009784.1.

In some embodiments, the DMPK targeting oligonucleotide comprises a nucleotide sequence comprising a region complementary to a target region that is at least 10 continuous nucleotides (e.g., at least 10, at least 12, at least 14, at least 16, or more continuous nucleotides) in SEQ ID NO: 15.

In some embodiments, the DMPK targeting oligonucleotide comprise a gapmer motif. "Gapmer" means a chimeric antisense compound in which an internal region having a plurality of nucleotides that support RNase H cleavage is positioned between external regions having one or more nucleotides, wherein the nucleotides comprising the internal region are chemically distinct from the nucleotide or nucleotides comprising the external regions. The internal region can be referred to as a "gap segment" and the external regions can be referred to as "wing segments." In some embodiments, the DMPK targeting oligonucleotide comprises one or more modified nucleotides, and/or one or more modified internucleotide linkages. In some embodiments, the internucleotide linkage is a phosphorothioate linkage. In some embodiments, the oligonucleotide comprises a full phosphorothioate backbone. In some embodiments, the oligonucleotide is a DNA gapmer with cET ends (e.g., 3-10-3; cET-DNA-cET). In some embodiments, the DMPK targeting oligonucleotide comprises one or more 6'-(S)—CH$_3$ biocyclic nucleotides, one or more D-D-2'-deoxyribonucleotides, and/or one or more 5-methylcytosine nucleotides.

a. Oligonucleotide Size/Sequence

Oligonucleotides may be of a variety of different lengths, e.g., depending on the format. In some embodiments, an oligonucleotide is 7, 8, 9, 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some embodiments, the oligonucleotide is 8 to 50 nucleotides in length, 8 to 40 nucleotides in length, 8 to 30 nucleotides in length, 10 to 15 nucleotides in length, 10 to 20 nucleotides in length, 15 to 25 nucleotides in length, 21 to 23 nucleotides in lengths, etc.

In some embodiments, a complementary nucleic acid sequence of an oligonucleotide for purposes of the present disclosure is specifically hybridizable or specific for the target nucleic acid when binding of the sequence to the target molecule (e.g., mRNA) interferes with the normal function of the target (e.g., mRNA) to cause a loss of activity (e.g., inhibiting translation) or expression (e.g., degrading a target mRNA) and there is a sufficient degree of complementarity to avoid non-specific binding of the sequence to non-target sequences under conditions in which avoidance of non-specific binding is desired, e.g., under physiological conditions in the case of in vivo assays or therapeutic treatment, and in the case of in vitro assays, under conditions in which the assays are performed under suitable conditions of stringency. Thus, in some embodiments, an oligonucleotide may be at least 80%, at least 85%, at least 90%, at least 91%, at least 92%, at least 93%, at least 94%, at least 95%, at least 96%, at least 97%, at least 98%, at least 99% or 100% complementary to the consecutive nucleotides of an target nucleic acid. In some embodiments a complementary nucleotide sequence need not be 100% complementary to that of its target to be specifically hybridizable or specific for a target nucleic acid.

In some embodiments, an oligonucleotide comprises region of complementarity to a target nucleic acid that is in the range of 8 to 15, 8 to 30, 8 to 40, or 10 to 50, or 5 to 50, or 5 to 40 nucleotides in length. In some embodiments, a region of complementarity of an oligonucleotide to a target nucleic acid is 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides in length. In some embodiments, the region of complementarity is complementary with at least 8 consecutive nucleotides of a target nucleic acid. In some embodiments, an oligonucleotide may contain 1, 2 or 3 base mismatches compared to the portion of the consecutive nucleotides of target nucleic acid. In some embodiments the oligonucleotide may have up to 3 mismatches over 15 bases, or up to 2 mismatches over 10 bases.

In some embodiments, an oligonucleotide comprises at least 10, 11, 12, 13, 14, 15, 16, 17, 18, 19, or 20 consecutive nucleotides of a sequence comprising any one of SEQ ID NO: 45-280. In some embodiments, an oligonucleotide comprises a sequence comprising any one of SEQ ID NO: 45-280. In some embodiments, an oligonucleotide comprises a sequence that shares at least 70%, 75%, 80%, 85%, 90%, 95%, or 97% sequence identity with at least 12 or at least 15 consecutive nucleotides of any one of SEQ ID NO: 45-280.

In some embodiments, an oligonucleotide comprises a sequence that targets a DMPK sequence comprising any one of SEQ ID NO: 281-516. In some embodiments, an oligonucleotide comprises at least 10, 11, 12, 13, 14, 15, 16, 17, 18, 19, or 20 nucleotides (e.g., consecutive nucleotides) that are complementary to a DMPK sequence comprising any one of SEQ ID NO: 281-516. In some embodiments, an oligonucleotide comprises a sequence that is at least 70%, 75%, 80%, 85%, 90%, 95%, or 97% complementary with at least 12 or at least 15 consecutive nucleotides of any one of SEQ ID NO: 281-516.

b. Oligonucleotide Modifications

The oligonucleotides described herein may be modified, e.g., comprise a modified sugar moiety, a modified internucleoside linkage, a modified nucleotide and/or combinations thereof. In addition, in some embodiments, oligonucleotides may exhibit one or more of the following properties: do not mediate alternative splicing; are not immune stimulatory; are nuclease resistant; have improved cell uptake compared to unmodified oligonucleotides; are not toxic to cells or mammals; have improved endosomal exit internally in a cell; minimizes TLR stimulation; or avoid pattern recognition receptors. Any of the modified chemistries or formats of oligonucleotides described herein can be combined with each other. For example, one, two, three, four, five, or more different types of modifications can be included within the same oligonucleotide.

In some embodiments, certain nucleotide modifications may be used that make an oligonucleotide into which they are incorporated more resistant to nuclease digestion than the native oligodeoxynucleotide or oligoribonucleotide molecules; these modified oligonucleotides survive intact for a longer time than unmodified oligonucleotides. Specific examples of modified oligonucleotides include those comprising modified backbones, for example, modified internucleoside linkages such as phosphorothioates, phosphotriesters, methyl phosphonates, short chain alkyl or cycloalkyl intersugar linkages or short chain heteroatomic or heterocyclic intersugar linkages. Accordingly, oligonucleotides of the disclosure can be stabilized against nucleolytic degradation such as by the incorporation of a modification, e.g., a nucleotide modification.

In some embodiments, an oligonucleotide may be of up to 50 or up to 100 nucleotides in length in which 2 to 10, 2 to 15, 2 to 16, 2 to 17, 2 to 18, 2 to 19, 2 to 20, 2 to 25, 2 to 30, 2 to 40, 2 to 45, or more nucleotides of the oligonucleotide are modified nucleotides. The oligonucleotide may be of 8 to 30 nucleotides in length in which 2 to 10, 2 to 15, 2 to 16, 2 to 17, 2 to 18, 2 to 19, 2 to 20, 2 to 25, 2 to 30 nucleotides of the oligonucleotide are modified nucleotides. The oligonucleotide may be of 8 to 15 nucleotides in length in which 2 to 4, 2 to 5, 2 to 6, 2 to 7, 2 to 8, 2 to 9, 2 to 10, 2 to 11, 2 to 12, 2 to 13, 2 to 14 nucleotides of the oligonucleotide are modified nucleotides. Optionally, the oligonucleotides may have every nucleotide except 1, 2, 3, 4, 5, 6, 7, 8, 9, or 10 nucleotides modified. Oligonucleotide modifications are described further herein.

c. Modified Nucleotides

In some embodiments, an oligonucleotide include a 2-modified nucleotide, e.g., a 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA).

In some embodiments, an oligonucleotide can include at least one 2'-O-methyl-modified nucleotide, and in some embodiments, all of the nucleotides include a 2'-O-methyl modification. In some embodiments, an oligonucleotide comprises modified nucleotides in which the ribose ring comprises a bridge moiety connecting two atoms in the ring, e.g., connecting the 2'-O atom to the 4'-C atom. In some embodiments, the oligonucleotides are "locked," e.g., comprise modified nucleotides in which the ribose ring is "locked" by a methylene bridge connecting the 2'-O atom and the 4'-C atom. Examples of LNAs are described in International Patent Application Publication WO/2008/043753, published on Apr. 17, 2008, and entitled "RNA Antagonist Compounds For The Modulation Of PCSK9", the contents of which are incorporated herein by reference in its entirety.

Other modifications that may be used in the oligonucleotides disclosed herein include ethylene-bridged nucleic acids (ENAs). ENAs include, but are not limited to, 2'-0,4'-C-ethylene-bridged nucleic acids. Examples of ENAs are provided in International Patent Publication No. WO 2005/042777, published on May 12, 2005, and entitled "APP/ENA Antisense"; Morita et al., Nucleic Acid Res., Suppl 1:241-242, 2001; Surono et al., Hum. Gene Ther., 15:749-757, 2004; Koizumi, Cuff. Opin. Mol. Ther., 8:144-149, 2006 and Horie et al., Nucleic Acids Symp. Ser (Oxf), 49:171-172, 2005; the disclosures of which are incorporated herein by reference in their entireties.

In some embodiments, the oligonucleotide may comprise a bridged nucleotide, such as a locked nucleic acid (LNA) nucleotide, a constrained ethyl (cEt) nucleotide, or an ethylene bridged nucleic acid (ENA) nucleotide. In some embodiments, the oligonucleotide comprises a modified nucleotide disclosed in one of the following United States Patent or Patent Application Publications: U.S. Pat. No. 7,399,845, issued on Jul. 15, 2008, and entitled "6-Modified Bicyclic Nucleic Acid Analogs"; U.S. Pat. No. 7,741,457, issued on Jun. 22, 2010, and entitled "6-Modified Bicyclic Nucleic Acid Analogs"; U.S. Pat. No. 8,022,193, issued on Sep. 20, 2011, and entitled "6-Modified Bicyclic Nucleic Acid Analogs"; U.S. Pat. No. 7,569,686, issued on Aug. 4, 2009, and entitled "Compounds And Methods For Synthesis Of Bicyclic Nucleic Acid Analogs"; U.S. Pat. No. 7,335,765, issued on Feb. 26, 2008, and entitled "Novel Nucleoside And Oligonucleotide Analogues"; U.S. Pat. No. 7,314,923, issued on Jan. 1, 2008, and entitled "Novel Nucleoside And Oligonucleotide Analogues"; U.S. Pat. No. 7,816,333, issued on Oct. 19, 2010, and entitled "Oligonucleotide Analogues And Methods Utilizing The Same" and US Publication Number 2011/0009471 now U.S. Pat. No. 8,957,201, issued on Feb. 17, 2015, and entitled "Oligonucleotide Analogues And Methods Utilizing The Same", the entire contents of each of which are incorporated herein by reference for all purposes.

In some embodiments, the oligonucleotide comprises at least one nucleotide modified at the 2 position of the sugar, preferably a 2'-O-alkyl, 2'-O-alkyl-O-alkyl or 2'-fluoro-modified nucleotide. In other preferred embodiments, RNA modifications include 2'-fluoro, 2'-amino and 2' O-methyl modifications on the ribose of pyrimidines, abasic residues or an inverted base at the 3' end of the RNA.

In some embodiments, the oligonucleotide may have at least one modified nucleotide that results in an increase in Tm of the oligonucleotide in a range of 1° C., 2° C., 3° C., 4° C., or 5° C. compared with an oligonucleotide that does not have the at least one modified nucleotide. The oligonucleotide may have a plurality of modified nucleotides that result in a total increase in Tm of the oligonucleotide in a range of 2° C., 3° C., 4° C., 5° C., 6° C., 7° C., 8° C., 9° C., 10° C., 15° C., 20° C., 25° C., 30° C., 35° C., 40° C., 45° C. or more compared with an oligonucleotide that does not have the modified nucleotide.

The oligonucleotide may comprise alternating nucleotides of different kinds. For example, an oligonucleotide may comprise alternating deoxyribonucleotides or ribonucleotides and 2'-fluoro-deoxyribonucleotides. An oligonucleotide may comprise alternating deoxyribonucleotides or ribonucleotides and 2'-O-methyl nucleotides. An oligonucleotide may comprise alternating 2'-fluoro nucleotides and 2'-O-methyl nucleotides. An oligonucleotide may comprise alternating bridged nucleotides and 2'-fluoro or 2'-O-methyl nucleotides.

d. Internucleotide Linkages/Backbones

In some embodiments, oligonucleotide may contain a phosphorothioate or other modified internucleotide linkage. In some embodiments, the oligonucleotide comprises phosphorothioate internucleoside linkages. In some embodiments, the oligonucleotide comprises phosphorothioate internucleoside linkages between at least two nucleotides. In some embodiments, the oligonucleotide comprises phosphorothioate internucleoside linkages between all nucleotides. For example, in some embodiments, oligonucleotides comprise modified internucleotide linkages at the first, second, and/or third internucleoside linkage at the 5' or 3' end of the nucleotide sequence.

Phosphorus-containing linkages that may be used include, but are not limited to, phosphorothioates, chiral phosphorothioates, phosphorodithioates, phosphotriesters, aminoalkylphosphotriesters, methyl and other alkyl phosphonates comprising 3'alkylene phosphonates and chiral phosphonates, phosphinates, phosphoramidates comprising 3'-amino phosphoramidate and aminoalkylphosphoramidates, thionophosphoramidates, thionoalkylphosphonates, thionoalkylphosphotriesters, and boranophosphates having normal 3'-5' linkages, 2-5' linked analogs of these, and those having inverted polarity wherein the adjacent pairs of nucleoside units are linked 3'-5' to 5'-3' or 2'-5' to 5'-2'; see U.S. Pat. Nos. 3,687,808; 4,469,863; 4,476,301; 5,023,243; 5, 177, 196; 5,188,897; 5,264,423; 5,276,019; 5,278,302; 5,286, 717; 5,321,131; 5,399,676; 5,405,939; 5,453,496; 5,455, 233; 5,466,677; 5,476,925; 5,519,126; 5,536,821; 5,541, 306; 5,550,111; 5,563, 253; 5,571,799; 5,587,361; and 5,625,050.

In some embodiments, oligonucleotides may have heteroatom backbones, such as methylene(methylimino) or MMI backbones; amide backbones (see De Mesmaeker et al. Ace. Chem. Res. 1995, 28:366-374); morpholino backbones (see Summerton and Weller, U.S. Pat. No. 5,034,506); or peptide nucleic acid (PNA) backbones (wherein the phosphodiester backbone of the oligonucleotide is replaced with a polyamide backbone, the nucleotides being bound directly or indirectly to the aza nitrogen atoms of the polyamide backbone, see Nielsen et al., Science 1991, 254, 1497).

e. Stereospecific Oligonucleotides

In some embodiments, internucleotidic phosphorus atoms of oligonucleotides are chiral, and the properties of the oligonucleotides by adjusted based on the configuration of the chiral phosphorus atoms. In some embodiments, appropriate methods may be used to synthesize P-chiral oligonucleotide analogs in a stereocontrolled manner (e.g., as described in Oka N, Wada T. Stereocontrolled synthesis of oligonucleotide analogs containing chiral internucleotidic phosphorus atoms. Chem Soc Rev. 2011 December; 40(12): 5829-43.) In some embodiments, phosphorothioate containing oligonucleotides comprise nucleoside units that are joined together by either substantially all Sp or substantially all Rp phosphorothioate intersugar linkages are provided. In some embodiments, such phosphorothioate oligonucleotides having substantially chirally pure intersugar linkages are prepared by enzymatic or chemical synthesis, as described, for example, in U.S. Pat. No. 5,587,261, issued on Dec. 12, 1996, the contents of which are incorporated herein by reference in their entirety. In some embodiments, chirally controlled oligonucleotides provide selective cleavage patterns of a target nucleic acid. For example, in some embodiments, a chirally controlled oligonucleotide provides single site cleavage within a complementary sequence of a nucleic acid, as described, for example, in US Patent Application Publication 20170037399 A1, published on Feb. 2, 2017, entitled "CHIRAL DESIGN", the contents of which are incorporated herein by reference in their entirety.

f. Morpholinos

In some embodiments, the oligonucleotide may be a morpholino-based compounds. Morpholino-based oligomeric compounds are described in Dwaine A. Braasch and David R. Corey, Biochemistry, 2002, 41(14), 4503-4510); Genesis, volume 30, issue 3, 2001; Heasman, J., Dev. Biol., 2002, 243, 209-214; Nasevicius et al., Nat. Genet., 2000, 26, 216-220; Lacerra et al., Proc. Natl. Acad. Sci., 2000, 97, 9591-9596; and U.S. Pat. No. 5,034,506, issued Jul. 23, 1991. In some embodiments, the morpholino-based oligomeric compound is a phosphorodiamidate morpholino oligomer (PMO) (e.g., as described in Iverson. Curr. Opin. Mol. Ther., 3:235-238, 2001; and Wang et al., J. Gene Med., 12:354-364, 2010; the disclosures of which are incorporated herein by reference in their entireties).

g. Peptide Nucleic Acids (PNAs)

In some embodiments, both a sugar and an internucleoside linkage (the backbone) of the nucleotide units of an oligonucleotide are replaced with novel groups. In some embodiments, the base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, for example, an aminoethylglycine backbone. The nucleobases are retained and are bound directly or indirectly to aza nitrogen atoms of the amide portion of the backbone. Representative publication that report the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., Science, 1991, 254, 1497-1500.

h. Gapmers

In some embodiments, the oligonucleotide is a gapmer. A gapmer oligonucleotide generally has the formula 5'-X-Y-Z-3', with X and Z as flanking regions around a gap region Y. In some embodiments, the Y region is a contiguous stretch of nucleotides, e.g., a region of at least 6 DNA nucleotides, which are capable of recruiting an RNAse, such as RNAse H. In some embodiments, the gapmer binds to the target nucleic acid, at which point an RNAse is recruited and can then cleave the target nucleic acid. In some embodiments, the Y region is flanked both 5' and 3' by regions X and Z comprising high-affinity modified nucleotides, e.g., one to six modified nucleotides. Examples of modified nucleotides include, but are not limited to, 2' MOE or 2'OMe or Locked Nucleic Acid bases (LNA). The flanking sequences X and Z may be of one to twenty nucleotides, one to eight nucleotides or one to five nucleotides in length, in some embodiments. The flanking sequences X and Z may be of similar length or of dissimilar lengths. The gap-segment Y may be a nucleotide sequence of five to twenty nucleotides, size to twelve nucleotides or six to ten nucleotides in length, in some embodiments.

In some embodiments, the gap region of the gapmer oligonucleotides may contain modified nucleotides known to be acceptable for efficient RNase H action in addition to DNA nucleotides, such as C4'-substituted nucleotides, acyclic nucleotides, and arabino-configured nucleotides. In some embodiments, the gap region comprises one or more unmodified internucleosides. In some embodiments, one or both flanking regions each independently comprise one or more phosphorothioate internucleoside linkages (e.g., phosphorothioate internucleoside linkages or other linkages) between at least two, at least three, at least four, at least five or more nucleotides. In some embodiments, the gap region and two flanking regions each independently comprise modified internucleoside linkages (e.g., phosphorothioate internucleoside linkages or other linkages) between at least two, at least three, at least four, at least five or more nucleotides.

A gapmer may be produced using appropriate methods. Representative U.S. patents, U.S. patent publications, and PCT publications that teach the preparation of gapmers include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; 5,700,922; 5,898,031; 7,432,250; and 7,683,036; U.S. patent publication Nos. US20090286969, US20100197762, and US20110112170; and PCT publication Nos. WO2008049085 and WO2009090182, each of which is herein incorporated by reference in its entirety.

i. Mixmers

In some embodiments, an oligonucleotide described herein may be a mixmer or comprise a mixmer sequence pattern. In general, mixmers are oligonucleotides that comprise both naturally and non-naturally occurring nucleotides or comprise two different types of non-naturally occurring nucleotides typically in an alternating pattern. Mixmers generally have higher binding affinity than unmodified oligonucleotides and may be used to specifically bind a target molecule, e.g., to block a binding site on the target molecule. Generally, mixmers do not recruit an RNAse to the target molecule and thus do not promote cleavage of the target molecule. Such oligonucleotides that are incapable of recruiting RNAse H have been described, for example, see WO2007/112754 or WO2007/112753.

In some embodiments, the mixmer comprises or consists of a repeating pattern of nucleotide analogues and naturally occurring nucleotides, or one type of nucleotide analogue and a second type of nucleotide analogue. However, a mixmer need not comprise a repeating pattern and may instead comprise any arrangement of modified nucleotides and naturally occurring nucleotides or any arrangement of one type of modified nucleotide and a second type of modified nucleotide. The repeating pattern, may, for instance be every second or every third nucleotide is a modified nucleotide, such as LNA, and the remaining nucleotides are naturally occurring nucleotides, such as DNA, or are a 2' substituted nucleotide analogue such as 2'MOE or 2' fluoro analogues, or any other modified nucleotide described herein. It is recognized that the repeating pattern of modified nucleotide, such as LNA units, may be combined with modified nucleotide at fixed positions—e.g. at the 5' or 3' termini.

In some embodiments, a mixmer does not comprise a region of more than 5, more than 4, more than 3, or more than 2 consecutive naturally occurring nucleotides, such as DNA nucleotides. In some embodiments, the mixmer comprises at least a region consisting of at least two consecutive modified nucleotide, such as at least two consecutive LNAs. In some embodiments, the mixmer comprises at least a region consisting of at least three consecutive modified nucleotide units, such as at least three consecutive LNAs.

In some embodiments, the mixmer does not comprise a region of more than 7, more than 6, more than 5, more than 4, more than 3, or more than 2 consecutive nucleotide analogues, such as LNAs. In some embodiments, LNA units may be replaced with other nucleotide analogues, such as those referred to herein.

Mixmers may be designed to comprise a mixture of affinity enhancing modified nucleotides, such as in non-limiting example LNA nucleotides and 2'-O-methyl nucleotides. In some embodiments, a mixmer comprises modified internucleoside linkages (e.g., phosphorothioate internucleoside linkages or other linkages) between at least two, at least three, at least four, at least five or more nucleotides.

A mixmer may be produced using any suitable method. Representative U.S. patents, U.S. patent publications, and PCT publications that teach the preparation of mixmers include U.S. patent publication Nos. US20060128646, US20090209748, US20090298916, US20110077288, and US20120322851, and U.S. Pat. No. 7,687,617.

j. RNA Interference (RNAi)

In some embodiments, oligonucleotides provided herein may be in the form of small interfering RNAs (siRNA), also known as short interfering RNA or silencing RNA. SiRNA, is a class of double-stranded RNA molecules, typically about 20-25 base pairs in length that target nucleic acids (e.g., mRNAs) for degradation via the RNA interference (RNAi) pathway in cells. Specificity of siRNA molecules may be determined by the binding of the antisense strand of the molecule to its target RNA. Effective siRNA molecules are generally less than 30 to 35 base pairs in length to prevent the triggering of non-specific RNA interference pathways in the cell via the interferon response, although longer siRNA can also be effective.

Following selection of an appropriate target RNA sequence, siRNA molecules that comprise a nucleotide sequence complementary to all or a portion of the target sequence, i.e. an antisense sequence, can be designed and prepared using appropriate methods (see, e.g., PCT Publication Number WO 2004/016735; and U.S. Patent Publication Nos. 2004/0077574 and 2008/0081791).

The siRNA molecule can be double stranded (i.e. a dsRNA molecule comprising an antisense strand and a complementary sense strand) or single-stranded (i.e. a ssRNA molecule comprising just an antisense strand). The siRNA molecules can comprise a duplex, asymmetric duplex, hairpin or asymmetric hairpin secondary structure, having self-complementary sense and antisense strands.

Double-stranded siRNA may comprise RNA strands that are the same length or different lengths. Double-stranded siRNA molecules can also be assembled from a single oligonucleotide in a stem-loop structure, wherein self-complementary sense and antisense regions of the siRNA molecule are linked by means of a nucleic acid based or non-nucleic acid-based linker(s), as well as circular single-stranded RNA having two or more loop structures and a stem comprising self-complementary sense and antisense strands, wherein the circular RNA can be processed either in vivo or in vitro to generate an active siRNA molecule capable of mediating RNAi. Small hairpin RNA (shRNA) molecules thus are also contemplated herein. These molecules comprise a specific antisense sequence in addition to the reverse complement (sense) sequence, typically separated by a spacer or loop sequence. Cleavage of the spacer or loop provides a single-stranded RNA molecule and its reverse complement, such that they may anneal to form a dsRNA molecule (optionally with additional processing steps that may result in addition or removal of one, two, three or more nucleotides from the 3' end and/or the 5' end of either or both strands). A spacer can be of a sufficient length to permit the antisense and sense sequences to anneal and form a double-stranded structure (or stem) prior to cleavage of the spacer (and, optionally, subsequent processing steps that may result in addition or removal of one, two, three, four, or more nucleotides from the 3' end and/or the 5' end of either or both strands). A spacer sequence is may be an unrelated nucleotide sequence that is situated between two complementary nucleotide sequence regions which, when annealed into a double-stranded nucleic acid, comprise a shRNA.

The overall length of the siRNA molecules can vary from about 14 to about 100 nucleotides depending on the type of siRNA molecule being designed. Generally between about 14 and about 50 of these nucleotides are complementary to the RNA target sequence, i.e. constitute the specific antisense sequence of the siRNA molecule. For example, when the siRNA is a double- or single-stranded siRNA, the length can vary from about 14 to about 50 nucleotides, whereas when the siRNA is a shRNA or circular molecule, the length can vary from about 40 nucleotides to about 100 nucleotides.

An siRNA molecule may comprise a 3' overhang at one end of the molecule, The other end may be blunt-ended or have also an overhang (5' or 3'). When the siRNA molecule comprises an overhang at both ends of the molecule, the length of the overhangs may be the same or different. In one embodiment, the siRNA molecule of the present disclosure comprises 3' overhangs of about 1 to about 3 nucleotides on both ends of the molecule.

k. microRNA (miRNAs)

In some embodiments, an oligonucleotide may be a microRNA (miRNA). MicroRNAs (referred to as "miRNAs") are small non-coding RNAs, belonging to a class of regulatory molecules that control gene expression by binding to complementary sites on a target RNA transcript. Typically, miRNAs are generated from large RNA precursors (termed pri-miRNAs) that are processed in the nucleus into approximately 70 nucleotide pre-miRNAs, which fold into imperfect stem-loop structures. These pre-miRNAs typically undergo an additional processing step within the cytoplasm where mature miRNAs of 18-25 nucleotides in length are excised from one side of the pre-miRNA hairpin by an RNase III enzyme, Dicer.

As used herein, miRNAs including pri-miRNA, pre-miRNA, mature miRNA or fragments of variants thereof that retain the biological activity of mature miRNA. In one embodiment, the size range of the miRNA can be from 21 nucleotides to 170 nucleotides. In one embodiment the size range of the miRNA is from 70 to 170 nucleotides in length. In another embodiment, mature miRNAs of from 21 to 25 nucleotides in length can be used.

l. Aptamers

In some embodiments, oligonucleotides provided herein may be in the form of aptamers. Generally, in the context of molecular payloads, aptamer is any nucleic acid that binds specifically to a target, such as a small molecule, protein, nucleic acid in a cell. In some embodiments, the aptamer is a DNA aptamer or an RNA aptamer. In some embodiments, a nucleic acid aptamer is a single-stranded DNA or RNA (ssDNA or ssRNA). It is to be understood that a single-stranded nucleic acid aptamer may form helices and/or loop structures. The nucleic acid that forms the nucleic acid aptamer may comprise naturally occurring nucleotides, modified nucleotides, naturally occurring nucleotides with hydrocarbon linkers (e.g., an alkylene) or a polyether linker (e.g., a PEG linker) inserted between one or more nucleotides, modified nucleotides with hydrocarbon or PEG linkers inserted between one or more nucleotides, or a combination of thereof. Exemplary publications and patents describing aptamers and method of producing aptamers include, e.g., Lorsch and Szostak, 1996; Jayasena, 1999; U.S. Pat. Nos. 5,270,163; 5,567,588; 5,650,275; 5,670,637; 5,683,867; 5,696,249; 5,789,157; 5,843,653; 5,864,026; 5,989,823; 6,569,630; 8,318,438 and PCT application WO 99/31275, each incorporated herein by reference.

m. Ribozymes

In some embodiments, oligonucleotides provided herein may be in the form of a ribozyme. A ribozyme (ribonucleic acid enzyme) is a molecule, typically an RNA molecule, that is capable of performing specific biochemical reactions, similar to the action of protein enzymes. Ribozymes are molecules with catalytic activities including the ability to cleave at specific phosphodiester linkages in RNA molecules to which they have hybridized, such as mRNAs, RNA-containing substrates, lncRNAs, and ribozymes, themselves.

Ribozymes may assume one of several physical structures, one of which is called a "hammerhead." A hammerhead ribozyme is composed of a catalytic core containing nine conserved bases, a double-stranded stem and loop structure (stem-loop II), and two regions complementary to the target RNA flanking regions the catalytic core. The flanking regions enable the ribozyme to bind to the target RNA specifically by forming double-stranded stems I and III. Cleavage occurs in cis (i.e., cleavage of the same RNA molecule that contains the hammerhead motif) or in trans (cleavage of an RNA substrate other than that containing the ribozyme) next to a specific ribonucleotide triplet by a transesterification reaction from a 3',5'-phosphate diester to a 2',3'-cyclic phosphate diester. Without wishing to be bound by theory, it is believed that this catalytic activity requires the presence of specific, highly conserved sequences in the catalytic region of the ribozyme.

Modifications in ribozyme structure have also included the substitution or replacement of various non-core portions of the molecule with non-nucleotidic molecules. For example, Benseler et al. (J. Am. Chem. Soc. (1993) 115: 8483-8484) disclosed hammerhead-like molecules in which two of the base pairs of stem II, and all four of the nucleotides of loop II were replaced with non-nucleoside linkers based on hexaethylene glycol, propanediol, bis(triethylene glycol) phosphate, tris(propanediol)bisphosphate, or bis(propanediol) phosphate. Ma et al. (Biochem. (1993) 32:1751-1758; Nucleic Acids Res. (1993) 21:2585-2589) replaced the six nucleotide loop of the TAR ribozyme hairpin with non-nucleotidic, ethylene glycol-related linkers. Thomson et al. (Nucleic Acids Res. (1993) 21:5600-5603) replaced loop II with linear, non-nucleotidic linkers of 13, 17, and 19 atoms in length.

Ribozyme oligonucleotides can be prepared using well known methods (see, e.g., PCT Publications WO9118624; WO9413688; WO9201806; and WO 92/07065; and U.S. Pat. Nos. 5,436,143 and 5,650,502) or can be purchased from commercial sources (e.g., US Biochemicals) and, if desired, can incorporate nucleotide analogs to increase the resistance of the oligonucleotide to degradation by nucleases in a cell. The ribozyme may be synthesized in any known manner, e.g., by use of a commercially available synthesizer produced, e.g., by Applied Biosystems, Inc. or Milligen. The ribozyme may also be produced in recombinant vectors by conventional means. See, Molecular Cloning: A Laboratory Manual, Cold Spring Harbor Laboratory (Current edition). The ribozyme RNA sequences maybe synthesized conventionally, for example, by using RNA polymerases such as T7 or SP6.

n. Guide Nucleic Acids

In some embodiments, oligonucleotides are guide nucleic acid, e.g., guide RNA (gRNA) molecules. Generally, a guide RNA is a short synthetic RNA composed of (1) a scaffold sequence that binds to a nucleic acid programmable DNA binding protein (napDNAbp), such as Cas9, and (2) a nucleotide spacer portion that defines the DNA target sequence (e.g., genomic DNA target) to which the gRNA binds in order to bring the nucleic acid programmable DNA binding protein in proximity to the DNA target sequence. In some embodiments, the napDNAbp is a nucleic acid-programmable protein that forms a complex with (e.g., binds or associates with) one or more RNA(s) that targets the nucleic acid-programmable protein to a target DNA sequence (e.g., a target genomic DNA sequence). In some embodiments, a nucleic acid-programmable nuclease, when in a complex with an RNA, may be referred to as a nuclease:RNA complex. Guide RNAs can exist as a complex of two or more RNAs, or as a single RNA molecule.

Guide RNAs (gRNAs) that exist as a single RNA molecule may be referred to as single-guide RNAs (sgRNAs), though gRNA is also used to refer to guide RNAs that exist as either single molecules or as a complex of two or more molecules. Typically, gRNAs that exist as a single RNA species comprise two domains: (1) a domain that shares homology to a target nucleic acid (i.e., directs binding of a Cas9 complex to the target); and (2) a domain that binds a Cas9 protein. In some embodiments, domain (2) corresponds to a sequence known as a tracrRNA and comprises a stem-loop structure. In some embodiments, domain (2) is identical or homologous to a tracrRNA as provided in Jinek et al., Science 337:816-821 (2012), the entire contents of which is incorporated herein by reference.

In some embodiments, a gRNA comprises two or more of domains (1) and (2), and may be referred to as an extended gRNA. For example, an extended gRNA will bind two or more Cas9 proteins and bind a target nucleic acid at two or more distinct regions, as described herein. The gRNA comprises a nucleotide sequence that complements a target site, which mediates binding of the nuclease/RNA complex to said target site, providing the sequence specificity of the nuclease:RNA complex. In some embodiments, the RNA-programmable nuclease is the (CRISPR-associated system) Cas9 endonuclease, for example, Cas9 (Csn1) from *Streptococcus pyogenes* (see, e.g., "Complete genome sequence of an M1 strain of *Streptococcus pyogenes*." Ferretti J. J., McShan W. M., Ajdic D. J., Savic D. J., Savic G., Lyon K., Primeaux C., Sezate S., Suvorov A. N., Kenton S., Lai H. S., Lin S. P., Qian Y., Jia H. G., Najar F. Z., Ren Q., Zhu H., Song L., White J., Yuan X., Clifton S. W., Roe B. A., McLaughlin R. E., Proc. Natl. Acad. Sci. U.S.A. 98:4658-4663 (2001); "CRISPR RNA maturation by trans-encoded small RNA and host factor RNase III." Deltcheva E., Chylinski K., Sharma C. M., Gonzales K., Chao Y., Pirzada Z. A., Eckert M. R., Vogel J., Charpentier E., Nature 471:602-607 (2011); and "A programmable dual-RNA-guided DNA endonuclease in adaptive bacterial immunity." Jinek M., Chylinski K., Fonfara I., Hauer M., Doudna J. A., Charpentier E. Science 337:816-821 (2012), the entire contents of each of which are incorporated herein by reference.

o. Multimers

In some embodiments, molecular payloads may comprise multimers (e.g., concatemers) of 2 or more oligonucleotides connected by a linker. In this way, in some embodiments, the oligonucleotide loading of a complex/conjugate can be increased beyond the available linking sites on a targeting agent (e.g., available thiol sites on an antibody) or otherwise tuned to achieve a particular payload loading content. Oligonucleotides in a multimer can be the same or different (e.g., targeting different genes or different sites on the same gene or products thereof).

In some embodiments, multimers comprise 2 or more oligonucleotides linked together by a cleavable linker. However, in some embodiments, multimers comprise 2 or more oligonucleotides linked together by a non-cleavable linker. In some embodiments, a multimer comprises 2, 3, 4, 5, 6, 7, 8, 9, 10 or more oligonucleotides linked together. In some embodiments, a multimer comprises 2 to 5, 2 to 10 or 4 to 20 oligonucleotides linked together.

In some embodiments, a multimer comprises 2 or more oligonucleotides linked end-to-end (in a linear arrangement). In some embodiments, a multimer comprises 2 or more oligonucleotides linked end-to-end via a oligonucleotide based linker (e.g., poly-dT linker, an abasic linker). In some embodiments, a multimer comprises a 5' end of one oligonucleotide linked to a 3' end of another oligonucleotide. In some embodiments, a multimer comprises a 3' end of one oligonucleotide linked to a 3' end of another oligonucleotide. In some embodiments, a multimer comprises a 5' end of one oligonucleotide linked to a 5' end of another oligonucleotide. Still, in some embodiments, multimers can comprise a branched structure comprising multiple oligonucleotides linked together by a branching linker.

Further examples of multimers that may be used in the complexes provided herein are disclosed, for example, in US Patent Application Number 2015/0315588 A1, entitled Methods of delivering multiple targeting oligonucleotides to a cell using cleavable linkers, which was published on Nov. 5, 2015; US Patent Application Number 2015/0247141 A1, entitled Multimeric Oligonucleotide Compounds, which was published on Sep. 3, 2015, US Patent Application Number US 2011/0158937 A1, entitled Immunostimulatory Oligonucleotide Multimers, which was published on Jun. 30, 2011; and U.S. Pat. No. 5,693,773, entitled Triplex-Forming Antisense Oligonucleotides Having Abasic Linkers Targeting Nucleic Acids Comprising Mixed Sequences Of Purines And Pyrimidines, which issued on Dec. 2, 1997, the contents of each of which are incorporated herein by reference in their entireties.

ii. Small Molecules

Any suitable small molecule may be used as a molecular payload, as described herein. In some embodiments, the small molecule is as described in US Patent Application Publication 2016052914A1, published on Feb. 25, 2016, entitled "Compounds And Methods For Myotonic Dystrophy Therapy". Further examples of small molecule payloads are provided in Lopez-Morato M, et al., Small Molecules Which Improve Pathogenesis of Myotonic Dystrophy Type 1, (Review) Front. Neurol., 18 May 2018. For example, in some embodiments, the small molecule is an MBNL1 upregulator such as phenylbuthazone, ketoprofen, ISOX, or vorinostat. In some embodiments, the small molecule is an H-Ras pathway inhibitor such as manumycin A. In some embodiments, the small molecule is a protein kinase modulator such as Ro-318220, C16, C51, Metformin, AICAR, lithium chloride, TDZD-8 or Bio. In some embodiments, the small molecule is a plant alkaloid such as harmine. In some embodiments, the small molecule is a transcription inhibitor such as pentamidine, propamidine, heptamidiine or actinomycin D. In some embodiments, the small molecule is an inhibitor of Glycogen synthase kinase 3 beta (GSK3β), for example, as disclosed in Jones K, et al., GSK3β mediates muscle pathology in myotonic dystrophy. J Clin Invest. 2012 December; 122(12):4461-72; and Wei C, et al., GSK3β is a new therapeutic target for myotonic dystrophy type 1. Rare Dis. 2013; 1: e26555; and Palomo V, et al., Subtly Modulating Glycogen Synthase Kinase 3 β: Allosteric Inhibitor Development and Their Potential for the Treatment of Chronic Diseases. J Med Chem. 2017 Jun. 22; 60(12):4983-5001, the contents of each of which are incorporated herein by reference in their entireties. In some embodiments, the small molecule is a substituted pyrido[2,3-d]pyrimidines and pentamidine-like compound, as disclosed in Gonzalez A L, et al., In silico discovery of substituted pyrido[2,3-d] pyrimidines and pentamidine-like compounds with biological activity in myotonic dystrophy models. PLoS One. 2017 Jun. 5; 12(6):e0178931, the contents of which are incorporated herein by reference in its entirety. In some embodiments, the small molecule is an MBNL1 modulator, for example, as disclosed in: Zhange F, et al., A flow cytometry-based screen identifies MBNL1 modulators that rescue splicing defects in myotonic dystrophy type I. Hum Mol Genet. 2017 Aug. 15; 26(16):3056-3068, the contents of which are incorporated herein by reference in its entirety.

iii. Peptides

Any suitable peptide or protein may be used as a molecular payload, as described herein. A peptide or protein payload may correspond to a sequence of a protein that preferentially binds to a nucleic acid, e.g. a disease-associated repeat, or a protein, e.g. MBNL1, found in muscle cells. In some embodiments, peptides or proteins may be produced, synthesized, and/or derivatized using several methodologies, e.g. phage displayed peptide libraries, one-bead one-compound peptide libraries, or positional scanning synthetic peptide combinatorial libraries. Exemplary methodologies have been characterized in the art and are incorporated by reference (Gray, B. P. and Brown, K. C. "Combinatorial Peptide Libraries: Mining for Cell-Binding Peptides" Chem Rev. 2014, 114:2, 1020-1081.; Samoylova, T. I. and Smith, B. F. "Elucidation of muscle-binding peptides by phage display screening." Muscle Nerve, 1999, 22:4, 460-6.).

In some embodiments, the peptide is as described in US Patent Application 2018/0021449, published on Jan. 25, 2018, "Antisense conjugates for decreasing expression of DMPK". In some embodiments, the peptide is as described in Garcia-Lopez et al., "In vivo discovery of a peptide that prevents CUG-RNA hairpin formation and reverses RNA toxicity in myotonic dystrophy models", PNAS Jul. 19, 2011, 108 (29) 11866-11871. In some embodiments, the peptide or protein may target, e.g., bind to, a disease-associated repeat, e.g. a RNA CUG repeat expansion.

In some embodiments, the peptide or protein comprises a fragment of an MBNL protein, e.g., MBNL1. In some embodiments, the peptide or protein comprises at least one zinc finger. In some embodiments, the peptide or protein may comprise about 2-25 amino acids, about 2-20 amino acids, about 2-15 amino acids, about 2-10 amino acids, or about 2-5 amino acids. The peptide or protein may comprise naturally-occurring amino acids, e.g. cysteine, alanine, or non-naturally-occurring or modified amino acids. Non-naturally occurring amino acids include p-amino acids, homo-amino acids, proline derivatives, 3-substituted alanine derivatives, linear core amino acids, N-methyl amino acids, and others known in the art. In some embodiments, the peptide may be linear; in other embodiments, the peptide may be cyclic, e.g. bicyclic.

iv. Nucleic Add Constructs

Any suitable gene expression construct may be used as a molecular payload, as described herein. In some embodiments, a gene expression construct may be a vector or a cDNA fragment. In some embodiments, a gene expression construct may be messenger RNA (mRNA). In some embodiments, a mRNA used herein may be a modified mRNA, e.g., as described in U.S. Pat. No. 8,710,200, issued on Apr. 24, 2014, entitled "Engineered nucleic acids encoding a modified erythropoietin and their expression". In some embodiments, a mRNA may comprise a 5' methyl cap. In some embodiments, a mRNA may comprise a polyA tail, optionally of up to 160 nucleotides in length. A gene expression construct may encode a sequence of a protein that preferentially binds to a nucleic acid, e.g. a disease-associated repeat, or a protein, e.g. MBNL1, found in muscle cells. In some embodiments, the gene expression construct may be expressed, e.g., overexpressed, within the nucleus of a muscle cell. In some embodiments, the gene expression construct encodes a MBNL protein, e.g., MBNL1. In some embodiments, the gene expression constructs encodes a protein that comprises at least one zinc finger. In some embodiments, the gene expression construct encodes a protein that binds to a disease-associated repeat. In some embodiments, the gene expression construct encodes a protein that leads to a reduction in the expression of a disease-associated repeat. In some embodiments, the gene expression construct encodes a gene editing enzyme. Additional examples of nucleic acid constructs that may be used as molecular payloads are provided in International Patent Application Publication WO2017152149A1, published on Sep. 19, 2017, entitled, "Closed-Ended Linear Duplex Dna For Non-Viral Gene Transfer"; U.S. Pat. No. 8,853,377B2, issued on Oct. 7, 2014, entitled, "mRNA For Use In Treatment Of Human Genetic Diseases"; and U.S. Pat. No. 8,822,663B2, issued on Sep. 2, 2014. Engineered Nucleic Acids And Methods Of Use Thereof," the contents of each of which are incorporated herein by reference in their entireties.

C. Linkers

Complexes described herein generally comprise a linker that connects a muscle-targeting agent to a molecular payload. A linker comprises at least one covalent bond. In some embodiments, a linker may be a single bond, e.g., a disulfide bond or disulfide bridge, that connects a muscle-targeting agent to a molecular payload. However, in some embodiments, a linker may connect a muscle-targeting agent to a molecular through multiple covalent bonds. In some embodiments, a linker may be a cleavable linker. However, in some embodiments, a linker may be a non-cleavable linker. A linker is generally stable in vitro and in vivo, and may be stable in certain cellular environments. Additionally, generally a linker does not negatively impact the functional properties of either the muscle-targeting agent or the molecular payload. Examples and methods of synthesis of linkers are known in the art (see, e.g. Kline, T. et al. "Methods to Make Homogenous Antibody Drug Conjugates." Pharmaceutical Research, 2015, 32:11, 3480-3493.; Jain, N. et al. "Current ADC Linker Chemistry" Pharm Res. 2015, 32:11, 3526-3540.; McCombs, J. R. and Owen, S. C. "Antibody Drug Conjugates: Design and Selection of Linker, Payload and Conjugation Chemistry" AAPS J. 2015, 17:2, 339-351.).

A precursor to a linker typically will contain two different reactive species that allow for attachment to both the muscle-targeting agent and a molecular payload. In some embodiments, the two different reactive species may be a nucleophile and/or an electrophile. In some embodiments, a linker is connected to a muscle-targeting agent via conjugation to a lysine residue or a cysteine residue of the muscle-targeting agent. In some embodiments, a linker is connected to a cysteine residue of a muscle-targeting agent via a maleimide-containing linker, wherein optionally the maleimide-containing linker comprises a maleimidocaproyl or maleimidomethyl cyclohexane-1-carboxylate group. In some embodiments, a linker is connected to a cysteine residue of a muscle-targeting agent or thiol functionalized molecular payload via a 3-arylpropionitrile functional group. In some embodiments, a linker is connected to a muscle-targeting agent and/or a molecular payload via an amide bond, a hydrazide, a trizaole, a thioether, or a disulfide bond.

i. Cleavable Linkers

A cleavable linker may be a protease-sensitive linker, a pH-sensitive linker, or a glutathione-sensitive linker. These linkers are generally cleavable only intracellularly and are preferably stable in extracellular environments, e.g. extracellular to a muscle cell.

Protease-sensitive linkers are cleavable by protease enzymatic activity. These linkers typically comprise peptide sequences and may be 2-10 amino acids, about 2-5 amino acids, about 5-10 amino acids, about 10 amino acids, about 5 amino acids, about 3 amino acids, or about 2 amino acids in length. In some embodiments, a peptide sequence may comprise naturally-occurring amino acids, e.g. cysteine, alanine, or non-naturally-occurring or modified amino acids. Non-naturally occurring amino acids include β-amino acids, homo-amino acids, proline derivatives, 3-substituted alanine derivatives, linear core amino acids, N-methyl amino acids, and others known in the art. In some embodiments, a protease-sensitive linker comprises a valine-citrulline or alanine-citrulline dipeptide sequence. In some embodiments, a protease-sensitive linker can be cleaved by a lysosomal protease, e.g. cathepsin B, and/or an endosomal protease.

A pH-sensitive linker is a covalent linkage that readily degrades in high or low pH environments. In some embodiments, a pH-sensitive linker may be cleaved at a pH in a range of 4 to 6. In some embodiments, a pH-sensitive linker comprises a hydrazone or cyclic acetal. In some embodiments, a pH-sensitive linker is cleaved within an endosome or a lysosome.

In some embodiments, a glutathione-sensitive linker comprises a disulfide moiety. In some embodiments, a glutathione-sensitive linker is cleaved by an disulfide exchange reaction with a glutathione species inside a cell. In some embodiments, the disulfide moiety further comprises at least one amino acid, e.g. a cysteine residue.

In some embodiments, the linker is a Val-cit linker (e.g., as described in U.S. Pat. No. 6,214,345, incorporated herein by reference). In some embodiments, before conjugation, the val-cit linker has a structure of:

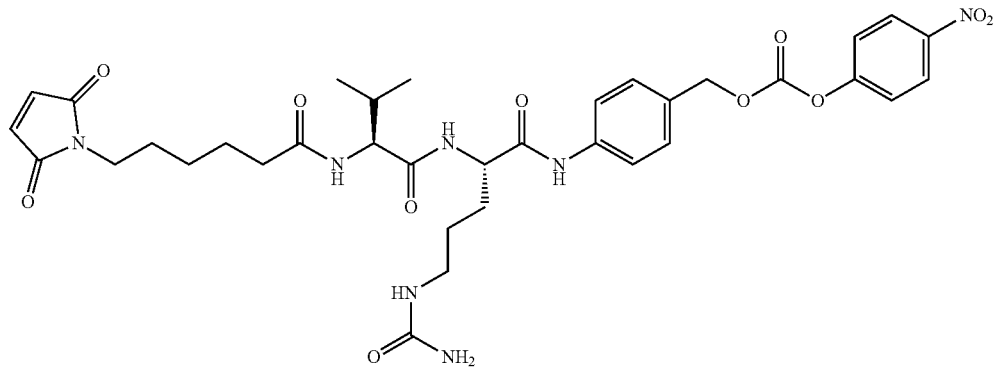 [SMILES: CC(C)[C@H](NC(=O)CCCCCN1C(=O)C=CC1=O)C(=O)N[C@@H](CCCNC(N)=O)C(=O)Nc1ccc(COC(=O)Oc2ccc([N+](=O)[O-])cc2)cc1]

In some embodiments, after conjugation, the val-cit linker has a structure of: —S

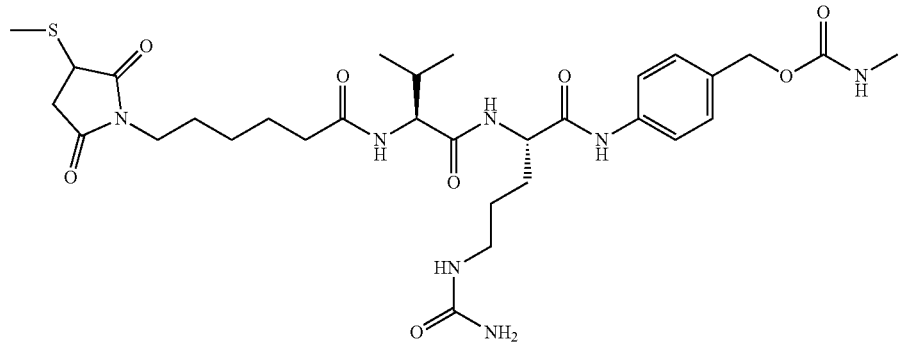

ii. Non-Cleavable Linkers

In some embodiments, non-cleavable linkers may be used. Generally, a non-cleavable linker cannot be readily degraded in a cellular or physiological environment. In some embodiments, a non-cleavable linker comprises an optionally substituted alkyl group, wherein the substitutions may include halogens, hydroxyl groups, oxygen species, and other common substitutions. In some embodiments, a linker may comprise an optionally substituted alkyl, an optionally substituted alkylene, an optionally substituted arylene, a heteroarylene, a peptide sequence comprising at least one non-natural amino acid, a truncated glycan, a sugar or sugars that cannot be enzymatically degraded, an azide, an alkyne-azide, a peptide sequence comprising a LPXT sequence, a thioether, a biotin, a biphenyl, repeating units of polyethylene glycol or equivalent compounds, acid esters, acid amides, sulfamides, and/or an alkoxy-amine linker. In some embodiments, sortase-mediated ligation will be utilized to covalently link a muscle-targeting agent comprising a LPXT sequence to a molecular payload comprising a $(G)_n$ sequence (see, e.g. Proft T. Sortase-mediated protein ligation: an emerging biotechnology tool for protein modification and immobilization. Biotechnol Lett. 2010, 32(1):1-10.).

In some embodiments, a linker may comprise a substituted alkylene, an optionally substituted alkenylene, an optionally substituted alkynylene, an optionally substituted cycloalkylene, an optionally substituted cycloalkenylene, an optionally substituted arylene, an optionally substituted heteroarylene further comprising at least one heteroatom selected from N, O, and S, an optionally substituted heterocyclylene further comprising at least one heteroatom selected from N, O, and S, an imino, an optionally substituted nitrogen species, an optionally substituted oxygen species O, an optionally substituted sulfur species, or a poly(alkylene oxide), e.g. polyethylene oxide or polypropylene oxide.

iii. Linker conjugation

In some embodiments, a linker is connected to a muscle-targeting agent and/or molecular payload via a phosphate, thioether, ether, carbon-carbon, or amide bond. In some embodiments, a linker is connected to an oligonucleotide through a phosphate or phosphorothioate group, e.g. a terminal phosphate of an oligonucleotide backbone. In some embodiments, a linker is connected to an muscle-targeting agent, e.g. an antibody, through a lysine or cysteine residue present on the muscle-targeting agent In some embodiments, a linker is connected to a muscle-targeting agent and/or molecular payload by a cycloaddition reaction between an azide and an alkyne to form a triazole, wherein the azide and the alkyne may be located on the muscle-targeting agent, molecular payload, or the linker. In some embodiments, an alkyne may be a cyclic alkyne, e.g., a cyclooctyne. In some embodiments, an alkyne may be bicyclononyne (also known as bicyclo[6.1.0]nonyne or BCN) or substituted bicyclononyne. In some embodiments, a cyclooctane is as described in International Patent Application Publication WO2011136645, published on Nov. 3, 2011, entitled, "Fused Cyclooctyne Compounds And Their Use In Metal-free Click Reactions". In some embodiments, an azide may be a sugar or carbohydrate molecule that comprises an azide. In some embodiments, an azide may be 6-azido-6-deoxygalactose or 6-azido-N-acetylgalactosamine. In some embodiments, a sugar or carbohydrate molecule that comprises an azide is as described in International Patent Application Publication WO2016170186, published on Oct. 27, 2016, entitled, "Process For The Modification Of A Glycoprotein Using A Glycosyltransferase That Is Or Is Derived From A β(1,4)—N-Acetylgalactosaminyltransferase". In some embodiments, a cycloaddition reaction between an azide and an alkyne to form a triazole, wherein the azide and the alkyne may be located on the muscle-targeting agent, molecular payload, or the linker is as described in International Patent Application Publication WO2014065661, published on May 1, 2014, entitled. "Modified antibody, antibody-conjugate and process for the preparation thereof"; or International Patent Application Publication WO2016170186, published on Oct. 27, 2016, entitled, "Process For The Modification Of A Glycoprotein Using A Glycosyltransferase That Is Or Is Derived From A β(1,4)—N-Acetylgalactosaminyltransferases".

In some embodiments, a linker further comprises a spacer, e.g., a polyethylene glycol spacer or an acyl/carbomoyl sulfamide spacer, e.g., a HydraSpace™ spacer. In some embodiments, a spacer is as described in Verkade, J. M. M. et al., "A Polar Sulfamide Spacer Significantly Enhances the Manufacturability, Stability, and Therapeutic Index of Antibody-Drug Conjugates", Antibodies, 2018, 7, 12.

In some embodiments, a linker is connected to a muscle-targeting agent and/or molecular payload by the Diels-Alder reaction between a dienophile and a diene/hetero-diene, wherein the dienophile and the diene/hetero-diene may be located on the muscle-targeting agent, molecular payload, or the linker. In some embodiments a linker is connected to a muscle-targeting agent and/or molecular payload by other pericyclic reactions, e.g. ene reaction. In some embodiments, a linker is connected to a muscle-targeting agent and/or molecular payload by an amide, thioamide, or sulfonamide bond reaction. In some embodiments, a linker is connected to a muscle-targeting agent and/or molecular payload by a condensation reaction to form an oxime, hydrazone, or semicarbazide group existing between the linker and the muscle-targeting agent and/or molecular payload.

In some embodiments, a linker is connected to a muscle-targeting agent and/or molecular payload by a conjugate addition reactions between a nucleophile, e.g. an amine or a hydroxyl group, and an electrophile, e.g. a carboxylic acid or an aldehyde. In some embodiments, a nucleophile may exist on a linker and an electrophile may exist on a muscle-targeting agent or molecular payload prior to a reaction between a linker and a muscle-targeting agent or molecular payload. In some embodiments, an electrophile may exist on a linker and a nucleophile may exist on a muscle-targeting agent or molecular payload prior to a reaction between a linker and a muscle-targeting agent or molecular payload. In some embodiments, an electrophile may be an azide, a silicon centers, a carbonyl, a carboxylic acid, an anhydride, an isocyanate, a thioisocyanate, a succinimidyl ester, a sulfosuccinimidyl ester, a maleimide, an alkyl halide, an alkyl pseudohalide, an epoxide, an episulfide, an aziridine, an aryl, an activated phosphorus center, and/or an activated sulfur center. In some embodiments, a nucleophile may be an optionally substituted alkene, an optionally substituted alkyne, an optionally substituted aryl, an optionally substituted heterocyclyl, a hydroxyl group, an amino group, an alkylamino group, an anilido group, or a thiol group.

D. Examples of Antibody-Molecular Payload Complexes

Other aspects of the present disclosure provide complexes comprising any one the muscle targeting agent (e.g., a transferrin receptor antibodies) described herein covalently linked to any of the molecular payloads (e.g., an oligonucleotide) described herein. In some embodiments, the muscle targeting agent (e.g., a transferrin receptor antibody) is covalently linked to a molecular payload (e.g., an oligonucleotide) via a linker. Any of the linkers described herein may be used. In some embodiments, the linker is linked to the 5' end, the 3' end, or internally of the oligonucleotide. In some embodiments, the linker is linked to the antibody via a thiol-reactive linkage (e.g., via a cysteine in the antibody).

An exemplary structure of a complex comprising a transferrin receptor antibody covalently linked to an oligonucleotide via a Val-cit linker is provided below:

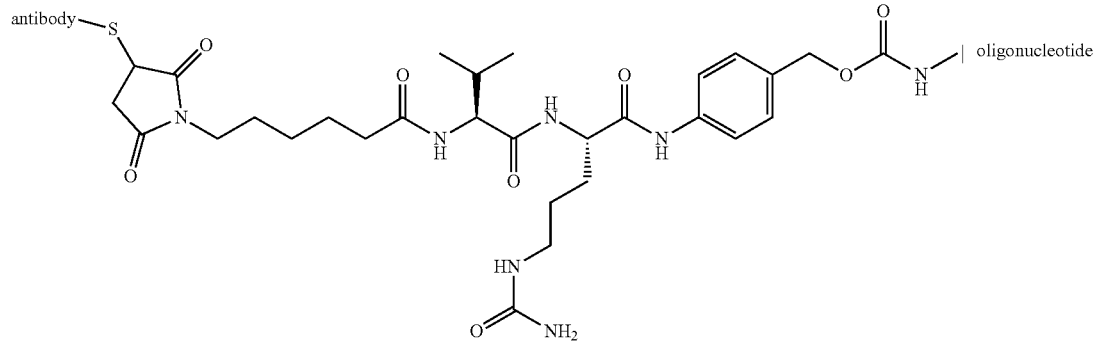

wherein the linker is linked to the 5' end, the 3' end, or internally of the oligonucleotide, and wherein the linker is linked to the antibody via a thiol-reactive linkage (e.g., via a cysteine in the antibody).

It should be appreciated that antibodies can be linked to oligonucleotides with different stochiometries, a property that may be referred to as a drug to antibody ratios (DAR) with the "drug" being the oligonucleotide. In some embodiments, one oligonucleotide is linked to an antibody (DAR=1). In some embodiments, two oligonucleotides are linked to an antibody (DAR=2). In some embodiments, three oligonucleotides are linked to an antibody (DAR=3). In some embodiments, four oligonucleotides are linked to an antibody (DAR=4). In some embodiments, a mixture of different complexes, each having a different DAR, is provided. In some embodiments, an average DAR of complexes in such a mixture may be in a range of 1 to 3, 1 to 4, 1 to 5 or more. DAR may be increased by conjugating oligonucleotides to different sites on an antibody and/or by conjugating multimers to one or more sites on antibody. For example, a DAR of 2 may be achieved by conjugating a single oligonucleotide to two different sites on an antibody or by conjugating a dimer oligonucleotide to a single site of an antibody.

In some embodiments, the complex described herein comprises a transferrin receptor antibody (e.g., an antibody or any variant thereof as described herein) covalently linked to an oligonucleotide targeting DMPK (e.g., an oligonucleotide having a region of complementarity to a DMPK gene sequence as set forth in SEQ ID NO: 15 or SEQ ID NO: 16). In some embodiments, the complex described herein comprises a transferrin receptor antibody (e.g., an antibody or any variant thereof as described herein) covalently linked to an oligonucleotide targeting DMPK (e.g., an oligonucleotide having a region of complementarity to a DMPK gene sequence as set forth in SEQ ID NO: 15 or SEQ ID NO: 16) via a linker (e.g., a Val-cit linker). In some embodiments, the linker (e.g., a Val-cit linker) is linked to the 5' end, the 3' end, or internally of the nucleotide targeting DMPK (e.g., an oligonucleotide having a region of complementarity to a DMPK gene sequence as set forth in SEQ ID NO: 15 or SEQ ID NO: 16). In some embodiments, the linker (e.g., a Val-cit linker) is linked to the antibody (e.g., an antibody or any variant thereof as described herein) via a thiol-reactive linkage (e.g., via a cysteine in the antibody).

In some embodiments, the complex described herein comprises a transferrin receptor antibody covalently linked to a DMPK targeting oligonucleotide, wherein the transferrin receptor antibody comprises a CDR-H1, a CDR-H2, and a CDR-H3 that are the same as the CDR-H1, CDR-H2, and CDR-H3 shown in Table 1.1; and a CDR-L1, a CDR-L2, and a CDR-L3 that are the same as the CDR-L1, CDR-L2, and CDR-L3 shown in Table 1.1.

In some embodiments, the complex described herein comprises a transferrin receptor antibody covalently linked to a DMPK targeting oligonucleotide, wherein the transferrin receptor antibody comprises a VH having the amino acid sequence of SEQ ID NO: 33 and a VL having the amino acid sequence of SEQ ID NO: 34. In some embodiments, the complex described herein comprises a transferrin receptor antibody covalently linked to a DMPK targeting oligonucleotide, wherein the transferrin receptor antibody comprises a VH having the amino acid sequence of SEQ ID NO: 35 and a VL having the amino acid sequence of SEQ ID NO: 36.

In some embodiments, the complex described herein comprises a transferrin receptor antibody covalently linked to a DMPK targeting oligonucleotide, wherein the transferrin receptor antibody comprises a heavy chain having the amino acid sequence of SEQ ID NO: 39 and a light chain having the amino acid sequence of SEQ ID NO: 40. In some embodiments, the complex described herein comprises a transferrin receptor antibody covalently linked to a DMPK targeting oligonucleotide, wherein the transferrin receptor antibody comprises a heavy chain having the amino acid sequence of SEQ ID NO: 41 and a light chain having the amino acid sequence of SEQ ID NO: 42.

In some embodiments, the complex described herein comprises a transferrin receptor antibody covalently linked to a DMPK targeting oligonucleotide via a linker (e.g., a Val-cit linker), wherein the transferrin receptor antibody comprises a CDR-H1, a CDR-H2, and a CDR-H3 that are the same as the CDR-H1, CDR-H2, and CDR-H3 shown in Table 1.1; and a CDR-L1, a CDR-L2, and a CDR-L3 that are the same as the CDR-L1, CDR-L2, and CDR-L3 shown in Table 1.1.

In some embodiments, the complex described herein comprises a transferrin receptor antibody covalently linked to a DMPK targeting oligonucleotide via a linker (e.g., a Val-cit linker), wherein the transferrin receptor antibody comprises a VH having the amino acid sequence of SEQ ID NO: 33 and a VL having the amino acid sequence of SEQ ID NO: 34. In some embodiments, the complex described herein comprises a transferrin receptor antibody covalently linked to a DMPK targeting oligonucleotide via a linker (e.g., a Val-cit linker), wherein the transferrin receptor antibody comprises a VH having the amino acid sequence of SEQ ID NO: 35 and a VL having the amino acid sequence of SEQ ID NO: 36.

In some embodiments, the complex described herein comprises a transferrin receptor antibody covalently linked to a DMPK targeting oligonucleotide via a linker (e.g., a Val-cit linker), wherein the transferrin receptor antibody comprises a heavy chain having the amino acid sequence of SEQ ID NO: 39 and a light chain having the amino acid sequence of SEQ ID NO: 40. In some embodiments, the complex described herein comprises a transferrin receptor antibody covalently linked to a DMPK targeting oligonucleotide via a linker (e.g., a Val-cit linker), wherein the transferrin receptor antibody comprises a heavy chain having the amino acid sequence of SEQ ID NO: 41 and a light chain having the amino acid sequence of SEQ ID NO: 42.

In some embodiments, the complex described herein comprises a transferrin receptor antibody covalently linked to a DMPK targeting oligonucleotide via a Val-cit linker, wherein the transferrin receptor antibody comprises a CDR-H1, a CDR-H2, and a CDR-H3 that are the same as the CDR-H1, CDR-H2, and CDR-H3 shown in Table 1.1; and a CDR-L1, a CDR-L2, and a CDR-L3 that are the same as the CDR-L1, CDR-L2, and CDR-L3 shown in Table 1.1, and wherein the complex comprises the structure of:

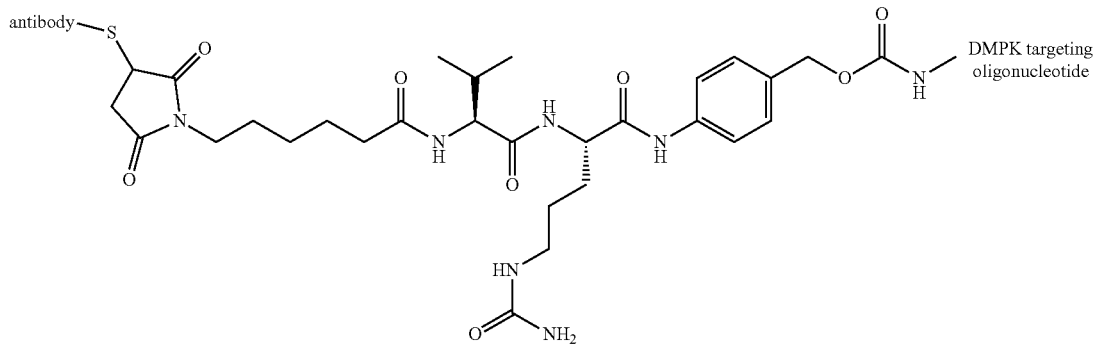

wherein the linker Val-cit linker is linked to the 5' end, the 3' end, or internally of the DMPK targeting oligonucleotide, and wherein the Val-cit linker is linked to the antibody (e.g., an antibody or any variant thereof as described herein) via a thiol-reactive linkage (e.g., via a cysteine in the antibody).

In some embodiments, the complex described herein comprises a transferrin receptor antibody covalently linked to a DMPK targeting oligonucleotide via a Val-cit linker, wherein the transferrin receptor antibody comprises a VH having the amino acid sequence of SEQ ID NO: 33 and a VL having the amino acid sequence of SEQ ID NO: 34, and wherein the complex comprises the structure of:

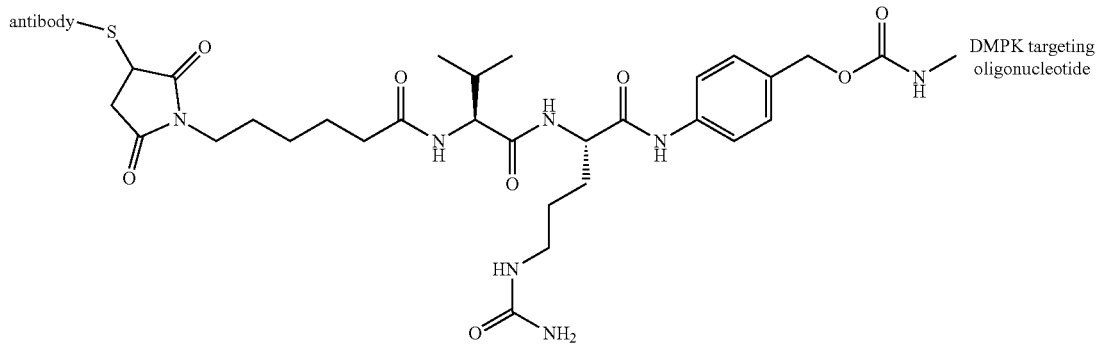

wherein the linker Val-cit linker is linked to the 5' end, the 3' end, or internally of DMPK targeting oligonucleotide, and wherein the Val-cit linker is linked to the antibody (e.g., an antibody or any variant thereof as described herein) via a thiol-reactive linkage (e.g., via a cysteine in the antibody).

In some embodiments, the complex described herein comprises a transferrin receptor antibody covalently linked to a DMPK targeting oligonucleotide via a Val-cit linker, wherein the transferrin receptor antibody comprises a VH having the amino acid sequence of SEQ ID NO: 35 and a VL having the amino acid sequence of SEQ ID NO: 36, and wherein the complex comprises the structure of:

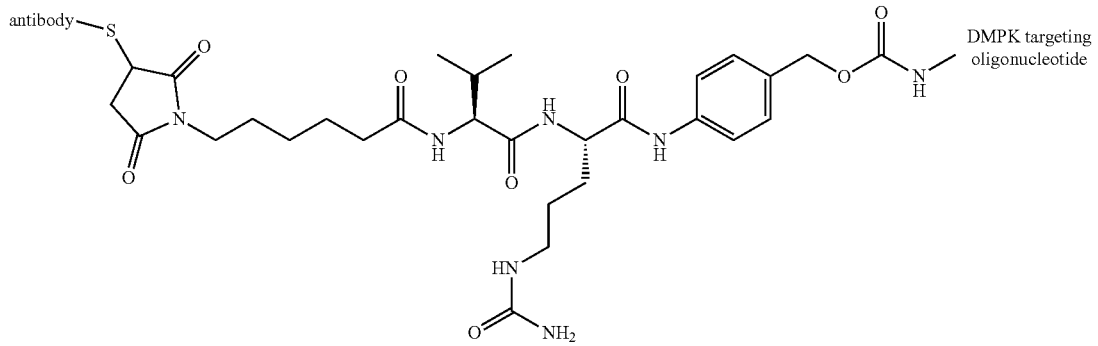

wherein the linker Val-cit linker is linked to the 5' end, the 3' end, or internally of the DMPK targeting oligonucleotide, and wherein the Val-cit linker is linked to the antibody (e.g., an antibody or any variant thereof as described herein) via a thiol-reactive linkage (e.g., via a cysteine in the antibody).

In some embodiments, the complex described herein comprises a transferrin receptor antibody covalently linked to a DMPK targeting oligonucleotide via a Val-cit linker, wherein the transferrin receptor antibody comprises a heavy chain having the amino acid sequence of SEQ ID NO: 39 and a light chain having the amino acid sequence of SEQ ID NO: 40, and wherein the complex comprises the structure of:

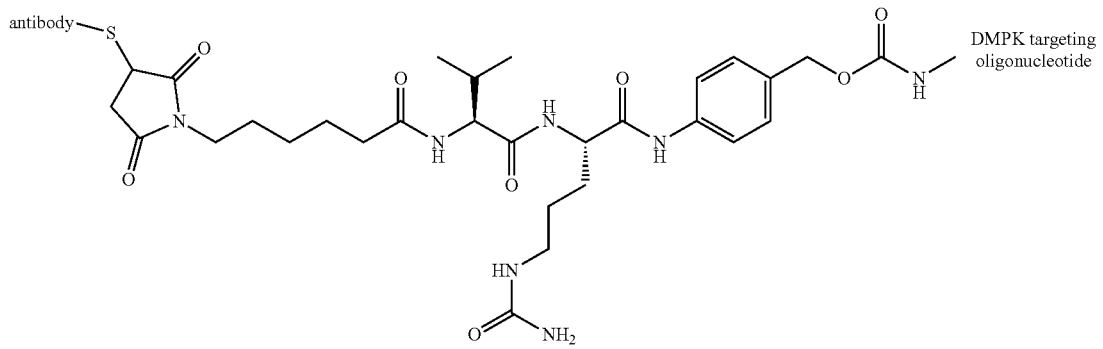

wherein the linker Val-cit linker is linked to the 5' end, the 3' end, or internally of DMPK targeting oligonucleotide, and wherein the Val-cit linker is linked to the antibody (e.g., an antibody or any variant thereof as described herein) via a thiol-reactive linkage (e.g., via a cysteine in the antibody).

In some embodiments, the complex described herein comprises a transferrin receptor antibody covalently linked to a DMPK targeting oligonucleotide via a Val-cit linker, wherein the transferrin receptor antibody comprises a heavy chain having the amino acid sequence of SEQ ID NO: 41 and a light chain having the amino acid sequence of SEQ ID NO: 42, and wherein the complex comprises the structure of:

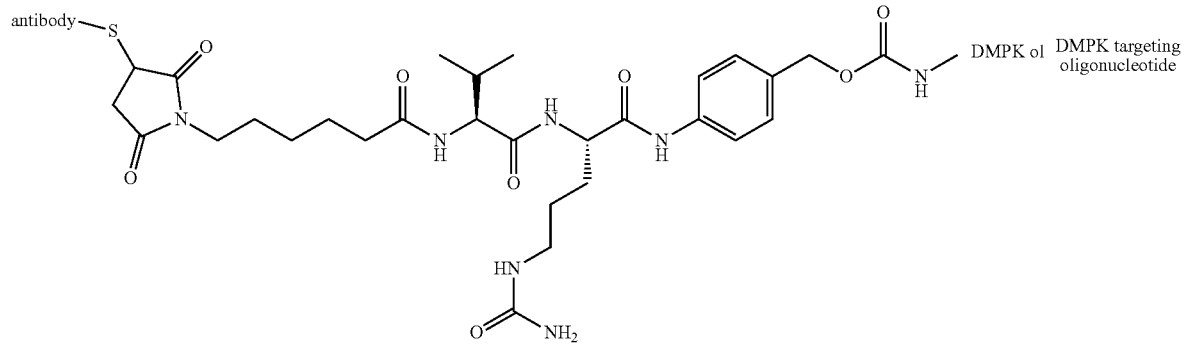

wherein the linker Val-cit linker is linked to the 5' end, the 3' end, or internally of DMPK targeting oligonucleotide, and wherein the Val-cit linker is linked to the antibody (e.g., an antibody or any variant thereof as described herein) via a thiol-reactive linkage (e.g., via a cysteine in the antibody).

III. Formulations

Complexes provided herein may be formulated in any suitable manner. Generally, complexes provided herein are formulated in a manner suitable for pharmaceutical use. For example, complexes can be delivered to a subject using a formulation that minimizes degradation, facilitates delivery and/or uptake, or provides another beneficial property to the complexes in the formulation. In some embodiments, provided herein are compositions comprising complexes and pharmaceutically acceptable carriers. Such compositions can be suitably formulated such that when administered to a subject, either into the immediate environment of a target cell or systemically, a sufficient amount of the complexes enter target muscle cells. In some embodiments, complexes are formulated in buffer solutions such as phosphate-buffered saline solutions, liposomes, micellar structures, and capsids.

It should be appreciated that, in some embodiments, compositions may include separately one or more components of complexes provided herein (e.g., muscle-targeting agents, linkers, molecular payloads, or precursor molecules of any one of them).

In some embodiments, complexes are formulated in water or in an aqueous solution (e.g., water with pH adjustments). In some embodiments, complexes are formulated in basic buffered aqueous solutions (e.g., PBS). In some embodiments, formulations as disclosed herein comprise an excipient. In some embodiments, an excipient confers to a composition improved stability, improved absorption, improved solubility and/or therapeutic enhancement of the active ingredient. In some embodiments, an excipient is a buffering agent (e.g., sodium citrate, sodium phosphate, a tris base, or sodium hydroxide) or a vehicle (e.g., a buffered solution, petrolatum, dimethyl sulfoxide, or mineral oil).

In some embodiments, a complex or component thereof (e.g., oligonucleotide or antibody) is lyophilized for extending its shelf-life and then made into a solution before use (e.g., administration to a subject). Accordingly, an excipient in a composition comprising a complex, or component thereof, described herein may be a lyoprotectant (e.g., mannitol, lactose, polyethylene glycol, or polyvinyl pyrolidone), or a collapse temperature modifier (e.g., dextran, ficoll, or gelatin).

In some embodiments, a pharmaceutical composition is formulated to be compatible with its intended route of administration. Examples of routes of administration include parenteral, e.g., intravenous, intradermal, subcutaneous, administration. Typically, the route of administration is intravenous or subcutaneous.

Pharmaceutical compositions suitable for injectable use include sterile aqueous solutions (where water soluble) or dispersions and sterile powders for the extemporaneous preparation of sterile injectable solutions or dispersions. The carrier can be a solvent or dispersion medium containing, for example, water, ethanol, polyol (for example, glycerol, propylene glycol, and liquid polyethylene glycol, and the like), and suitable mixtures thereof. In some embodiments, formulations include isotonic agents, for example, sugars, polyalcohols such as mannitol, sorbitol, and sodium chloride in the composition. Sterile injectable solutions can be prepared by incorporating the a complexes in a required amount in a selected solvent with one or a combination of ingredients enumerated above, as required, followed by filtered sterilization.

In some embodiments, a composition may contain at least about 0.1% of the a complex, or component thereof, or more, although the percentage of the active ingredient(s) may be between about 1% and about 80% or more of the weight or volume of the total composition. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

IV. Methods of Use/Treatment

Complexes comprising a muscle-targeting agent covalently to a molecular payload as described herein are effective in treating myotonic dystrophy. In some embodiments, complexes are effective in treating myotonic dystrophy type 1 (DM1). In some embodiments, DM1 is associated with an expansion of a CTG trinucleotide repeat in the 3' non-coding region of DMPK. In some embodiments, the nucleotide expansions lead to toxic RNA repeats capable of forming hairpin structures that bind critical intracellular proteins, e.g., muscleblind-like proteins, with high affinity.

In some embodiments, a subject may be a human subject, a non-human primate subject, a rodent subject, or any suitable mammalian subject. In some embodiments, a subject may have myotonic dystrophy. In some embodiments, a subject has a DMPK allele, which may optionally contain a disease-associated repeat. In some embodiments, a subject may have a DMPK allele with an expanded disease-associated-repeat that comprises about 2-10 repeat units, about 2-50 repeat units, about 2-100 repeat units, about 50-1,000 repeat units, about 50-500 repeat units, about 50-250 repeat units, about 50-100 repeat units, about 500-10,000 repeat units, about 500-5,000 repeat units, about 500-2,500 repeat units, about 500-1,000 repeat units, or about 1,000-10,000 repeat units. In some embodiments, a subject is suffering from symptoms of DM1, e.g. muscle atrophy or muscle loss. In some embodiments, a subject is not suffering from symptoms of DM1. In some embodiments, subjects have congenital myotonic dystrophy.

An aspect of the disclosure includes a methods involving administering to a subject an effective amount of a complex as described herein. In some embodiments, an effective amount of a pharmaceutical composition that comprises a complex comprising a muscle-targeting agent covalently to a molecular payload can be administered to a subject in need of treatment. In some embodiments, a pharmaceutical composition comprising a complex as described herein may be administered by a suitable route, which may include intravenous administration, e.g., as a bolus or by continuous infusion over a period of time. In some embodiments, intravenous administration may be performed by intramuscular, intraperitoneal, intracerebrospinal, subcutaneous, intra-articular, intrasynovial, or intrathecal routes. In some embodiments, a pharmaceutical composition may be in solid form, aqueous form, or a liquid form. In some embodiments, an aqueous or liquid form may be nebulized or lyophilized. In some embodiments, a nebulized or lyophilized form may be reconstituted with an aqueous or liquid solution.

Compositions for intravenous administration may contain various carriers such as vegetable oils, dimethylactamide, dimethyformamide, ethyl lactate, ethyl carbonate, isopropyl myristate, ethanol, and polyols (glycerol, propylene glycol, liquid polyethylene glycol, and the like). For intravenous injection, water soluble antibodies can be administered by the drip method, whereby a pharmaceutical formulation containing the antibody and a physiologically acceptable excipients is infused. Physiologically acceptable excipients may include, for example, 5% dextrose, 0.9% saline, Ringer's solution or other suitable excipients. Intramuscular preparations, e.g., a sterile formulation of a suitable soluble salt form of the antibody, can be dissolved and administered in a pharmaceutical excipient such as Water-for-Injection, 0.9% saline, or 5% glucose solution.

In some embodiments, a pharmaceutical composition that comprises a complex comprising a muscle-targeting agent covalently to a molecular payload is administered via site-specific or local delivery techniques. Examples of these techniques include implantable depot sources of the complex, local delivery catheters, site specific carriers, direct injection, or direct application.

In some embodiments, a pharmaceutical composition that comprises a complex comprising a muscle-targeting agent covalently to a molecular payload is administered at an effective concentration that confers therapeutic effect on a subject. Effective amounts vary, as recognized by those skilled in the art, depending on the severity of the disease, unique characteristics of the subject being treated, e.g. age, physical conditions, health, or weight, the duration of the treatment, the nature of any concurrent therapies, the route of administration and related factors. These related factors are known to those in the art and may be addressed with no more than routine experimentation. In some embodiments, an effective concentration is the maximum dose that is considered to be safe for the patient. In some embodiments, an effective concentration will be the lowest possible concentration that provides maximum efficacy.

Empirical considerations, e.g. the half-life of the complex in a subject, generally will contribute to determination of the concentration of pharmaceutical composition that is used for treatment. The frequency of administration may be empirically determined and adjusted to maximize the efficacy of the treatment.

Generally, for administration of any of the complexes described herein, an initial candidate dosage may be about 1 to 100 mg/kg, or more, depending on the factors described above, e.g. safety or efficacy. In some embodiments, a treatment will be administered once. In some embodiments, a treatment will be administered daily, biweekly, weekly, bimonthly, monthly, or at any time interval that provide maximum efficacy while minimizing safety risks to the subject. Generally, the efficacy and the treatment and safety risks may be monitored throughout the course of treatment The efficacy of treatment may be assessed using any suitable methods. In some embodiments, the efficacy of treatment may be assessed by evaluation of observation of symptoms associated with DM1, e.g. muscle atrophy or muscle weakness, through measures of a subject's self-reported outcomes, e.g. mobility, self-care, usual activities, pain/discomfort, and anxiety/depression, or by quality-of-life indicators, e.g. lifespan.

In some embodiments, a pharmaceutical composition that comprises a complex comprising a muscle-targeting agent covalently to a molecular payload described herein is administered to a subject at an effective concentration sufficient to inhibit activity or expression of a target gene by at least 10%, at least 20%, at least 30%, at least 40%, at least 50%, at least 60%, at least 70%, at least 80%, at least 90% or at least 95% relative to a control, e.g. baseline level of gene expression prior to treatment.

In some embodiments, a single dose or administration of a pharmaceutical composition that comprises a complex comprising a muscle-targeting agent covalently to a molecular payload described herein to a subject is sufficient to inhibit activity or expression of a target gene for at least 1-5, 1-10, 5-15, 10-20, 15-30, 20-40, 25-50, or more days. In some embodiments, a single dose or administration of a pharmaceutical composition that comprises a complex comprising a muscle-targeting agent covalently to a molecular payload described herein to a subject is sufficient to inhibit activity or expression of a target gene for at least 1, 2, 3, 4, 5, 6, 7, 8, 9, 10, 11, or 12 weeks. In some embodiments, a single dose or administration of a pharmaceutical composition that comprises a complex comprising a muscle-targeting agent covalently to a molecular payload described herein to a subject is sufficient to inhibit activity or expression of a target gene for at least 1, 2, 3, 4, 5, or 6 months.

In some embodiments, a pharmaceutical composition may comprises more than one complex comprising a muscle-targeting agent covalently to a molecular payload. In some embodiments, a pharmaceutical composition may further comprise any other suitable therapeutic agent for treatment of a subject, e.g. a human subject having DM1. In some embodiments, the other therapeutic agents may enhance or supplement the effectiveness of the complexes described herein. In some embodiments, the other therapeutic agents may function to treat a different symptom or disease than the complexes described herein.

EXAMPLES

Example 1: Targeting DMPK with Transfected Antisense Oligonucleotides

A gapmer antisense oligonucleotide that targets both wild-type and mutant alleles of DMPK (DTX-P-060) was tested in vitro for its ability to reduce expression levels of DMPK in an immortalized cell line. Briefly, Hepa 1-6 cells were transfected with the DTX-P-060 (100 nM) formulated with lipofectamine 2000. DMPK expression levels were evaluated 72 hours following transfection. A control experiment was also performed in which vehicle (phosphate-buffered saline) was delivered to Hepa 1-6 cells in culture and the cells were maintained for 72 hours. As shown in FIG. 1, it was found that the DTX-P-060 reduced DMPK expression levels by ~90% compared with controls.

Example 2: Targeting DMPK with a Muscle-Targeting Complex

A muscle-targeting complex was generated comprising the DMPK ASO used in Example 1 (DTX-P-060) covalently linked, via a cathepsin cleavable linker, to DTX-A-002 (RI7 217 (Fab)), an anti-transferrin receptor antibody.

Briefly, a maleimidocaproyl-L-valine-L-citrulline-p-aminobenzyl alcohol p-nitrophenyl carbonate (MC-Val-Cit-PABC-PNP) linker molecule was coupled to $NH_2$—$C_6$-DTX-P-060 using an amide coupling reaction. Excess linker and organic solvents were removed by gel permeation chromatography. The purified Val-Cit-linker-DTX-P-060 was then coupled to a thiol-reactive anti-transferrin receptor antibody (DTX-A-002).

Figure 2A:
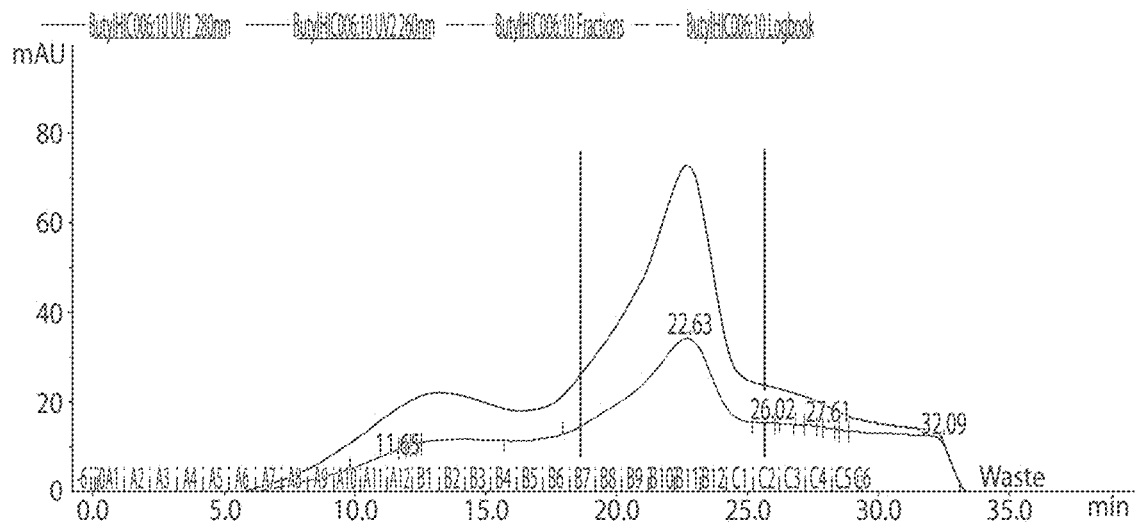
FIG. 2A depicts a non-limiting schematic showing an HIL-HPLC trace obtained during purification of a muscle targeting complex comprising an anti-transferrin receptor antibody covalently linked to a DMPK antisense oligonucleotide.
Figure 2B:
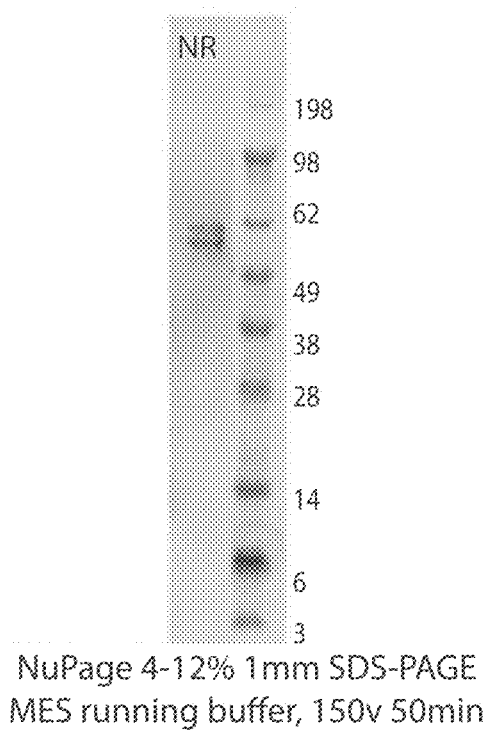
FIG. 2B depicts a non-limiting image of an SDS-PAGE analysis of a muscle targeting complex.

The product of the antibody coupling reaction was then subjected to hydrophobic interaction chromatography (HIC-HPLC). FIG. 2A shows a resulting HIC-HPLC chromatogram, in which fractions B7-C2 of the chromatogram (denoted by vertical lines) contained antibody-oligonucleotide complexes (referred to as DTX-C-008) comprising one or two DMPK ASO molecules covalently attached to DTX-A-002, as determined by SDS-PAGE. These HIC-HPLC fractions were combined and densitometry confirmed that this sample of DTX-C-008 complexes had an average ASO to antibody ratio of 1.48. SDS-PAGE analysis demonstrated that 86.4% of this sample of DTX-C-008 complexes comprised DTX-A-002 linked to either one or two DMPK ASO molecules (FIG. 2B).

Using the same methods as described above, a control complex was generated comprising the DMPK ASO used in Example 1 (DTX-P-060) covalently linked via a Val-Cit linker to an IgG2a (Fab) antibody (DTX-C-007).

Figure 3:
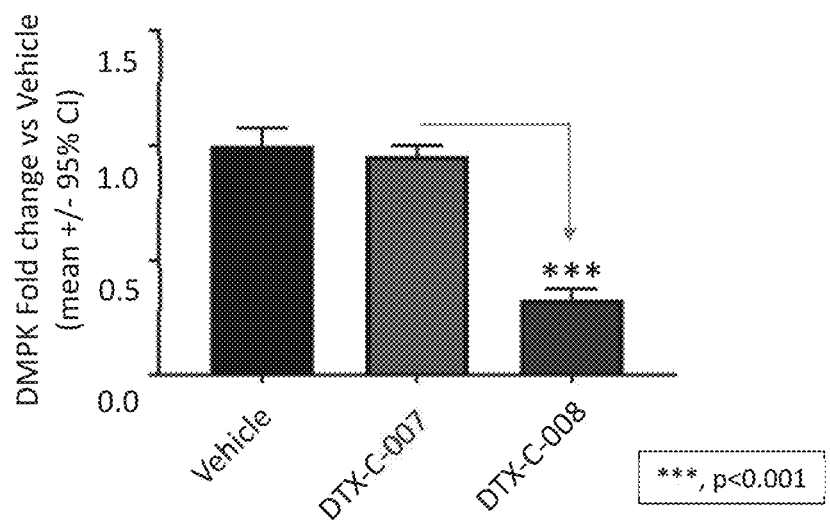
FIG. 3 depicts a non-limiting schematic showing the ability of a muscle targeting complex (DTX-C-008) comprising DTX-P-060 to reduce expression levels of DMPK.
Figure 4A:
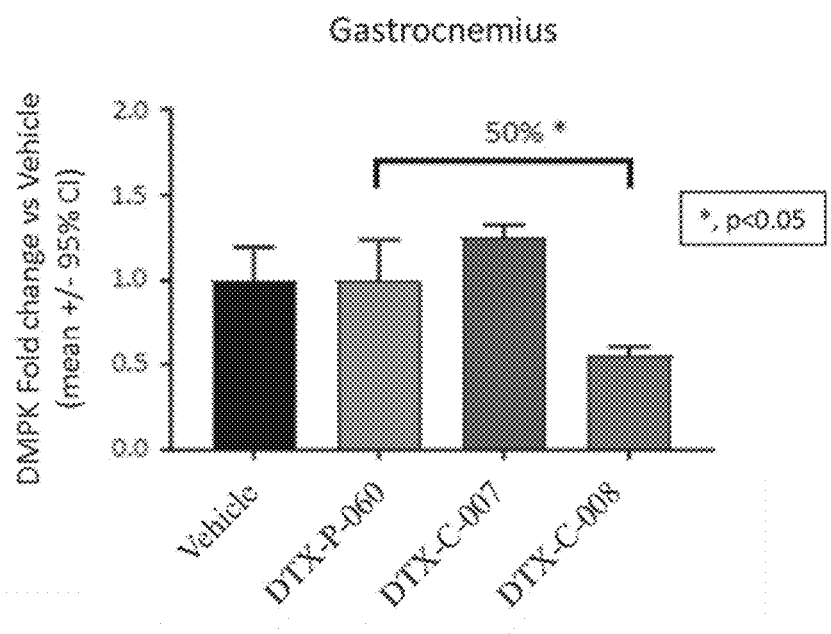
FIGS. 4A-4E depict non-limiting schematics showing the ability of a muscle targeting complex (DTX-C-008) comprising DTX-P-060 to reduce expression levels of DMPK in mouse muscle tissues in vivo, relative to a vehicle experiment. (N=3 C57Bl/6 WT mice)
Figure 4B:
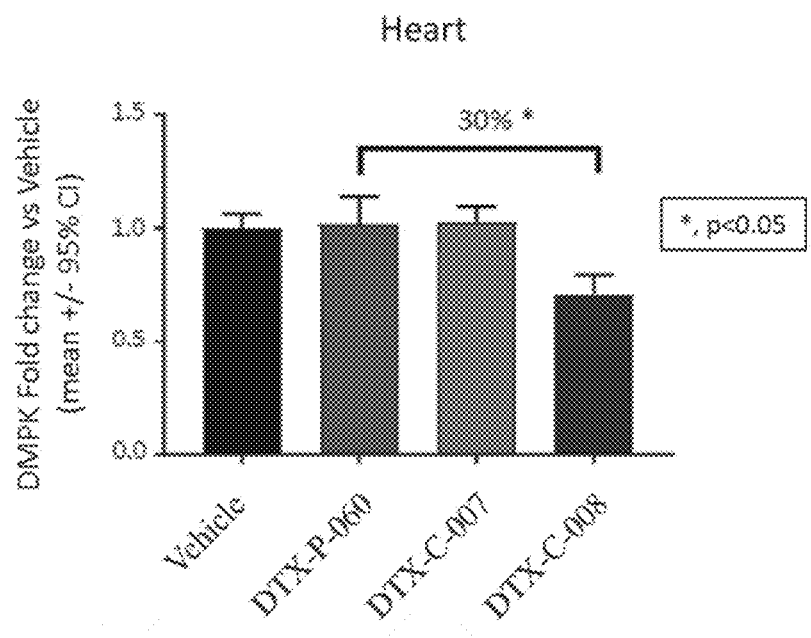
Figure 4C:
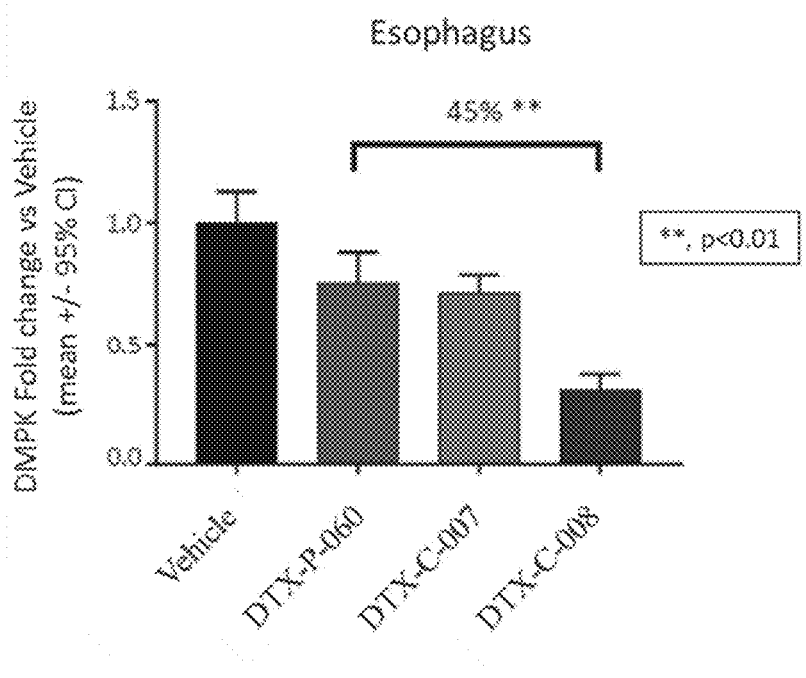
Figure 4D:
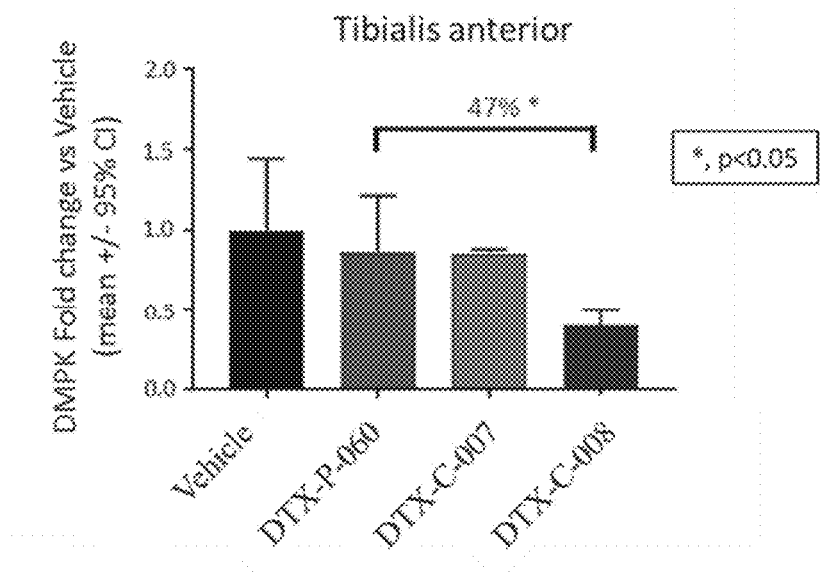
Figure 4E:
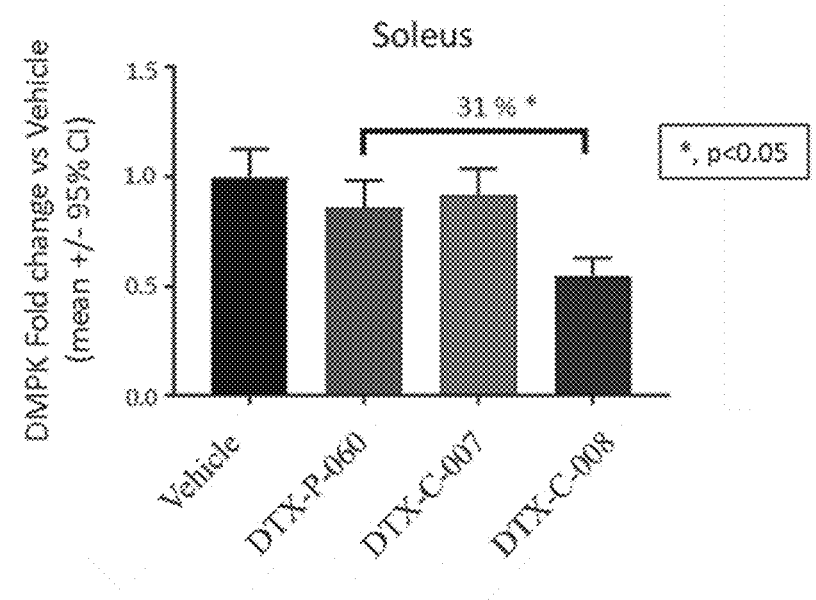

The purified DTX-C-008 was then tested for cellular internalization and inhibition of DMPK. Hepa 1-6 cells, which have relatively high expression levels of transferrin receptor, were incubated in the presence of vehicle control, DTX-C-008 (100 nM), or DTX-C-007 (100 nM) for 72 hours. After the 72 hour incubation, the cells were isolated and assayed for expression levels of DMPK (FIG. 3). Cells treated with the DTX-C-008 demonstrated a reduction in DMPK expression by ~65% relative to the cells treated with the vehicle control. Meanwhile, cells treated with the DTX-C-007 had DMPK expression levels comparable to the vehicle control (no reduction in DMPK expression). These data indicate that the anti-transferrin receptor antibody of the DTX-C-008 enabled cellular internalization of the complex, thereby allowing the DMPK ASO to inhibit expression of DMPK.

Example 3: Targeting DMPK in Mouse Muscle Tissues with a Muscle-Targeting Complex The muscle-targeting complex described in Example 2, DTX-C-008, was tested for inhibition of DMPK in mouse tissues. C57BL/6 wild-type mice were intravenously injected with a single dose of a vehicle control, DTX-P-060 (3 mg/kg of RNA), DTX-C-008 (3 mg/kg of RNA, corresponding to 20 mg/kg antibody conjugate), or DTX-C-007 (3 mg/kg of RNA, corresponding to 20 mg/kg antibody conjugate). DTX-P-060, the DMPK ASO as described in Example 1, was used as a control. Each experimental condition was replicated in three individual C57BL/6 wild-type mice. Following a seven-day period after injection, the mice were euthanized and segmented into isolated tissue types. Individual tissue samples were subsequently assayed for expression levels of DMPK (FIGS. 4A-4E and 5A-5B).

Mice treated with the DTX-C-008 complex demonstrated a reduction in DMPK expression in a variety of skeletal, cardiac, and smooth muscle tissues. For example, as shown in FIGS. 4A-4E, DMPK expression levels were significantly reduced in gastrocnemius (50% reduction), heart (30% reduction), esophagus (45% reduction), tibialis anterior (47% reduction), and soleus (31% reduction) tissues, relative to the mice treated with the vehicle control. Meanwhile, mice treated with the DTX-C-007 complex had DMPK expression levels comparable to the vehicle control (no reduction in DMPK expression) for all assayed muscle tissue types.

Figure 5A:
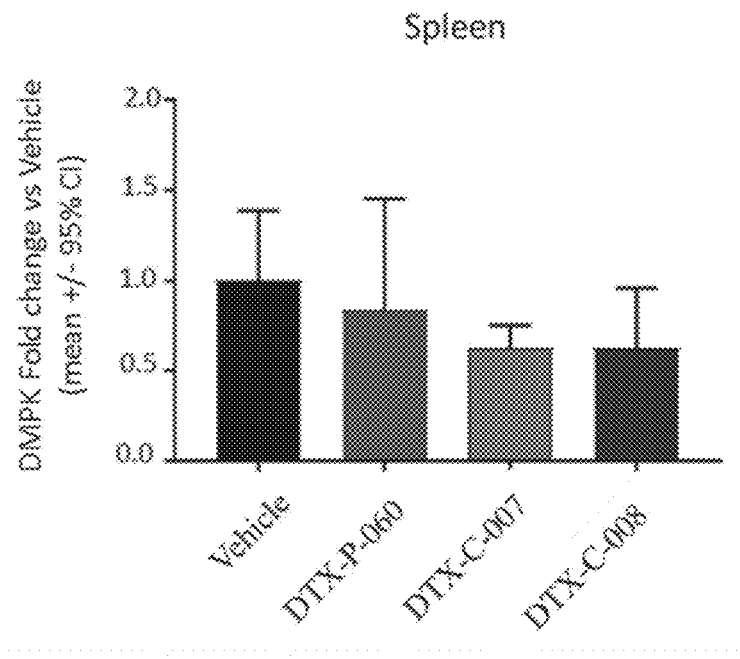
FIGS. 5A-5B depict non-limiting schematics showing the tissue selectivity of a muscle targeting complex (DTX-C-008) comprising DTX-P-060. The muscle targeting complex (DTX-C-008) comprising DTX-P-060 does not reduce expression levels of DMPK in mouse brain or spleen tissues in vivo, relative to a vehicle experiment. (N=3 C57Bl/16 WT mice)
Figure 5B:
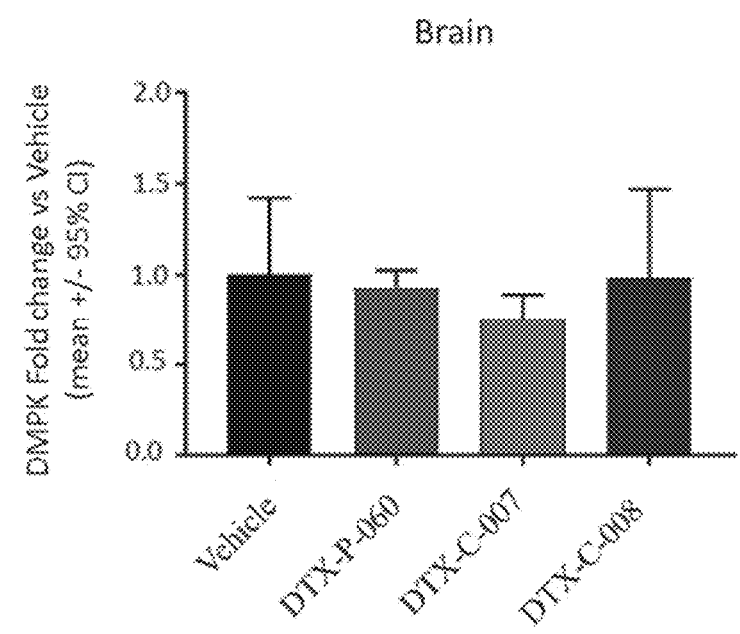
Figure 6A:
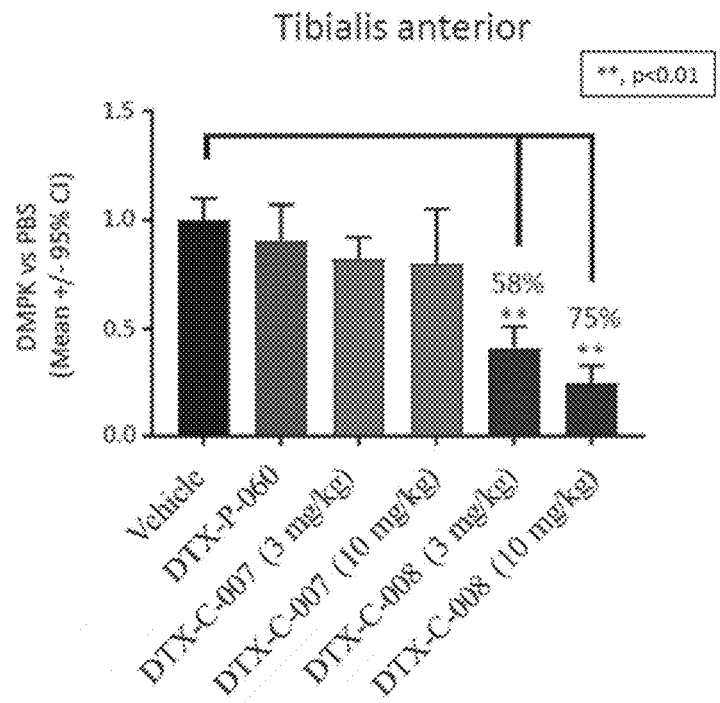
FIGS. 6A-6F depict non-limiting schematics showing the ability of a muscle targeting complex (DTX-C-008) comprising DTX-P-060 to reduce expression levels of DMPK in mouse muscle tissues in vivo, relative to a vehicle experiment. (N=5 C57Bl/6 WT mice)
Figure 6B:
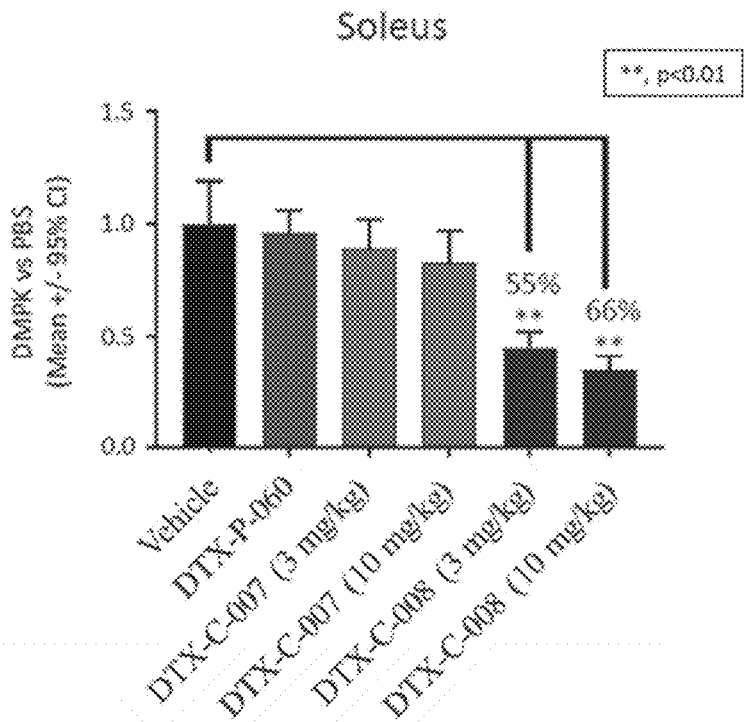
Figure 6C:
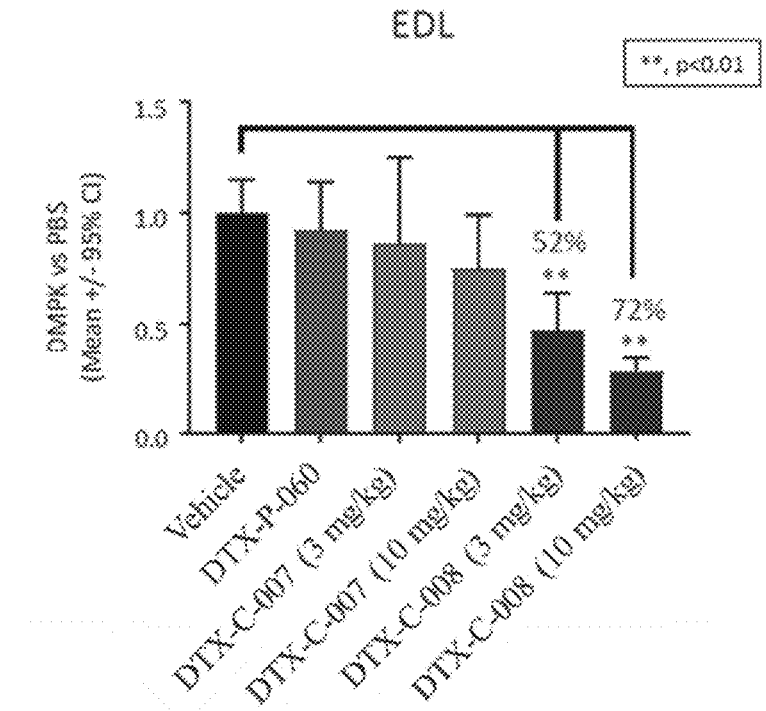
Figure 6D:
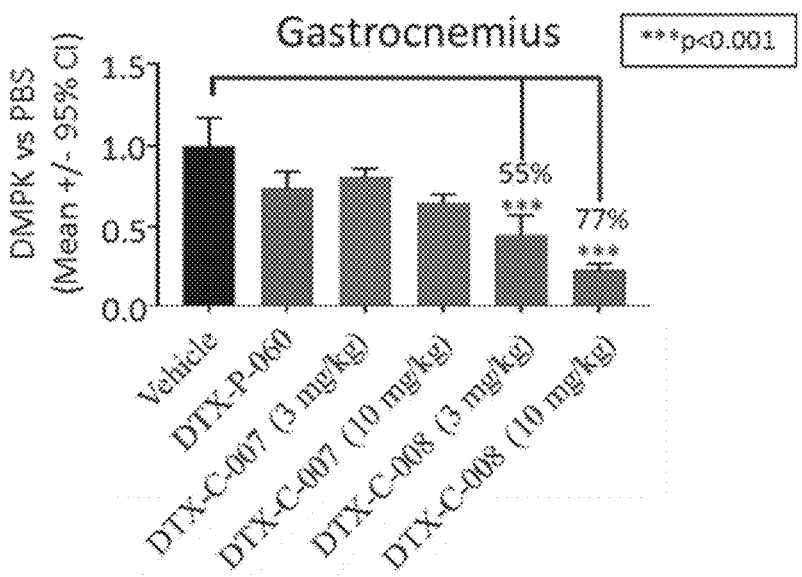
Figure 6E:
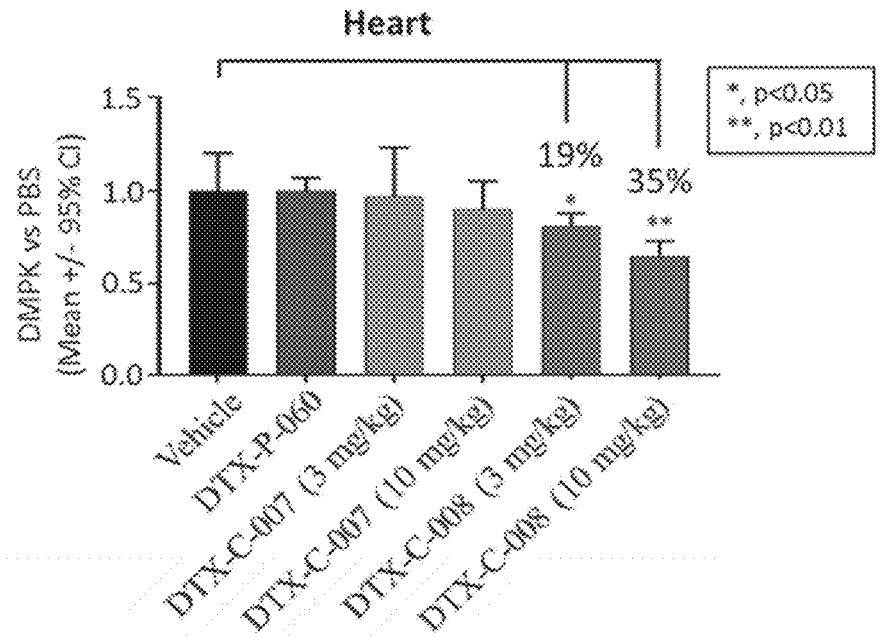
Figure 6F:
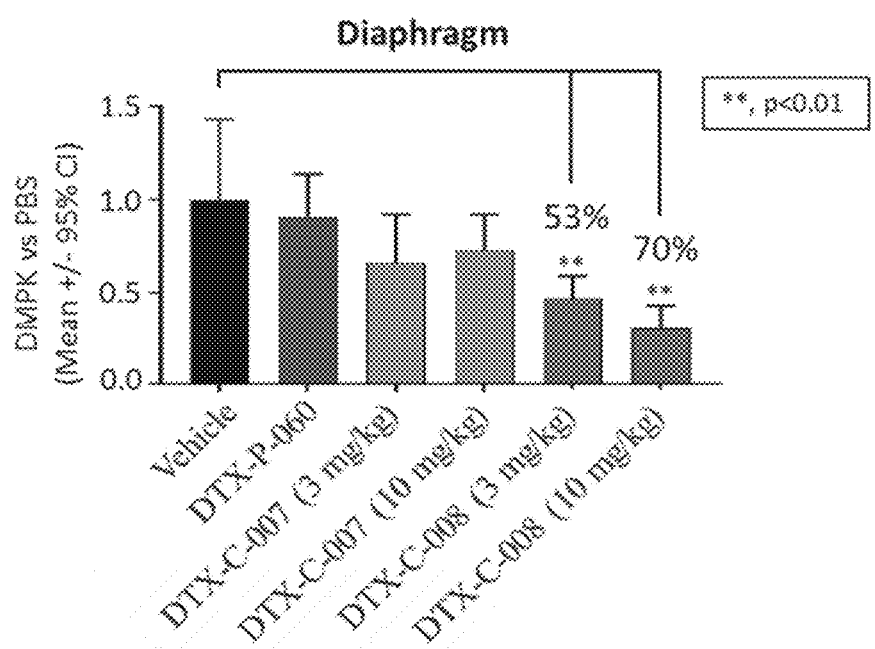

Mice treated with the DTX-C-008 complex demonstrated no change in DMPK expression in non-muscle tissues such as spleen and brain tissues (FIGS. 5A and 5B).

These data indicate that the anti-transferrin receptor antibody of the DTX-C-008 enabled cellular internalization of the complex into muscle-specific tissues in an in vivo mouse model, thereby allowing the DMPK ASO to inhibit expression of DMPK. These data further demonstrate that the DTX-C-008 complex is capable of specifically targeting muscle tissues.

Example 4: Targeting DMPK in Mouse Muscle Tissues with a Muscle-Targeting Complex The muscle-targeting complex described in Example 2, DTX-C-008, was tested for dose-dependent inhibition of DMPK in mouse tissues. C57BL/6 wild-type mice were intravenously injected with a single dose of a vehicle control (phosphate-buffered saline, PBS), DTX-P-060 (10 mg/kg of RNA), DTX-C-008 (3 mg/kg or 10 mg/kg of RNA, wherein 3 mg/kg corresponds to 20 mg/kg antibody conjugate), or DTX-C-007 (3 mg/kg or 10 mg/kg of RNA, wherein 3 mg/kg corresponds to 20 mg/kg antibody conjugate). DTX-P-060, the DMPK ASO as described in Example 1, was used as a control. Each experimental condition was replicated in five individual C57BL/6 wild-type mice. Following a seven-day period after injection, the mice were euthanized and segmented into isolated tissue types. Individual tissue samples were subsequently assayed for expression levels of DMPK (FIGS. 6A-6F).

Mice treated with the DTX-C-008 complex demonstrated a reduction in DMPK expression in a variety of skeletal muscle tissues. As shown in FIGS. 6A-6F, DMPK expression levels were significantly reduced in tibialis anterior (58% and 75% reduction for 3 mg/kg and 10 mg/kg DTX-C-008, respectively), soleus (55% and 66% reduction for 3 mg/kg and 10 mg/kg DTX-C-008, respectively), extensor digitorum longus (EDL) (52% and 72% reduction for 3 mg/kg and 10 mg/kg DTX-C-008, respectively), gastrocnemius (55% and 77% reduction for 3 mg/kg and 10 mg/kg DTX-C-008, respectively), heart (19% and 35% reduction for 3 mg/kg and 10 mg/kg DTX-C-008, respectively), and diaphragm (53% and 70% reduction for 3 mg/kg and 10 mg/kg DTX-C-008, respectively) tissues, relative to the mice treated with the vehicle control. Notably, all assayed muscle tissue types experienced dose-dependent inhibition of DMPK, with greater reduction in DMPK levels at 10 mg/kg antibody conjugate relative to 3 mg/kg antibody conjugate.

Meanwhile, mice treated with the control DTX-C-007 complex had DMPK expression levels comparable to the vehicle control (no reduction in DMPK expression) for all assayed muscle tissue types. These data indicate that the anti-transferrin receptor antibody of the DTX-C-008 enabled cellular internalization of the complex into muscle-specific tissues in an in vivo mouse model, thereby allowing the DMPK ASO to inhibit expression of DMPK. These data further demonstrate that the DTX-C-008 complex is capable of specifically targeting muscle tissues for dose-dependent inhibition of DMPK.

Example 5: Targeting DMPK in Cynomolgus Monkey Muscle Tissues with a Muscle-Targeting Complex A muscle-targeting complex comprising DTX-P-060 (DTX-C-012), was generated and purified using methods described in Example 2. DTX-C-012 is a complex comprising a human anti-transferrin antibody covalently linked, via a cathepsin cleavable Val-Cit linker, to DTX-P-060, an antisense oligonucleotide that targets DMPK. Following HIC-HPLC purification, densitometry confirmed that DTX-C-012 had an average ASO to antibody ratio of 1.32, and SDS-PAGE revealed a purity of 92.3%.

DTX-C-012 was tested for dose-dependent inhibition of DMPK in male cynomolgus monkey tissues. Male cynomolgus monkeys (19-31 months; 2-3 kg) were intravenously injected with a single dose of a saline control, DTX-P-060 (naked DMPK ASO) (10 mg/kg of RNA), or DTX-C-012 (10 mg/kg of RNA) on Day 0. Each experimental condition was replicated in three individual male cynomolgus monkeys. On Day 7 after injection, tissue biopsies (including muscle tissues) were collected. DMPK mRNA expression levels, ASO detection assays, serum clinical chemistries, tissue histology, clinical observations, and body weights were analyzed. The monkeys were euthanized on Day 14.

Figure 7A:
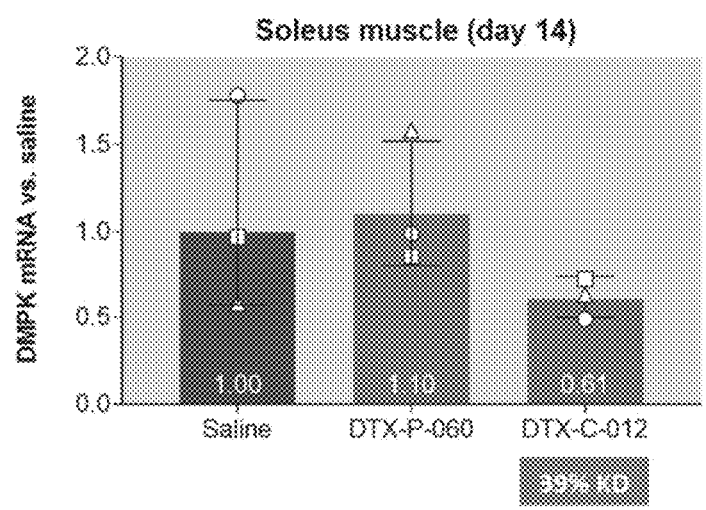
FIGS. 7A-7L depict non-limiting schematics showing the ability of a muscle targeting complex (DTX-C-012) comprising DTX-P-060 to reduce expression levels of DMPK in cynomolgus monkey muscle tissues in vivo, relative to a vehicle experiment and compared to a naked DMPK ASO (DTX-P-060). (N=3 male cynomolgus monkeys)
Figure 7B:
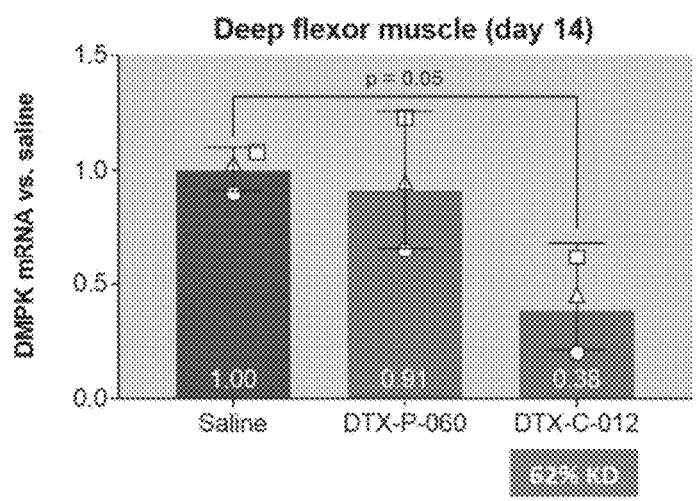
Figure 7C:
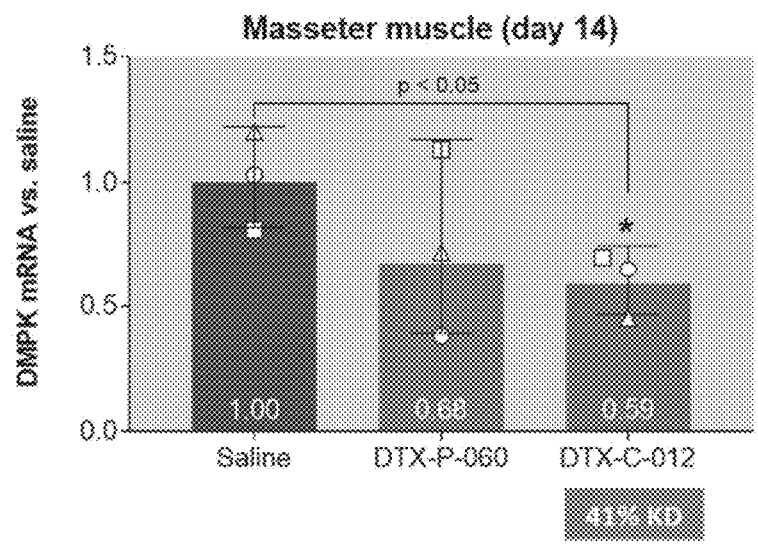
Figure 7D:
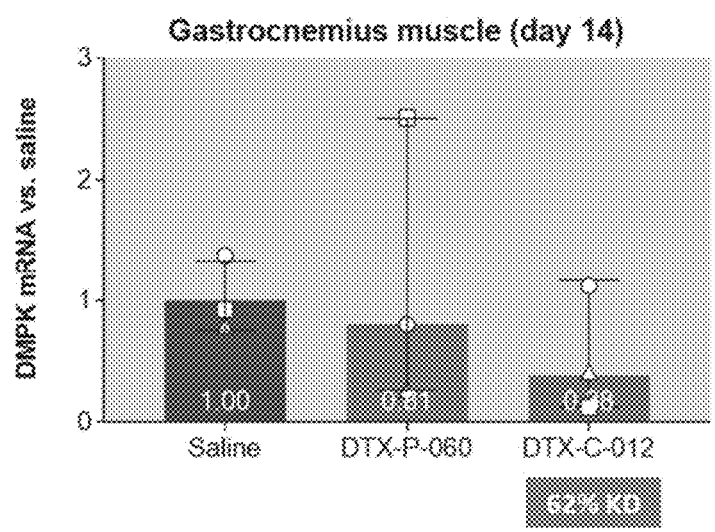
Figure 7E:
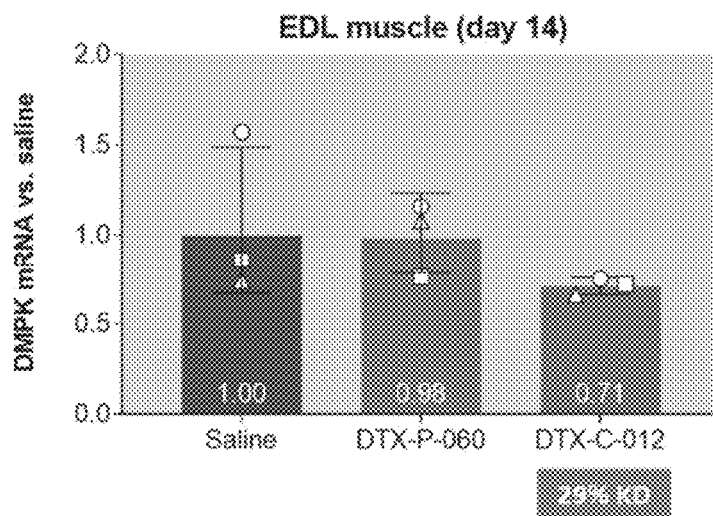
Figure 7F:
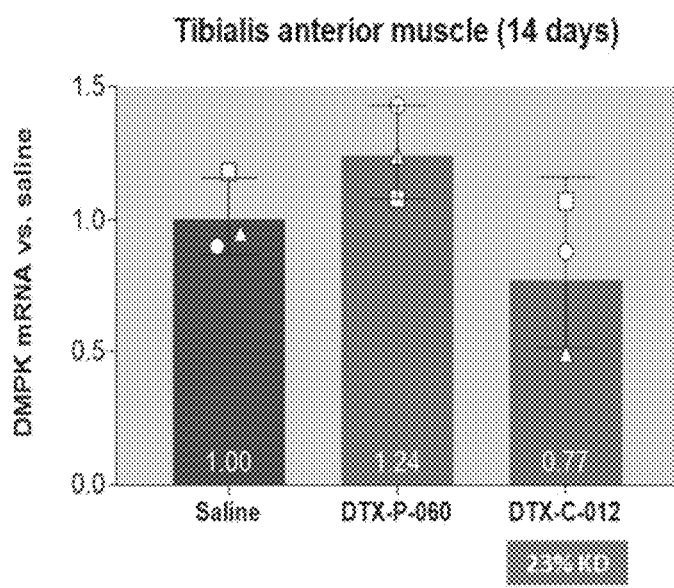
Figure 7G:
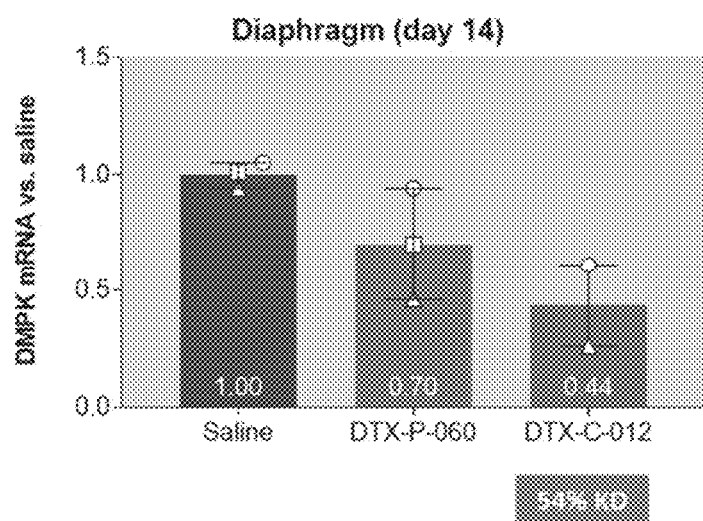
Figure 7H:
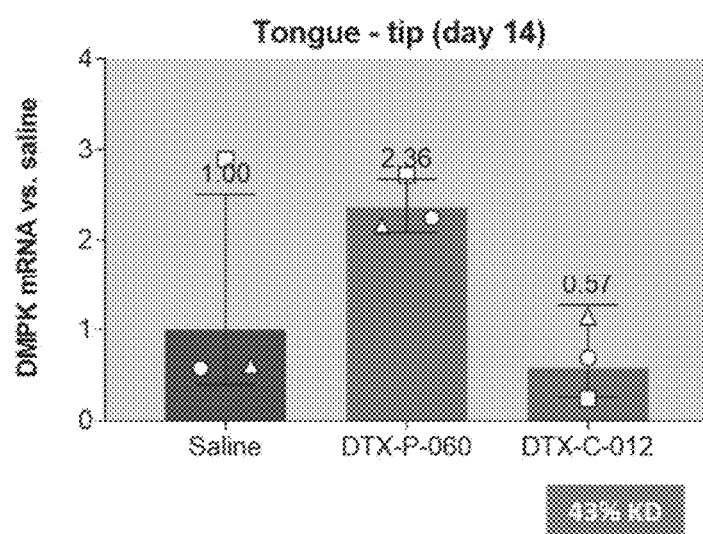
Figure 7I:
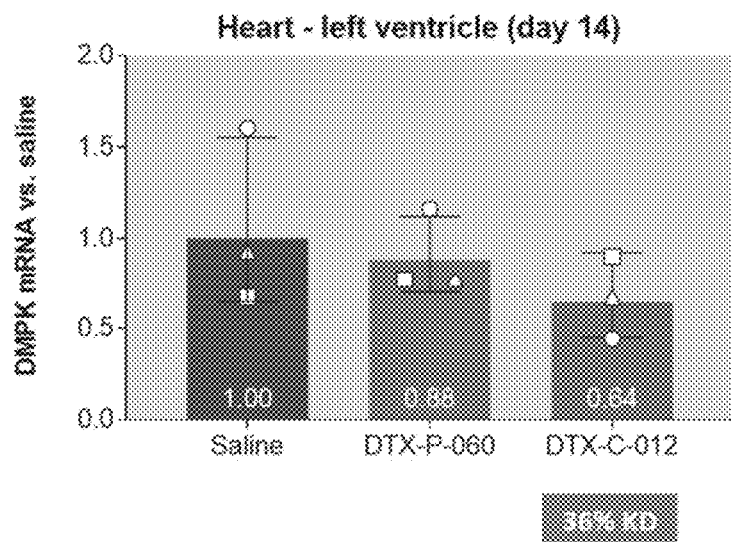
Figure 7J:
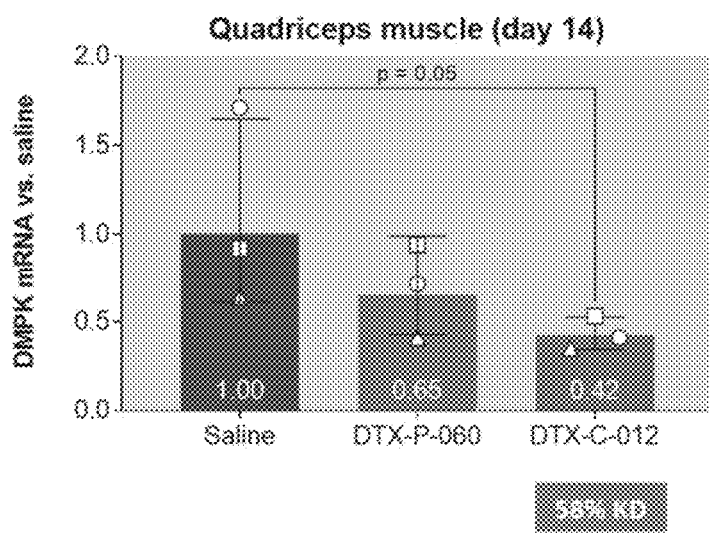
Figure 7K:
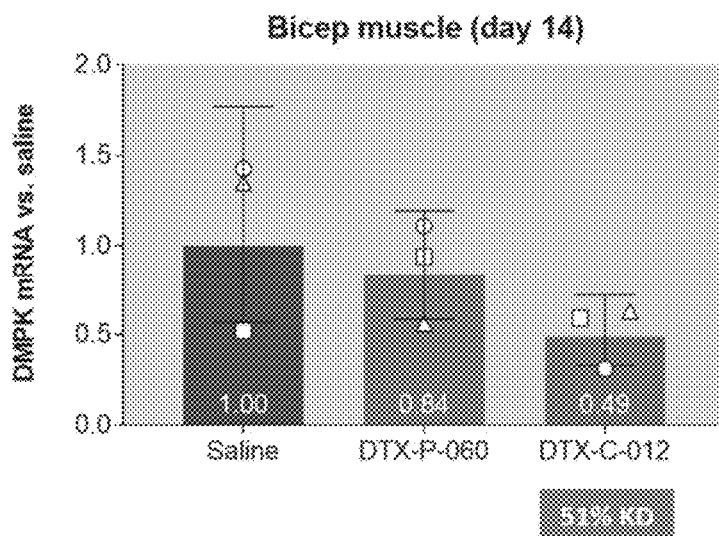
Figure 7L:
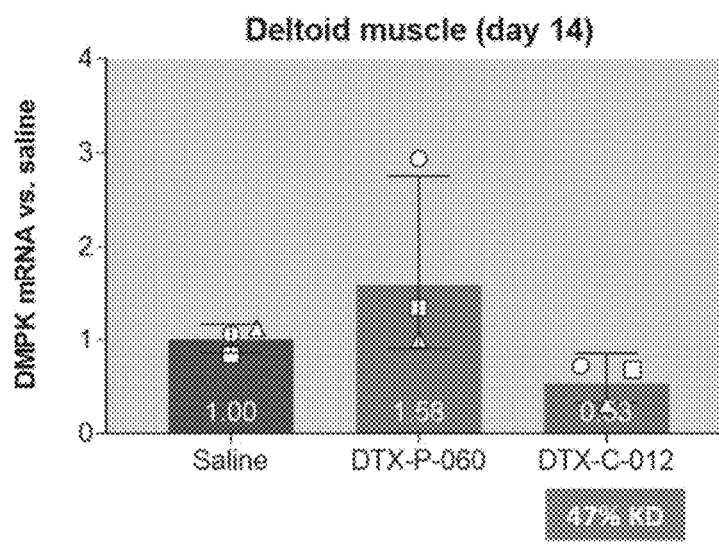
Figure 8A:
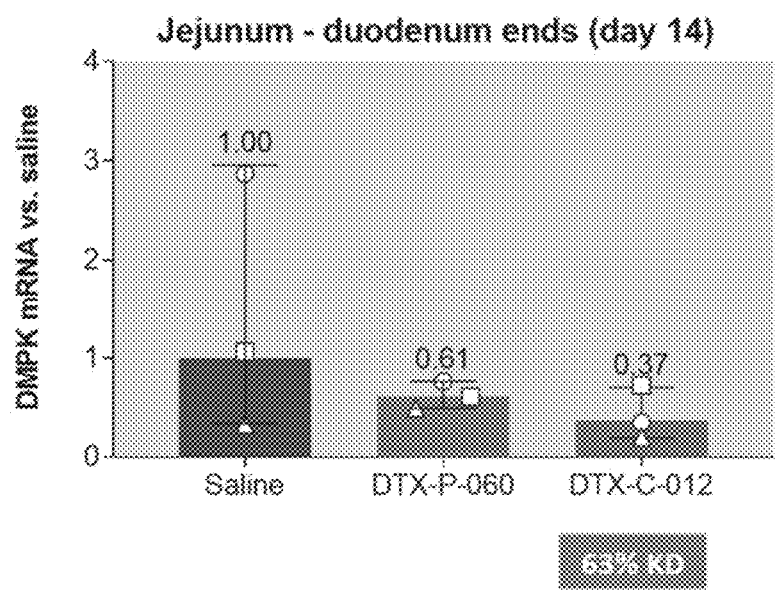
FIGS. 8A-8B depict non-limiting schematics showing the ability of a muscle targeting complex (DTX-C-012) comprising DTX-P-060 to reduce expression levels of DMPK in cynomolgus monkey smooth muscle tissues in vivo, relative to a vehicle experiment and compared to a naked DMPK ASO (DTX-P-060). (N=3 male cynomolgus monkeys)
Figure 8B:
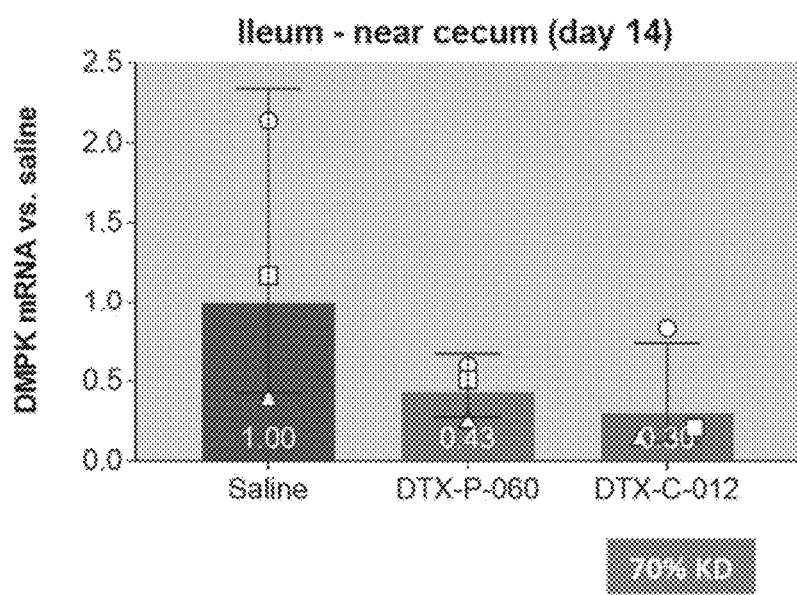
Figure 9A:
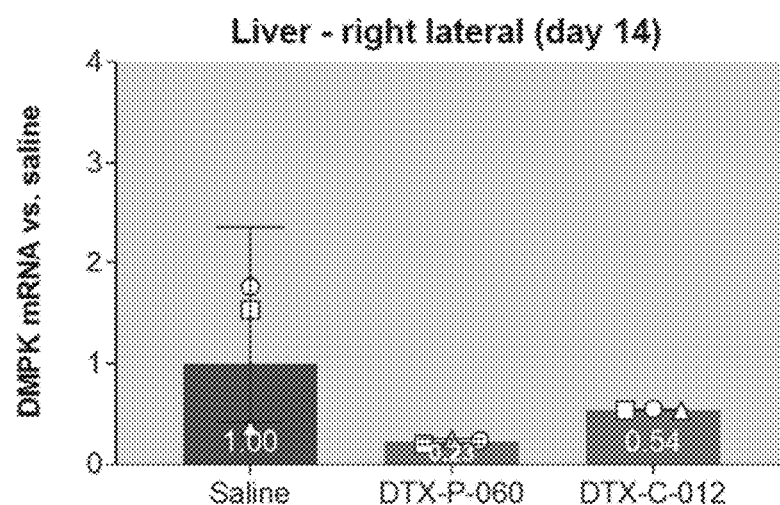
FIGS. 9A-9D depict non-limiting schematics showing the tissue selectivity of a muscle targeting complex (DTX-C-012) comprising DTX-P-060. The muscle targeting complex comprising DMPK-ASO does not reduce expression levels of DMPK in cynomolgus monkey liver, kidney, brain, or spleen tissues in vivo, relative to a vehicle experiment. (N=3 male cynomolgus monkeys)
Figure 9B:
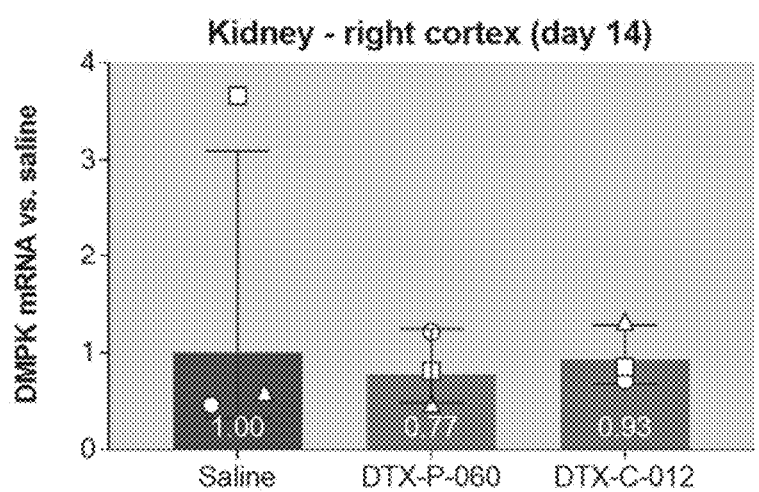
Figure 9C:
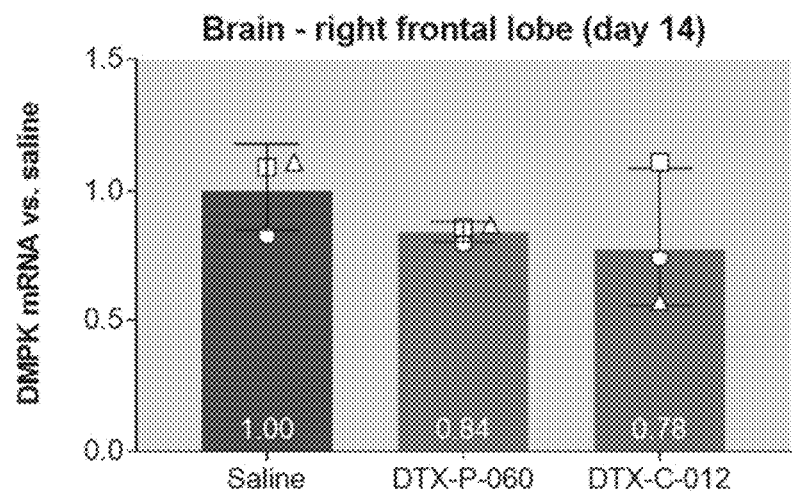
Figure 9D:
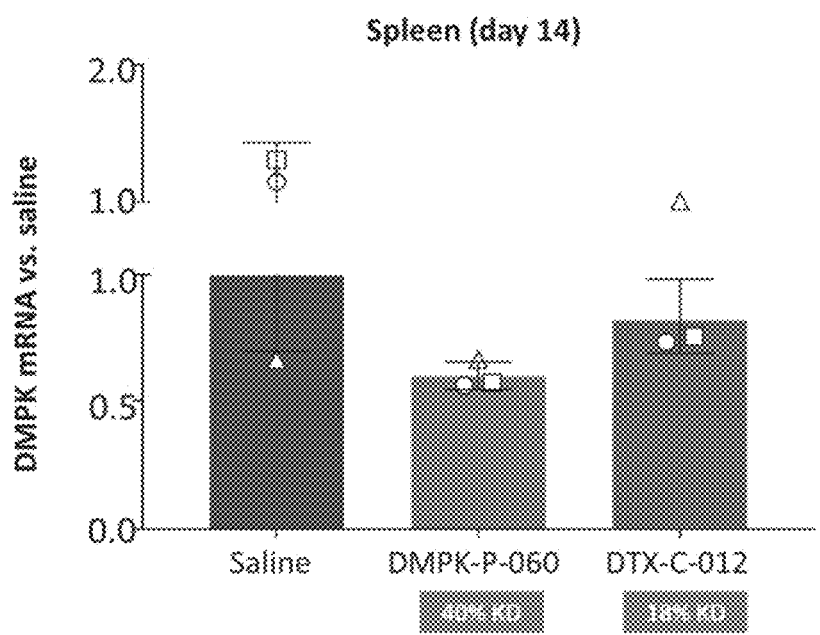
Figure 10:
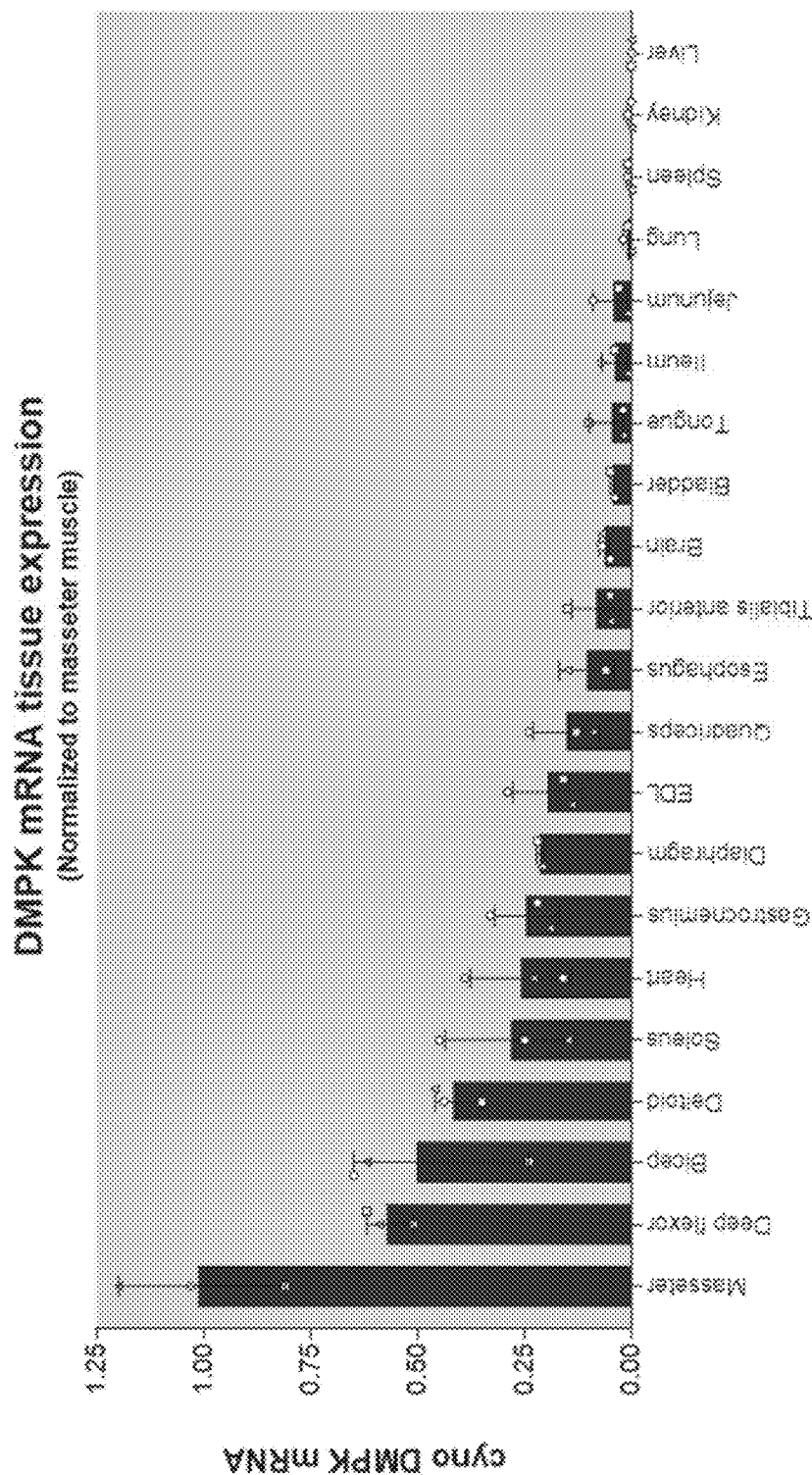
FIG. 10 shows normalized DMPK mRNA tissue expression levels across several tissue types in cynomolgus monkeys. (N=3 male cynomolgus monkeys)

Significant knockdown (KD) of DMPK mRNA expression using DTX-C-012 was observed in soleus, deep flexor, and masseter muscles relative to saline control, with 39% KD, 62% KD, and 41% KD, respectively (FIGS. 7A-7C). Robust knockdown of DMPK mRNA expression DTX-C-012 was further observed in gastrocnemius (62% KD; FIG. 7D), EDL (29% KD; FIG. 7E), tibialis anterior muscle (23% KD; FIG. 7F), diaphragm (54% KD; FIG. 7G), tongue (43% KD; FIG. 7H), heart muscle (36% KD; FIG. 7I), quadriceps (58% KD; FIG. 7J), bicep (51% KD; FIG. 7K), and deltoid muscles (47% KD; FIG. 7L). Knockdown of DMPK mRNA expression DTX-C-012 in smooth muscle was also observed in the intestine, with 63% KD at jejunum-duodenum ends (FIG. 8A) and 70% KD in ileum (FIG. 8B). Notably, naked DMPK ASO (i.e., not linked to a muscle-targeting agent), DTX-P-060, had minimal effects on DMPK expression levels relative to the vehicle control (i.e., little or no reduction in DMPK expression) for all assayed muscle tissue types. Monkeys treated with the DTX-C-012 complex demonstrated no change in DMPK expression in non-muscle tissues, such as liver, kidney, brain, and spleen tissues (FIGS. 9A-9D). Additional tissues were examined, as depicted in FIG. 10, which shows normalized DMPK mRNA tissue expression levels across several tissue types in cynomolgus monkeys. (N=3 male cynomolgus monkeys)

Figure 12:
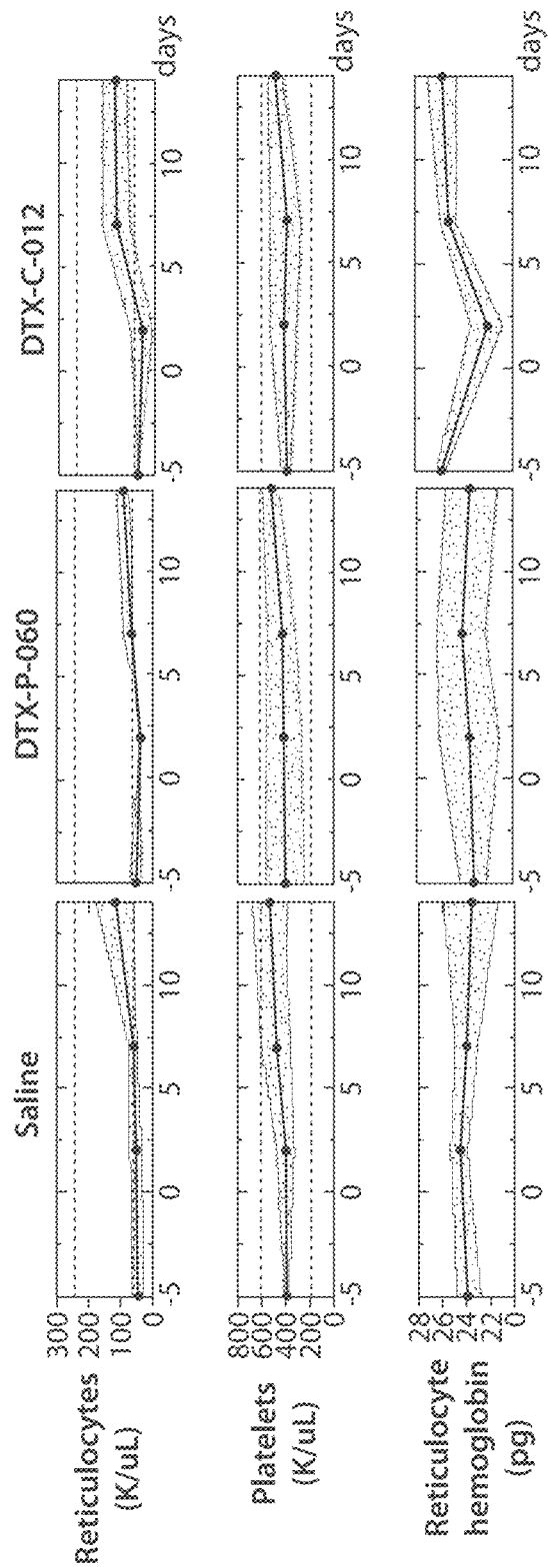
FIG. 12 shows that a single dose of a muscle targeting complex (DTX-C-012) comprising DTX-P-060 is safe and tolerated in cynomolgus monkeys. (N=3 male cynomolgus monkeys)

Prior to euthanization, all monkeys were tested for reticulocyte levels, platelet levels, hemoglobin expression, alanine aminotransferase (ALT) expression, aspartate aminotransferase (AST) expression, and blood urea nitrogen (BUN) levels on days 2, 7, and 14 after dosing. As shown in FIG. 12, monkeys dosed with antibody-oligonucleotide complex had normal reticulocyte levels, platelet levels, hemoglobin expression, alanine aminotransferase (ALT) expression, aspartate aminotransferase (AST) expression, and blood urea nitrogen (BUN) levels throughout the length of the experiment. These data show that a single dose of a complex comprising DTX-P-060 is safe and tolerated in cynomolgus monkeys.

These data demonstrate that the anti-transferrin receptor antibody of the DTX-C-012 complex enabled cellular internalization of the complex into muscle-specific tissues in an in vivo cynomolgus monkey model, thereby allowing the DMPK ASO (DTX-P-060) to inhibit expression of DMPK. These data further demonstrate that the DTX-C-012 complex is capable of specifically targeting muscle tissues for dose-dependent inhibition of DMPK without substantially impacting non-muscle tissues. This is direct contrast with the limited ability of DTX-P-060, a naked DMPK ASO (not linked to a muscle-targeting agent), to inhibit expression of DMPK in muscle tissues of an in vivo cynomolgus monkey model.

Figure 11A:
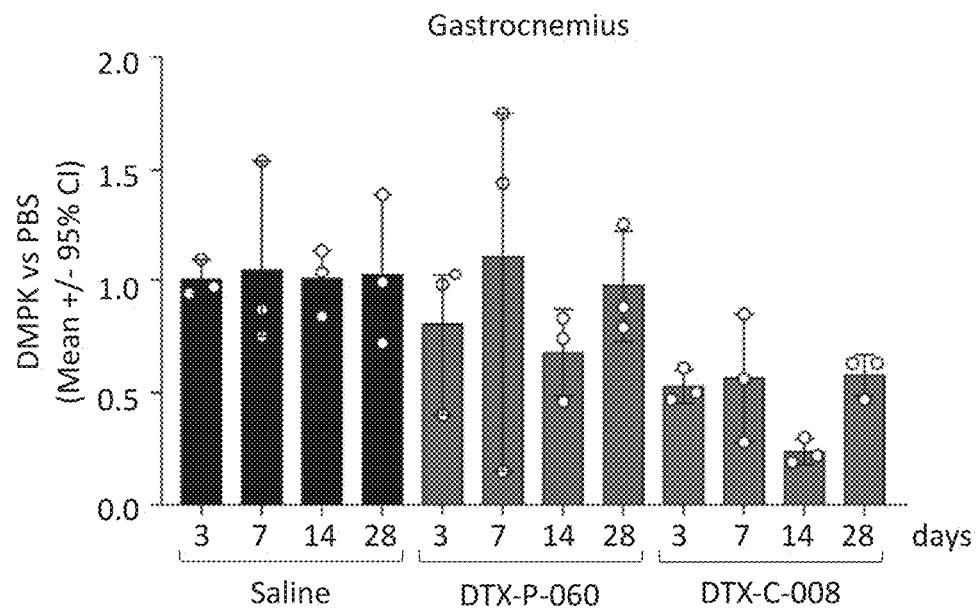
FIGS. 11A-11B depict non-limiting schematics showing the ability of a muscle targeting complex (DTX-C-008) comprising DTX-P-060 to reduce expression levels of DMPK in mouse muscle tissues in vivo for up to 28 days after dosing with DTX-C-008, relative to a vehicle experiment and compared to a naked DMPK ASO (DTX-P-060).
Figure 11B:
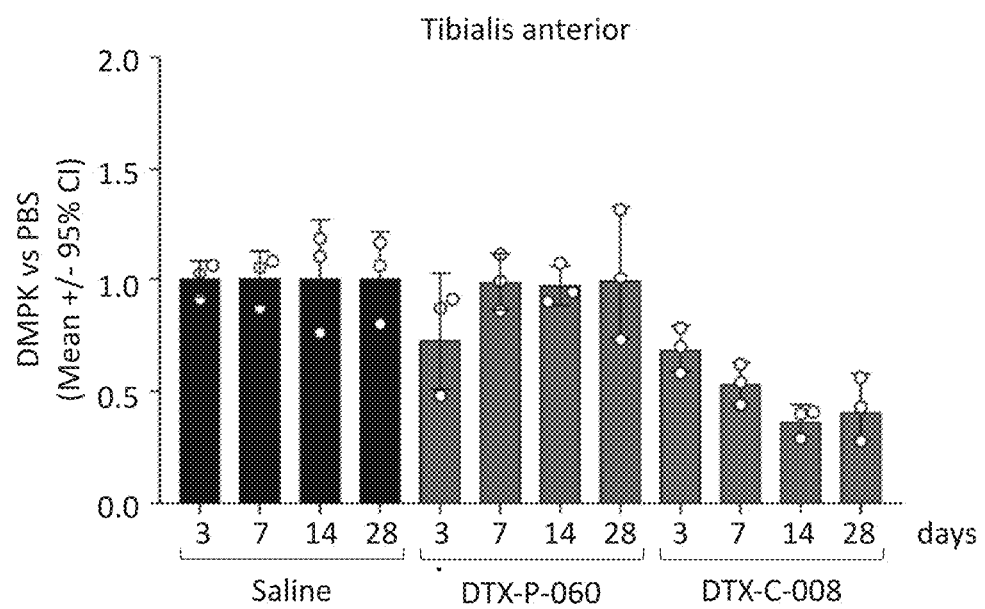

Example 6: Targeting DMPK in Mouse Muscle Tissues with a Muscle-Targeting Complex The muscle-targeting complex described in Example 2, DTX-C-008, was tested for time-dependent inhibition of DMPK in mouse tissues. C57BL/6 wild-type mice were intravenously injected with a single dose of a vehicle control (saline), DTX-P-060 (10 mg/kg of RNA), or DTX-C-008 (10 mg/kg of RNA) and euthanized after a prescribed period of time, as described in Table 2. Following euthanization, the mice were segmented into isolated tissue types and tissue samples were subsequently assayed for expression levels of DMPK (FIGS. 11A-11B).

TABLE 2

Experimental conditions

| Group | Dosage | Days after injection before euthanization | Number of mice |
| --- | --- | --- | --- |
| 1 | Vehicle (saline) | 3 days | 3 |
| 2 | Vehicle (saline) | 7 days | 3 |
| 3 | Vehicle (saline) | 14 days | 3 |
| 4 | Vehicle (saline) | 28 days | 3 |
| 5 | DTX-P-060 | 3 days | 3 |
| 6 | DTX-P-060 | 7 days | 3 |
| 7 | DTX-P-060 | 14 days | 3 |
| 8 | DTX-P-060 | 28 days | 3 |
| 9 | DTX-C-008 | 3 days | 3 |
| 10 | DTX-C-008 | 7 days | 3 |
| 11 | DTX-C-008 | 14 days | 3 |
| 12 | DTX-C-008 | 28 days | 3 |

Mice treated with the DTX-C-008 complex demonstrated approximately 50% reduction in DMPK expression in gastrocnemius (FIG. 11A) and tibialis anterior (FIG. 11B) muscles for all of Groups 9-12 (3-28 days between injection and euthanization), relative to vehicle. Mice treated with the DTX-P-060 naked oligonucleotide did not demonstrate significant reduction in DMPK expression.

These data indicate that the DTX-C-008 complex was capable of providing persistent reduction in DMPK expression for up to 28 days following dosage of mice with said DTX-C-008 complex.

Example 7: Evaluation of Antisense Oligonucleotides that Target DMPK in Immortalized Myoblasts Two hundred and thirty-six oligonucleotides for targeting DMPK were generated using in silico analysis. Each individual oligonucleotide was evaluated for their ability to target DMPK in cellulo at two doses—0.5 nM (low dose) and 50 nM (high dose).

Briefly, DM1 C15 immortalized myoblasts were cultured in T-75 flasks until near confluency (~80% confluent). Myoblasts were then disrupted with trypsin and seeded into 96-well microplates at a density of 50,000 cells/well. Cells were allowed to recover overnight before the growth media was washed out and replaced with a no-serum media to induce differentiation into myotubes. Differentiation proceeded for seven days prior to treatment with DMPK-targeting oligonucleotides.

On day seven following induction of differentiation, DM1 C15 myotubes were transfected with an individual oligonucleotide using 0.3 µL of Lipofectamine MessengerMax per well. All oligonucleotides were tested at both 0.5 nM and 50 nM final concentrations in biological triplicates. After treatment with oligonucleotides, cells were incubated for 72 hours prior to being harvested for total RNA. cDNA was synthesized from the total RNA extracts and qPCR was performed to determine expression levels of DMPK in technical quadruplicate. All qPCR data were analyzed using a traditional ΔΔCT method and were normalized to a plate-based negative control that comprised cells treated with vehicle control (0.3 µL/well Lipofectamine MessengerMax without any oligonucleotide). Results from these experiments are shown in Table 3. 'Normalized DMPK Remaining' for each antisense oligonucleotide in Table 3 refers to the expression level of DMPK in cell treated with said antisense oligonucleotide relative to the negative control that comprised cells treated with vehicle control (wherein the expression level of the negative control has been normalized to equal 1.00)

The majority of tested DMPK-targeting antisense oligonucleotides demonstrated a reduction in DMPK expression in differentiated myotubes at both the low and high dose concentrations (0.5 nM and 50 nM, respectively). These data demonstrate that the antisense oligonucleotides shown in Table 3 are capable of targeting DMPK in cellulo, suggesting that muscle-targeting complexes comprising these antisense oligonucleotides would be capable of targeting DMPK in muscle tissues in vivo.

TABLE 3

Ability of DMPK-targeting antisense oligonucleotides to reduce expression of DMPK in cellulo

| | | | | 0.5 nM | | 50 nM | |
|---|---|---|---|---|---|---|---|
| Antisense Oligonucleotide Sequence | SEQ ID NO: | DMPK Target Sequence | SEQ ID NO: | Normalized DMPK Remaining | Percent DMPK Reduction | Normalized DMPK Remaining | Percent DMPK Reduction |
| GGACGGCCCGGCUUGCUGCC | 45 | GGCAGCAAGCCGGGCCGTCC | 281 | 0.42 | 58.25 | 0.31 | 69.30 |
| GGGCCCGGAUCACAGGACUG | 46 | CAGTCCTGTGATCCGGGCCC | 282 | 0.42 | 57.97 | 0.38 | 61.96 |
| CAAACUUGCUCAGCAGUGUC | 47 | GACACTGCTGAGCAAGTTTG | 283 | 0.69 | 31.45 | 0.46 | 53.93 |
| AAACUUGCUCAGCAGUGUCA | 48 | TGACACTGCTGAGCAAGTTT | 284 | 0.69 | 30.85 | 0.49 | 50.69 |
| CGGAUGGCCUCCAUCUCCCG | 49 | CGGGAGATGGAGGCCATCCG | 285 | 0.71 | 28.92 | 0.44 | 55.57 |
| CUCGGCCGGAAUCCGCUCCC | 50 | GGGAGCGGATTCCGGCCGAG | 286 | 0.71 | 28.64 | 0.35 | 64.75 |
| UCUCGGCCGGAAUCCGCUCC | 51 | GGAGCGGATTCCGGCCGAGA | 287 | 0.72 | 27.88 | 0.33 | 67.46 |
| UGCUCAGCAGUGUCAGCAGG | 52 | CCTGCTGACACTGCTGAGCA | 288 | 0.73 | 27.08 | 0.34 | 65.78 |
| UUGUCGGGUUUGAUGUCCCU | 53 | AGGGACATCAAACCCGACAA | 289 | 0.66 | 34.16 | 0.44 | 55.56 |
| GUUGCGGGUUUGAUGUCCC | 54 | GGGACATCAAACCGACAAC | 290 | 0.67 | 33.31 | 0.39 | 61.07 |
| UCCGCCAGGUAGAAGCGCGC | 55 | GCGCGCTTCTACCTGGCGGA | 291 | 0.72 | 27.99 | 0.20 | 80.06 |
| CAUGGCAUACACCUGGCCCG | 56 | CGGGCCAGGTGTATGCCATG | 292 | 0.68 | 31.63 | 0.26 | 74.03 |

TABLE 3-continued

Ability of DMPK-targeting antisense oligonucleotides to reduce expression of DMPK in cellulo

| Antisense Oligonucleotide Sequence | SEQ ID NO: | DMPK Target Sequence | SEQ ID NO: | 0.5 nM | | 50 nM | |
|---|---|---|---|---|---|---|---|
| | | | | Normalized DMPK Remaining | Percent DMPK Reduction | Normalized DMPK Remaining | Percent DMPK Reduction |
| AACUUGCUCAGCAGUGUCAG | 57 | CTGACACTGCTGAGCAAGTT | 293 | 0.80 | 19.81 | 0.47 | 52.64 |
| CAGCUGCGUGAUCCACCGCC | 58 | GGCGGTGGATCACGCAGCTG | 294 | 0.81 | 19.03 | 0.32 | 68.34 |
| CGAAUGUCCGACAGUGUCUC | 59 | GAGACACTGTCGGACATTCG | 295 | 0.60 | 40.21 | 0.36 | 64.42 |
| GAAGUCGGCCAGGCGGAUGU | 60 | ACATCCGCCTGGCCGACTTC | 296 | 0.82 | 18.36 | 0.56 | 44.04 |
| UGUCGGGUUUGAUGUCCCUG | 61 | CAGGGACATCAAACCCGACA | 297 | 0.70 | 30.09 | 0.32 | 68.14 |
| GGAUGGCCUCCAUCUCCCGG | 62 | CCGGGAGATGGAGGCCATCC | 298 | 0.75 | 24.93 | 0.39 | 60.77 |
| AGGAUGUUGUCGGGUUUGAU | 63 | ATCAAACCCGACAACATCCT | 299 | 0.76 | 24.19 | 0.61 | 39.48 |
| GUCGGGUUUGAUGUCCCUGU | 64 | ACAGGGACATCAAACCCGAC | 300 | 0.71 | 28.89 | 0.36 | 64.15 |
| AAUACUCCAUGACCAGGUAC | 65 | GTACCTGGTCATGGAGTATT | 301 | 0.71 | 28.86 | 0.48 | 52.07 |
| CUUGUUCAUGAUCUUCAUGG | 66 | CCATGAAGATCATGAACAAG | 302 | 0.84 | 16.06 | 0.51 | 49.47 |
| UCAGUGCAUCCAAAACGUGG | 67 | CCACGTTTTGGATGCACTGA | 303 | 0.84 | 15.76 | 0.58 | 42.06 |
| CUGUCCCGGAGACCAUCCCA | 68 | TGGGATGGTCTCCGGGACAG | 304 | 0.64 | 35.85 | 0.49 | 50.78 |
| GGGCCUGGGACCUCACUGUC | 69 | GACAGTGAGGTCCCAGGCCC | 305 | 0.63 | 37.19 | 0.23 | 76.81 |
| CCCACGUAAUACUCCAUGAC | 70 | GTCATGGAGTATTACGTGGG | 306 | 0.72 | 28.21 | 0.54 | 45.94 |
| CUCUGCCGCAGGGACAGCCG | 71 | CGGCTGTCCCTGCGGCAGAG | 307 | 0.63 | 37.09 | 0.06 | 93.59 |
| CUGUGCACGUAGCCAAGCCG | 72 | CGGCTTGGCTACGTGCACAG | 308 | 0.74 | 25.67 | 0.30 | 70.10 |
| UGCCCAUCCACGUCAGGGCC | 73 | GGCCCTGACGTGGATGGGCA | 309 | 0.86 | 13.63 | 0.67 | 33.09 |
| AGCGCCUCCGAUAGGCCAGG | 74 | CCTGGCCTATCGGAGGCGCT | 310 | 0.79 | 21.19 | 0.38 | 61.91 |
| UGUGCACGUAGCCAAGCCGG | 75 | CCGGCTTGGCTACGTGCACA | 311 | 0.75 | 24.74 | 0.25 | 75.09 |
| GACCAGGUACAGGUAGUUCU | 76 | AGAACTACCTGTACCTGGTC | 312 | 0.57 | 42.85 | 0.29 | 70.95 |
| CCAUCUCGGCCGGAAUCCGC | 77 | GCGGATTCCGGCCGAGATGG | 313 | 0.79 | 20.50 | 0.40 | 59.76 |
| CAUCUCGGCCGGAAUCCGCU | 78 | AGCGGATTCCGGCCGAGATG | 314 | 0.80 | 20.21 | 0.41 | 59.40 |
| UUGCCAUAGGUCUCCGCCGU | 79 | ACGGCGGAGACCTATGGCAA | 315 | 0.64 | 36.30 | 0.40 | 60.12 |
| ACAGCGGUCCAGCAGGAUGU | 80 | ACATCCTGCTGGACCGCTGT | 316 | 0.80 | 19.94 | 0.45 | 55.14 |

TABLE 3-continued

Ability of DMPK-targeting antisense oligonucleotides to reduce expression of DMPK in cellulo

| Antisense Oligonucleotide Sequence | SEQ ID NO: | DMPK Target Sequence | SEQ ID NO: | 0.5 nM | | 50 nM | |
|---|---|---|---|---|---|---|---|
| | | | | Normalized DMPK Remaining | Percent DMPK Reduction | Normalized DMPK Remaining | Percent DMPK Reduction |
| AAAGCGCCUCCG AUAGGCCA | 81 | TGGCCTATCGGA GGCGCTTT | 317 | 0.80 | 19.89 | 0.38 | 62.04 |
| GCCAAAGAAGAA GGGAUGUG | 82 | CACATCCCTTCTT CTTTGGC | 318 | 0.75 | 24.87 | 0.44 | 56.19 |
| CACGUAAUACUC CAUGACCA | 83 | TGGTCATGGAGT ATTACGTG | 319 | 0.76 | 24.40 | 0.54 | 46.50 |
| AUCUCGGCCGGA AUCCGCUC | 84 | GAGCGGATTCCG GCCGAGAT | 320 | 0.88 | 11.61 | 0.34 | 65.98 |
| GCUUCAUCUUCA CUACCGCU | 85 | AGCGGTAGTGAA GATGAAGC | 321 | 0.69 | 31.44 | 0.48 | 51.78 |
| GCCAUCUCGGCC GGAAUCCG | 86 | CGGATTCCGGCC GAGATGGC | 322 | 0.81 | 18.56 | 0.14 | 86.39 |
| CAGGGACAGCCG CUGGAACU | 87 | AGTTCCAGCGGC TGTCCCTG | 323 | 0.68 | 32.09 | 0.41 | 58.84 |
| AUGACAAUCUCC GCCAGGUA | 88 | TACCTGGCGGAG ATTGTCAT | 324 | 0.58 | 42.38 | 0.40 | 60.47 |
| GGCCAUGACAAU CUCCGCCA | 89 | TGGCGGAGATTG TCATGGCC | 325 | 0.58 | 42.38 | 0.25 | 75.00 |
| AUACUCCAUGAC CAGGUACA | 90 | TGTACCTGGTCAT GGAGTAT | 326 | 0.77 | 23.07 | 0.43 | 56.84 |
| GCCUCUGCCUCG CGUAGUUG | 91 | CAACTACGCGAG GCAGAGGC | 327 | 0.65 | 35.38 | 0.19 | 81.18 |
| GAAUGUCCGACA GUGUCUCC | 92 | GGAGACACTGTC GGACATTC | 328 | 0.70 | 30.09 | 0.37 | 63.41 |
| CGUUCCAUCUGC CCGCAGCU | 93 | AGCTGCGGGCAG ATGGAACG | 329 | 0.66 | 33.74 | 0.31 | 68.72 |
| CCUUGUAGUGGA CGAUCUUG | 94 | CAAGATCGTCCA CTACAAGG | 330 | 0.83 | 17.20 | 0.34 | 65.91 |
| AUCUCCGCCAGG UAGAAGCG | 95 | CGCTTCTACCTGG CGGAGAT | 331 | 0.58 | 42.37 | 0.35 | 65.50 |
| CUCAGGCUCUGC CGGGUGAG | 96 | CTCACCCGGCAG AGCCTGAG | 332 | 0.70 | 30.13 | 0.37 | 63.07 |
| UGCUUCAUCUUC ACUACCGC | 97 | GCGGTAGTGAAG ATGAAGCA | 333 | 0.71 | 28.82 | 0.40 | 60.24 |
| GCAGGAUGUUGU CGGGUUUG | 98 | CAAACCCGACAA CATCCTGC | 334 | 0.56 | 44.39 | 0.22 | 78.03 |
| GGCCUCAGCCUC UGCCGCAG | 99 | CTGCGGCAGAGG CTGAGGCC | 335 | 0.80 | 20.12 | 0.29 | 71.28 |
| UGUUGUCGGGUU UGAUGUCC | 100 | GGACATCAAACC CGACAACA | 336 | 0.79 | 21.00 | 0.58 | 42.19 |
| CCACGUAAUACU CCAUGACC | 101 | GGTCATGGAGTA TTACGTGG | 337 | 0.79 | 20.84 | 0.50 | 50.06 |
| CCGUUCCAUCUG CCCGCAGC | 102 | GCTGCGGGCAGA TGGAACGG | 338 | 0.68 | 31.74 | 0.23 | 77.46 |
| UUCCCGAGUAAG CAGGCAGA | 103 | TCTGCCTGCTTAC TCGGGAA | 339 | 0.69 | 31.49 | 0.50 | 49.81 |

TABLE 3-continued

Ability of DMPK-targeting antisense oligonucleotides to reduce expression of DMPK in cellulo

|                              |               |                      |               | 0.5 nM | | 50 nM | |
|---|---|---|---|---|---|---|---|
| Antisense Oligonucleotide Sequence | SEQ ID NO: | DMPK Target Sequence | SEQ ID NO: | Normalized DMPK Remaining | Percent DMPK Reduction | Normalized DMPK Remaining | Percent DMPK Reduction |
| UGAUCUUCAUGGCAUACACC | 104 | GGTGTATGCCATGAAGATCA | 340 | 0.72 | 27.70 | 0.10 | 89.68 |
| AGGGACAGCCGCUGGAACTG | 105 | CAGTTCCAGCGGCTGTCCCT | 341 | 0.71 | 28.72 | 0.55 | 45.34 |
| GGGUUUGAUGUCCCUGUGCA | 106 | TGCACAGGGACATCAAACCC | 342 | 0.60 | 40.12 | 0.37 | 62.61 |
| UGACAAUCUCCGCCAGGUAG | 107 | CTACCTGGCGGAGATTGTCA | 343 | 0.61 | 38.86 | 0.33 | 66.56 |
| CACAGCGGUCCAGCAGGAUG | 108 | CATCCTGCTGGACCGCTGTG | 344 | 0.93 | 6.62 | 0.40 | 59.58 |
| GCGUAGAAGGGCGUCUGCCC | 109 | GGGCAGACGCCCTTCTACGC | 345 | 0.60 | 39.53 | 0.22 | 77.91 |
| CUCAGCCUCUGCCGCAGGGA | 110 | TCCCTGCGGCAGAGGCTGAG | 346 | 0.82 | 17.86 | 0.20 | 79.58 |
| GUCUCAGUGCAUCCAAAACG | 111 | CGTTTTGGATGCACTGAGAC | 347 | 0.81 | 18.85 | 0.54 | 46.13 |
| GGACGAUCUUGCCAUAGGUC | 112 | GACCTATGGCAAGATCGTCC | 348 | 0.70 | 29.82 | 0.51 | 48.97 |
| UCAGCAGUGUCAGCAGGUCC | 113 | GGACCTGCTGACACTGCTGA | 349 | 0.67 | 33.46 | 0.39 | 61.11 |
| GCUCCUGGGCGGCGCCAGAC | 114 | GTCTGGCGCCGCCCAGGAGC | 350 | 0.91 | 8.52 | 0.21 | 78.79 |
| AGCAGGAUGUUGUCGGGUUU | 115 | AAACCCGACAACATCCTGCT | 351 | 0.59 | 41.05 | 0.26 | 74.02 |
| AUCCGCUCCUGCAACUGCCG | 116 | CGGCAGTTGCAGGAGCGGAT | 352 | 0.87 | 12.80 | 0.60 | 40.06 |
| AGGAGCAGGGAAAGCGCCUC | 117 | GAGGCGCTTTCCCTGCTCCT | 353 | 0.67 | 33.24 | 0.38 | 62.37 |
| ACACCUGGCCCGUCUGCUUC | 118 | GAAGCAGACGGGCCAGGTGT | 354 | 0.67 | 33.00 | 0.45 | 55.40 |
| CCCAGCGCCCACCAGUCACA | 119 | TGTGACTGGTGGGCGCTGGG | 355 | 0.62 | 37.93 | 0.32 | 67.82 |
| GCUCCCUCUGCCUGCAGCAA | 120 | TTGCTGCAGGCAGAGGGAGC | 356 | 0.74 | 26.41 | 0.30 | 70.15 |
| GCUCAGGCUCUGCCGGGUGA | 121 | TCACCCGGCAGAGCCTGAGC | 357 | 0.74 | 25.69 | 0.39 | 60.71 |
| UUGAUGUCCCUGUGCACGUA | 122 | TACGTGCACAGGGACATCAA | 358 | 0.74 | 25.67 | 0.45 | 55.13 |
| GCCUCAGCCUCUGCCGCAGG | 123 | CCTGCGGCAGAGGCTGAGGC | 359 | 0.84 | 16.37 | 0.54 | 46.42 |
| GGUAGUUCUCAUCCUGGAAG | 124 | CTTCCAGGATGAGAACTACC | 360 | 0.75 | 25.48 | 0.44 | 56.15 |
| CAGCGCCCACCAGUCACACU | 125 | AGTGTGACTGGTGGGCGCTG | 361 | 0.63 | 37.28 | 0.35 | 64.93 |
| CCCAAACUUGCUCAGCAGUG | 126 | CACTGCTGAGCAAGTTTGGG | 362 | 0.63 | 37.02 | 0.38 | 61.78 |

TABLE 3-continued

Ability of DMPK-targeting antisense oligonucleotides to reduce expression of DMPK in cellulo

| Antisense Oligonucleotide Sequence | SEQ ID NO: | DMPK Target Sequence | SEQ ID NO: | 0.5 nM | | 50 nM | |
|---|---|---|---|---|---|---|---|
| | | | | Normalized DMPK Remaining | Percent DMPK Reduction | Normalized DMPK Remaining | Percent DMPK Reduction |
| CUUGCCAUAGGU CUCCGCCG | 127 | CGGCGGAGACCT ATGGCAAG | 363 | 0.73 | 27.04 | 0.29 | 71.05 |
| UACACCUGGCCC GUCUGCUU | 128 | AAGCAGACGGGC CAGGTGTA | 364 | 0.69 | 31.10 | 0.43 | 57.43 |
| CCAGCGCCACC AGUCACAC | 129 | GTGTGACTGGTG GGCGCTGG | 365 | 0.64 | 36.17 | 0.29 | 70.96 |
| GGCCUCAGCCUG GCCGAAAG | 130 | CTTTCGGCCAGGC TGAGGCC | 366 | 0.86 | 14.49 | 0.35 | 64.80 |
| AAUCUCCGCCAG GUAGAAGC | 131 | GCTTCTACCTGGC GGAGATT | 367 | 0.64 | 35.85 | 0.35 | 65.27 |
| AUGGCAUACACC UGGCCCGU | 132 | ACGGGCCAGGTG TATGCCAT | 368 | 0.86 | 14.31 | 0.50 | 49.63 |
| CCAUGACAAUCU CCGCCAGG | 133 | CCTGGCGGAGAT TGTCATGG | 369 | 0.65 | 34.53 | 0.24 | 76.46 |
| UCCCCAAACUUG CUCAGCAG | 134 | CTGCTGAGCAAG TTTGGGGA | 370 | 0.94 | 5.73 | 0.55 | 44.67 |
| GAUGUUGUCGGG UUUGAUGU | 135 | ACATCAAACCCG ACAACATC | 371 | 0.90 | 10.06 | 0.58 | 42.42 |
| GUUUGCCCAUCC ACGUCAGG | 136 | CCTGACGTGGAT GGGCAAAC | 372 | 0.66 | 34.36 | 0.46 | 54.49 |
| CGGACGGCCCGG CUUGCUGC | 137 | GCAGCAAGCCGG GCCGTCCG | 373 | 0.95 | 5.42 | 0.70 | 30.41 |
| CUCCGCCAGGUA GAAGCGCG | 138 | CGCGCTTCTACCT GGCGGAG | 374 | 0.70 | 30.22 | 0.22 | 78.14 |
| GUACAGGUAGUU CUCAUCCU | 139 | AGGATGAGAACT ACCTGTAC | 375 | 0.68 | 31.52 | 0.34 | 65.57 |
| AGGGCGUCUGCC CAUAGAAC | 140 | GTTCTATGGGCA GACGCCCT | 376 | 0.87 | 13.23 | 0.41 | 58.98 |
| UGGCCACAGCGG UCCAGCAG | 141 | CTGCTGGACCGCT GTGGCCA | 377 | 0.70 | 29.59 | 0.31 | 69.44 |
| CGUAGUUGACUG GCGAAGUU | 142 | AACTTCGCCAGTC AACTACG | 378 | 0.75 | 25.26 | 0.38 | 61.52 |
| UCUGCCGCAGGG ACAGCCGC | 143 | GCGGCTGTCCCTG CGGCAGA | 379 | 0.77 | 22.97 | 0.18 | 82.10 |
| AAGCGCCUCCGA UAGGCCAG | 144 | CTGGCCTATCGG AGGCGCTT | 380 | 0.91 | 8.91 | 0.56 | 43.93 |
| GACAGAACAACG GCGAACAG | 145 | CTGTTCGCCGTTG TTCTGTC | 381 | 0.79 | 21.41 | 0.30 | 70.49 |
| GCUCAGCAGUGU CAGCAGGU | 146 | ACCTGCTGACACT GCTGAGC | 382 | 0.71 | 29.18 | 0.27 | 73.46 |
| AUGAUCUUCAUG GCAUACAC | 147 | GTGTATGCCATG AAGATCAT | 383 | 0.87 | 12.76 | 0.60 | 39.97 |
| UUUGCCCAUCCA CGUCAGGG | 148 | CCCTGACGTGGA TGGGCAAA | 384 | 0.6 | 32.79 | 0.41 | 59.36 |

TABLE 3-continued

Ability of DMPK-targeting antisense oligonucleotides to reduce expression of DMPK in cellulo

| Antisense Oligonucleotide Sequence | SEQ ID NO: | DMPK Target Sequence | SEQ ID NO: | 0.5 nM | | 50 nM | |
|---|---|---|---|---|---|---|---|
| | | | | Normalized DMPK Remaining | Percent DMPK Reduction | Normalized DMPK Remaining | Percent DMPK Reduction |
| ACUUGCUCAGCAGUGUCAGC | 149 | GCTGACACTGCTGAGCAAGT | 385 | 0.72 | 27.84 | 0.39 | 60.71 |
| UGAUGUCCCUGUGCACGUAG | 150 | CTACGTGCACAGGGACATCA | 386 | 0.79 | 20.58 | 0.41 | 59.00 |
| AAAUACCGAGGAAUGUCGGG | 151 | CCCGACATTCCTCGGTATTT | 387 | 0.89 | 11.25 | 0.49 | 50.91 |
| GGCGAAUACACCCAGCGCCC | 152 | GGGCGCTGGGTGTATTCGCC | 388 | 0.80 | 19.77 | 0.31 | 68.72 |
| AGACAAUAAAUACCGAGGAA | 153 | TTCCTCGGTATTTATTGTCT | 389 | 0.71 | 29.37 | 0.52 | 48.20 |
| CCCGUCUGCUUCAUCUUCAC | 154 | GTGAAGATGAAGCAGACGGG | 390 | 0.80 | 20.31 | 0.56 | 43.97 |
| CUGCCUGCAGCAACUCCAUC | 155 | GATGGAGTTGCTGCAGGCAG | 391 | 0.7 | 23.10 | 0.53 | 46.69 |
| CCUCAGCCUCUGCCGCAGGG | 156 | CCCTGCGGCAGAGGCTGAGG | 392 | 0.89 | 10.87 | 0.45 | 55.22 |
| GUGUCCGGAAGUCGCCUGCU | 157 | AGCAGGCGACTTCCGGACAC | 393 | 0.77 | 22.99 | 0.26 | 73.65 |
| UGCACGUGUGGCUCAAGCAG | 158 | CTGCTTGAGCCACACGTGCA | 394 | 0.89 | 10.81 | 0.36 | 64.18 |
| GACAAUAAAUACCGAGGAAU | 159 | ATTCCTCGGTATTTATTGTC | 395 | 0.71 | 28.97 | 0.52 | 47.51 |
| GCCAUGACAAUCUCCGCCAG | 160 | CTGGCGGAGATTGTCATGGC | 396 | 0.69 | 30.96 | 0.19 | 81.00 |
| GCUGUCCCGGAGACCAUCCC | 161 | GGGATGGTCTCCGGGACAGC | 397 | 0.77 | 22.57 | 0.34 | 66.27 |
| CAUGACCAGGUACAGGUAGU | 162 | ACTACCTGTACCTGGTCATG | 398 | 0.81 | 19.39 | 0.41 | 59.09 |
| AGCGCCCACCAGUCACACUC | 163 | GAGTGTGACTGGTGGGCGCT | 399 | 0.70 | 30.36 | 0.36 | 63.67 |
| UCUCAGUGCAUCCAAAACGU | 164 | ACGTTTTGGATGCACTGAGA | 400 | 0.89 | 10.88 | 0.49 | 51.34 |
| UUUGGGCAGAUGGAGGGCCU | 165 | AGGCCCTCCATCTGCCCAAA | 401 | 0.65 | 35.14 | 0.30 | 70.00 |
| GAUGUCCCUGUGCACGUAGC | 166 | GCTACGTGCACAGGGACATC | 402 | 0.81 | 18.99 | 0.38 | 62.46 |
| CAGCAGUGUCAGCAGGUCCC | 167 | GGGACCTGCTGACACTGCTG | 403 | 0.74 | 25.67 | 0.48 | 51.97 |
| CAUGACAAUCUCCGCCAGGU | 168 | ACCTGGCGGAGATTGTCATG | 404 | 0.71 | 29.45 | 0.29 | 70.52 |
| ACUUGUUCAUGAUCUUCAUG | 169 | CATGAAGATCATGAACAAGT | 405 | 0.75 | 25.47 | 0.47 | 52.89 |
| GUGGAAUCCGCGUAGAAGGG | 170 | CCCTTCTACGCGGATTCCAC | 406 | 0.69 | 30.55 | 0.51 | 49.34 |
| UGGCCAUGACAAUCUCCGCC | 171 | GGCGGAGATTGTCATGGCCA | 407 | 0.70 | 30.46 | 0.27 | 72.55 |

TABLE 3-continued

Ability of DMPK-targeting antisense oligonucleotides to reduce expression of DMPK in cellulo

| Antisense Oligonucleotide Sequence | SEQ ID NO: | DMPK Target Sequence | SEQ ID NO: | 0.5 nM | | 50 nM | |
|---|---|---|---|---|---|---|---|
| | | | | Normalized DMPK Remaining | Percent DMPK Reduction | Normalized DMPK Remaining | Percent DMPK Reduction |
| GGGACAGACAAU AAAUACCG | 172 | CGGTATTTATTGT CTGTCCC | 408 | 0.73 | 27.19 | 0.49 | 50.50 |
| CCGCUCCCCAAA CUUGCUCA | 173 | TGAGCAAGTTTG GGGAGCGG | 409 | 1.00 | 0.28 | 0.43 | 56.82 |
| CGGCUCAGGCUC UGCCGGGU | 174 | ACCCGGCAGAGC CTGAGCCG | 410 | 0.82 | 17.97 | 0.31 | 69.03 |
| GGCUCCUGGGCG GCGCCAGA | 175 | TCTGGCGCCGCCC AGGAGCC | 411 | 1.00 | 0.05 | 0.04 | 96.23 |
| UUUCCCGAGUAA GCAGGCAG | 176 | CTGCCTGCTTACT CGGGAAA | 412 | 0.79 | 20.69 | 0.55 | 44.89 |
| GGAUGUUGUCGG GUUUGAUG | 177 | CATCAAACCCGA CAACATCC | 413 | 0.96 | 4.26 | 0.59 | 40.81 |
| CAGGUAGUUCUC AUCCUGGA | 178 | TCCAGGATGAGA ACTACCTG | 414 | 0.74 | 25.92 | 0.23 | 76.71 |
| UGCCCAUAGAAC AUUUCAUA | 179 | TATGAAATGTTCT ATGGGCA | 415 | 0.92 | 7.67 | 0.65 | 34.56 |
| UAGUUCUCAUCC UGGAAGGC | 180 | GCCTTCCAGGAT GAGAACTA | 416 | 0.83 | 16.83 | 0.56 | 43.88 |
| AUGUCCCUGUGC ACGUAGCC | 181 | GGCTACGTGCAC AGGGACAT | 417 | 0.83 | 16.78 | 0.51 | 49.29 |
| CGGGCCCGGAUC ACAGGACU | 182 | AGTCCTGTGATCC GGGCCCG | 418 | 0.83 | 17.45 | 0.33 | 67.11 |
| UGGACGAUCUUG CCAUAGGU | 183 | ACCTATGGCAAG ATCGTCCA | 419 | 0.81 | 19.20 | 0.57 | 42.52 |
| GUUGGCCGGCGU GGGCCACC | 184 | GGTGGCCCACGC CGGCCAAC | 420 | 1.02 | -1.82 | 0.56 | 43.57 |
| CUCAGUGCAUCC AAAACGUG | 185 | CACGTTTTGGATG CACTGAG | 421 | 0.92 | 7.65 | 0.46 | 54.26 |
| UCGAAGUUGCAU GUGUCGGU | 186 | ACCGACACATGC AACTTCGA | 422 | 0.77 | 22.96 | 0.42 | 58.15 |
| UGGAACACGGAC GGCCCGGC | 187 | GCCGGGCCGTCC GTGTTCCA | 423 | 1.02 | -1.90 | 0.39 | 60.96 |
| CCGAGAGCAGCG CAAGUGAG | 188 | CTCACTTGCGCTG CTCTCGG | 424 | 0.84 | 16.13 | 0.59 | 40.93 |
| UCCUGCAACUGC CGGACGUG | 189 | CACGTCCGGCAG TTGCAGGA | 425 | 0.84 | 16.06 | 0.55 | 44.61 |
| UCACCAACACGU CCCUCUCC | 190 | GGAGAGGGACGT GTTGGTGA | 426 | 0.53 | 47.12 | 0.16 | 84.09 |
| UGCCUGCAGCAA CUCCAUCC | 191 | GGATGGAGTTGC TGCAGGCA | 427 | 0.86 | 13.99 | 0.50 | 49.75 |
| UUGGCCGGCGUG GGCCACCA | 192 | TGGTGGCCCACG CCGGCCAA | 428 | 1.03 | 3.19 | 0.56 | 44.37 |
| GAGCCUCUGCCU CGCGUAGU | 193 | ACTACGCGAGGC AGAGGCTC | 429 | 0.81 | 18.77 | 0.22 | 77.78 |
| AAGGGCGUCUGC CCAUAGAA | 194 | TTCTATGGGCAG ACGCCCTT | 430 | 0.87 | 13.15 | 0.65 | 34.56 |

TABLE 3-continued

Ability of DMPK-targeting antisense oligonucleotides to reduce expression of DMPK in cellulo

| Antisense Oligonucleotide Sequence | SEQ ID NO: | DMPK Target Sequence | SEQ ID NO: | 0.5 nM | | 50 nM | |
|---|---|---|---|---|---|---|---|
| | | | | Normalized DMPK Remaining | Percent DMPK Reduction | Normalized DMPK Remaining | Percent DMPK Reduction |
| ACAGACAAUAAA UACCGAGG | 195 | CCTCGGTATTTAT TGTCTGT | 431 | 1.04 | -3.95 | 0.26 | 74.02 |
| GGACAGACAAUA AAUACCGA | 196 | TCGGTATTTATTG TCTGTCC | 432 | 0.77 | 22.57 | 0.47 | 52.51 |
| ACGUGUGCCUCU AGGUCCCG | 197 | CGGGACCTAGAG GCACACGT | 433 | 0.84 | 16.47 | 0.22 | 77.73 |
| GGCACGAGACAG AACAACGG | 198 | CCGTTGTTCTGTC TCGTGCC | 434 | 0.84 | 16.10 | 0.32 | 68.01 |
| UGACCAGGUACA GGUAGUUC | 199 | GAACTACCTGTA CCTGGTCA | 435 | 0.78 | 22.00 | 0.36 | 63.73 |
| CUCUGCCGGGUG AGCACCUC | 200 | GAGGTGCTCACC CGGCAGAG | 436 | 0.75 | 25.25 | 0.26 | 74.36 |
| GACAAUCUCCGC CAGGUAGA | 201 | TCTACCTGGCGG AGATTGTC | 437 | 0.76 | 23.70 | 0.50 | 49.82 |
| UCUCCGCCAGGU AGAAGCGC | 202 | GCGCTTCTACCTG GCGGAGA | 438 | 0.80 | 19.59 | 0.33 | 66.52 |
| CUCUGCCUCGCG UAGUUGAC | 203 | GTCAACTACGCG AGGCAGAG | 439 | 0.83 | 16.61 | 0.09 | 91.21 |
| CUUUGGGCAGAU GGAGGGCC | 204 | GGCCCTCCATCTG CCCAAAG | 440 | 0.72 | 28.06 | 0.33 | 67.50 |
| ACAGGUAGUUCU CAUCCUGG | 205 | CCAGGATGAGAA CTACCTGT | 441 | 0.79 | 20.51 | 0.15 | 85.36 |
| CCAAACUUGCUC AGCAGUGU | 206 | ACACTGCTGAGC AAGTTTGG | 442 | 0.76 | 23.64 | 0.42 | 57.70 |
| UCGGGUUUGAUG UCCCUGUG | 207 | CACAGGGACATC AAACCCGA | 443 | 0.78 | 22.49 | 0.43 | 57.16 |
| GGCUUGCUGCCU UCCCAGGC | 208 | GCCTGGGAAGGC AGCAAGCC | 444 | 1.06 | -6.32 | 0.52 | 48.15 |
| UACAGGUAGUUC UCAUCCUG | 209 | CAGGATGAGAAC TACCTGTA | 445 | 0.80 | 19.83 | 0.27 | 72.51 |
| UUGCCCAUCCAC GUCAGGGC | 210 | GCCCTGACGTGG ATGGGCAA | 446 | 0.78 | 22.23 | 0.33 | 67.15 |
| AGGUACAGGUAG UUCUCAUC | 211 | GATGAGAACTAC CTGTACCT | 447 | 0.81 | 18.68 | 0.41 | 58.92 |
| GACAGACAAUAA AUACCGAG | 212 | CTCGGTATTTATT GTCTGTC | 448 | 0.82 | 18.26 | 0.62 | 38.07 |
| UAGAACAUUUCA UAGGCGAA | 213 | TTCGCCTATGAAA TGTTCTA | 449 | 0.80 | 20.23 | 0.56 | 43.67 |
| AGGGCCUUUUAU UCGCGAGG | 214 | CCTCGCGAATAA AAGGCCCT | 450 | 0.86 | 13.63 | 0.34 | 66.43 |
| GCCUCGCGUAGU UGACUGGC | 215 | GCCAGTCAACTA CGCGAGGC | 451 | 0.87 | 12.98 | 0.09 | 91.10 |
| CCAGCAGGAUGU UGUCGGGU | 216 | ACCCGACAACAT CCTGCTGG | 452 | 0.60 | 40.29 | 0.10 | 89.59 |
| GUAGUUGACUGG CGAAGUUC | 217 | GAACTTCGCCAG TCAACTAC | 453 | 0.93 | 7.50 | 0.55 | 45.33 |

TABLE 3-continued

Ability of DMPK-targeting antisense oligonucleotides to reduce expression of DMPK in cellulo

| Antisense Oligonucleotide Sequence | SEQ ID NO: | DMPK Target Sequence | SEQ ID NO: | 0.5 nM | | 50 nM | |
|---|---|---|---|---|---|---|---|
| | | | | Normalized DMPK Remaining | Percent DMPK Reduction | Normalized DMPK Remaining | Percent DMPK Reduction |
| UGCGGAUGGCCU CCAUCUCC | 218 | GGAGATGGAGGC CATCCGCA | 454 | 0.60 | 40.15 | 0.16 | 84.43 |
| ACAAUCUCCGCC AGGUAGAA | 219 | TTCTACCTGGCGG AGATTGT | 455 | 0.81 | 19.09 | 0.50 | 49.75 |
| GCGAAUACACCC AGCGCCCA | 220 | TGGGCGCTGGGT GTATTCGC | 456 | 0.93 | 6.94 | 0.30 | 69.72 |
| GUAGUUCUCAUC CUGGAAGG | 221 | CCTTCCAGGATG AGAACTAC | 457 | 0.93 | 7.43 | 0.45 | 55.09 |
| GGCUCAGGCUCU GCCGGGUG | 222 | CACCCGGCAGAG CCTGAGCC | 458 | 0.93 | 7.38 | 0.34 | 65.82 |
| CCAUUCACCAAC ACGUCCCU | 223 | AGGGACGTGTTG GTGAATGG | 459 | 0.61 | 39.26 | 0.13 | 86.83 |
| ACCAGGUACAGG UAGUUCUC | 224 | GAGAACTACCTG TACCTGGT | 460 | 0.84 | 16.09 | 0.23 | 76.96 |
| CTGCAGUUUGCC CAUCCACG | 225 | CGTGGATGGGCA AACTGCAG | 461 | 1.11 | −10.69 | 0.40 | 60.08 |
| UUGUUCAUGAUC UUCAUGGC | 226 | GCCATGAAGATC ATGAACAA | 462 | 0.86 | 14.13 | 0.55 | 45.23 |
| UUGAUGUCCCUG UGCACGU | 227 | ACGTGCACAGGG ACATCAAA | 463 | 0.93 | 6.92 | 0.57 | 43.07 |
| GCGGUCCAGCAG GAUGUUGU | 228 | ACAACATCCTGCT GGACCGC | 464 | 0.61 | 38.84 | 0.16 | 83.64 |
| GUCUAUGGCCAU GACAAUCU | 229 | AGATTGTCATGG CCATAGAC | 465 | 1.11 | −11.00 | 0.27 | 73.11 |
| GGAGCAGGGAAA GCGCCUCC | 230 | GGAGGCGCTTTC CCTGCTCC | 466 | 0.79 | 21.46 | 0.12 | 88.35 |
| UGCCUCGCGUAG UUGACUGG | 231 | CCAGTCAACTAC GCGAGGCA | 467 | 0.89 | 11.03 | 0.12 | 88.02 |
| GCGGAUGGCCUC CAUCUCCC | 232 | GGGAGATGGAGG CCATCCGC | 468 | 0.79 | 21.25 | 0.28 | 71.77 |
| UUUCAUAGGCGA AUACACCC | 233 | GGGTGTATTCGCC TATGAAA | 469 | 0.94 | 5.56 | 0.47 | 53.28 |
| GCCUGUCAGCGA GUCGGAGG | 234 | CCTCCGACTCGCT GACAGGC | 470 | 0.89 | 10.81 | 0.24 | 75.67 |
| CCACUUCAGCUG UUUCAUCC | 235 | GGATGAAACAGC TGAAGTGG | 471 | 0.78 | 22.40 | 0.36 | 64.20 |
| CAUCCGCUCCUG CAACUGCC | 236 | GGCAGTTGCAGG AGCGGATG | 472 | 0.79 | 21.04 | 0.23 | 76.81 |
| UCUAGGGUUCAG GGAGCGCG | 237 | CGCGCTCCCTGA ACCCTAGA | 473 | 0.78 | 21.81 | 0.17 | 83.22 |
| CACCAACACGUC CCUCUCCU | 238 | AGGAGAGGGACG TGTTGGTG | 474 | 0.62 | 37.51 | 0.18 | 81.57 |
| CAGGAGCAGGGA AAGCGCCU | 239 | AGGCGCTTTCCCT GCTCCTG | 475 | 0.88 | 12.48 | 0.48 | 51.82 |
| CAAUCUCCGCCA GGUAGAAG | 240 | CTTCTACCTGGCG GAGATTG | 476 | 0.84 | 15.95 | 0.51 | 49.25 |

TABLE 3-continued

Ability of DMPK-targeting antisense oligonucleotides to reduce expression of DMPK in cellulo

| Antisense Oligonucleotide Sequence | SEQ ID NO: | DMPK Target Sequence | SEQ ID NO: | 0.5 nM | | 50 nM | |
|---|---|---|---|---|---|---|---|
| | | | | Normalized DMPK Remaining | Percent DMPK Reduction | Normalized DMPK Remaining | Percent DMPK Reduction |
| AUGUUGUCGGGU UUGAUGUC | 241 | GACATCAAACCC GACAACAT | 477 | 0.83 | 16.93 | 0.47 | 52.83 |
| CCAUCCGCUCCU GCAACUGC | 242 | GCAGTTGCAGGA GCGGATGG | 478 | 0.80 | 19.53 | 0.28 | 71.62 |
| GCGUCACCUCGG CCUCAGCC | 243 | GGCTGAGGCCGA GGTGACGC | 479 | 0.80 | 20.02 | 0.19 | 81.27 |
| GAGGGCCUUUUA UUCGCGAG | 244 | CTCGCGAATAAA AGGCCCTC | 480 | 0.92 | 8.23 | 0.38 | 62.2 |
| AGCGGCAGAGAG AGGUGCUC | 245 | GAGCACCTCTCT TGCCGCT | 481 | 0.80 | 19.75 | 0.09 | 90.71 |
| CAUCCAAAACGU GGAUUGGG | 246 | CCCAATCCACGTT TTGGATG | 482 | 0.81 | 19.12 | 0.22 | 77.98 |
| UUGGGCAGAUGG AGGGCCUU | 247 | AAGGCCCTCCAT CTGCCCAA | 483 | 0.81 | 19.08 | 0.22 | 78.39 |
| CCUCUGCCUCGC GUAGUUGA | 248 | TCAACTACGCGA GGCAGAGG | 484 | 0.93 | 7.39 | 0.15 | 85.33 |
| ACAGAACAACGG CGAACAGG | 249 | CCTGTTCGCCGTT GTTCTGT | 485 | 0.98 | 2.07 | 0.44 | 55.96 |
| CAGGAUGUUGUC GGGUUUGA | 250 | TCAAACCCGACA ACATCCTG | 486 | 0.83 | 17.17 | 0.21 | 79.31 |
| CGGCCUCAGCCU CUGCCGCA | 251 | TGCGGCAGAGGC TGAGGCCG | 487 | 0.93 | 6.71 | 0.40 | 60.06 |
| CAGCAGGAUGUU GUCGGGUU | 252 | AACCCGACAACA TCCTGCTG | 488 | 0.66 | 34.18 | 0.15 | 84.54 |
| GCAGAGAGAGGU GCUCCUUG | 253 | CAAGGAGCACCT CTCTCTGC | 489 | 0.83 | 17.29 | 0.14 | 85.95 |
| UCCAGUUCCAUG GGUGUGGG | 254 | CCCACACCCATG GAACTGGA | 490 | 0.84 | 15.66 | 0.22 | 78.48 |
| CCUCAGCCUGGC CGAAAGAA | 255 | TTCTTTCGGCCAG GCTGAGG | 491 | 0.83 | 16.83 | 0.36 | 63.99 |
| GGGCCUUUUAUU CGCGAGGG | 256 | CCCTCGCGAATA AAAGGCCC | 492 | 0.95 | 5.11 | 0.49 | 50.65 |
| GUCGGCCAGGCG GAUGUGGC | 257 | GCCACATCCGCCT GGCCGAC | 493 | 0.85 | 15.35 | 0.25 | 74.59 |
| GCUUGCUGCCUU CCCAGGCC | 258 | GGCCTGGGAAGG CAGCAAGC | 494 | 0.99 | 1.14 | 0.19 | 81.01 |
| GGUCCAGCAGGA UGUUGUCG | 259 | CGACAACATCCT GCTGGACC | 495 | 0.68 | 31.78 | 0.20 | 79.93 |
| CGGAGACCAUCC CAGUCGAG | 260 | CTCGACTGGGAT GGTCTCCG | 496 | 0.86 | 14.08 | 0.20 | 79.93 |
| UCUGCCUCGCGU AGUGACU | 261 | AGTCAACTACGC GAGGCAGA | 497 | 0.96 | 3.53 | 0.13 | 86.86 |
| AGGUAGUUCUCA UCCUGGAA | 262 | TTCCAGGATGAG AACTACCT | 498 | 0.93 | 7.36 | 0.37 | 62.62 |
| UCCUUGUAGUGG ACGAUCUU | 263 | AAGATCGTCCAC TACAAGGA | 499 | 0.87 | 12.96 | 0.15 | 84.87 |

TABLE 3-continued

Ability of DMPK-targeting antisense oligonucleotides to reduce expression of DMPK in cellulo

| Antisense Oligonucleotide Sequence | SEQ ID NO: | DMPK Target Sequence | SEQ ID NO: | 0.5 nM | | 50 nM | |
|---|---|---|---|---|---|---|---|
| | | | | Normalized DMPK Remaining | Percent DMPK Reduction | Normalized DMPK Remaining | Percent DMPK Reduction |
| GCAUCCAAAACGUGGAUUGG | 264 | CCAATCCACGTTTTGGATGC | 500 | 0.97 | 2.54 | 0.27 | 72.69 |
| GUCCAGCAGGAUGUGUCGG | 265 | CCGACAACATCCTGCTGGAC | 501 | 0.70 | 30.00 | 0.17 | 82.64 |
| AGCUCCCGCAGCGUCACCUC | 266 | GAGGTGACGCTGCGGGAGCT | 502 | 0.86 | 13.72 | 0.20 | 80.40 |
| CGAGAGCAGCGCAAGUGAGG | 267 | CCTCACTTGCGCTGCTCTCG | 503 | 1.02 | -2.19 | 0.63 | 37.11 |
| CAGGGAAAGCGCCUCCGAUA | 268 | TATCGGAGGCGCTTTCCCTG | 504 | 0.89 | 11.10 | 0.08 | 91.59 |
| AUUUCAUAGGCGAAUACACC | 269 | GGTGTATTCGCCTATGAAAT | 505 | 1.05 | -4.54 | 0.56 | 44.15 |
| UCGGCCAGGCGGAUGUGGCC | 270 | GGCCACATCCGCCTGGCCGA | 506 | 0.73 | 26.53 | 0.17 | 83.04 |
| AAGGGAUGUGUCCGGAAGUC | 271 | GACTTCCGGACACATCCCTT | 507 | 0.90 | 10.37 | 0.26 | 73.52 |
| CUUGUAGUGGACGAUCUUGC | 272 | GCAAGATCGTCCACTACAAG | 508 | 0.76 | 24.09 | 0.11 | 89.16 |
| AGUCGGCCAGGCGGAUGUGG | 273 | CCACATCCGCCTGGCCGACT | 509 | 0.94 | 6.15 | 0.33 | 67.44 |
| GCCUCAGCCUGGCCGAAAGA | 274 | TCTTTCGGCCAGGCTGAGGC | 510 | 1.05 | 4.82 | 0.37 | 63.11 |
| AGCGUCACCUCGGCCUCAGC | 275 | GCTGAGGCCGAGGTGACGCT | 511 | 0.78 | 22.10 | 0.35 | 64.70 |
| CAGCGGCAGAGAGAGGUGCT | 276 | AGCACCTCTCTCTGCCGCTG | 512 | 0.96 | 4.49 | 0.14 | 86.00 |
| CCAGCGGCAGAGAGAGGUGC | 277 | GCACCTCTCTCTGCCGCTGG | 513 | 0.97 | 3.23 | 0.15 | 84.55 |
| UUGUAGUGGACGAUCUUGCC | 278 | GGCAAGATCGTCCACTACAA | 514 | 0.83 | 17.22 | 0.19 | 81.05 |
| AGGGAAAGCGCCUCCGAUAG | 279 | CTATCGGAGGCGCTTTCCCT | 515 | 1.01 | -1.12 | 0.25 | 75.50 |
| GGGAAAGCGCCUCCGAUAGG | 280 | CCTATCGGAGGCGCTTTCCC | 516 | 0.90 | 10.02 | 0.23 | 76.79 |

Example 8: Selected Antisense Oligonucleotides Provided Dose-Dependent Reduction in DMPK Expression in Immortalized Myoblasts Eighteen oligonucleotides from Example 7 were selected to be evaluated for their ability to reduce DMPK expression in a dose-responsive manner. DM1 C15 myoblasts were prepared as in Example 7 to yield differentiated myotubes in 96-well microplates. After seven days of differentiation, cells were transfected with individual oligonucleotides using Lipofectamine MessengerMax. Each oligonucleotide was tested in triplicate at concentrations of 0.046 nM, 0.137 nM, 0.412 nM, 1.235 nM, 3.704 nM, 11.11 nM, 33.33 nM, and 100 nM by 3-fold serial dilutions using 0.3 µL of Lipofectamine MessengerMax per well.

Following addition of oligonucleotide, cells were incubated for 72 hours prior to harvesting for total RNA. cDNA was synthesized from the total RNA extracts and qPCR was performed to determine expression levels of DMPK using a commercially available Taqman probeset in technical quadruplicate. All qPCR data were analyzed using a traditional ΔΔCT method and were normalized to a plate-based negative control that comprised of cells treated with vehicle control (0.3 µL/well Lipofectamine MessengerMax without any oligonucleotide). Data for each oligonucleotide to was fit to sigmoidal curve in order to determine an effective concentration of each oligonucleotide that provided a half-maximal response (EC-50). Results from these experiments are shown in Table 4.

Each of the eighteen antisense oligonucleotides selected for dose-dependent experimentation were capable of dose-dependently reducing DMPK in differentiated myotubes. Further, each of the tested antisense oligonucleotides reduced DMPK with EC-50 values below 25 nM. For example, antisense oligonucleotides comprising SEQ ID NOs: 161, 112, 119, 87, and 109 resulted in EC-50 values of 3.27 nM, 3.59 nM, 5.45 nM, 6.04 nM, and 24.59 nM, respectively. These data demonstrate that the antisense oligonucleotides shown in Table 4 are capable of dose-dependent reduction of DMPK in cellulo, suggesting that muscle-targeting complexes comprising these antisense oligonucleotides would be capable of targeting DMPK in muscle tissues in vivo.

TABLE 4

Ability of DMPK-targeting antisense oligonucleotides to reduce expression of DMPK in dose-dependent manner in cellulo

| Antisense Oligonucleotide Sequence | SEQ ID NO: | DMPK Target Sequence | SEQ ID NO: | EC-50 (nM) | Percent DMPK reduction at 100 nM |
|---|---|---|---|---|---|
| GCAGGAUGUUGUCGGGUUUG | 98 | CAAACCCGACAACATCCTGC | 334 | 0.1679 | 89.77 |
| AGCAGGAUGUUGUCGGGUUU | 115 | AAACCCGACAACATCCTGCT | 351 | 0.2266 | 85.81 |
| GCGUAGAAGGGCGUCUGCCC | 109 | GGGCAGACGCCCTTCTACGC | 345 | 24.59 | 95.13 |
| CCCAGCGCCCACCAGUCACA | 119 | TGTGACTGGTGGGCGCTGGG | 355 | 5.454 | 63.69 |
| CCAUCUCGGCCGGAAUCCGC | 77 | GCGGATTCCGGCCGAGATGG | 313 | 0.44 | 95.42 |
| CGUUCCAUCUGCCCGCAGCU | 93 | AGCTGCGGGCAGATGGAACG | 329 | 0.19 | 89.97 |
| CAGGGACAGCCGCUGGAACU | 87 | AGTTCCAGCGGCTGTCCCTG | 323 | 6.04 | 90.59 |
| CAUGGCAUACACCUGGCCCG | 56 | CGGGCCAGGTGTATGCCATG | 292 | 0.42 | 75.28 |
| GCUUCAUCUUCACUACCGCU | 85 | AGCGGTAGTGAAGATGAAGC | 321 | 0.03 | 64.06 |
| GAAUGUCCGACAGUGUCUCC | 92 | GGAGACACTGTCGGACATTC | 328 | 0.07 | 97.23 |
| GGACGAUCUUGCCAUAGGUC | 112 | GACCTATGGCAAGATCGTCC | 348 | 3.59 | 92.18 |
| GCUGUCCCGGAGACCAUCCC | 161 | GGGATGGTCTCCGGGACAGC | 397 | 3.27 | 93.07 |
| GACAGAACAACGGCGAACAG | 145 | CTGTTCGCCGTTGTTCTGTC | 381 | 0.08 | 94.32 |
| UGUUGUCGGGUUUGAUGUCC | 100 | GGACATCAAACCCGACAACA | 336 | 0.21 | 93.95 |
| CGAAUGUCCGACAGUGUCUC | 59 | GAGACACTGTCGGACATTCG | 295 | 0.18 | 95.93 |
| GGGCCUGGGACCUCACUGUC | 69 | GACAGTGAGGTCCCAGGCCC | 305 | 0.07 | 90.58 |
| CUCUGCCGCAGGGACAGCCG | 71 | CGGCTGTCCCTGCGGCAGAG | 307 | 0.42 | 93.66 |
| UUGCCAUAGGUCUCCGCCGU | 79 | ACGGCGGAGACCTATGGCAA | 315 | 0.37 | 93.70 |

EQUIVALENTS AND TERMINOLOGY

The disclosure illustratively described herein suitably can be practiced in the absence of any element or elements, limitation or limitations that are not specifically disclosed herein. Thus, for example, in each instance herein any of the terms "comprising", "consisting essentially of", and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the disclosure. Thus, it should be understood that although the present disclosure has been specifically disclosed by preferred embodiments, optional features, modification and variation of the concepts herein disclosed may be resorted to by those skilled in the art, and that such modifications and variations are considered to be within the scope of this disclosure.

In addition, where features or aspects of the disclosure are described in terms of Markush groups or other grouping of alternatives, those skilled in the art will recognize that the disclosure is also thereby described in terms of any individual member or subgroup of members of the Markush group or other group.

It should be appreciated that, in some embodiments, sequences presented in the sequence listing may be referred to in describing the structure of an oligonucleotide or other nucleic acid. In such embodiments, the actual oligonucleotide or other nucleic acid may have one or more alternative nucleotides (e.g., an RNA counterpart of a DNA nucleotide or a DNA counterpart of an RNA nucleotide) and/or one or more modified nucleotides and/or one or more modified internucleotide linkages and/or one or more other modification compared with the specified sequence while retaining essentially same or similar complementary properties as the specified sequence.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein. Variations of those embodiments may become apparent to those of ordinary skill in the art upon reading the foregoing description.

The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context. Those skilled in the art will recognize, or be able to ascertain using no more than routine experimentation, many equivalents to the specific embodiments of the invention described herein. Such equivalents are intended to be encompassed by the following claims.

What is claimed is:

1. A composition comprising a plurality of complexes, each complex comprising an anti-transferrin receptor antibody covalently linked, via a protease-sensitive linker, to an oligonucleotide that targets a DMPK RNA, wherein each complex is configured for delivering the oligonucleotide into muscle cells, wherein the oligonucleotide is 15, 16, 17, or 18 nucleotides in length and comprises a region of complementarity that is fully complementary, along a length of at least 14 contiguous nucleotides, to a coding region of a DMPK sequence as set forth in SEQ ID NO: 15, wherein the oligonucleotide is configured to bring about degradation of the DMPK RNA via RNase H mediated degradation, wherein the oligonucleotide comprises a 5'-X-Y-Z-3' formula, wherein X and Z are flanking regions comprising one or more 2'-modified nucleosides selected from the group consisting of: 2'-O-methyl, 2'-fluoro, 2'-O-methoxyethyl, and 2',4'-bridged nucleosides, wherein Y is a gap region and each nucleoside in Y is a 2'-deoxyribonucleoside, and wherein the oligonucleotide comprises one or more phosphorothioate internucleoside linkages; and wherein the anti-transferrin receptor antibody binds an extracellular domain of a transferrin receptor protein 1 (TfR1).

2. The composition of claim 1, wherein the 5' end of the oligonucleotide is covalently linked to a lysine in the anti-transferrin receptor antibody via the protease-sensitive linker.

3. The composition of claim 1, wherein the protease-sensitive linker comprises a cleavage site of a lysosomal and/or endosomal protease.

4. The composition of claim 3, wherein the lysosomal and/or endosomal protease is a cathepsin protease.

5. The composition of claim 1, wherein the protease-sensitive linker comprises a valine-citrulline sequence.

6. The composition of claim 1, wherein the protease sensitive linker comprises a triazole obtained by a cycloaddition reaction between an azide and an alkyne.

7. The composition of claim 6, wherein prior to the cycloaddition reaction, the azide is located on the protease sensitive linker that is covalently linked to the 5' end of the oligonucleotide and the alkyne is provided in a bicyclononyne moiety, and wherein the protease-sensitive linker further covalently links to the anti-transferrin receptor antibody.

8. The composition of claim 7, wherein the protease-sensitive linker further comprises one or more polyethylene glycol units.

9. The composition of claim 1, wherein each nucleotide in X and Z is a 2'-modified nucleoside.

10. The composition of claim 1, wherein each internucleoside linkage in the oligonucleotide is a phosphorothioate linkage.

11. The composition of claim 1, wherein the oligonucleotide is 16, 17 or 18 nucleotides in length.

12. The composition of claim 1, wherein the region of complementarity is fully complementary, along a length of at least 16 contiguous nucleotides, to the coding region of the DMPK sequence.

13. The composition of claim 1, wherein the anti-transferrin receptor antibody is in the form of a ScFv, Fab fragment, Fab' fragment, F(ab')2 fragment, or Fv fragment.

14. The composition of claim 13, wherein the anti-transferrin receptor antibody is in the form of a Fab fragment.

15. The composition of claim 1, wherein the DMPK RNA comprises 38 to 200 repeating CUG units.

16. The composition of claim 1, wherein administration of the composition to a subject results in reduction of DMPK RNA level by at least 50% in muscle cells of the subject.

17. The composition of claim 1, wherein administration of the composition to a subject rescues splicing defects in muscle cells of the subject.

18. The composition of claim 1, wherein the muscle cells are skeletal muscle cells, cardiac muscle cells, or smooth muscle cells.

19. The composition of claim 17, wherein the subject is human.

20. The composition of claim 17, wherein the subject is cynomolgus.

21. The composition of claim 1, further comprising a pharmaceutically acceptable carrier.

22. The composition of claim 1, wherein the composition is formulated for intravenous administration.

23. The composition of claim 1, wherein the complexes of the composition on average comprise 1 to 3 oligonucleotides.

24. The composition of claim 1, wherein the DMPK RNA contains a disease-associated repeat sequence in the 3'-UTR that is associated with myotonic dystrophy type 1 (DM1).

* * * * *